(12) United States Patent
Angibaud et al.

(10) Patent No.: US 9,757,364 B2
(45) Date of Patent: Sep. 12, 2017

(54) NAPHTHYRIDINE DERIVATIVE COMPOUNDS

(71) Applicant: ASTEX THERAPEUTICS LIMITED, Cambridge (GB)

(72) Inventors: Patrick René Angibaud, Fontaine-Bellenger (FR); Michel Obringer, Ostwald (FR); Julien Jérémie Joseph Marin, Kertzfeld (FR); Matthieu Jeanty, Louviers (FR)

(73) Assignee: ASTEX THERAPEUTICS LTD, Cambridge (GB)

( * ) Notice: Subject to any disclaimer, the term of this patent is extended or adjusted under 35 U.S.C. 154(b) by 0 days.

(21) Appl. No.: 15/339,148

(22) Filed: Oct. 31, 2016

(65) Prior Publication Data

US 2017/0105978 A1  Apr. 20, 2017

Related U.S. Application Data

(60) Continuation of application No. 14/855,986, filed on Sep. 16, 2015, now Pat. No. 9,527,844, which is a division of application No. 14/354,793, filed as application No. PCT/GB2012/052669 on Oct. 26, 2012, now Pat. No. 9,309,241.

(60) Provisional application No. 61/552,883, filed on Oct. 28, 2011.

(30) Foreign Application Priority Data

Oct. 28, 2011 (GB) .................................. 1118675.6

(51) Int. Cl.
*A61K 31/4375* (2006.01)
*A61K 31/506* (2006.01)
*A61K 31/4545* (2006.01)
*A61K 31/444* (2006.01)

(52) U.S. Cl.
CPC ........ *A61K 31/4375* (2013.01); *A61K 31/444* (2013.01); *A61K 31/4545* (2013.01); *A61K 31/506* (2013.01)

(58) Field of Classification Search
CPC .................................................. A61K 31/4375
USPC ....................................................... 514/300
See application file for complete search history.

(56) References Cited

U.S. PATENT DOCUMENTS

| | | |
|---|---|---|
| 2,940,972 A | 6/1960 | Roch |
| 4,666,828 A | 5/1987 | Gusella |
| 4,683,202 A | 7/1987 | Mullis |
| 4,801,531 A | 1/1989 | Frossard |
| 5,192,659 A | 3/1993 | Simons |
| 5,272,057 A | 12/1993 | Smulson et al. |
| 5,700,823 A | 12/1997 | Hirth et al. |
| 5,882,864 A | 3/1999 | An et al. |
| 6,218,529 B1 | 4/2001 | An et al. |
| 6,271,231 B1 | 8/2001 | Bergstrand et al. |
| 6,331,555 B1 | 12/2001 | Hirth et al. |
| 7,432,279 B2 * | 10/2008 | Green ................. C07D 471/04 514/300 |
| 8,895,601 B2 | 11/2014 | Saxty et al. |
| 9,145,367 B2 | 9/2015 | Tazi et al. |
| 9,221,804 B2 | 12/2015 | Leonard et al. |
| 9,290,478 B2 | 3/2016 | Saxty et al. |
| 9,303,029 B2 | 4/2016 | Woodhead et al. |
| 9,303,030 B2 | 4/2016 | Angibaud et al. |
| 9,309,241 B2 | 4/2016 | Angibaud et al. |
| 9,309,242 B2 | 4/2016 | Berdini et al. |
| 9,439,896 B2 | 9/2016 | Berdini et al. |
| 9,447,098 B2 | 9/2016 | Saxty et al. |
| 9,464,071 B2 | 10/2016 | Saxty et al. |
| 9,493,426 B2 | 11/2016 | Angibaud et al. |
| 9,527,844 B2 | 12/2016 | Angibaud et al. |
| 2003/0207886 A1 | 11/2003 | Plucker et al. |
| 2005/0261307 A1 | 11/2005 | Cai et al. |
| 2005/0272728 A1 | 12/2005 | Altenbach et al. |
| 2005/0272736 A1 | 12/2005 | Altenbach et al. |
| 2007/0123494 A1 | 5/2007 | Seipelt et al. |
| 2007/0149484 A1 | 6/2007 | Claus et al. |
| 2008/0116789 A1 | 5/2008 | Yamaguchi et al. |
| 2009/0054304 A1 | 2/2009 | Herbert et al. |
| 2009/0118261 A1 | 5/2009 | Aquila et al. |
| 2009/0221591 A1 | 9/2009 | Hartmann et al. |
| 2010/0234347 A1 | 9/2010 | Dollinger et al. |
| 2013/0072457 A1 | 3/2013 | Saxty et al. |
| 2013/0267525 A1 | 10/2013 | Saxty et al. |
| 2014/0288053 A1 | 9/2014 | Mis et al. |
| 2014/0296236 A1 | 10/2014 | Berdini |
| 2015/0031669 A1 | 1/2015 | Woodhead et al. |
| 2015/0057293 A1 | 2/2015 | Angibaud et al. |

(Continued)

FOREIGN PATENT DOCUMENTS

| | | |
|---|---|---|
| CA | 2524525 | 12/2004 |
| CA | 2524948 | 12/2004 |

(Continued)

OTHER PUBLICATIONS

International Search Report for PCT/GB2012/052669 dated Feb. 21, 2013.

(Continued)

*Primary Examiner* — Niloofar Rahmani

(74) *Attorney, Agent, or Firm* — Heslin Rothenberg Farley & Mesiti P.C.

(57) ABSTRACT

The invention relates to new naphthyridine derivative compounds, to pharmaceutical compositions comprising said compounds, to processes for the preparation of said compounds and to the use of said compounds in the treatment of diseases, e.g. cancer.

21 Claims, No Drawings

(56) References Cited

U.S. PATENT DOCUMENTS

| | | |
|---|---|---|
| 2015/0105368 A1 | 4/2015 | Saxty et al. |
| 2015/0239883 A1 | 8/2015 | Angibaud et al. |
| 2015/0291589 A1 | 10/2015 | Saxty et al. |
| 2016/0031856 A1 | 2/2016 | Saxty et al. |
| 2016/0075666 A1 | 3/2016 | Angibaud et al. |
| 2016/0108034 A1 | 4/2016 | Angibaud et al. |
| 2016/0213677 A1 | 7/2016 | Angibaud et al. |
| 2016/0220564 A1 | 8/2016 | Woodhead et al. |
| 2016/0235744 A1 | 8/2016 | Berdini et al. |
| 2016/0311800 A1 | 10/2016 | Saxty et al. |
| 2017/0000781 A1 | 1/2017 | Berdini et al. |
| 2017/0000796 A1 | 1/2017 | Saxty et al. |
| 2017/0100406 A1 | 4/2017 | Jovcheva et al. |
| 2017/0101396 A1 | 4/2017 | Vermeulen et al. |
| 2017/0119763 A1 | 5/2017 | Jovcheva et al. |

FOREIGN PATENT DOCUMENTS

| | | |
|---|---|---|
| CN | 1128496 A | 8/1996 |
| CN | 102036963 A | 4/2011 |
| EP | 0544445 A2 | 6/1993 |
| EP | 1001946 | 5/2000 |
| EP | 1990342 | 11/2008 |
| EP | 2332939 | 6/2011 |
| EP | 2650293 A1 | 10/2013 |
| JP | 2003213463 A | 7/2003 |
| JP | 2006516561 A | 7/2006 |
| JP | 2008530030 A | 8/2008 |
| JP | 2008540535 A | 11/2008 |
| JP | 2010514693 A | 5/2010 |
| RU | 2377241 C2 | 12/2009 |
| WO | 95/19169 A2 | 7/1995 |
| WO | 98/54156 A1 | 12/1998 |
| WO | 99/17759 A2 | 4/1999 |
| WO | 00/42026 A1 | 7/2000 |
| WO | 01/19825 A1 | 2/2001 |
| WO | 01/68047 A2 | 9/2001 |
| WO | 02/076985 A1 | 10/2002 |
| WO | 03/051833 A2 | 6/2003 |
| WO | 03/055491 A1 | 7/2003 |
| WO | 2004/006355 A2 | 1/2004 |
| WO | 2004/030635 A2 | 4/2004 |
| WO | 2004/043950 A1 | 5/2004 |
| WO | 2004/056822 A1 | 7/2004 |
| WO | 2004065378 A1 | 8/2004 |
| WO | 2004/098494 A2 | 11/2004 |
| WO | 2004/110350 A2 | 12/2004 |
| WO | 2005/007099 A2 | 1/2005 |
| WO | 2005/009437 A1 | 2/2005 |
| WO | 2005/039587 A1 | 5/2005 |
| WO | 2005/047244 A2 | 5/2005 |
| WO | 2005/054201 A1 | 6/2005 |
| WO | 2005054231 A1 | 6/2005 |
| WO | 2005/061463 A1 | 7/2005 |
| WO | 2006/040052 A1 | 4/2006 |
| WO | 2006/066361 A1 | 6/2006 |
| WO | 2006084338 A1 | 8/2006 |
| WO | 2006/092430 A1 | 9/2006 |
| WO | 2006124354 A2 | 11/2006 |
| WO | 2007/003419 A1 | 1/2007 |
| WO | 2007054556 A1 | 5/2007 |
| WO | 2007/075567 A1 | 7/2007 |
| WO | 2007/125405 A2 | 11/2007 |
| WO | 2007/132227 A1 | 11/2007 |
| WO | 2008/003702 A2 | 1/2008 |
| WO | 2008/076278 A1 | 6/2008 |
| WO | 2008/078091 A1 | 7/2008 |
| WO | 2008/082198 A1 | 7/2008 |
| WO | 2008079988 A2 | 7/2008 |
| WO | 2008080015 A2 | 7/2008 |
| WO | 2008/138878 A2 | 11/2008 |
| WO | 2008/141065 A1 | 11/2008 |
| WO | 2008/148867 A2 | 12/2008 |
| WO | 2008/150827 A1 | 12/2008 |
| WO | 2008/155378 A1 | 12/2008 |
| WO | 2009/019518 A1 | 2/2009 |
| WO | 2009/021083 A1 | 2/2009 |
| WO | 2009/064835 A1 | 5/2009 |
| WO | 2009/137378 A1 | 11/2009 |
| WO | 2009/141386 A1 | 11/2009 |
| WO | 2010059771 A1 | 5/2010 |
| WO | 2010/084152 A1 | 7/2010 |
| WO | 2010088177 A1 | 8/2010 |
| WO | 2010129570 A1 | 11/2010 |
| WO | 2011/026579 A1 | 3/2011 |
| WO | 2011/028947 A2 | 3/2011 |
| WO | 2011/064250 A1 | 6/2011 |
| WO | 2011/126903 A2 | 10/2011 |
| WO | 2011/135376 A1 | 11/2011 |
| WO | 2011/146591 A1 | 11/2011 |
| WO | 2011/149937 A1 | 12/2011 |
| WO | 2012/073017 A1 | 6/2012 |
| WO | 2012/104776 A1 | 8/2012 |
| WO | 2012/118492 A1 | 9/2012 |
| WO | 2012/148540 A1 | 11/2012 |
| WO | 2013/032951 A1 | 3/2013 |
| WO | 2013/040515 A1 | 3/2013 |
| WO | 2013/043935 A1 | 3/2013 |
| WO | 2013/052699 A2 | 4/2013 |
| WO | 2013/061074 A1 | 5/2013 |
| WO | 2013/061077 A1 | 5/2013 |
| WO | 2013/061080 A1 | 5/2013 |
| WO | 2013/061081 A1 | 5/2013 |
| WO | 2013/061305 A1 | 5/2013 |
| WO | 2013/063217 A1 | 5/2013 |
| WO | 2013/179033 A1 | 12/2013 |
| WO | 2013/179034 A1 | 12/2013 |
| WO | 2014/174307 A1 | 10/2014 |
| WO | 2015144803 A1 | 10/2015 |
| WO | 2015144804 A1 | 10/2015 |
| WO | 2015144808 A1 | 10/2015 |
| WO | 2016128411 A1 | 8/2016 |

OTHER PUBLICATIONS

GB Search Report for GB Application No. GB1118675.6 dated Feb. 27, 2012.

Yan, Lin et al. "An efficient synthesis of quinoxaline derivatives from 4-chloro-4-deoxy-α-D-galactose and their cytotoxic activities", *Bioorganic & Medicinal Chemistry Letters*, vol. 17, No. 3, 2006, pp. 609-612.

Thompson, Andrew M. et al. "Synthesis and Structure—Activity Relationships of 7-Substituted 3-(2,6-Dichlorophenyl)-1,6-napthyridin-2(1H)-ones as Selective Inhibitors of pp60$^{c-src}$", *Journal of Medicinal Chemistry*, vol. 43, No. 16, 2000, pp. 3134-3147.

Berge, Stephen M. et al. "Pharmaceutical Salts", *Journal of Pharmaceutical Sciences*, vol. 66, No. 1, 1977, pp. 1-19.

Deady, Leslie W. "Ring Nitrogen Oxidation of Amino Substituted Nitrogen Heterocycles with m-Chloroperbenzoic Acid", *Synthetic Communications*, vol. 7(8), 1977, pp. 509-514.

Knights, Victoria et al. "De-regulated FGF receptors as therapeutic targets in cancer", *Pharmacology & Therapeutics*, 2010; vol. 125(1), pp. 105-117.

Korc, M. et al. "The Role of Fibroblast Growth Factors in Tumor Growth", *Current Cancer Drug Targets*, vol. 9(5), 2009, pp. 639-651.

Angerer, Lynne M. et al. "Demonstration of Tissue-Specific Gene Expression by in Situ Hybridization", *Methods in Enzymology*, vol. 152, 1987, pp. 649-661.

Deprimo, Samuel E. et al. "Expression profiling of blood samples from an SU5416 Phase III metastatic colorectal cancer clinical trial: a novel strategy for biomarker identification", *BMC Cancer*, vol. 3, 2003; pp. 1-12.

Orre, Maxine and Rogers, Peter A.W. "VEGF, VEGFR-1, VEGFR-2, Microvessel Density and Endothelial Cell Proliferation in Tumours of the Ovary", *Int. J. Cancel (Pred. Oncol.)*, vol. 84(2), 1999, pp. 101-108.

Zhou, Wenjun et al., "A Structure-Guided Approach to Creating Covalent FGFR Inhibitors", *Chemistry & Biology*, vol. 17, pp. 285-295 (2010).

(56) References Cited

OTHER PUBLICATIONS

Avendaño, C., et al., "Drugs That Inhibit Signalling Pathways for Tumor Cell Growth and Proliferation", *Medicinal Chemistry of Anticancer Drugs*, pp. 251-305 (2008).
Garuti, L., et al., Irreversible Protein Kinase Inhibitors, *Current Medicinal Chemistry*, vol. 18, No. 20, Jul. 1, 2011, pp. 2981-2994.
Vippagunta, S.R. et al., Crystalline Solids, *Advanced Drug Delivery Reviews*, vol. 48, pp. 3-26 (2001).
Jordan, V.C., Tamoxifen: A Most Unlikely Pioneering Medicine, *Nature Reviews: Drug Discovery*, vol. 2, pp. 205-213 (2003).
Hackam, D.G., et al., Translation of Research Evidence From Animals to Humans, *JAMA*, vol. 14, pp. 1731-1732 (2006).
"Himicheskaja jenciklopedija" tom 4, str. 990-993, izdatel'stvo "Sovetskaja jencklopedija", Moskva, 1988 (In English: Chemical Encyclopedia, vol. 4, pp. 990-993, Publishing House "Soviet encyclopedia", Moscow, 1988).
V. Hikkinvottom, "Reakcii Organicheskih Soedinenij" Gosudarstvennoe ob#eninennoe nauchno-technicheskoe izdatel'stvo, Redakcija himicheskoj literatury, Moskva, stranicy 360-362, 1939 (In English: V. Hikkinbottom, "Reactions of Organic Compounds", State Associated Scientific-Technical Publishing House, Editor Office of Chemical Literature, pp. 360-362, Moscow, 1939).
"Himicheskaja jenciklopedija" tom. 1, stranicy 242-243, izdatel'stvo "Sovetskaja jencklopedija", Moskva, 1988 (In English: Chemical Encyclopedia (thesaurus), vol. 1, pp. 242-243, publishing house "Soviet encyclopedia", Moscow, 1988).
Dorwald, F.Z., Side Reactions in Organic Synthesis: A Guide to Successful Synthesis Design, Weinheim:WILEY-VCH Verlag GmbH & Co. KGaA, 2005, ISBN: 3-527-31021.5.
Lima, L.M., et al., "Bioisosterism: A Useful Strategy for Molecular Modification and Drug Design", *Current Medical Chemistry*, vol. 12(1), pp. 23-49 (2005).
Patani, G.A., et al., "Bioisosterism: A Rational Approach in Drug Design", *Chem. Rev.* vol. 96, pp. 3147-3176 (1996).
Dieci, M.V., et al., Fibroblast Growth Factor Receptor Inhibitors as a Cancer Treatment: From a Biologic Rationale to Medical Perspectives, Cancer Discovery, vol. 3, No. 3, pp. 264-279 (Feb. 2013).
Gallick, G.E., et al., Small-molecule protein tyrosine kinase inhibitors for the treatment of metastatic prostate cancer, Future Medicinal Chemistry, vol. 4, No. 1, pp. 107-119 (Jan. 2012).
Study to Assess the Relative Bioavailability of Orally Administered JNJ-42756493 Tablet Versus JNJ-42756493 Capsule in Healthy Participants, ClinicalTrials.gov, pp. 1-4 (2014).
Matsuda, Y., et al., Fibroblast Growth Factor Receptor-2 IIIc as a Novel Molecular Target in Colorectal Cancer, Current Colorectal Cancer Reports, vol. 10, No. 1, pp. 20-26 (2014).
Carneiro, B.A., et al., Emerging therapeutic targets in bladder cancer, Cancer Treatment Reviews, vol. 41, No. 2, pp. 170-178 (2015).
Fujita, M., et al., Generation of Formaldehyde by Pharmaceutical Excipients and Its Absorption by Meglumine, Chem. Pharm. Bull, vol. 57, No. 10, pp. 1096-1099 (2009).
Adcock, J., et al., Diversity oriented synthesis: substitution at C5 in unreactive pyrimidines by Claisen rearrangement and reactivity in nucleophilic substitution at C2 and C4 in pteridines and pyrido[2,3-d]pyrimidines, Tetrahedron, vol. 67, pp. 3226-3237 (2011).
Database Caplus, Grina, et al., Preparation of oxohydroquinazolinylaminophenylpropanesulfonamide derivatives and analogs for use as Raf inhibitors, Document No. 157:465574, Accession No. 2012:1301209 (2012).
Liang, G., et al., "Small molecule inhibition of fibroblast growth factor receptors in cancer", Cytokine & Growth Factor Reviews, vol. 24, pp. 467-475 (2013).
Golub, T.R., et al., "Molecular Classification of Cancer: Class Discovery and Class Prediction by Gene Expression Monitoring", Science, vol. 286, pp. 531-537 (1999).
Greulich, H., et al., "Targeting mutant fibroblast growth factor receptors in cancer", Trends in Molecular Medicine, vol. 17, No. 5, pp. 283-292 (2011).
Freshney, R.I., "Culture of Animal Cells, A Manual of Basic Technique", Published by Alan R. Liss, Inc, New York, pp. 1-6 (1983).
Cohen, P., "The development and therapeutic potential of protein kinase inhibitors", Current Opinion in Chemical Biology, vol. 3, pp. 459-465 (1999).
Cecil Textbook of Medicine, edited by Bennet, J.C., and Plum, F., 20th edition, vol. 1, pp. 1004-1010 (1996).
Hynes, N.E., et al., "Potential for Targeting the Fibroblast Growth Factor Receptors in Breast Cancer", Cancer Research, vol. 70, pp. 5199-5202 (2010).
Neidle, S., "Cancer Drug Design and Discovery", Elsevier/Academic Press, pp. 427-431 (2008).
Dermer, G.B., "Another Anniversary for the War on Cancer", Biotechnology, vol. 12, p. 320 (1994).
Katoh, Y., et al., "FGFR2-related pathogenesis and FGFR2-targeted therapeutics (Review)", International Journal of Molecular Medicine, vol. 23, pp. 307-311 (2009).
Jain, V.K., et al., "Challenges and opportunities in the targeting of fibroblast growth factor receptors in breast cancer", Breast Cancer Research, vol. 14, No. 208, pp. 1-9 (2012).

* cited by examiner

NAPHTHYRIDINE DERIVATIVE COMPOUNDS

CROSS REFERENCE TO RELATED APPLICATIONS

This application is a continuation of U.S. application Ser. No. 14/855,986, filed with the U.S. Patent and Trademark Office on Sep. 16, 2015, which is a divisional of U.S. application Ser. No. 14/354,793, filed with the U.S. Patent and Trademark Office on Apr. 28, 2014, which is a national stage filing under Section 371 of International Application No. PCT/GB2012/052669 filed on Oct. 26, 2012, and published in English as WO 2013/061077 A1 on May 2, 2013, and claims priority to British Application No. 1118675.6 filed on Oct. 28, 2011 and to U.S. Provisional Application No. 61/552,883 filed on Oct. 28, 2011. The entire disclosures of each of the prior applications are hereby incorporated herein by reference.

FIELD OF THE INVENTION

The invention relates to new naphthyridine derivative compounds, to pharmaceutical compositions comprising said compounds, to processes for the preparation of said compounds and to the use of said compounds in the treatment of diseases, e.g. cancer.

SUMMARY OF THE INVENTION

According to a first aspect of the invention there is provided compounds of formula (I):

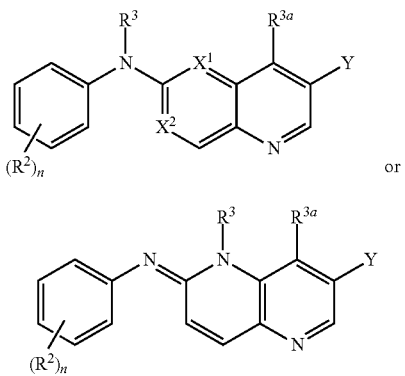

including any tautomeric or stereochemically isomeric form thereof, wherein $X^1$ is N and $X^2$ is $CR^{3a}$, or $X^2$ is N and $X^1$ is $CR^{3a}$;

each $R^2$ is independently selected from hydroxyl, halogen, cyano, $C_{1-4}$alkyl, $C_{2-4}$alkenyl, $C_{2-4}$alkynyl, $C_{1-4}$alkoxy, hydroxy$C_{1-4}$alkyl, hydroxy$C_{1-4}$alkoxy, halo$C_{1-4}$alkyl, halo$C_{1-4}$alkoxy, hydroxyhalo$C_{1-4}$alkyl, hydroxyhalo$C_{1-4}$alkoxy, $C_{1-4}$alkoxy$C_{1-4}$alkyl, halo$C_{1-4}$alkoxy$C_{1-4}$alkyl, $C_{1-4}$alkoxy$C_{1-4}$alkyl wherein each $C_{1-4}$alkyl may optionally be substituted with one or two hydroxyl groups, hydroxyhalo$C_{1-4}$alkoxy$C_{1-4}$alkyl, $R^{13}$, $C_{1-4}$alkyl substituted with $R^{13}$, $C_{1-4}$alkyl substituted with —C(=O)—$R^{13}$, $C_{1-4}$alkoxy substituted with $R^{13}$, $C_{1-4}$alkoxy substituted with —C(=O)—$R^{13}$, —C(=O)—$R^{13}$, $C_{1-4}$alkyl substituted with —C(=O)—NR$^7$R$^8$, $C_{1-4}$alkoxy substituted with —NR$^7$R$^8$, $C_{1-4}$alkoxy substituted with —C(=O)—NR$^7$R$^8$, —NR$^7$R$^8$ and —C(=O)—NR$^7$R$^8$; or when two $R^2$ groups are attached to adjacent carbon atoms they may be taken together to form a radical of formula:

—O—(C($R^{17}$)$_2$)$_p$—O—;

—X—CH=CH—; or

—X—CH=N—;

wherein $R^{17}$ represents hydrogen or fluorine, p represents 1 or 2 and X represents O or S;

Y represents —C$R^{18}$=N—O$R^{19}$ or -E-D;

D represents a 3 to 12 ring membered monocyclic or bicyclic carbocyclyl or a 3 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups;

E represents a bond, —(C$R^{22}R^{23}$)$_n$—, $C_{2-4}$alkenediyl optionally substituted with $R^{22}$, $C_{2-4}$alkynediyl optionally substituted with $R^{22}$, —CO—(C$R^{22}R^{23}$)$_s$—, —(C$R^{22}R^{23}$)$_s$—CO—, —NR$^{22}$—(C$R^{22}R^{23}$)$_s$—, —(C$R^{22}R^{23}$)$_s$—NR$^{22}$—, —O—(C$R^{22}R^{23}$)$_s$—, —(C$R^{22}R^{23}$)$_s$—O—, —S(O)$_m$—(C$R^{22}R^{23}$)$_s$—, —(C$R^{22}R^{23}$)$_s$—S(O)$_m$—, —(C$R^{22}R^{23}$)$_s$—CO—NR$^{22}$—(C$R^{22}R^{23}$)$_s$— or —(C$R^{22}R^{23}$)$_s$—NR$^{22}$—CO—(C$R^{22}R^{23}$)$_s$—;

$R^1$ represents hydrogen, halo, cyano, $C_{1-6}$alkyl, $C_{1-6}$alkoxy, —C(=O)—O—$C_{1-6}$alkyl, $C_{2-4}$alkenyl, hydroxy$C_{1-6}$alkyl, halo$C_{1-6}$alkyl, hydroxyhalo$C_{1-6}$alkyl, cyano$C_{1-4}$alkyl, $C_{1-6}$alkoxy$C_{1-6}$alkyl wherein each $C_{1-6}$alkyl may optionally be substituted with one or two hydroxyl groups, —NR$^4$R$^5$, $C_{1-6}$alkyl substituted with —O—C(=O)—$C_{1-6}$alkyl, $C_{1-6}$alkyl substituted with —NR$^4$R$^5$, —C(=O)—NR$^4$R$^5$, —C(=O)—$C_{1-6}$alkyl-NR$^4$R$^5$, $C_{1-6}$alkyl substituted with —C(=O)—NR$^4$R$^5$, —S(=O)$_2$—$C_{1-6}$alkyl, —S(=O)$_2$-halo$C_{1-6}$alkyl, —S(=O)$_2$—NR$^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—NR$^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NR$^{12}$—S(=O)$_2$—NR$^{14}R^{15}$, $R^6$, $C_{1-6}$alkyl substituted with $R^6$, —C(=O)—$R^6$, $C_{1-6}$alkyl substituted with —C(=O)—$R^6$, hydroxy$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$;

$R^{3a}$ represents hydrogen, chlorine, hydroxyl, or $C_{1-6}$alkoxy;
$R^3$ represents hydroxyl, $C_{1-6}$alkoxy, hydroxy$C_{1-6}$alkoxy, $C_{1-6}$alkoxy substituted with —NR$^{10}R^{11}$, $C_{1-6}$alkyl, $C_{2-6}$alkenyl, $C_{2-6}$alkynyl, halo$C_{1-6}$alkyl optionally substituted with —O—C(=O)—$C_{1-6}$alkyl, hydroxy$C_{1-6}$alkyl optionally substituted with —O—C(=O)—$C_{1-6}$alkyl, hydroxy$C_{2-6}$alkenyl, hydroxy$C_{2-6}$alkynyl, hydroxyhalo$C_{1-6}$alkyl, cyano$C_{1-6}$alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy$C_{1-6}$alkyl-O—C(=O)—, $C_{1-6}$alkyl substituted with $C_{1-6}$alkoxy$C_{1-6}$alkyl-C(=O)—, $C_{1-6}$alkyl substituted with —O—C(=O)—$C_{1-6}$alkyl, $C_{1-6}$alkoxy-$C_{1-6}$alkyl wherein each $C_{1-6}$alkyl may optionally be substituted with one or two hydroxyl groups or with —O—C(=O)—$C_{1-6}$alkyl, $C_{2-6}$alkenyl substituted with $C_{1-6}$alkoxy, $C_{2-6}$alkynyl substituted with $C_{1-6}$alkoxy, $C_{1-6}$alkyl substituted with $R^9$ and optionally substituted with —O—C(=O)—$C_{1-6}$alkyl, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —$NR^{10}R^{11}$, $C_{2-6}$alkenyl substituted with —$NR^{10}R^{11}$, $C_{2-6}$alkynyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, —$C_{1-6}$alkyl-$C(R^{12})$=N—O—$R^{12}$, $C_{1-6}$alkyl substituted with —$C$(=O)—$NR^{10}R^{11}$, $C_{1-6}$alkyl substituted with —O—$C$(=O)—$NR^{10}R^{11}$, —$S$(=O)$_2$—$C_{1-6}$alkyl, —$S$(=O)$_2$-halo$C_{1-6}$alkyl, —$S$(=O)$_2$—$NR^{14}R^{15}$, $C_{1-6}$alkyl substituted with —$S$(=O)$_2$—$C_{1-6}$alkyl, $C_{1-6}$alkyl substituted with —$S$(=O)$_2$-halo$C_{1-6}$alkyl, $C_{1-6}$alkyl substituted with —$S$(=O)$_2$—$NR^{14}R^{15}$, $C_{1-6}$alkyl substituted with —$NR^{12}$—$S$(=O)$_2$—$C_{1-6}$alkyl, $C_{1-6}$alkyl substituted with —NH—$S$(=O)$_2$-halo$C_{1-6}$alkyl, $C_{1-6}$alkyl substituted with —$NR^{12}$—$S$(=O)$_2$—$NR^{14}R^{15}$, $R^{13}$, $C_{1-6}$alkyl substituted with —$P$(=O)(OH)$_2$ or $C_{1-6}$alkyl substituted with —$P$(=O)(O$C_{1-6}$alkyl)$_2$;

$R^4$ and $R^5$ each independently represent hydrogen, $C_{1-6}$alkyl, $C_{1-6}$alkyl substituted with —$NR^{14}R^{15}$, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, —$S$(=O)$_2$—$C_{1-6}$alkyl, —$S$(=O)$_2$-halo$C_{1-6}$alkyl, —$S$(=O)$_2$—$NR^{14}R^{15}$, —$C$(=O)—$NR^{14}R^{15}$, —$C$(=O)—O—$C_{1-6}$alkyl, —$C$(=O)—$R^{13}$, $C_{1-6}$alkyl substituted with —$S$(=O)$_2$—$C_{1-6}$alkyl, $C_{1-6}$alkyl substituted with —$S$(=O)$_2$-halo$C_{1-6}$alkyl, $C_{1-6}$alkyl substituted with —$S$(=O)$_2$—$NR^{14}R^{15}$, $C_{1-6}$alkyl substituted with —NH—$S$(=O)$_2$—$C_{1-6}$alkyl, $C_{1-6}$alkyl substituted with —NH—$S$(=O)$_2$-halo$C_{1-6}$alkyl, $C_{1-6}$alkyl substituted with —NH—$S$(=O)$_2$—$NR^{14}R^{15}$, $R^{13}$ or $C_{1-6}$alkyl substituted with $R^{13}$;

$R^6$ represents $C_{3-8}$cycloalkyl, $C_{3-8}$cycloalkenyl, phenyl, 4 to 7-membered monocyclic heterocyclyl containing at least one heteroatom selected from N, O or S; said $C_{3-8}$cycloalkyl, $C_{3-8}$cycloalkenyl, phenyl, 4 to 7-membered monocyclic heterocyclyl, optionally and each independently being substituted by 1, 2, 3, 4 or 5 substituents, each substituent independently being selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O—$C$(=O)—, —$NR^{14}R^{15}$, —$C$(=O)—$NR^{14}R^{15}$, $C_{1-6}$alkyl substituted with —$NR^{14}R^{15}$, $C_{1-6}$alkyl substituted with —$C$(=O)—$NR^{14}R^{15}$, —$S$(=O)$_2$—$C_{1-6}$alkyl, —$S$(=O)$_2$-halo$C_{1-6}$alkyl, —$S$(=O)$_2$—$NR^{14}R^{15}$, $C_{1-6}$alkyl substituted with —$S$(=O)$_2$—$C_{1-6}$alkyl, $C_{1-6}$alkyl substituted with —$S$(=O)$_2$-halo$C_{1-6}$alkyl, $C_{1-6}$alkyl substituted with —$S$(=O)$_2$—$NR^{14}R^{15}$, $C_{1-6}$alkyl substituted with —NH—$S$(=O)$_2$—$C_{1-6}$alkyl, $C_{1-6}$alkyl substituted with —NH—$S$(=O)$_2$-halo$C_{1-6}$alkyl or $C_{1-6}$alkyl substituted with —NH—$S$(=O)$_2$—$NR^{14}R^{15}$;

$R^7$ and $R^8$ each independently represent hydrogen, $C_{1-6}$alkyl, hydroxy$C_{1-6}$alkyl, halo$C_{1-6}$alkyl, hydroxyhalo$C_{1-6}$alkyl or $C_{1-6}$alkoxy$C_{1-6}$alkyl;

$R^9$ represents $C_{3-8}$cycloalkyl, $C_{3-8}$cycloalkenyl, phenyl, naphthyl, or 3 to 12 membered monocyclic or bicyclic heterocyclyl containing at least one heteroatom selected from N, O or S, said $C_{3-8}$cycloalkyl, $C_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl-O—$C$(=O)—, $C_{1-4}$alkyl substituted with $C_{1-4}$alkyl-O—$C$(=O)—, $C_{1-4}$alkyl-$C$(=O)—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —$NR^{14}R^{15}$, —$C$(=O)—$NR^{14}R^{15}$, $C_{1-4}$alkyl substituted with —$NR^{14}R^{15}$, $C_{1-4}$alkyl substituted with —$C$(=O)—$NR^{14}R^{15}$, $C_{1-4}$alkoxy, —$S$(=O)$_2$—$C_{1-4}$alkyl, —$S$(=O)$_2$-halo$C_{1-4}$alkyl, —$S$(=O)$_2$—$NR^{14}R^{15}$, $C_{1-4}$alkyl substituted with —$S$(=O)$_2$—$NR^{14}R^{15}$, $C_{1-4}$alkyl substituted with —NH—$S$(=O)$_2$—$C_{1-4}$alkyl, $C_{1-4}$alkyl substituted with —NH—$S$(=O)$_2$-halo$C_{1-4}$alkyl, $C_{1-4}$alkyl substituted with —NH—$S$(=O)$_2$—$NR^{14}R^{15}$, $R^{13}$, —$C$(=O)—$R^{13}$, $C_{1-4}$alkyl substituted with $R^{13}$, phenyl optionally substituted with $R^{16}$ phenyl$C_{1-6}$alkyl wherein the phenyl is optionally substituted with $R^{16}$, a 5 or 6-membered aromatic monocyclic heterocyclyl containing at least one heteroatom selected from N, O or S wherein said heterocyclyl is optionally substituted with $R^{16}$;

or when two of the substituents of $R^9$ are attached to the same atom, they may be taken together to form a 4 to 7-membered saturated monocyclic heterocyclyl containing at least one heteroatom selected from N, O or S;

$R^{10}$ and $R^{11}$ each independently represent hydrogen, carboxyl, $C_{1-6}$alkyl, cyano$C_{1-6}$alkyl, $C_{1-6}$alkyl substituted with —$NR^{14}R^{15}$, $C_{1-6}$alkyl substituted with —$C$(=O)—$NR^{14}R^{15}$, halo$C_{1-6}$alkyl, hydroxy$C_{1-6}$alkyl, hydroxyhalo$C_{1-6}$alkyl, $C_{1-6}$alkoxy, $C_{1-6}$alkoxy$C_{1-6}$alkyl wherein each $C_{1-6}$alkyl may optionally be substituted with one or two hydroxyl groups, $R^6$, $C_{1-6}$alkyl substituted with $R^6$, —$C$(=O)—$R^6$, —$C$(=O)—$C_{1-6}$alkyl, —$C$(=O)-hydroxy$C_{1-6}$alkyl, —$C$(=O)-halo$C_{1-6}$alkyl, —$C$(=O)-hydroxyhalo$C_{1-6}$alkyl, $C_{1-6}$alkyl substituted with —$Si(CH_3)_3$, —$S$(=O)$_2$—$C_{1-6}$alkyl, —$S$(=O)$_2$-halo$C_{1-6}$alkyl, —$S$(=O)$_2$—$NR^{14}R^{15}$, $C_{1-6}$alkyl substituted with —$S$(=O)$_2$—$C_{1-6}$alkyl, $C_{1-6}$alkyl substituted with —$S$(=O)$_2$-halo$C_{1-6}$alkyl, $C_{1-6}$alkyl substituted with —$S$(=O)$_2$—$NR^{14}R^{15}$, $C_{1-6}$alkyl substituted with —NH—$S$(=O)$_2$—$C_{1-6}$alkyl, $C_{1-6}$alkyl substituted with —NH—$S$(=O)$_2$-halo$C_{1-6}$alkyl, $C_{1-6}$alkyl substituted with carboxyl, or $C_{1-6}$alkyl substituted with —NH—$S$(=O)$_2$—$NR^{14}R^{15}$;

$R^{12}$ represents hydrogen or $C_{1-4}$alkyl optionally substituted with $C_{1-4}$alkoxy;

$R^{13}$ represents $C_{3-8}$cycloalkyl or a saturated 4 to 6-membered monocyclic heterocyclyl containing at least one heteroatom selected from N, O or S, wherein said $C_{3-8}$cycloalkyl or monocyclic heterocyclyl is optionally substituted with 1, 2 or 3 substituents each independently selected from halogen, hydroxyl, $C_{1-6}$alkyl, halo$C_{1-6}$alkyl, =O, cyano, —$C$(=O)—$C_{1-6}$alkyl, $C_{1-6}$alkoxy, or —$NR^{14}R^{15}$;

$R^{14}$ and $R^{15}$ each independently represent hydrogen, or halo$C_{1-4}$alkyl, or $C_{1-4}$alkyl optionally substituted with a substituent selected from hydroxyl, $C_{1-4}$alkoxy, amino or mono- or di($C_{1-4}$alkyl)amino;

$R^{16}$ represents hydroxyl, halogen, cyano, $C_{1-4}$alkyl, $C_{1-4}$alkoxy, —$NR^{14}R^{15}$ or —$C$(=O)$NR^{14}R^{15}$;

$R^{18}$ represents hydrogen, $C_{1-6}$ alkyl, $C_{3-8}$ cycloalkyl, $C_{1-4}$alkyl substituted with $C_{3-8}$ cycloalkyl;

$R^{19}$ represents hydrogen; $C_{1-6}$ alkyl; $C_{3-8}$ cycloalkyl; $C_{1-6}$alkyl substituted with —O—$R^{20}$; —$(CH_2)_r$—CN; —$(CH_2)_r$—CONR$^{20}$R$^{21}$; —$(CH_2)_{r1}$—NR$^{20}$R$^{21}$; —$(CH_2)_{r1}$—NR$^{20}$COR$^{21}$; —$(CH_2)_{r1}$—NR$^{20}$—$(CH_2)_s$—SO$_2$—R$^{21}$; —$(CH_2)_r$—NH—SO$_2$—NR$^{20}$R$^{21}$; —$(CH_2)_{r1}$—NR$^{20}$CO$_2$R$^{21}$; —$(CH_2)_r$—SO$_2$NR$^{20}$R$^{21}$; phenyl optionally substituted with 1, 2, 3, 4 or 5 substituents each independently selected from halogen, $C_{1-4}$alkyl, $C_{1-4}$alkyloxy, cyano or amino; a 5- or 6-membered aromatic monocyclic heterocycle containing at least one heteroatom selected from N, O or S, said heterocycle being optionally substituted with 1, 2, 3 or 4 substituents each independently selected from halogen, $C_{1-4}$alkyl, $C_{1-4}$alkyloxy, cyano or amino; wherein said $C_{1-6}$ alkyl and $C_{3-8}$ cycloalkyl, may be optionally substituted by one or more $R^{20}$ groups $R^{20}$ and $R^{21}$ independently represent hydrogen, $C_{1-6}$ alkyl, hydroxy$C_{1-6}$alkyl, —$(CH_2)_n$—O—$C_{1-6}$alkyl, or when attached to a nitrogen atom $R^{20}$ and $R^{21}$ can be taken together to form with the nitrogen atom to which they are attached a monocyclic saturated 4, 5 or 6-membered ring which optionally contains a further heteroatom selected from O, S or N;

$R^{22}$ and $R^{23}$ independently represent hydrogen, $C_{1-6}$ alkyl, or hydroxy$C_{1-6}$alkyl;

m independently represents an integer equal to 0, 1 or 2;

n independently represents an integer equal to 0, 1, 2, 3 or 4;

s independently represents an integer equal to 0, 1, 2, 3 or 4;

r independently represent an integer equal to 1, 2, 3, or 4;

r1 independently represent an integer equal to 2, 3 or 4;

the N-oxides thereof, the pharmaceutically acceptable salts thereof or the solvates thereof.

WO2006/092430, WO2008/003702, WO01/68047, WO2005/007099, WO2004/098494, WO2009/141386, WO 2004/030635, WO 2008/141065, WO 2011/026579, WO 2011/028947, WO 00/42026, US2008/0116789, WO2010/084152, US2009/0054304, WO2008/150827, WO2006/066361, WO2011064250, WO2007/125405 and WO2011/135376 which each disclose a series of heterocyclyl derivatives.

DETAILED DESCRIPTION OF THE INVENTION

Unless the context indicates otherwise, references to formula (I) in all sections of this document (including the uses, methods and other aspects of the invention) include references to all other sub-formula, sub-groups (e.g. I-A, I-B, I-C or I-D), preferences, embodiments and examples as defined herein.

The prefix "$C_{x-y}$" (where x and y are integers) as used herein refers to the number of carbon atoms in a given group. Thus, a $C_{1-6}$alkyl group contains from 1 to 6 carbon atoms, a $C_{3-6}$cycloalkyl group contains from 3 to 6 carbon atoms, a $C_{1-4}$alkoxy group contains from 1 to 4 carbon atoms, and so on.

The term 'halo' or 'halogen' as used herein refers to a fluorine, chlorine, bromine or iodine atom.

The term '$C_{1-4}$alkyl', or '$C_{1-6}$alkyl' as used herein as a group or part of a group refers to a linear or branched saturated hydrocarbon group containing from 1 to 4 or 1 to 6 carbon atoms. Examples of such groups include methyl, ethyl, n-propyl, isopropyl, n-butyl, isobutyl, sec-butyl, tert-butyl, n-pentyl, isopentyl, neopentyl or hexyl and the like.

The term '$C_{2-4}$alkenyl' or '$C_{2-6}$alkenyl' as used herein as a group or part of a group refers to a linear or branched hydrocarbon group containing from 2 to 4 or 2 to 6 carbon atoms and containing a carbon carbon double bond.

The term '$C_{2-4}$alkenediyl' as used herein as a group or part of a group refers to a linear or branched bivalent hydrocarbon group containing from 2 to 4 carbon atoms and containing a carbon carbon double bond.

The term '$C_{2-4}$alkynyl' or '$C_{2-6}$alkynyl' as used herein as a group or part of a group refers to a linear or branched hydrocarbon group having from 2 to 4 or 2 to 6 carbon atoms and containing a carbon carbon triple bond.

The term '$C_{1-4}$alkoxy' or '$C_{1-6}$alkoxy' as used herein as a group or part of a group refers to an —O—$C_{1-4}$alkyl group or an —O—$C_{1-6}$alkyl group wherein $C_{1-4}$alkyl and $C_{1-6}$alkyl are as defined herein. Examples of such groups include methoxy, ethoxy, propoxy, butoxy, and the like.

The term '$C_{1-4}$alkoxy$C_{1-4}$alkyl' or '$C_{1-6}$alkoxy$C_{1-6}$alkyl' as used herein as a group or part of a group refers to a $C_{1-4}$alkyl-O—$C_{1-4}$alkyl group or a $C_{1-6}$alkyl-O—$C_{1-6}$alkyl group wherein $C_{1-4}$alkyl and $C_{1-6}$alkyl are as defined herein. Examples of such groups include methoxyethyl, ethoxyethyl, propoxymethyl, butoxypropyl, and the like.

The term '$C_{3-8}$cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term '$C_3$-8cycloalkenyl' as used herein refers to a monocyclic hydrocarbon ring of 3 to 8 carbon atoms having a carbon carbon double bond.

The term 'hydroxy$C_{1-4}$alkyl' or 'hydroxy$C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group. The terms 'hydroxy$C_{1-4}$alkyl' or 'hydroxy$C_{1-6}$alkyl' therefore include monohydroxy$C_{1-4}$alkyl, monohydroxy$C_{1-6}$alkyl and also polyhydroxy$C_{1-4}$alkyl and polyhydroxy$C_{1-6}$alkyl. There may be one, two, three or more hydrogen atoms replaced with a hydroxyl group, so the hydroxy$C_{1-4}$alkyl or hydroxy$C_{1-6}$alkyl may have one, two, three or more hydroxyl groups. Examples of such groups include hydroxymethyl, hydroxyethyl, hydroxypropyl and the like.

The term 'halo$C_{1-4}$alkyl' or 'halo$C_{1-6}$alkyl' as used herein as a group or part of a group refers to a $C_{1-4}$alkyl or $C_{1-6}$alkyl group as defined herein wherein one or more than one hydrogen atom is replaced with a halogen. The term 'halo$C_{1-4}$alkyl' or 'halo$C_{1-6}$alkyl' therefore include monohalo$C_{1-4}$alkyl, monohalo$C_{1-6}$alkyl and also polyhalo$C_{1-4}$alkyl and polyhalo$C_{1-6}$alkyl. There may be one, two, three or more hydrogen atoms replaced with a halogen, so the halo$C_{1-4}$alkyl or halo$C_{1-6}$alkyl may have one, two, three or more halogens. Examples of such groups include fluoroethyl, fluoromethyl, trifluoromethyl or trifluoroethyl and the like.

The term 'hydroxyhalo$C_{1-4}$alkyl' or 'hydroxyhalo$C_{1-6}$alkyl' as used herein as a group or part of a group refers to a $C_{1-4}$alkyl or $C_{1-6}$alkyl group as defined herein wherein one or more than one hydrogen atom is replaced with a hydroxyl group and one or more than one hydrogen atom is replaced with a halogen. The term 'hydroxyhalo$C_{1-4}$alkyl' or 'hydroxyhalo$C_{1-6}$alkyl' therefore refers to a $C_{1-4}$alkyl or $C_{1-6}$alkyl group wherein one, two, three or more hydrogen atoms are replaced with a hydroxyl group and one, two, three or more hydrogen atoms are replaced with a halogen.

The term 'hydroxy$C_{1-4}$alkoxy' or 'hydroxy$C_{1-6}$alkoxy' as used herein as a group or part of a group refers to an —O—$C_{1-4}$alkyl group or an —O—$C_{1-6}$alkyl group wherein the $C_{1-4}$alkyl and $C_{1-6}$alkyl group is as defined above and one or more than one hydrogen atom of the $C_{1-4}$alkyl or $C_{1-6}$alkyl group is replaced with a hydroxyl group. The term 'hydroxy-$C_{1-4}$alkoxy' or 'hydroxy$C_{1-6}$alkoxy' therefore include monohydroxy$C_{1-4}$alkoxy, monohydroxy$C_{1-6}$alkoxy and also polyhydroxy$C_{1-4}$alkoxy and polyhydroxy$C_{1-6}$alkoxy. There may be one, two, three or more hydrogen atoms replaced with a hydroxyl group so the hydroxy$C_{1-4}$alkoxy or hydroxy$C_{1-6}$alkoxy may have one, two, three or more hydroxyl groups. Examples of such groups include hydroxymethoxy, hydroxyethoxy, hydroxypropoxy and the like.

The term 'halo$C_{1-4}$alkoxy' or 'halo$C_{1-6}$alkoxy' as used herein as a group or part of a group refers to a —O—

$C_{1-4}$alkyl group or a —O—$C_{1-6}$ alkyl group as defined herein wherein one or more than one hydrogen atom is replaced with a halogen. The terms 'halo$C_{1-4}$alkoxy' or 'halo$C_{1-6}$alkoxy' therefore include monohalo$C_{1-4}$alkoxy, monohalo$C_{1-6}$alkoxy and also polyhalo$C_{1-4}$alkoxy and polyhalo$C_{1-6}$alkoxy. There may be one, two, three or more hydrogen atoms replaced with a halogen, so the halo-$C_{1-4}$alkoxy or halo$C_{1-6}$alkoxy may have one, two, three or more halogens. Examples of such groups include fluoroethyloxy, difluoromethoxy or trifluoromethoxy and the like.

The term 'hydroxyhalo$C_{1-4}$alkoxy' as used herein as a group or part of a group refers to an —O—$C_{1-4}$alkyl group wherein the $C_{1-4}$alkyl group is as defined herein and wherein one or more than one hydrogen atom is replaced with a hydroxyl group and one or more than one hydrogen atom is replaced with a halogen. The term 'hydroxyhalo$C_{1-4}$alkoxy' therefore refers to a —O—$C_{1-4}$alkyl group wherein one, two, three or more hydrogen atoms are replaced with a hydroxyl group and one, two, three or more hydrogen atoms are replaced with a halogen.

The term 'halo$C_{1-4}$alkoxy$C_{1-4}$alkyl' as used herein as a group or part of a group refers to a $C_{1-4}$alkyl-O—$C_{1-4}$alkyl group wherein $C_{1-4}$alkyl is as defined herein and wherein in one or both of the $C_{1-4}$alkyl groups one or more than one hydrogen atom is replaced with a halogen. The term 'halo$C_{1-4}$ alkoxy$C_{1-4}$alkyl' therefore refers to a $C_{1-4}$alkyl-O—$C_{1-4}$alkyl group wherein in one or both of the $C_{1-4}$alkyl groups one, two, three or more hydrogen atoms are replaced with a halogen and wherein $C_{1-4}$ alkyl is as defined herein. Preferably, in one of the $C_{1-4}$alkyl groups one or more than one hydrogen atom is replaced with a halogen. Preferably, halo$C_{1-4}$alkoxy$C_{1-4}$alkyl means $C_{1-4}$alkyl substituted with halo$C_{1-4}$alkoxy.

The term 'hydroxyhalo$C_{1-4}$alkoxy$C_{1-4}$alkyl' as used herein refers to a $C_{1-4}$alkyl-O—$C_{1-4}$alkyl group wherein $C_{1-4}$alkyl is as defined herein and wherein in one or both of the $C_{1-4}$alkyl groups one or more than one hydrogen atom is replaced with a hydroxyl group and one or more than one hydrogen atom is replaced with a halogen. The terms 'hydroxyhalo-$C_{1-4}$alkoxy$C_{1-4}$alkyl' therefore refers to a $C_{1-4}$alkyl-O—$C_{1-4}$alkyl group wherein in one or both of the $C_{1-4}$alkyl groups one, two, three or more hydrogen atoms are replaced with a hydroxyl group and one, two, three or more hydrogen atoms are replaced with a halogen and wherein $C_{1-4}$alkyl is as defined herein.

The term 'hydroxy$C_{2-6}$alkenyl' as used herein refers to a $C_{2-6}$alkenyl group wherein one or more than one hydrogen atom is replaced with a hydroxyl group and wherein $C_{2-6}$alkenyl is as defined herein.

The term 'hydroxy$C_{2-6}$alkynyl' as used herein refers to a $C_{2-6}$alkynyl group wherein one or more than one hydrogen atom is replaced with a hydroxyl group and wherein $C_{2-6}$alkynyl is as defined herein.

The term phenyl$C_{1-6}$alkyl as used herein refers to a $C_{1-6}$alkyl group as defined herein which is substituted with one phenyl group.

The term cyano$C_{1-4}$alkyl or cyano$C_{1-6}$alkyl as used herein refers to a $C_{1-4}$alkyl or $C_{1-6}$alkyl group as defined herein which is substituted with one cyano group.

The term "heterocyclyl" as used herein shall, unless the context indicates otherwise, include both aromatic and non-aromatic ring systems. Thus, for example, the term "heterocyclyl group" includes within its scope aromatic, non-aromatic, unsaturated, partially saturated and fully saturated heterocyclyl ring systems. In general, unless the context indicates otherwise, such groups may be monocyclic or bicyclic and may contain, for example, 3 to 12 ring members, more usually 5 to 10 ring members. Reference to 4 to 7 ring members include 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, and preferably 5, 6 or 7 ring members, more preferably 5 or 6 ring members. Examples of bicyclic groups are those containing 8, 9, 10, 11 and 12 ring members, and more usually 9 or 10 ring members. Where reference is made herein to heterocyclyl groups, the heterocyclyl ring can, unless the context indicates otherwise, be optionally substituted (i.e. unsubstituted or substituted) by one or more substituents as discussed herein.

The heterocyclyl groups can be heteroaryl groups having from 5 to 12 ring members, more usually from 5 to 10 ring members. The term "heteroaryl" is used herein to denote a heterocyclyl group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

Examples of heteroaryl groups are monocyclic and bicyclic groups containing from five to twelve ring members, and more usually from five to ten ring members. The heteroaryl group can be, for example, a five membered or six membered monocyclic ring or a bicyclic structure formed from fused five and six membered rings or two fused six membered rings, or two fused five membered rings. Each ring may contain up to about five heteroatoms typically selected from nitrogen, sulphur and oxygen. Typically the heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
  a) a benzene ring fused to a 5- or 6-membered ring containing 1, 2 or 3 ring heteroatoms;
  b) a pyridine ring fused to a 5- or 6-membered ring containing 0, 1, 2 or 3 ring heteroatoms;
  c) a pyrimidine ring fused to a 5- or 6-membered ring containing 0, 1 or 2 ring heteroatoms;
  d) a pyrrole ring fused to a 5- or 6-membered ring containing 0, 1, 2 or 3 ring heteroatoms;
  e) a pyrazole ring fused to a 5- or 6-membered ring containing 0, 1 or 2 ring heteroatoms;
  f) an imidazole ring fused to a 5- or 6-membered ring containing 0, 1 or 2 ring heteroatoms;
  g) an oxazole ring fused to a 5- or 6-membered ring containing 0, 1 or 2 ring heteroatoms;
  h) an isoxazole ring fused to a 5- or 6-membered ring containing 0, 1 or 2 ring heteroatoms;

i) a thiazole ring fused to a 5- or 6-membered ring containing 0, 1 or 2 ring heteroatoms;
j) an isothiazole ring fused to a 5- or 6-membered ring containing 0, 1 or 2 ring heteroatoms;
k) a thiophene ring fused to a 5- or 6-membered ring containing 0, 1, 2 or 3 ring heteroatoms;
l) a furan ring fused to a 5- or 6-membered ring containing 0, 1, 2 or 3 ring heteroatoms;
m) a cyclohexyl ring fused to a 5- or 6-membered ring containing 1, 2 or 3 ring heteroatoms; and
n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzthiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, chromene, isochromene, chroman, isochroman, benzodioxan, quinolizine, benzoxazine, benzodiazine, pyridopyridine, quinoxaline, quinazoline, cinnoline, phthalazine, naphthyridine and pteridine groups.

Examples of polycyclic heteroaryl groups containing an aromatic ring and a non-aromatic ring include, tetrahydroisoquinoline, tetrahydroquinoline, dihydrobenzthiene, dihydrobenzfuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), indoline and indane groups.

A nitrogen-containing heteroaryl ring must contain at least one ring nitrogen atom. Each ring may, in addition, contain up to about four other heteroatoms typically selected from nitrogen, sulphur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazole, benzthiazolyl and benzisothiazole, indolyl, 3H-indolyl, isoindolyl, indolizinyl, isoindolinyl, purinyl (e.g., adenine [6-aminopurine], guanine [2-amino-6-hydroxypurine]), indazolyl, quinolizinyl, benzoxazinyl, benzodiazinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "non-aromatic group" embraces, unless the context indicates otherwise, unsaturated ring systems without aromatic character, partially saturated and fully saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated heterocyclyl groups include piperidine, morpholine, thiomorpholine, piperazine. Partially saturated heterocyclyl groups include pyrazolines, for example 2-pyrazoline and 3-pyrazoline.

Examples of non-aromatic heterocyclyl groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulphur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulphones (e.g. as in sulpholane and sulpholene), cyclic sulphoxides, cyclic sulphonamides and combinations thereof (e.g. thiomorpholine).

Particular examples include morpholine, piperidine (e.g. 1-piperidinyl, 2-piperidinyl, 3-piperidinyl and 4-piperidinyl), piperidone, pyrrolidine (e.g. 1-pyrrolidinyl, 2-pyrrolidinyl and 3-pyrrolidinyl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. 4-tetrahydro pyranyl), imidazoline, imidazolidinone, oxazoline, thiazoline, 2-pyrazoline, pyrazolidine, piperazone, piperazine, and N-alkyl piperazines such as N-methyl piperazine. In general, preferred non-aromatic heterocyclyl groups include saturated groups such as piperidine, pyrrolidine, azetidine, morpholine, piperazine and N-alkyl piperazines.

In a nitrogen-containing non-aromatic heterocyclyl ring the ring must contain at least one ring nitrogen atom. The heterocylic groups can contain, for example cyclic amine moieties (e.g. as in pyrrolidine), cyclic amides (such as a pyrrolidinone, piperidone or caprolactam), cyclic sulphonamides (such as an isothiazolidine 1,1-dioxide, [1,2]thiazinane 1,1-dioxide or [1,2]thiazepane 1,1-dioxide) and combinations thereof. Particular examples of nitrogen-containing non-aromatic heterocyclyl groups include aziridine, morpholine, thiomorpholine, piperidine (e.g. 1-piperidinyl, 2-piperidinyl, 3-piperidinyl and 4-piperidinyl), pyrrolidine (e.g. 1-pyrrolidinyl, 2-pyrrolidinyl and 3-pyrrolidinyl), pyrrolidone, dihydrothiazole, imidazoline, imidazolidinone, oxazoline, thiazoline, 6H-1,2,5-thiadiazine, 2-pyrazoline, 3-pyrazoline, pyrazolidine, piperazine, and N-alkyl piperazines such as N-methyl piperazine.

The heterocyclyl groups can be polycyclic fused ring systems or bridged ring systems such as the oxa- and aza analogues of bicycloalkanes, tricycloalkanes (e.g. adamantane and oxa-adamantane). For an explanation of the distinction between fused and bridged ring systems, see

*Advanced Organic Chemistry*, by Jerry March, 4$^{th}$ Edition, Wiley Interscience, pages 131-133, 1992.

The heterocyclyl groups can each be unsubstituted or substituted by one or more substituent groups. For example, heterocyclyl groups can be unsubstituted or substituted by 1, 2, 3 or 4 substituents. Where the heterocyclyl group is monocyclic or bicyclic, typically it is unsubstituted or has 1, 2 or 3 substituents.

The term "carbocyclyl" as used herein shall, unless the context indicates otherwise, include both aromatic and non-aromatic ring systems. Thus, for example, the term "carbocyclyl group" includes within its scope aromatic, non-aromatic, unsaturated, partially saturated and fully saturated carbocyclyl ring systems. In general, unless the context indicates otherwise, such groups may be monocyclic or bicyclic and may contain, for example, 3 to 12 ring members, more usually 5 to 10 ring members. Reference to 4 to 7 ring members include 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, and preferably 5, 6 or 7 ring members, more preferably 5 or 6 ring members. Examples of bicyclic groups are those containing 8, 9, 10, 11 and 12 ring members, and more usually 9 or 10 ring members. Where reference is made herein to carbocyclyl groups, the carbocyclyl ring can, unless the context indicates otherwise, be optionally substituted (i.e. unsubstituted or substituted) by one or more substituents as discussed herein.

The term carbocyclyl comprises aryl, $C_{3-8}$cycloalkyl, $C_{3-8}$cycloalkenyl.

The term aryl as used herein refers to carbocyclyl aromatic groups including phenyl, naphthyl, indenyl, and tetrahydronaphthyl groups.

Whenever used hereinbefore or hereinafter that substituents can be selected each independently out of a list of numerous definitions, all possible combinations are intended which are chemically possible. Whenever used hereinbefore or hereinafter that a particular substituent is further substituted with two or more groups, such as for example hydroxyhalo$C_{1-4}$alkyl, hydroxyhalo$C_{1-4}$alkoxy, all possible combinations are intended which are chemically possible.

In one embodiment, the invention relates to a compound of formula (I-A).

In one embodiment, the invention relates to a compound of formula (I-A) wherein $X^1$ is N, and $X^2$ is $CR^{3a}$, in particular wherein $R^{3a}$ represents hydrogen. In one embodiment, the invention relates to a compound of formula (I-A) wherein $X^2$ is N and $X^1$ is $CR^{3a}$; in particular wherein $R^{3a}$ represents hydrogen.

In one embodiment, the invention relates to a compound of formula (I-B), in particular wherein $R^{3a}$ represents hydrogen.

In one embodiment, Y represents —$CR^{18}$=N—$OR^{19}$. In particular wherein $R^{18}$ and $R^{19}$ represent $C_{1-6}$alkyl.

In one embodiment, Y represents -E-D wherein E represents a bond.

In one embodiment, Y represents a 3 to 12 ring membered monocyclic or bicyclic carbocyclyl or a 3 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups.

In one embodiment, Y represents a 5 to 12 ring membered monocyclic or bicyclic carbocyclyl or a 5 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups.

In one embodiment, Y represents an aromatic 3 to 12, in particular an aromatic 5 to 12, ring membered monocyclic or bicyclic carbocyclyl or an aromatic 3 to 12, in particular an aromatic 5 to 12, ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups.

In one embodiment, Y represents an aromatic 3 to 12 (e.g. 5 to 10) ring membered monocyclic or bicyclic carbocyclyl, wherein said carbocyclyl may be optionally substituted by one or more (e.g. 1, 2 or 3) $R^1$ groups.

In one embodiment, Y represents phenyl or naphthyl, wherein said phenyl or naphthyl may each be optionally substituted by one or more (e.g. 1, 2 or 3) $R^1$ groups.

In one embodiment, Y represents a 5 to 12 ring membered monocyclic or bicyclic heterocyclyl containing at least one heteroatom selected from N, O or S, wherein said heterocyclyl may each be optionally substituted by one or more (e.g. 1, 2 or 3) $R^1$ groups.

In one embodiment, Y represents an aromatic 5 to 12 ring membered monocyclic heterocyclyl containing at least one heteroatom selected from N, O or S, wherein said heterocyclyl group may each be optionally substituted by one or more (e.g. 1, 2 or 3) $R^1$ groups.

In one embodiment, Y represents a 5 or 6 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, Y represents an aromatic 5 or 6 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, Y represents a 5 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, Y represents a 5 ring membered monocyclic aromatic heterocyclyl containing at least one heteroatom selected from N, O or S, wherein said heterocyclyl may each be optionally substituted by one or more (e.g. 1, 2 or 3) $R^1$ groups.

In one embodiment, Y represents pyrazolyl (e.g. pyrazol-4yl), wherein said pyrazolyl may each be optionally substituted by one or more (e.g. 1, 2 or 3) $R^1$ groups.

In one embodiment, Y represents a 6 ring membered monocyclic heterocyclyl containing at least one heteroatom selected from N, O or S, wherein said heterocyclyl may each be optionally substituted by one or more (e.g. 1, 2 or 3) $R^1$ groups.

In one embodiment, Y represents a 6 ring membered monocyclic aromatic heterocyclyl containing at least one heteroatom selected from N, O or S, wherein said heterocyclyl may each be optionally substituted by one or more (e.g. 1, 2 or 3) $R^1$ groups.

In one embodiment, Y represents a 12 ring membered bicyclic heterocyclyl containing at least one heteroatom selected from N, O or S, wherein said heterocyclyl may each be optionally substituted by one or more (e.g. 1, 2 or 3) $R^1$ groups.

In one embodiment, Y represents a 12 ring membered bicyclic aromatic heterocyclyl containing at least one heteroatom selected from N, O or S, wherein said heterocyclyl may each be optionally substituted by one or more (e.g. 1, 2 or 3) $R^1$ groups.

In one embodiment Y represents

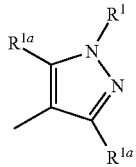

wherein $R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, cyano$C_{1-4}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —$C(=O)$—$NR^4R^5$, —$S(=O)_2$—$C_{1-6}$alkyl, —$S(=O)_2$-halo$C_{1-6}$alkyl, —$S(=O)_2$—$NR^{14}R^{15}$, $C_{1-6}$alkyl substituted with —$S(=O)_2$—$C_{1-6}$alkyl, $C_{1-6}$alkyl substituted with —$S(=O)_2$-halo$C_{1-6}$alkyl, $C_{1-6}$alkyl substituted with —$S(=O)_2$—$NR^{14}R^{15}$, $C_{1-6}$alkyl substituted with —NH—$S(=O)_2$—$C_{1-6}$alkyl, $C_{1-6}$alkyl substituted with —NH—$S(=O)_2$-halo$C_{1-6}$alkyl, $C_{1-6}$alkyl substituted with —$NR^{12}$—$S(=O)_2$—$NR^{14}R^{15}$, $R^6$, $C_{1-6}$alkyl substituted with $R^6$, $C_{1-6}$alkyl substituted with —$C(=O)$—$R^6$, hydroxy-$C_{1-6}$alkyl substituted with $R^6$, $C_{1-6}$alkyl substituted with —$Si(CH_3)_3$, $C_{1-6}$alkyl substituted with —$P(=O)(OH)_2$ or $C_{1-6}$alkyl substituted with —$P(=O)(OC_{1-6}alkyl)_2$; and each $R^{1a}$ is independently selected from hydrogen, $C_{1-4}$alkyl, hydroxy$C_{1-4}$alkyl, $C_{1-4}$alkyl substituted with amino or mono- or di($C_{1-4}$alkyl)amino or —$NH(C_{3-8}$cycloalkyl), cyano$C_{1-4}$alkyl, $C_{1-4}$alkoxy$C_{1-4}$alkyl, and $C_{1-4}$alkyl substituted with one or more fluoro atoms. In one embodiment $R^{1a}$ is independently selected from hydrogen and $C_{1-4}$alkyl. In one embodiment $R^{1a}$ is hydrogen.

In one embodiment, Y represents

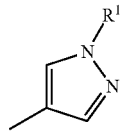

wherein $R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —$C(=O)$—$NR^4R^5$, —$S(=O)_2$—$C_{1-6}$alkyl, —$S(=O)_2$-halo$C_{1-6}$alkyl, —$S(=O)_2$—$NR^{14}R^{15}$, $C_{1-6}$alkyl substituted with —$S(=O)_2$—$C_{1-6}$alkyl, $C_{1-6}$alkyl substituted with —$S(=O)_2$-halo$C_{1-6}$alkyl, $C_{1-6}$alkyl substituted with —$S(=O)_2$—$NR^{14}R^{15}$, $C_{1-6}$alkyl substituted with —NH—$S(=O)_2$—$C_{1-6}$alkyl, $C_{1-6}$alkyl substituted with —NH—$S(=O)_2$-halo$C_{1-6}$alkyl, $C_{1-6}$alkyl substituted with —$NR^{12}$—$S(=O)_2$—$NR^{14}R^{15}$, $R^6$, $C_{1-6}$alkyl substituted with $R^6$, $C_{1-6}$alkyl substituted with —$C(=O)$—$R^6$, hydroxy-$C_{1-6}$alkyl substituted with $R^6$, $C_{1-6}$alkyl substituted with —$Si(CH_3)_3$, $C_{1-6}$alkyl substituted with —$P(=O)(OH)_2$ or $C_{1-6}$alkyl substituted with —$P(=O)(OC_{1-6}alkyl)_2$.

In one embodiment, E represents a bond, $C_{2-4}$alkenediyl optionally substituted with $R^{22}$, —CO—$(CR^{22}R^{23})_s$—, —$(CR^{22}R^{23})_s$—CO—, —$NR^{22}$—$(CR^{22}R^{23})_s$—, —$(CR^{22}R^{23})_s$—$NR^{22}$—, —O—$(CR^{22}R^{23})_s$—, —$(CR^{22}R^{23})_s$—CO—$NR^{22}$—$(CR^{22}R^{23})_s$— or —$(CR^{22}R^{23})_s$—$NR^{22}$—CO—$(CR^{22}R^{23})_s$—.

In one embodiment, E represents a bond, $C_{2-4}$alkenediyl, —CO—$(CR^{22}R^{23})_s$—, —$(CR^{22}R^{23})_s$—CO—, —$NR^{22}$—$(CR^{22}R^{23})_s$—, —$(CR^{22}R^{23})_s$—$NR^{22}$—, —$(CR^{22}R^{23})_s$—CO—$NR^{22}$—$(CR^{22}R^{23})_s$— or —$(CR^{22}R^{23})_s$—$NR^{22}$—CO—$(CR^{22}R^{23})_s$—.

In one embodiment, E represents $C_{2-4}$alkenediyl, —CO—$(CR^{22}R^{23})_s$—, —$(CR^{22}R^{23})_s$—CO—, —$NR^{22}$—$(CR^{22}R^{23})_s$—, —$(CR^{22}R^{23})_s$—$NR^{22}$—, —$(CR^{22}R^{23})_s$—CO—$NR^{22}$—$(CR^{22}R^{23})_s$— or —$(CR^{22}R^{23})_s$—$NR^{22}$—CO—$(CR^{22}R^{23})_s$—.

In one embodiment, E represents a bond.

In one embodiment, Y represents -E-D, wherein E is other than a bond.

In one embodiment, Y represents -E-D, wherein E is other than a bond and D represents any one of the following:

a 3 to 12 ring membered monocyclic or bicyclic carbocyclyl or a 3 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups;

a 5 to 12 ring membered monocyclic or bicyclic carbocyclyl or a 5 to 12 ring membered monocyclic or bicyclic heterocyclyl containing at least one heteroatom selected from N, O or S, wherein said carbocyclyl and heterocyclyl may each be optionally substituted by one or more (e.g. 1, 2 or 3) $R^1$ groups;

phenyl or naphthyl, wherein said phenyl or naphthyl may each be optionally substituted by one or more (e.g. 1, 2 or 3) $R^1$ groups;

a 5 to 12 ring membered monocyclic or bicyclic heterocyclyl containing at least one heteroatom selected from N, O or S, wherein said heterocyclyl may each be optionally substituted by one or more (e.g. 1, 2 or 3) $R^1$ groups;

a 5 or 6 ring membered monocyclic heterocyclyl containing at least one heteroatom selected from N, O or S, wherein said heterocyclyl may each be optionally substituted by one or more (e.g. 1, 2 or 3) $R^1$ groups;

a 5 ring membered monocyclic heterocyclyl containing at least one heteroatom selected from N, O or S, wherein said heterocyclyl may each be optionally substituted by one or more (e.g. 1, 2 or 3) $R^1$ groups;

a 5 ring membered monocyclic aromatic heterocyclyl containing at least one heteroatom selected from N, O or S, wherein said heterocyclyl group may each be optionally substituted by one or more (e.g. 1, 2 or 3) $R^1$ groups;

a 6 ring membered monocyclic heterocyclyl containing at least one heteroatom selected from N, O or S, wherein said heterocyclyl may each be optionally substituted by one or more (e.g. 1, 2 or 3) $R^1$ groups;

a 6 ring membered monocyclic aromatic heterocyclyl containing at least one heteroatom selected from N, O or S, wherein said heterocyclyl may each be optionally substituted by one or more (e.g. 1, 2 or 3) $R^1$ groups;

a 12 ring membered bicyclic heterocyclyl containing at least one heteroatom selected from N, O or S, wherein said heterocyclyl may each be optionally substituted by one or more (e.g. 1, 2 or 3) $R^1$ groups;

a 12 ring membered bicyclic aromatic heterocyclyl containing at least one heteroatom selected from N, O or S, wherein said heterocyclyl may each be optionally substituted by one or more (e.g. 1, 2 or 3) $R^1$ groups;

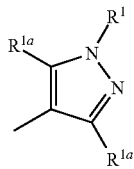

wherein $R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, cyano$C_{1-4}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —$C(=O)$—$NR^4R^5$, —$S(=O)_2$—$C_{1-6}$alkyl, —$S(=O)_2$-halo$C_{1-6}$alkyl, —$S(=O)_2$—$NR^{14}R^{15}$, $C_{1-6}$alkyl substituted with —$S(=O)_2$—$C_{1-6}$alkyl, $C_{1-6}$alkyl substituted with —$S(=O)_2$-halo$C_{1-6}$alkyl, $C_{1-6}$alkyl substituted with —$S(=O)_2$—$NR^{14}R^{15}$, $C_{1-6}$alkyl substituted with —NH—$S(=O)_2$—$C_{1-6}$alkyl, $C_{1-6}$alkyl substituted with —NH—$S(=O)_2$-halo$C_{1-6}$alkyl, $C_{1-6}$alkyl substituted with —$NR^{12}$—$S(=O)_2$—$NR^{14}R^{15}$, $R^6$, $C_{1-6}$alkyl substituted with $R^6$, $C_{1-6}$alkyl substituted with —$C(=O)$—$R^6$, hydroxy-$C_{1-6}$alkyl substituted with $R^6$, $C_{1-6}$alkyl substituted with —$Si(CH_3)_3$, $C_{1-6}$alkyl substituted with —$P(=O)(OH)_2$ or $C_{1-6}$alkyl substituted with —$P(=O)(OC_{1-6}alkyl)_2$; and each $R^{1a}$ is independently selected from hydrogen, $C_{1-4}$alkyl, hydroxy$C_{1-4}$alkyl, $C_{1-4}$alkyl substituted with amino or mono- or di($C_{1-4}$alkyl)amino or —$NH(C_{3-8}$cycloalkyl), cyano$C_{1-4}$alkyl, $C_{1-4}$alkoxy$C_{1-4}$alkyl, and $C_{1-4}$alkyl substituted with one or more fluoro atoms;

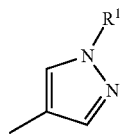

wherein $R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —$C(=O)$—$NR^4R^5$, —$S(=O)_2$—$C_{1-6}$alkyl, —$S(=O)_2$-halo$C_{1-6}$alkyl, —$S(=O)_2$—$NR^{14}R^{15}$, $C_{1-6}$alkyl substituted with —$S(=O)_2$—$C_{1-6}$alkyl, $C_{1-6}$alkyl substituted with —$S(=O)_2$-halo$C_{1-6}$alkyl, $C_{1-6}$alkyl substituted with —$S(=O)_2$—$NR^{14}R^{15}$, $C_{1-6}$alkyl substituted with —NH—$S(=O)_2$—$C_{1-6}$alkyl, $C_{1-6}$alkyl substituted with —NH—$S(=O)_2$-halo$C_{1-6}$alkyl, $C_{1-6}$alkyl substituted with —$NR^{12}$—$S(=O)_2$—$NR^{14}R^{15}$, $R^6$, $C_{1-6}$alkyl substituted with $R^6$, $C_{1-6}$alkyl substituted with —$C(=O)$—$R^6$, hydroxy-$C_{1-6}$alkyl substituted with $R^6$, $C_{1-6}$alkyl substituted with —$Si(CH_3)_3$, $C_{1-6}$alkyl substituted with —$P(=O)(OH)_2$ or $C_{1-6}$alkyl substituted with —$P(=O)(OC_{1-6}alkyl)_2$.

In one embodiment, D is other than pyrazolyl, in particular D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrolidinyl, thiadiazolyl, oxadiazolyl, said rings being optionally substituted. Said optional substituents may represent halo, cyano, $C_{1-6}$alkyl, $C_{1-6}$alkoxy, —$C(=O)$—O—$C_{1-6}$alkyl, hydroxy$C_{1-6}$alkyl, —$NR^4R^5$, $C_{1-6}$alkyl substituted with —O—$C(=O)$—$C_{1-6}$alkyl, $C_{1-6}$alkyl substituted with —$NR^4R^5$, —$C(=O)$—$NR^4R^5$, —$C(=O)$—$C_{1-6}$alkyl-$NR^4R^5$, $R^6$, $C_{1-6}$alkyl substituted with $R^6$.

In one embodiment, E is other than a bond and D is other than pyrazolyl, in particular D is piperidinyl, pyridinyl, phenyl, pyrrolyl, imidazolyl, triazolyl, pyrrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrrolidinyl, thiadiazolyl, oxadiazolyl, said rings being optionally substituted.

In one embodiment E is a bond and D is an optionally substituted 5 or 6 membered aromatic heterocycle. In one embodiment E is a bond and D is an optionally substituted membered aromatic heterocycle, such as for example pyrazolyl, optionally substituted with $C_{1-6}$alkyl. In one embodiment E is a bond and D is an optionally substituted 6 membered aromatic heterocycle, such as for example substituted pyridyl or unsubstituted pyridyl.

In one embodiment, E is a bond and D is optionally substituted 4-pyrazolyl. In one embodiment, E is a bond and D is 4-pyrazolyl substituted at the 1 position with $C_{1-6}$alkyl for example methyl.

In one embodiment, E is a bond and D is 1-pyrazolyl or 2-pyrazolyl, both may optionally be substituted. In one embodiment, E is other than a bond and D is 1-pyrazolyl or 2-pyrazolyl, both may optionally be substituted.

In one embodiment, E is other than a bond and D is optionally substituted pyrazolyl. In one embodiment, E is a bond and D is optionally substituted pyrazolyl.

In one embodiment $R^1$ represents hydrogen, $C_{1-6}$alkyl, $C_{2-4}$alkenyl, hydroxy$C_{1-6}$alkyl, halo$C_{1-6}$alkyl, hydroxyhalo$C_{1-6}$alkyl, cyano$C_{1-4}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —$C(=O)$—$NR^4R^5$, —$S(=O)_2$—$C_{1-6}$alkyl, —$S(=O)_2$-halo$C_{1-6}$alkyl, —$S(=O)_2$—$NR^{14}R^{15}$, $C_{1-6}$alkyl substituted with —$S(=O)_2$—$C_{1-6}$alkyl, $C_{1-6}$alkyl substituted with —$S(=O)_2$-halo$C_{1-6}$alkyl, $C_{1-6}$alkyl substituted with —$S(=O)_2$—$NR^{14}R^{15}$, $C_{1-6}$alkyl substituted with —NH—$S(=O)_2$—$C_{1-6}$alkyl, $C_{1-6}$alkyl substituted with —NH—$S(=O)_2$-halo$C_{1-6}$alkyl, $C_{1-6}$alkyl substituted with —$NR^{12}$—$S(=O)_2$—$NR^{14}R^{15}$, $R^6$, $C_{1-6}$alkyl substituted with $R^6$, $C_{1-6}$alkyl substituted with —$C(=O)$—$R^6$, hydroxy-$C_{1-6}$alkyl substituted with $R^6$, $C_{1-6}$alkyl substituted with —$Si(CH_3)_3$, $C_{1-6}$alkyl substituted with —$P(=O)(OH)_2$ or $C_{1-6}$alkyl substituted with —$P(=O)(OC_{1-6}alkyl)_2$.

In one embodiment $R^1$ represents hydrogen, $C_{1-6}$alkyl, $C_{2-4}$alkenyl, hydroxy$C_{1-6}$alkyl, halo$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with —$NR^4R^5$, $C_{1-6}$alkyl substituted with —$C(=O)$—$NR^4R^5$, —$S(=O)_2$—$C_{1-6}$alkyl, —$S(=O)_2$—$NR^{14}R^{15}$, $C_{1-6}$alkyl substituted with —$S(=O)_2$—$C_{1-6}$alkyl, $C_{1-6}$alkyl substituted with —NH—$S(=O)_2$—$C_{1-6}$alkyl, $R^6$, $C_{1-6}$alkyl substituted with $R^6$, $C_{1-6}$alkyl substituted with —$C(=O)$—$R^6$, hydroxy$C_{1-6}$alkyl substituted with $R^6$, or $C_{1-6}$alkyl substituted with —$Si(CH_3)_3$.

In one embodiment $R^1$ represents hydrogen.

In one embodiment $R^1$ represents $C_{1-6}$alkyl, such as for example methyl, ethyl or isopropyl. In one embodiment $R^1$ represents methyl.

In one embodiment each $R^2$ is independently selected from hydroxyl, halogen, cyano, $C_{1-4}$alkyl, $C_{2-4}$alkenyl, $C_{1-4}$alkoxy, hydroxy$C_{1-4}$alkyl, hydroxy$C_{1-4}$alkoxy, halo$C_{1-4}$alkyl, halo$C_{1-4}$alkoxy, $C_{1-4}$alkoxy$C_{1-4}$alkyl, $R^{13}$, $C_{1-4}$alkyl substituted with $R^{13}$, —C(=O)—$R^{13}$, $C_{1-4}$alkyl substituted with $NR^7R^8$, $C_{1-4}$alkoxy substituted with $NR^7R^8$, —$NR^7R^8$ and —C(=O)—$NR^7R^8$; or when two $R^2$ groups are attached to adjacent carbon atoms they may be taken together to form a radical of formula —O—(C($R^{17}$)$_2$)$_p$—O— wherein $R^{17}$ represents hydrogen or fluorine and p represents 1 or 2.

In one embodiment each $R^2$ is independently selected from hydroxyl, halogen, cyano, $C_{1-4}$alkyl, $C_{2-4}$alkenyl, $C_{1-4}$alkoxy, hydroxy$C_{1-4}$alkyl, hydroxy$C_{1-4}$alkoxy, halo$C_{1-4}$alkoxy, $C_{1-4}$alkoxy$C_{1-4}$alkyl, $R^{13}$, $C_{1-4}$alkoxy substituted with $R^{13}$, —C(=O)—$R^{13}$, $C_{1-4}$alkyl substituted with $NR^7R^8$, $C_{1-4}$alkoxy substituted with $NR^7R^8$, —$NR^7R^8$ or —C(=O)—$NR^7R^8$.

In one embodiment one or more $R^2$ represents $C_{1-4}$alkoxy, for example $CH_3O$—, or halogen, for example fluoro or chloro.

In one embodiment one or more $R^2$ represents $CH_3O$— or fluoro.

In one embodiment one or more $R^2$ represents $C_{1-4}$alkoxy, for example $CH_3O$—.

In one embodiment n is equal to 0. In one embodiment n is equal to 1. In one embodiment n is equal to 2. In one embodiment n is equal to 3. In one embodiment n is equal to 4.

In one embodiment, n is equal to 2, 3 or 4.

In one embodiment n is equal to 2 and one $R^2$ is present at the 3-position and the other is present at the 5-position.

In one embodiment n is equal to 2 and one $R^2$ is present at the 3-position and the other is present at the 5-position and each $R^2$ represents $C_{1-4}$alkoxy, for example each $R^2$ represents $CH_3O$—.

In one embodiment n is equal to 3 and one $R^2$ is present at the 2-position, one $R^2$ is present at the 3-position and one $R^2$ is present at the 5-position.

In one embodiment n is equal to 3 and one $R^2$ is present at the 3-position and represents $C_{1-4}$alkoxy, for example $CH_3O$—; one $R^2$ is present at the 5-position and represents $C_{1-4}$alkoxy, for example $CH_3O$—; one $R^2$ is present at the 2-position and represents halogen, for example fluoro.

In one embodiment n is equal to 4 and one $R^2$ is present at the 2-position, one $R^2$ is present at the 3-position, one $R^2$ is present at the 5-position and one $R^2$ is present at the 6-position.

In one embodiment n is equal to 4 and one $R^2$ is present at the 3-position and represents $C_{1-4}$alkoxy, for example $CH_3O$—; one $R^2$ is present at the 5-position and represents $C_{1-4}$alkoxy, for example $CH_3O$—; one $R^2$ is present at the 2-position and represents halogen, for example fluoro, and one $R^2$ is present at the 6-position and represents halogen, for example fluoro.

In one embodiment, $R^3$ represents $C_{1-6}$alkyl, hydroxy$C_{1-6}$alkyl, hydroxyhalo$C_{1-6}$alkyl, hydroxy$C_{2-6}$alkynyl, halo$C_{1-6}$alkyl, halo$C_{1-6}$alkyl optionally substituted (e.g. substituted) with —O—C(=O)—$C_{1-6}$alkyl, $C_{1-6}$alkyl substituted with —C(=O)—$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{1-6}$alkyl substituted with $R^9$, $C_{1-6}$alkyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, $C_{1-6}$alkyl substituted with —C(=O)—O—$C_{1-6}$alkyl, $C_{1-6}$alkyl substituted with —C(=O)—$NR^{10}R^{11}$, $C_{1-6}$alkyl substituted with carboxyl, $C_{1-6}$alkyl substituted with —O—C(=O)—$NR^{10}R^{11}$, $C_{1-6}$alkyl substituted with —$NR^{12}$—S(=O)$_2$—$C_{1-6}$alkyl, $C_{1-6}$alkyl substituted with —$NR^{12}$—S(=O)$_2$—$NR^{14}R^{15}$, $C_{1-6}$alkyl substituted with $R^9$ and optionally substituted with —O—C(=O)—$C_{1-6}$alkyl, $C_{1-6}$alkyl substituted with hydroxyl and $R^9$, —$C_{1-6}$alkyl-C($R^{12}$)=N—O—$R^{12}$, —S(=O)$_2$—$NR^{14}R^{15}$, $C_{1-6}$alkyl substituted with —S(=O)$_2$—$C_{1-6}$alkyl, $C_{1-6}$alkyl substituted with —C(=O)—$NR^{10}R^{11}$, $C_{1-6}$alkyl substituted with —C(=O)—$R^9$, $C_{2-6}$alkenyl substituted with $R^{9g}$, $C_{2-6}$alkynyl substituted with $R^9$, hydroxy$C_{1-6}$alkoxy, $C_{2-6}$alkenyl, $C_{2-6}$alkynyl, $R^{13}$, $C_{1-6}$alkyl substituted with $C_{1-6}$alkoxy$C_{1-6}$alkyl-C(=O)— or $C_{1-6}$alkyl substituted with —P(=O)(O$C_{1-6}$alkyl)$_2$.

In one embodiment $R^3$ represents $C_{1-6}$alkyl, hydroxy$C_{1-6}$alkyl, hydroxyhalo$C_{1-6}$alkyl, halo$C_{1-6}$alkyl, $C_{1-6}$alkyl substituted with —C(=O)—$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with $R^9$, $C_{1-6}$alkyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, $C_{1-6}$alkyl substituted with —C(=O)—O—$C_{1-6}$alkyl, $C_{1-6}$alkyl substituted with —C(=O)—$NR^{10}R^{11}$, $C_{1-6}$alkyl substituted with carboxyl, $C_{1-6}$alkyl substituted with —O—C(=O)—$NR^{10}R^{11}$, $C_{1-6}$alkyl substituted with —$NR^{12}$—S(=O)$_2$—$C_{1-6}$alkyl, $C_{1-6}$alkyl substituted with —$NR^{12}$—S(=O)$_2$—$NR^{14}R^{15}$, $C_{1-6}$alkyl substituted with hydroxyl and $R^9$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —C(=O)—$R^9$, $C_{2-6}$alkynyl substituted with $R^9$, hydroxy$C_{1-6}$alkoxy, $C_{2-6}$alkenyl, $C_{2-6}$alkynyl, $R^{13}$ or $C_{1-6}$alkyl substituted with $C_{1-6}$alkoxy$C_{1-6}$alkyl-C(=O)—.

In one embodiment $R^3$ represents $C_{1-6}$alkyl, hydroxy$C_{1-6}$alkyl, halo$C_{1-6}$alkyl, halo$C_{1-6}$alkyl optionally substituted with —O—C(=O)—$C_{1-6}$alkyl, hydroxyhalo$C_{1-6}$alkyl, hydroxy$C_{2-6}$alkynyl, $C_{1-6}$alkyl substituted with —C(=O)—$C_{1-6}$alkyl, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{1-6}$alkyl substituted with $R^9$, cyano$C_{1-6}$alkyl, $C_{1-6}$alkyl substituted with —$NR^{10}R^{11}$, $C_{1-6}$alkyl substituted with hydroxyl and —$NR^{10}R^{11}$, $C_{1-6}$alkyl substituted with one or two halo atoms and —$NR^{10}R^{11}$, $C_{1-6}$alkyl substituted with —C(=O)—O—$C_{1-6}$alkyl, $C_{1-6}$alkyl substituted with $C_{1-6}$alkoxy$C_{1-6}$alkyl-C(=O)—, $C_{1-6}$alkyl substituted with —C(=O)—$NR^{10}R^{11}$, $C_{1-6}$alkyl substituted with —C(=O)—$NR^{14}R^{15}$, $C_{1-6}$alkyl substituted with carboxyl, $C_{1-6}$alkyl substituted with —O—C(=O)—$NR^{10}R^{11}$, $C_{1-6}$alkyl substituted with —$NR^{12}$—S(=O)$_2$—$C_{1-6}$alkyl, $C_{1-6}$alkyl substituted with —$NR^{12}$—S(=O)$_2$—$NR^{14}R^{15}$, $C_{1-6}$alkyl substituted with $R^9$ and substituted with —O—C(=O)—$C_{1-6}$alkyl, $C_{1-6}$alkyl substituted with hydroxyl and $R^9$, —$C_{1-6}$alkyl-C($R^{12}$)=N—O—$R^{12}$, —S(=O)$_2$—$NR^{14}R^{15}$, $C_{1-6}$alkyl substituted with —S(=O)$_2$—$C_{1-6}$alkyl, $C_{1-6}$alkyl substituted with —C(=O)—$R^9$, $C_{2-6}$alkenyl substituted with $R^9$, $C_{2-6}$alkynyl substituted with $R^9$, $C_{1-6}$alkyloxy$C_{1-6}$alkyl wherein each $C_{1-6}$alkyl may optionally be substituted with one or two hydroxyl groups, $C_{2-6}$alkenyl, $C_{2-6}$alkynyl, $R^{13}$, or $C_{1-6}$alkyl substituted with —P(=O)(O$C_{1-6}$alkyl)$_2$.

In one embodiment, $R^3$ represents $C_{1-6}$alkyl, hydroxy$C_{1-6}$alkyl, hydroxyhalo$C_{1-6}$alkyl, halo$C_{1-6}$alkyl, $C_{1-6}$alkyl substituted with —C(=O)—$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with $R^9$, $C_{1-6}$alkyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, $C_{1-6}$alkyl substituted with —C(=O)—O—$C_{1-6}$alkyl, $C_{1-6}$alkyl substituted with —O—C(=O)—$NR^{10}R^{11}$, $C_{1-6}$alkyl substituted with carboxyl, $C_{1-6}$alkyl substituted with —$NR^{12}$—S(=O)$_2$—$C_{1-6}$alkyl, $C_{1-6}$alkyl substituted with —$NR^{12}$—S(=O)$_2$—$NR^{14}R^{15}$, $C_{1-6}$alkyl substituted with hydroxyl and $R^9$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —C(=O)—$R^9$, $C_{2-6}$alkynyl substituted with $R^9$, hydroxy$C_{1-6}$alkoxy, $C_{2-6}$alkenyl, $C_{2-6}$alkynyl or $R^{13}$.

In one embodiment $R^3$ represents $C_{2-6}$alkynyl, halo-$C_{1-6}$alkyl optionally substituted with —O—C(=O)—$C_{1-6}$alkyl, hydroxy$C_{1-6}$alkyl optionally substituted with —O—C(=O)—$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{1-6}$alkyl substituted with $R^9$, $C_{2-6}$alkynyl substituted with $R^9$, $C_{1-6}$alkyl substituted with —$NR^{10}R^{11}$, or $C_{1-6}$alkyl substituted with —O—C(=O)—$NR^{10}R^{11}$.

In one embodiment $R^3$ represents hydroxy$C_{1-6}$alkyl, hydroxyhalo$C_{1-6}$alkyl, $C_{1-6}$alkyl substituted with $R^9$, $C_{1-6}$alkyl substituted with —$NR^{10}R^{11}$, $C_{2-6}$alkynyl substituted with $R^9$, or $C_{2-6}$alkynyl.

In one embodiment $R^3$ represents hydroxy$C_{1-6}$alkyl, hydroxyhalo$C_{1-6}$alkyl, $C_{1-6}$alkyl substituted with $R^9$, $C_{1-6}$alkyl substituted with —$NR^{10}R^{11}$, $C_{1-6}$alkoxy$C_{1-6}$alkyl wherein each $C_{1-6}$alkyl may optionally be substituted with one or two hydroxyl groups or with —O—C(=O)—$C_{1-6}$alkyl, or $C_{2-6}$alkynyl substituted with $R^9$, $C_{2-6}$alkynyl.

In one embodiment $R^3$ represents hydroxy$C_{1-6}$alkyl, halo$C_{1-6}$alkyl, $C_{1-6}$alkyl substituted with $R^9$, $C_{1-6}$alkyl substituted with —$NR^{10}R^{11}$, $C_{1-6}$alkoxy$C_{1-6}$alkyl, or $C_{2-6}$alkynyl.

In one embodiment $R^3$ represents hydroxy$C_{1-6}$alkyl, cyano$C_{1-6}$alkyl, halo$C_{1-6}$alkyl, $C_{1-6}$alkyl substituted with $R^9$, $C_{1-6}$alkyl substituted with —$NR^{10}R^{11}$, $C_{1-6}$alkoxy$C_{1-6}$alkyl, $C_{1-6}$alkyl substituted with —C(=O)—$NR^{10}R^{11}$, $C_{2-6}$alkynyl or $R^{13}$.

In one embodiment $R^3$ represents $C_{1-6}$alkyl substituted with $R^9$, $C_{1-6}$alkyl substituted with —$NR^{10}R^{11}$ or $R^{13}$.

In one embodiment $R^3$ represents $C_{2-6}$alkynyl. $R^3$ may represent —$CH_2$—C≡C—H In one embodiment when $R^3$ represents $C_{1-6}$alkyl (e.g. $C_{1-4}$alkyl) substituted with $R^9$. $R^9$ represents an optionally substituted aromatic 5 or 6 membered monocyclic heterocyclyl, for example optionally substituted imidazolyl.

In one embodiment when $R^3$ represents $C_{1-6}$alkyl (e.g. $C_{1-4}$alkyl) substituted with $R^9$, wherein $R^9$ represents an optionally substituted aromatic 5 membered monocyclic heterocyclyl containing one or two nitrogen heteroatom, for example imidazolyl.

In one embodiment when $R^3$ represents $C_{1-4}$alkyl (e.g. methyl) substituted with $R^9$, wherein $R^9$ represents unsubstituted imidazolyl (e.g. imidazol-2-yl) or imidazolyl substituted with —S(O)$_2$—N(CH$_3$)$_2$.

In one embodiment $R^3$ represents $C_{1-6}$alkyl substituted with hydroxyl, halo and/or —$NR^{10}R^{11}$. In one embodiment $R^3$ represents $C_{1-6}$alkyl substituted with hydroxyl, halo or —$NR^{10}R^{11}$, wherein the $C_{1-6}$alkyl group is a straight chain alkyl group e.g. 2-ethyl, n-propyl, n-butyl. In a further embodiment $R^3$ represents $C_{1-6}$alkyl substituted with hydroxyl or —$NR^{10}R^{11}$.

In one embodiment $R^3$ represents hydroxy$C_{1-6}$alkyl. $R^3$ may represent —$CH_2CH_2OH$ or —$CH_2CH_2CH_2OH$.

In one embodiment $R^3$ represents $C_{1-6}$alkyloxy$C_{1-6}$alkyl. $R^3$ may represent —$CH_2CH_2OCH_3$.

In a yet further embodiment $R^3$ represents $C_{1-6}$alkyl substituted with —$NR^{10}R^{11}$. In one embodiment $R^3$ represents $C_{1-4}$alkyl substituted with —$NR^{10}R^{11}$. In one embodiment $R^3$ represents $C_{1-4}$alkyl substituted —$NR^{10}R^{11}$, wherein the $C_{1-4}$alkyl group is a straight chain alkyl group e.g. 2-ethyl, n-propyl. In one embodiment $R^3$ represents $C_{1-4}$alkyl substituted with —$NR^{10}R^{11}$, wherein the $C_{1-4}$alkyl group is an ethyl group (—$CH_2CH_2$—).

In one embodiment when $R^3$ represents $C_{1-6}$alkyl (e.g. 2-ethyl, n-propyl) substituted with —$NR^{10}R^{11}$, wherein $R^{10}$ and $R^{11}$ are independently selected from hydrogen, $C_{1-6}$alkyl and halo$C_{1-6}$alkyl (e.g. hydrogen, iso-propyl or —$CH_2CF_3$).

In one embodiment when $R^3$ represents $C_{1-6}$alkyl (e.g. 2-ethyl, n-propyl) substituted with —$NR^{10}R^{11}$, wherein $R^{10}$ and $R^{11}$ are independently selected from hydrogen, $C_{1-6}$alkyl and $C_{1-6}$alkyl substituted with —$NR^{14}R^{15}$. In one embodiment $R^{14}$ and $R^{15}$ each independently represent hydrogen, or $C_{1-4}$alkyl.

In one embodiment when $R^3$ represents $C_{1-6}$alkyl (e.g. 2-ethyl, n-propyl) substituted with —$NR^{10}R^{11}$, wherein $R^{10}$ and $R^{11}$ are independently selected from hydrogen, and $C_{1-6}$alkyl (e.g. hydrogen or iso-propyl).

In one embodiment when $R^3$ represents $C_{1-6}$alkyl substituted with —$NR^{10}R^{11}$, and one of $R^{10}$ and $R^{11}$ represents hydrogen and the other represents $C_{1-6}$alkyl substituted with —$NR^{14}R^{15}$ (e.g. —$NR^{14}R^{15}$ represents —NHCH(CH$_3$)$_2$). $R^3$ may represent —$CH_2CH_2N(CH(CH_3)_2)CH_2CH_2NHCH(CH_3)_2$ or —$CH_2CH_2NHCH(CH_3)_2$.

In one embodiment when $R^3$ represents $C_{1-6}$alkyl substituted with —$NR^{10}R^{11}$, and one of $R^{10}$ and $R^{11}$ represents hydrogen and the other represents $C_{1-6}$alkyl, for example —CH(CH$_3$)$_2$. $R^3$ may represent —$CH_2CH_2NHCH(CH_3)_2$.

In one embodiment $R^3$ represents —$CH_2CH_2NHCH(CH_3)_2$.

In one embodiment $R^3$ represents halo$C_{1-6}$alkyl. In one embodiment $R^3$ represents halo$C_{1-4}$alkyl. In one embodiment $R^3$ represents —$CH_2CH_2$—Br.

In one embodiment $R^{3a}$ represents hydrogen.
In one embodiment $R^{3a}$ represents chlorine.
In one embodiment, $R^9$ is selected from:
an optionally substituted $C_{3-8}$cycloalkyl,
an optionally substituted aromatic 5 membered monocyclic heterocyclyl, an optionally substituted saturated 6 membered monocyclic heterocyclyl,
a saturated or an aromatic 3, 4, 5 or 6 membered monocyclic heterocyclyl containing one or two oxygen heteroatoms,
an optionally substituted 4 membered heterocyclyl containing one oxygen heteroatom,
an optionally substituted aromatic 6 membered monocyclic heterocycle containing one or two nitrogen heteroatoms,
a partially saturated 6 membered monocyclic heterocyclyl containing one nitrogen heteroatom which may optionally be substituted,
an optionally substituted saturated 4 membered monocyclic heterocyclyl containing one nitrogen heteroatom,
a saturated 5 membered monocyclic heterocyclyl containing one nitrogen heteroatom,
a saturated 6 membered monocyclic heterocyclyl containing one nitrogen heteroatom,
a bicyclic heterocyclyl containing a benzene ring fused to a 5- or 6-membered ring containing 1, 2 or 3 ring heteroatoms,
a 4, 5 or 6 membered monocyclic saturated heterocycle substituted with two substituents which are attached to the same atom and which are taken together to form a 4 to 7-membered saturated monocyclic heterocyclyl containing at least one heteroatom selected from N, O or S,
an optionally substituted aromatic 5 membered monocyclic heterocyclyl containing one sulphur heteroatom,
an optionally substituted aromatic 5 membered monocyclic heterocyclyl containing one sulphur and one nitrogen heteroatom,
a saturated 6 membered monocyclic heterocyclyl containing two nitrogen heteroatoms,
an aromatic 5 membered monocyclic heterocyclyl containing four nitrogen heteroatoms,
an aromatic 5 membered monocyclic heterocyclyl containing one oxygen and two nitrogen heteroatoms,
an optionally substituted aromatic 5 membered monocyclic heterocyclyl containing two nitrogen heteroatoms,
an optionally substituted aromatic 5 membered monocyclic heterocyclyl containing three nitrogen heteroatoms,
a saturated 5 membered monocyclic heterocyclyl containing one nitrogen and one oxygen heteroatom,
a saturated 6 membered monocyclic heterocyclyl containing one nitrogen and one sulphur heteroatom,
a saturated 7 membered monocyclic heterocyclyl containing two nitrogen heteroatoms,
a saturated 7 membered monocyclic heterocyclyl containing one nitrogen and one oxygen heteroatom, and
phenyl or naphthyl, in particular phenyl.

In one embodiment, $R^9$ represents an optionally substituted 5 membered aromatic heterocycle, such as for example imidazolyl, or an optionally substituted 6 membered aromatic heterocycle, such as for example pyridyl, pyrimidinyl or pyrazinyl. Optional substituents may represent $C_{1-4}$alkoxy or $-S(=O)_2-NR^{14}R^{15}$.

In one embodiment, $R^9$ represents $C_{3-6}$cycloalkyl, such as for example cyclopropyl, a 3 membered saturated heterocyclyl, such as for example oxiranyl, an optionally substituted 5 membered saturated heterocycle, such as for example pyrolidinonyl, an optionally substituted 6 membered aromatic or saturated heterocycle, such as for example pyridyl, pyrimidinyl, pyrazinyl, piperazinyl, or morpholinyl, an optionally substituted bicyclic heterocycle, such as for example 1H-isoindol-1,3-dione. Optional substituents may represent =O, $C_{1-4}$alkoxy, $C_{1-4}$alkyl substituted with $-NR^{14}R^{15}$, hydroxy$C_{1-4}$alkyl, or $C_{1-4}$alkyl-C(=O)—.

In one embodiment, $R^9$ represents an optionally substituted 6 membered aromatic heterocycle, such as for example pyridinyl or pyrimidinyl. Optional substituents may represent $C_{1-4}$alkoxy.

In one embodiment, $R^9$ represents an optionally substituted 5 membered aromatic or saturated heterocycle, such as for example imidazolyl, pyrolidinyl, oxazolidinyl. Optional substituents may represent =O, a 5 or 6-membered aromatic monocyclic heterocyclyl containing at least one heteroatom selected from N, O or S wherein said heterocyclyl is optionally substituted with $R^{16}$; or $-S(=O)_2-NR^{14}R^{15}$.

In one embodiment, $R^9$ represents an optionally substituted 5 membered aromatic heterocycle, such as for example imidazolyl. Optional substituents may represent $-S(=O)_2-NR^{14}R^{15}$.

In one embodiment, $R^9$ represents an optionally substituted 5 membered aromatic heterocycle, such as for example imidazolyl, pyrazolyl, oxazolyl or triazolyl; or an optionally substituted 5 membered saturated heterocycle, such as for example pyrrolidinonyl or tetrahydrofuranyl; or an optionally substituted 6 membered aromatic heterocyle, such as for example pyrimidinyl. Optional substituents may represent $C_{1-4}$alkyl, oxo, benzyl or $-S(=O)_2-NR^{14}R^{15}$.

In one embodiment, $R^9$ represents an optionally substituted 5 membered aromatic heterocycle, such as for example imidazolyl or triazolyl; or an optionally substituted 5 membered saturated heterocycle, such as for example pyrrolidinonyl.

In one embodiment $R^{10}$ represents hydrogen or $C_{1-6}$alkyl.
In one embodiment $R^{10}$ is hydrogen.
In one embodiment $R^{11}$ represents hydrogen, $C_{1-6}$alkyl, halo$C_{1-6}$alkyl, $-C(=O)-C_{1-6}$alkyl, $-S(=O)_2-C_{1-6}$alkyl, $-S(=O)_2-NR^{14}R^{15}$, hydroxy$C_{1-6}$alkyl, $-C(=O)$-hydroxyhalo$C_{1-6}$alkyl, $-C(=O)-R^6$, cyano-$C_{1-6}$alkyl, $R^6$, $-C(=O)-R^6$, $C_{1-6}$alkyl substituted with $R^6$, $-C(=O)$-halo-$C_{1-6}$alkyl, $C_{1-6}$alkyl substituted with $-Si(CH_3)_3$, $C_{1-6}$alkyl substituted with $-NR^{14}R^{15}$, $C_{1-6}$alkyl substituted with $-C(=O)-NR^{14}R^{15}$, $C_{1-6}$alkoxy, hydroxyhalo$C_{1-6}$alkyl, carboxyl, or $C_{1-6}$alkoxy$C_{1-6}$alkyl.

In one embodiment, $R^{10}$ and $R^{11}$ represent hydrogen or $C_{1-6}$alkyl, such as for example methyl or isopropyl.

In one embodiment, $R^6$ represents a 6-membered monocyclic saturated heterocyclyl which is optionally substituted. For example piperazinyl or morpholinyl or tetrahydropyranyl, optionally substituted with halogen, $C_{1-6}$alkyl, or $C_{1-6}$alkyl-O—C(=O)—.

In one embodiment, $R^6$ represents a 6-membered monocyclic aromatic heterocyclyl which is optionally substituted.

For example pyridinyl, optionally substituted with halogen, $C_{1-6}$alkyl, or $C_{1-6}$alkyl-O—C(=O)—.

In one embodiment, $R^{12}$ represents hydrogen or $C_{1-4}$alkyl optionally substituted with $C_{1-4}$alkyloxy. In one embodiment, $R^{13}$ represents a saturated 4 to 6-membered monocyclic heterocyclyl containing at least one heteroatom selected from N or O.

In one embodiment, $R^{13}$ represents a saturated 6-membered monocyclic heterocyclyl containing at least one heteroatom selected from N or O, such as for example piperidinyl.

In one embodiment, $R^{14}$ and $R^{15}$ each independently represent hydrogen or $C_{1-4}$alkyl.

In one embodiment, $R^{14}$ and $R^{15}$ each independently represent $C_{1-4}$alkyl, such as for example methyl.

In one embodiment, $R^{22}$ and $R^{23}$ each independently represent hydrogen.

In one embodiment of the invention, $X^1$ represents N and $X^2$ represents CH; n represents an integer equal to 2; and each $R^2$ represents $C_{1-4}$alkoxy, for example $CH_3O$—; $R^3$ represents hydroxy$C_{1-6}$alkyl, halo$C_{1-6}$alkyl, $C_{1-6}$alkyl substituted with $R^9$, $C_{1-6}$alkyl substituted with —$NR^{10}R^{11}$, $C_{1-6}$alkoxy$C_{1-6}$alkyl, $C_{2-6}$alkynyl; Y represents -E-D wherein E represents a bond and D represents optionally substituted pyrazolyl.

In one embodiment of the invention, $X^1$ represents N and $X^2$ represents CH or $X^1$ represents CH and $X^2$ represents N; n represents an integer equal to 2, 3 or 4; and each $R^2$ represents $C_{1-4}$alkoxy, for example $CH_3O$—, or halo, for example fluoro or chloro; $R^{3a}$ represents hydrogen or chlorine; $R^3$ represents hydroxy$C_{1-6}$alkyl, cyano$C_{1-6}$alkyl, halo$C_{1-6}$alkyl, $C_{1-6}$alkyl substituted with $R^9$, $C_{1-6}$alkyl substituted with —$NR^{10}R^{11}$, $C_{1-6}$alkoxy$C_{1-6}$alkyl, $C_{1-6}$alkyl substituted with —C(=O)—$NR^{10}R^{11}$, $C_{2-6}$alkynyl or $R^{13}$; Y represents -E-D wherein E represents a bond and D represents an optionally substituted 5 or 6 membered aromatic heterocycle.

In one embodiment of the invention, $X^1$ represents N and $X^2$ represents CH or $X^1$ represents CH and $X^2$ represents N; n represents an integer equal to 2, 3 or 4; and each $R^2$ represents $C_{1-4}$alkoxy, for example $CH_3O$—, or halo, for example fluoro or chloro; $R^{3a}$ represents hydrogen or chlorine; $R^3$ represents hydroxy$C_{1-6}$alkyl, cyano$C_{1-6}$alkyl, halo$C_{1-6}$alkyl, $C_{1-6}$alkyl substituted with $R^9$, $C_{1-6}$alkyl substituted with —$NR^{10}R^{11}$, $C_{1-6}$alkoxy$C_{1-6}$alkyl, $C_{1-6}$alkyl substituted with —C(=O)—$NR^{10}R^{11}$, $C_{2-6}$alkynyl or $R^{13}$; Y represents -E-D wherein E represents a bond and D represents an optionally substituted 5 or 6 membered aromatic heterocycle, such as for example optionally substituted pyrazolyl or pyridyl; $R^1$ represents hydrogen or $C_{1-6}$alkyl, for example methyl, ethyl or isopropyl; $R^9$ represents an optionally substituted 5 membered aromatic heterocycle, such as for example imidazolyl, pyrazolyl, oxazolyl or triazolyl; or an optionally substituted 5 membered saturated heterocycle, such as for example pyrrolidinonyl or tetrahydrofuranyl; or an optionally substituted 6 membered aromatic heterocycle, such as for example pyrimidinyl; $R^{10}$ and $R^{11}$ represent hydrogen or $C_{1-6}$alkyl, such as for example methyl or isopropyl; $R^{13}$ represents a saturated 6-membered monocyclic heterocyclyl containing at least one heteroatom selected from N or O. In particular, the optional substituents for $R^9$ are selected from $C_{1-4}$alkyl, oxo, benzyl or —S(=O)$_2$—$NR^{14}R^{15}$, wherein $R^{14}$ and $R^{15}$ for instance each independently represent $C_{1-4}$alkyl, such as for example methyl.

In one embodiment of the invention, $X^1$ represents N and $X^2$ represents CH, n represents an integer equal to 2; and each $R^2$ represents $C_{1-4}$alkoxy, for example $CH_3O$—; $R^3$ represents hydroxy$C_{1-6}$alkyl, halo$C_{1-6}$alkyl, $C_{1-6}$alkyl substituted with $R^9$, $C_{1-6}$alkyl substituted with —$NR^{10}R^{11}$, $C_{1-6}$alkoxy$C_{1-6}$alkyl, $C_{2-6}$alkynyl; Y represents -E-D wherein E represents a bond and D represents pyrazolyl substituted with $C_{1-6}$alkyl; $R^{10}$ and $R^{11}$ represent hydrogen or $C_{1-6}$alkyl; $R^9$ represents an optionally substituted 5 membered aromatic heterocycle, such as for example optionally substituted imidazolyl.

In one embodiment, Y is -E-D, wherein E is a bond and D is a 5 or 6 membered monocyclic aromatic heterocyclyl, wherein said heterocyclyl may optionally be substituted by one or more (e.g. 1, 2 or 3) $R^1$ groups, and wherein one or more of the following applies:

n is 2;

$R^2$ is $C_{1-6}$alkyloxy;

$R^2$ is placed in position 3 and 5.

In one embodiment, Y is -E-D, wherein E is a bond and D is piperidinyl, pyridinyl, phenyl, pyrrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrrolyl, pyrimidinyl, pyrrolidinyl, thiadiazolyl, oxadiazolyl, said rings being optionally substituted, more in particular D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrrolidinyl, thiadiazolyl, oxadiazolyl, said rings being optionally substituted and n is 2, even more in particular D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrrolidinyl, thiadiazolyl, oxadiazolyl, said rings being optionally substituted; n is 2, $R^2$ is $C_{1-6}$alkyloxy, even further in particular D is piperidinyl, pyridinyl, phenyl, pyrolyl, imidazolyl, triazolyl, pyrolopyridinyl, 1,3-benzodioxolyl, indolyl, thiazolyl, cyclopentyl, azetidinyl, morpholinyl, tetrazolyl, oxazolyl, piperazinyl, 1,2,3,6-tetrahydropyridinyl, 2,5-dihydropyrolyl, pyrimidinyl, pyrrolidinyl, thiadiazolyl, oxadiazolyl, said rings being optionally substituted; n is 2, $R^2$ is $C_{1-6}$alkyloxy and said $R^2$ is placed in position 3 and 5.

In one embodiment there is provided compounds of formula (I-A) or (I-B) including any tautomeric or stereochemically isomeric form thereof, wherein
$X^1$ is N and $X^2$ is $CR^{3a}$;
each $R^2$ represents $C_{1-4}$alkoxy, for example $CH_3O$—;
Y represents -E-D;
D represents a 3 to 12 ring membered monocyclic or bicyclic carbocyclyl or a 3 to 12 ring membered monocyclic or bicyclic heterocyclyl containing at least one heteroatom selected from N, O or S, for example pyrazolyl, wherein said carbocyclyl and heterocyclyl may each be optionally substituted by one or more (e.g. 1, 2 or 3) $R^1$ groups;
E represents a bond;
$R^1$ represents $C_{1-6}$alkyl, for example —$CH_3$;
$R^{3a}$ represents hydrogen or chlorine;
$R^3$ represents hydroxy$C_{1-6}$alkyl for example —$CH_2CH_2OH$ or —$CH_2CH_2CH_2OH$, halo$C_{1-6}$alkyl, for example —CH2CH2Br, $C_{1-6}$alkyl substituted with $R^9$ for example —$CH_2$-substituted with imidazol-2-yl or with imidazol-2-yl substituted in the 3 position with —$S(O)_2$—$N(CH_3)_2$, $C_{1-6}$alkyl substituted with —$NR^{10}R^{11}$ for example —$CH_2CH_2N(CH(CH_3)_2)CH_2CH_2NHCH(CH_3)_2$ or —$CH_2CH_2NHCH(CH_3)_2$, $C_{1-6}$alkoxy$C_{1-6}$alkyl for example —$CH_2CH_2OCH_3$, or $C_{2-6}$alkynyl; for example —$CH_2C{\equiv}C$—H;
n independently represents an integer equal to 2;
the N-oxides thereof, the pharmaceutically acceptable salts thereof or the solvates thereof.

In one embodiment the compound of formula (I-A) is a compound of formula (I-C):

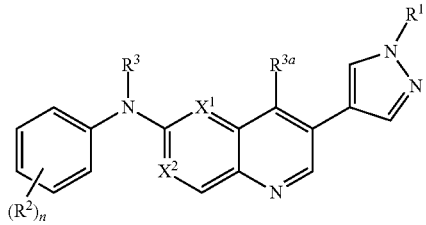

(I-C)

wherein n, $X^1$, $X^2$, $R^1$, $R^2$, $R^3$ and $R^{3a}$ are as defined herein. In one embodiment the compound of formula (I-A) is a compound of formula (I-C) wherein $R^{3a}$ is hydrogen.

In one embodiment the compound of formula (I-A) is a compound of formula (I-D):

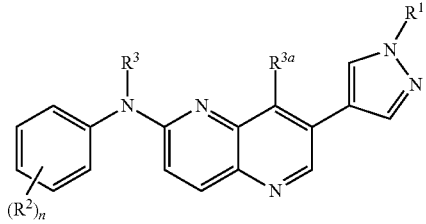

(I-D)

wherein n, $R^1$, $R^2$, $R^3$ and $R^{3a}$ are as defined herein. In one embodiment the compound of formula (I-A) is a compound of formula (I-D) wherein $R^{3a}$ is hydrogen.

In one embodiment the compound of formula (I-B) is a compound of formula (I-E):

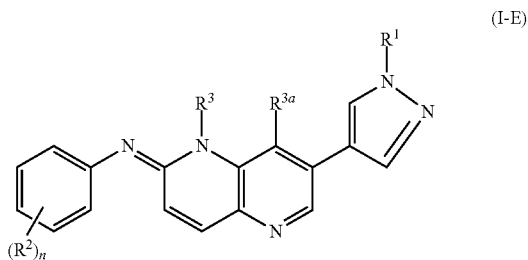

(I-E)

wherein n, $R^1$, $R^2$, $R^3$ and $R^{3a}$ are as defined herein. In one embodiment the compound of formula (I-B) is a compound of formula (I-D) wherein $R^{3a}$ is hydrogen.

In one embodiment, the present invention relates to any one of the following compounds

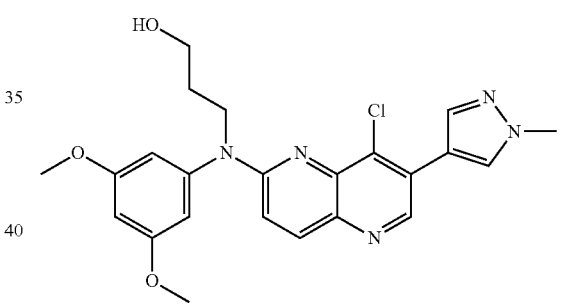

or

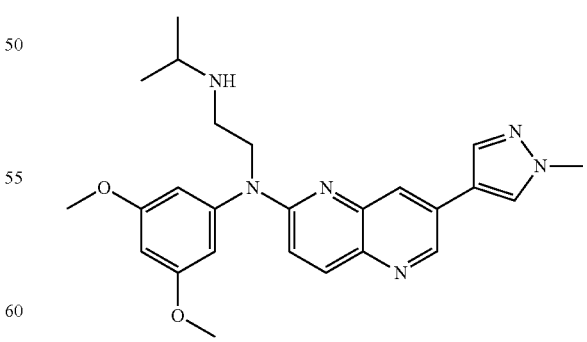

a N-oxide thereof, a pharmaceutically acceptable salt thereof or a solvate thereof.

In one embodiment, the present invention relates to any one of the following compounds

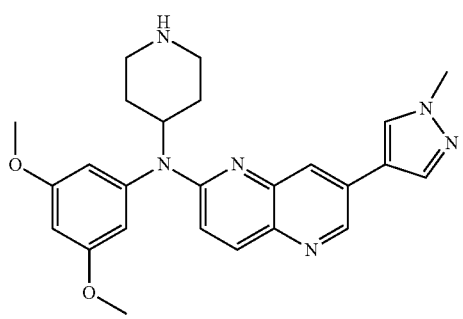
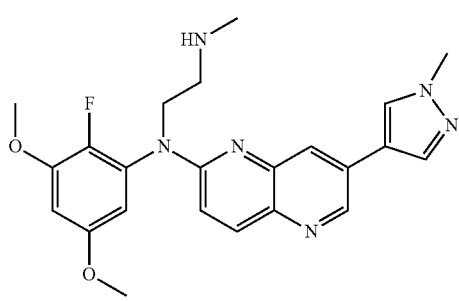
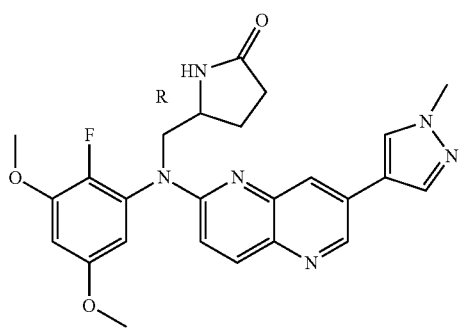
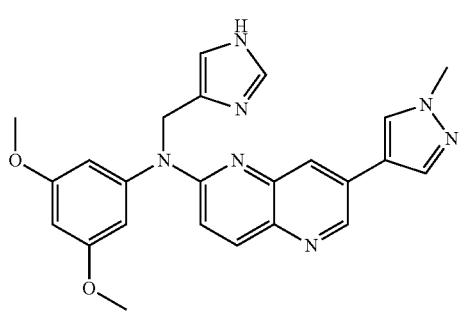
-continued
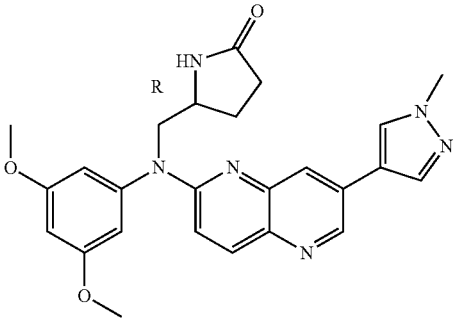
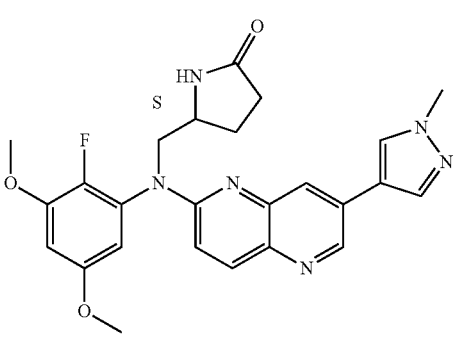
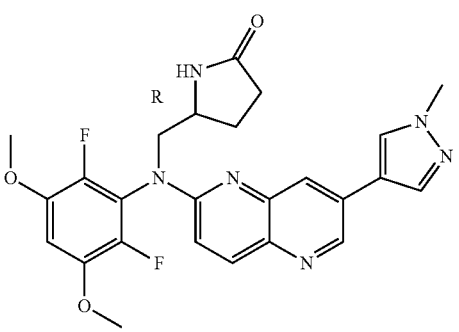

-continued

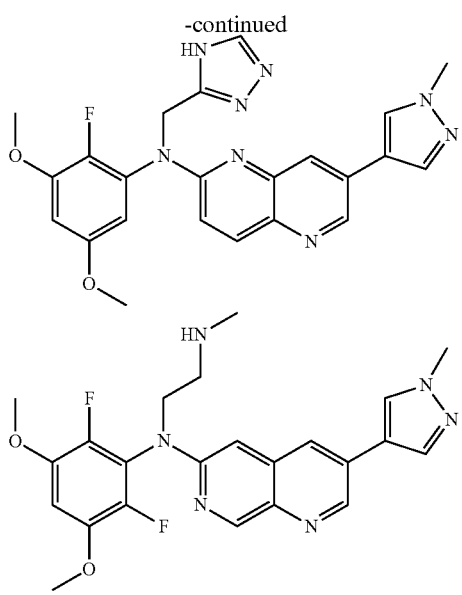

a N-oxide thereof, a pharmaceutically acceptable salt thereof or a solvate thereof.

For the avoidance of doubt, it is to be understood that each general and specific preference, embodiment and example for one substituent may be combined, whenever possible, with each general and specific preference, embodiment and example for one or more, preferably, all other substituents as defined herein and that all such embodiments are embraced by this application.

Methods for the Preparation of Compounds of Formula (I)

In this section, as in all other sections of this application unless the context indicates otherwise, references to formula (I) also include all other sub-groups and examples thereof as defined herein.

In general, compounds of formula (I-A) wherein $X^1$ is N, and $X^2$ is $CR^{3a}$; $R^{3a}$ is hydrogen, Y is D (E is a bond), said compounds being represented by formula (I-Aa), can be prepared according to the following reaction Scheme 1.

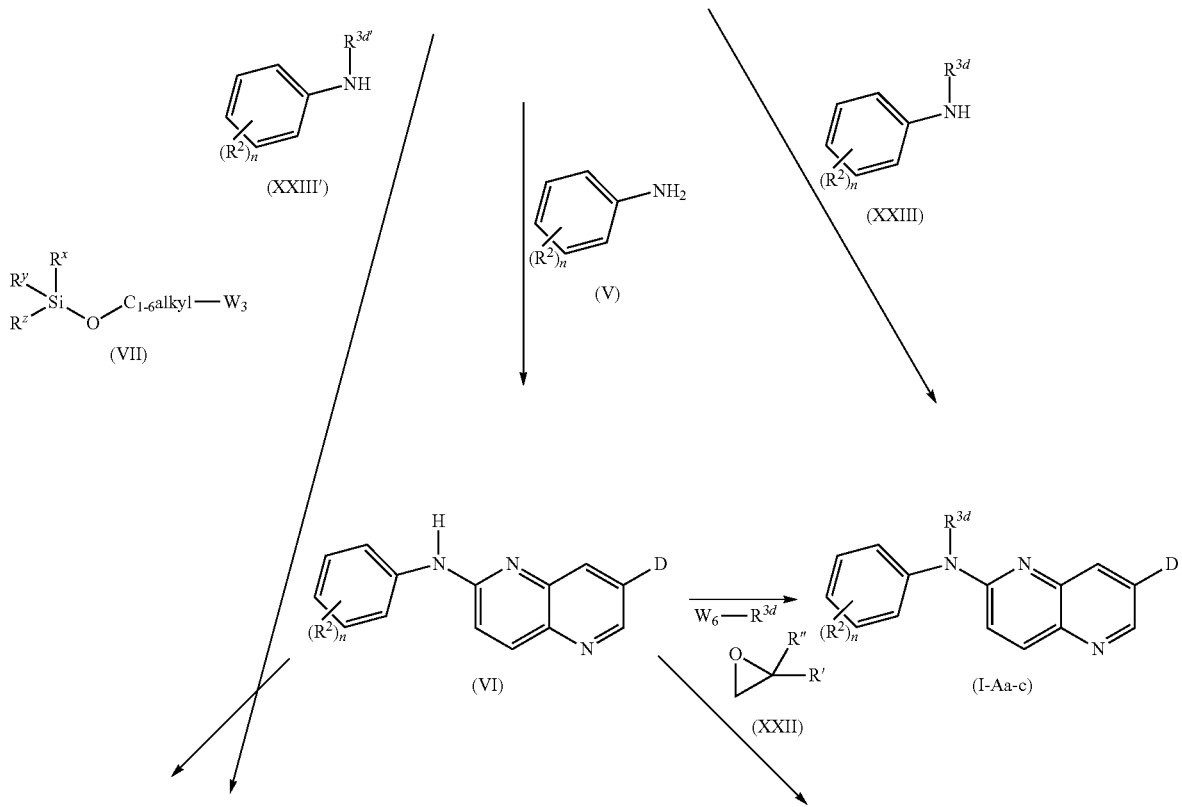

-continued
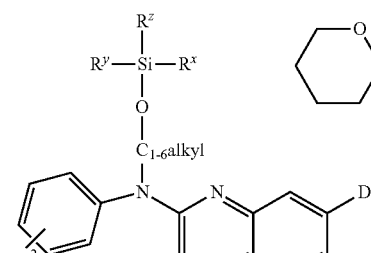
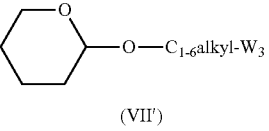
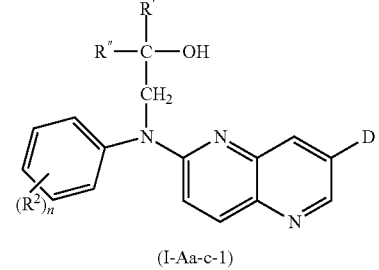
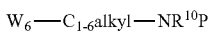
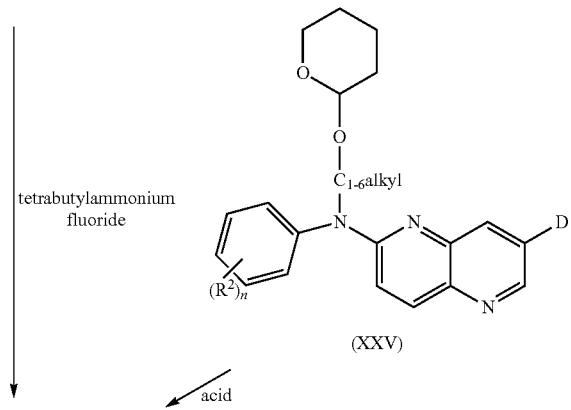
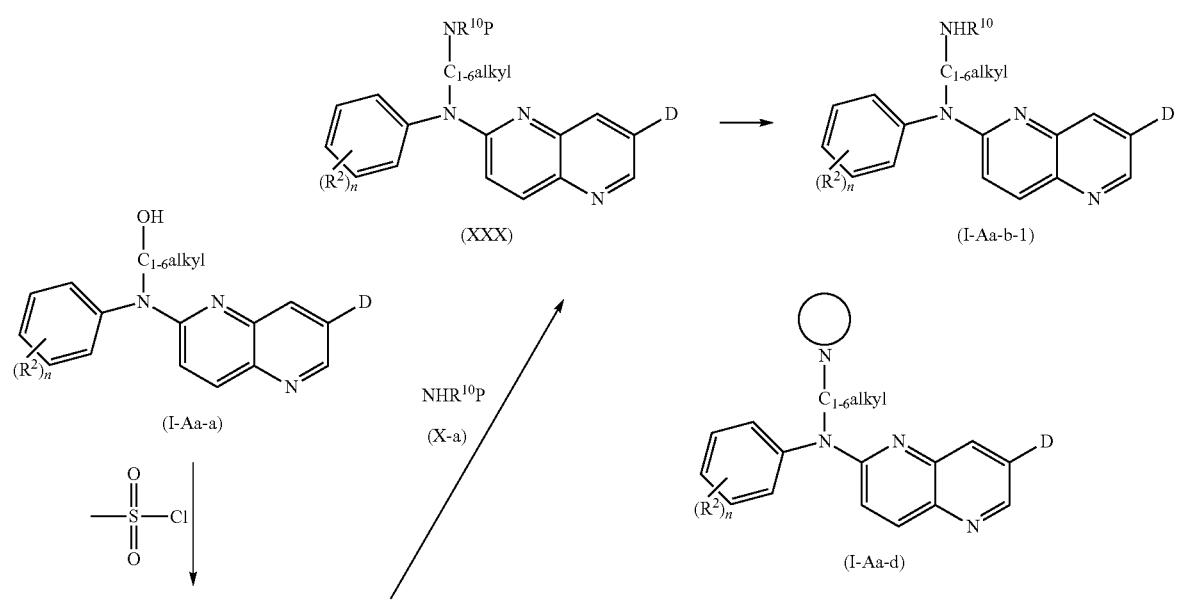

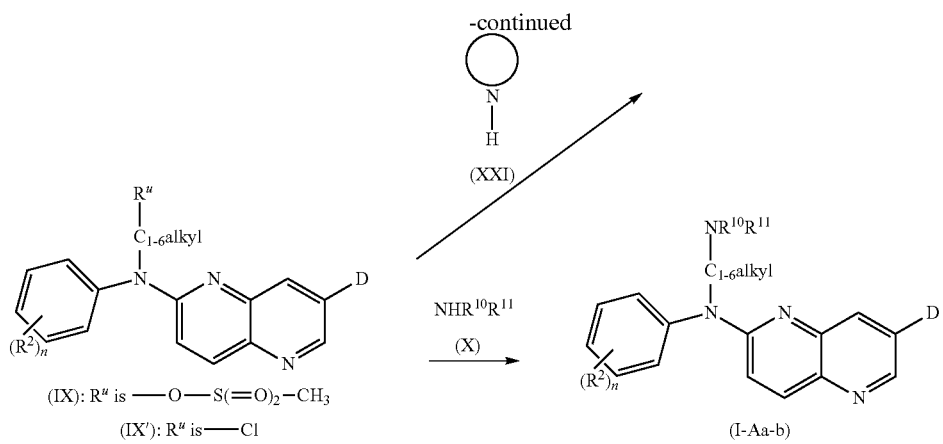

In scheme 1, an intermediate of formula (IV) wherein $W_2$ represents a suitable leaving group, such as for example halo, e.g. chloro and the like, or —O—SO$_2$—CF$_3$, is reacted with an intermediate of formula (V) in the presence of a suitable catalyst, such as for example palladium (II) acetate or Pd$_2$dba$_3$, a suitable base, such as sodium tert-butoxide or Cs$_2$CO$_3$, a suitable ligand, such as for example 1,1'-[1,1'-binaphthalene]-2,2'-diylbis[1,1-diphenylphosphine] or xantphos, and a suitable solvent or solvent mixture, such as for example dioxane or ethylene glycol dimethylether and water or N-methyl-pyrrolidone, or tetrahydrofuran or toluene or a mixture of dioxane and toluene, resulting in an intermediate of formula (VI). This reaction can also be performed in the presence of a suitable deprotonating agent, such as for example potassium bis(trimethylsilyl)amide, and a suitable solvent, such as for example tetrahydrofuran. Or alternatively an intermediate of formula (IV) is reacted with an intermediate of formula (V) in the presence of a suitable solvent, such as for example an alcohol, e.g. n-propanol. Said intermediate of formula (VI) can then be reacted with an intermediate of formula (VII) wherein $W_3$ represents a suitable leaving group, such as for example halo, e.g. bromo and wherein $R^x$ and $R^y$ represent $C_{1-4}$alkyl, and $R^z$ represent $C_{1-4}$alkyl or phenyl, for instance $R^x$ and $R^y$ represent CH$_3$ and $R^z$ represents C(CH$_3$)$_3$ or phenyl, in the presence of a suitable base, such as for example sodium hydride, and a suitable solvent, such as for example N,N-dimethylformamide or N,N-dimethylacetamide, resulting in an intermediate of formula (VIII). Intermediates of formula (VIII) or intermediates of formula (VIII) wherein the $R^1$ substituent carries a suitable protective group can also be prepared by reacting an intermediate of formula (IV) or an intermediate of formula (IV) wherein the $R^1$ substituent carries a suitable protective group with an intermediate of formula (XXIII') wherein $R^{3d'}$ represent —C$_{1-6}$alkyl-O—Si(RX)(R$^y$)(R$^z$) in the presence of a suitable catalyst, such as for example palladium (II) acetate, a suitable ligand, such as for example racemic-2,2'-bis(diphenylphosphino)-1,1'-binaphtyl, a suitable base, such as for example Cs$_2$CO$_3$, and a suitable solvent, such as for example 1,2-dimethoxyethane. Intermediates of formula (VIII) can be converted into a compound of formula (I) wherein $R^3$ represents —C$_{1-6}$alkyl-OH, said compounds being represented by formula (I-Aa-a) or compounds of formula (I-Aa) wherein the $R^1$ substituent carries a suitable protective group, by reaction with tetrabutylammonium fluoride in the presence of a suitable solvent, such as for example tetrahydrofuran. This type of reaction can also be performed in the presence of a suitable acid, such as for example acetic acid or HCl, and a suitable solvent, such as for example tetrahydrofurane or dioxane. Alternatively, an intermediate of formula (VI) can react with an intermediate of formula (VII') wherein $W_3$ represents a suitable leaving group, such as for example halo, e.g. bromo and the like, in the presence of a suitable base, such as for example sodium hydride, and a suitable solvent, such as for example N,N-dimethylformamide or N,N-dimethylacetamide, resulting in an intermediate of formula (XXV) which can then be deprotected in the presence of a suitable acid, such as for example HCl, and a suitable solvent, such as for example an alcohol, e.g. methanol or isopropanol, to give a compound of formula (I-Aa-a). The compounds of formula (I-Aa-a) or compounds of formula (I-Aa-a) wherein the $R^1$ substituent carries a suitable protective group can be reacted with methanesulfonyl chloride in the presence of a suitable base, such as for example triethylamine, diisopropylethanamine or N,N-dimethyl-4-aminopyridine, and a suitable solvent, such as for example dichloromethane or tetrahydrofuran, to result in an intermediate of formula (IX) (mesylate derivative) or an intermediate of formula (IX') (chloride derivative) or intermediates of formula (IX) or (IX') wherein the $R^1$ substituent carries a suitable protective group. In particular, this type of reaction is used to prepare intermediates of formula (IX) or (IX') wherein C$_{1-6}$alkyl represents C$_{3-6}$alkyl. For some variants of intermediates of formula (IX) or (IX'), e.g. wherein C$_{1-6}$alkyl represents C$_{1-2}$alkyl it might be preferred to perform the reaction in non basic conditions. Intermediates of formula (IX) or (IX') can then be reacted with an intermediate of formula (X) to obtain a compound of formula (Ia) wherein $R^3$ represents C$_{1-6}$alkyl substituted with NR$^{10}$R$^{11}$, said compounds being represented by formula (I-Aa-b) or compounds of formula (I-Aa-b) wherein the $R^1$ substituent carries a suitable protective group. This reaction may optionally be performed in the presence of a suitable base, such as for example triethylamine, K$_2$CO$_3$, Na$_2$CO$_3$ or sodium hydride and optionally a suitable solvent, such as for example acetonitrile, tetrahydrofuran, dioxane, N,N-dimethylformamide, 1-methyl-pyrrolidinone, a suitable alcohol, e.g. 1-butanol and the like. This type of reaction can also be performed with a suitable salt of the intermediate of formula (X), e.g. HCl salt of intermediate of formula (X), or may be performed in the presence of potassium iodide. In this way compounds wherein $R^3$ represents iodoC$_{1-6}$alkyl can be obtained. Compounds of formula (Ia-b) wherein the $R^1$ substituent carries a suitable protective group can be converted in a compound of formula (I-Aa-b) by reaction with a suitable acid, such as for example trifluoroacetic acid, in the presence of a suitable solvent, such as for example dichloromethane.

Intermediates of formula (IX) can also react with a suitable nitrogen containing ring within the definition of $R^9$, said ring being represented by formula (XXI) or a suitable salt of an intermediate of formula (XXI), in the presence of a suitable solvent, such as for example acetonitrile, 1-methyl-2-pyrrolidinone, or an alcohol, e.g. 1-butanol, optionally in the presence of potassium iodide or a suitable base, such as for example $Na_2CO_3$, $K_2CO_3$ or triethylamine, resulting in a compound of formula (I-Aa-d). Intermediates of formula (IX) can also react with an intermediate of formula (X-a) wherein P represents a suitable protective group, such as for example $—C(=O)—O—C(CH_3)_3$, in the presence of a suitable base, such as for example sodium hydride, and a suitable solvent, such as for example dimethylacetamide, resulting in an intermediate of formula (XXX) which can be deprotected to a compound of formula (I-Aa-b-1) in the presence of a suitable acid, such as for example HCl or trifluoroacetic acid, and a suitable solvent, such as for example dichloromethane or an alcohol, e.g. methanol. Intermediates of formula (XXX) can also be prepared by reacting an intermediate of formula (VI) with an intermediate of formula $W_6—C_{1-6}alkyl-NR^{10}P$ wherein $W_6$ represents a suitable leaving group, such as for example halo, e.g. bromo and the like, or $—O—S(=O)_2—CH_3$, and P is as defined above, in the presence of a suitable base, such as for example sodium hydride, and a suitable solvent, e.g. N,N-dimethylformamide or N,N-dimethylacetamide. Alternatively compounds of formula (I-Aa-d) or (I-Aa-b-1) can also be prepared by reacting respectively an intermediate of formula (VI) with an intermediate of formula $W_6—C_{1-6}alkyl-Ncycle$ or $W_6—C_{1-6}alkyl-NHR^{10}$ wherein $W_6$ is as defined above. Intermediates of formula (VI) can react with $W_6—R^{3d}$ wherein $W_6$ represents a suitable leaving group, such as for example halo, e.g. bromo and the like, or $—O—S(=O)_2—CH_3$ or p-toluenesulfonate, and $R^{3d}$ represents optionally substituted $C_{1-6}alkyl$, such as for example $—CH_2—C_3H_5$, in the presence of a suitable base, such as for example sodium hydride, $Cs_2CO_3$ or potassium hydroxide and a suitable phase transfer agent, such as for example tetrabutylammonium bromide or and a suitable solvent, such as for example N,N-dimethylformamide, N,N-dimethylacetamide, 2-methyltetrahydrofuran, water or acetonitrile, resulting in a compound of formula (I-Aa-c). $W_6—R^{3d}$ can also be used in an appropriate salt form, e.g. a hydrochloric acid salt of $W_6—R^{3d}$. In this way, compounds of formula (I-Aa-c) wherein $R^3$ represents $—S(=O)_2—N(CH_3)_2$ can also be prepared by reacting an intermediate of formula (VI) with dimethylsulfamoyl chloride, in the presence of a suitable base, such as for example NaH, and a suitable solvent, such as for example N,N-dimethylformamide. This type of reaction can also be used to prepare an intermediate wherein the $R^{3d}$ moiety is protected by an appropriate protective group, such as for example triphenylmethyl or $—CH_2—O—CH_2—CH_2—Si(CH_3)_3$, which can then be deprotected to a compound of formula (I-Aa-c) in the presence of a suitable acid, such as for example HCl or trifluoroacetic acid, in a suitable solvent, such as for example dichloromethane or acetonitrile, or by reaction with a suitable desilylating agent, such as for example tetrabutylammonium fluoride in the presence of a suitable solvent, such as for example tetrahydrofuran. This type of reaction can also be used to prepare a compound of formula (I-Ba) (see hereinafter). Compounds of formula (I-Aa-c) wherein the $C_{1-6}alkyl$ chain within the definition of R3d represents-CH2-(C0-5alkyl) can also be prepared by reacting an intermediate of formula (VI) with HC(=O)—R3d' in the presence of sodium cyanoborohydride, and a suitable solvent, such as for example an alcohol, e.g. methanol, and dichloromethane.

Compounds of formula (I-Aa-c) wherein $R^{3d}$ represents $—CH_2—C(OH)(R')(R'')$ wherein R' represents optionally substituted $C_{1-4}alkyl$ and R" represents hydrogen or optionally substituted $C_{1-4}alkyl$, said compounds being represented by formula (I-Aa-c-1), can be prepared by reacting the intermediate of formula (VI) with an intermediate of formula (XXII) in the presence of a suitable base, such as for example sodium hydride, $Cs_2CO_3$, or potassium hydroxide, and a suitable solvent, such as for example N,N-dimethylformamide, N,N-dimethylacetamide, acetonitrile or water.

Intermediates of formula (IV) can also react with an intermediate of formula (XXIII) in the presence of a suitable catalyst, such as for example palladium (II) acetate or tris(dibenzylideneacetone)dipalladium (0), a suitable base, such as for example sodium tert-butoxide or $Cs_2CO_3$, a suitable ligand, such as for example 1,1'-[1,1'-binaphthalene]-2,2'-diylbis[1, 1-diphenylphosphine] or 2-dicyclohexylphosphino-2'-(N,N-dimethyl-amino)biphenyl or dicyclohexyl(2',6'-diisopropoxy-2-biphenylyl)phosphine, and a suitable solvent, such as for example dioxane, resulting in a compound of formula (I-Aa-c). Intermediates of formula (XXIII) can also react in a form wherein the $R^{3d}$ moiety is in protected form, e.g. protected with $—C(=O)—O—C_{1-6}alkyl$. The resulting product can then be deprotected, for instance in the presence of a suitable acid, such as for example HCl, and a suitable solvent, such as for example dichloromethane.

Compounds of formula (I-Aa-b) wherein $R^{11}$ is $C_{1-6}alkyl$ substituted with amino, said compounds being represented by formula (I-Aa-b-2), can also be prepared according to the following reaction Scheme 1A.

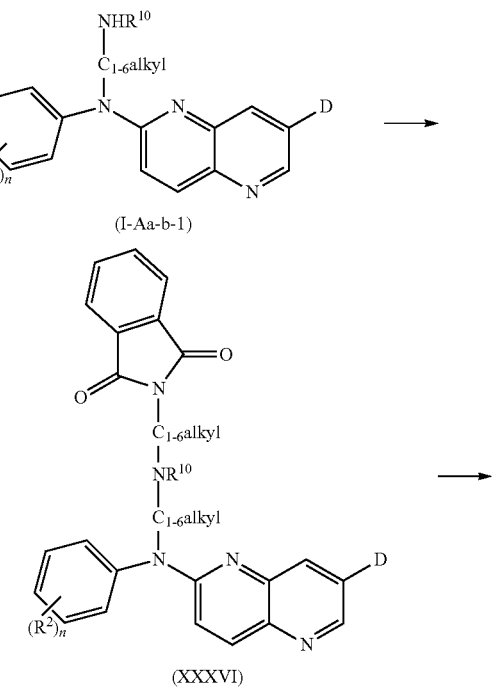

Scheme 1A

-continued

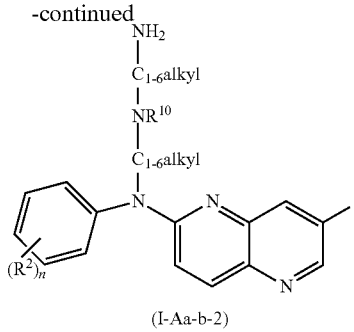

(I-Aa-b-2)

Scheme 1B

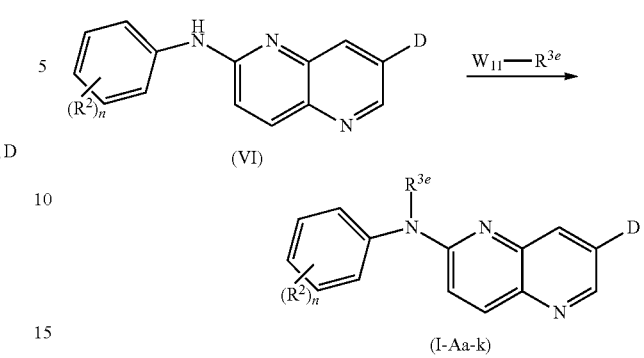

In Scheme 1A, a compound of formula (I-Aa-b-1) is reacted with N-(haloC$_{1-6}$alkyl)-phtalimide in the presence of a suitable base, such as for example potassium carbonate, and a suitable solvent, such as for example acetonitrile, resulting in an intermediate of formula (XXXVI) which can be converted into a compound of formula (I-Aa-b-2) by reaction with hydrazine in the presence of a suitable solvent, such as for example an alcohol, e.g. ethanol.

Compounds of formula (I-Aa) wherein $R^3$ represents optionally substituted C$_{2-6}$alkynyl, said compounds being represented by formula (I-Aa-k), can be prepared according to reaction Scheme 1B.

In Scheme 1B, an intermediate of formula (VI) is reacted with an intermediate of formula $W_{11}$—$R^{3e}$ wherein $R^{3e}$ represents optionally substituted C$_{2-6}$alkynyl and $W_{11}$ represents a suitable leaving group such as for example halo, e.g. chloro, or —O—S(=O)$_2$—CH$_3$, in the presence of a suitable base, such as for example NaH, and a suitable solvent, such as for example N,N-dimethylformamide. The intermediate $W_{11}$—$R^{3e}$ wherein $W_{11}$ represents —O—S(=O)$_2$—CH$_3$, can be prepared by reacting the corresponding alcohol derivative with methanesulfonyl chloride in the presence of a suitable base, such as for example triethylamine or 4-dimethylaminopyridine, and a suitable solvent, such as for example dichloromethane.

Compounds of formula (I-Aa-k), wherein $R^{3e}$ represents C$_{2-6}$alkynyl substituted with hydroxyl, said compounds being represented by formula (I-Aa-k-1), can be prepared according to the following reaction Scheme 1C.

Scheme 1C

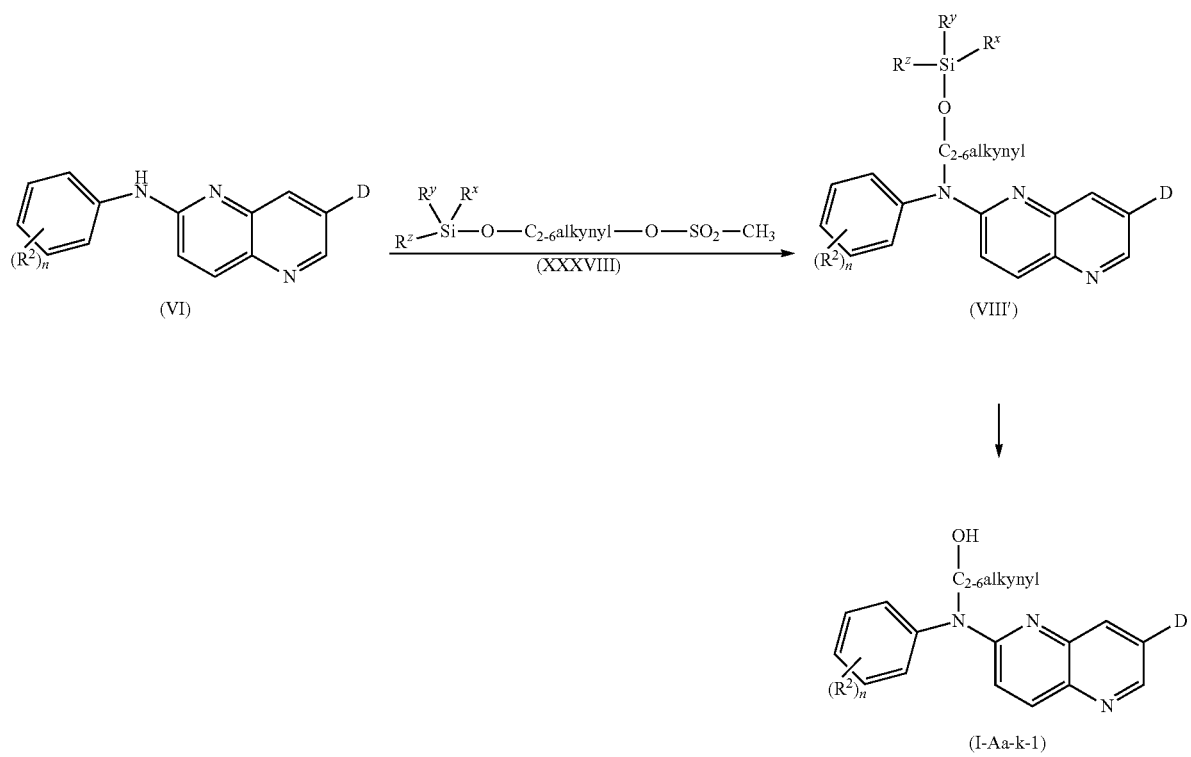

In Scheme 1C, an intermediate of formula (VI) is reacted with an intermediate of formula (XXXVIII) in the presence of a suitable base, such as for example NaH, and a suitable solvent, such as for example N,N-dimethylformamide, resulting in an intermediate of formula (VIII'), which is converted into a compound of formula (I-Aa-k-1) by reaction with a suitable acid, such as for example trifluoroacetic acid, in the presence of a suitable solvent, such as for example tetrahydrofuran. This reaction can also be performed with tetrabutyl ammonium fluoride in the presence of a suitable solvent such as for example tetrqahydrofuran.

Alternatively, instead of an intermediate of formula (XXXVIII), halo-$C_{2-6}$alkynyl-O—Si($R^x$)($R^y$)($R^z$) can also be used.

Compounds of formula (I-Aa-k), wherein $R^{3e}$ represents $C_{2-6}$alkynyl, said compounds being represented by formula (I-Aa-k-2), can be prepared according to the following reaction Scheme 1D.

In Scheme 1 D, a compound of formula (I-Aa-k-2) is prepared by deprotecting an intermediate of formula (XXXXII) in the presence of a suitable base, such as for example $K_2CO_3$, and a suitable solvent, such as for example an alcohol, e.g. methanol and the like. Said intermediate of formula (XXXXII) can be prepared by reacting an intermediate of formula (VI) with $W_{13}$—$C_{2-6}$alkynyl-Si($CH_3$)$_3$ wherein $W_{13}$ is a suitable leaving group, such as for example halogen, in the presence of a suitable base, such as for example NaH, and a suitable solvent, such as for example N,N-dimethylformamide.

Compounds of formula (I-Aa), wherein $R^3$ represents ethyl substituted with —P(=O)(O$C_{1-6}$alkyl)$_2$, said compounds being represented by formula (I-Aa-I), can be prepared according to the following reaction Scheme 1E.

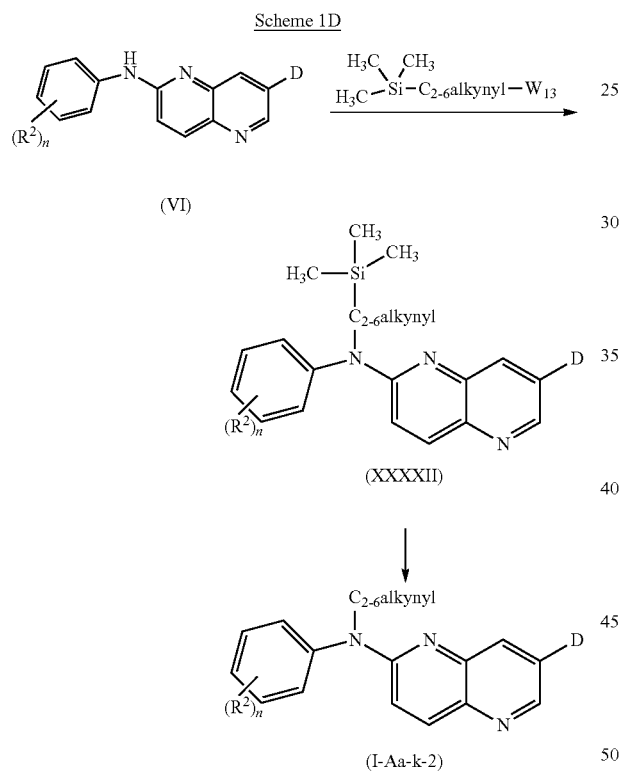

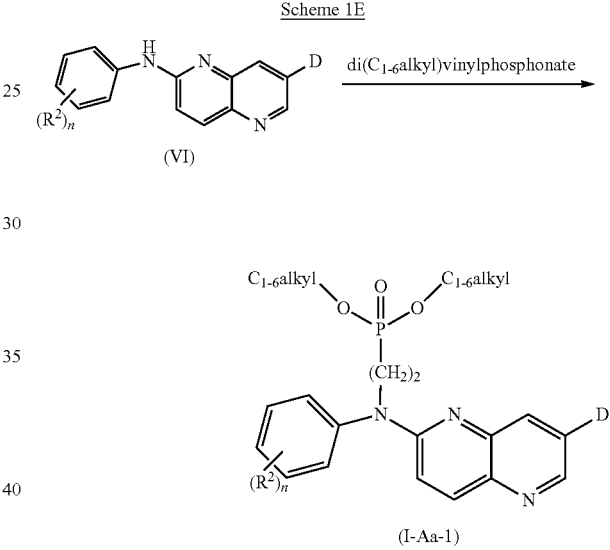

In scheme 1E, an intermediate of formula (VI) is reacted with di($C_{1-6}$alkyl)vinylphosphonate in the presence of a suitable catalyst, such as for example tri-N-butylphosphine, and a suitable solvent, such as for example acetonitrile resulting in a compound of formula (Ia-I).

Intermediates of formula (IV) can be prepared according to the following reaction Scheme 2.

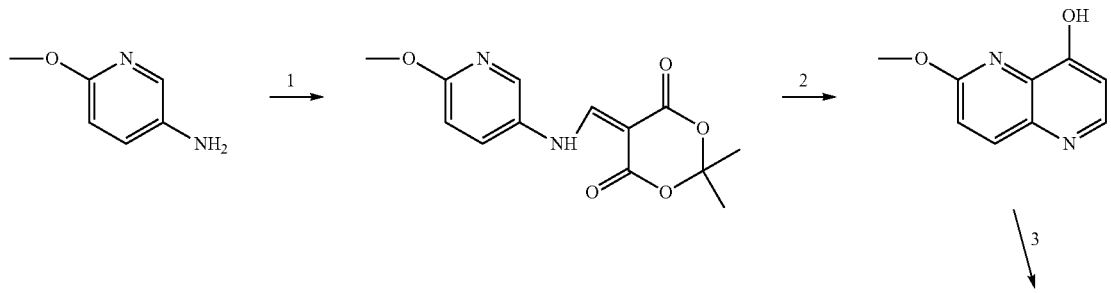

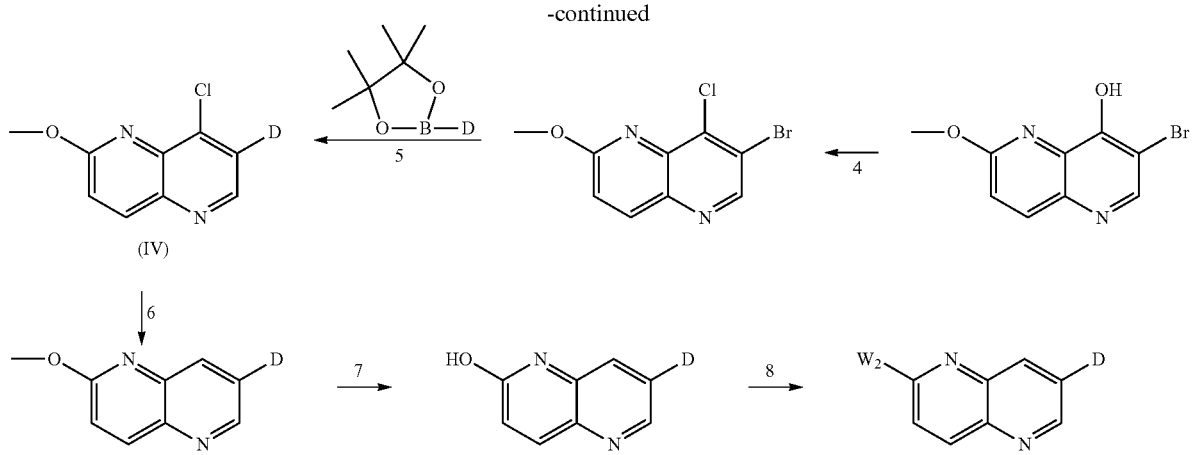

In Scheme 2, the following reaction conditions apply:
1: in the presence of a Meldrum's acid and triethyl orthoformate, and a suitable solvent, such as for example an alcohol, e.g. ethanol;
2: in the presence of diphenyl ether or dowtherm A;
3: in the presence of N-bromo-succinimide, and acetic acid;
4: in the presence of phosphoryl chloride, and a suitable solvent, such as for example chloroform;
5: in the presence of a suitable base, such as for example sodium carbonate, a suitable catalyst, such as for example $PdCl_2(pddf).CH_2Cl_2$, and a suitable solvent, such as for example dioxane and water;
6: in the presence of catalyst, such as for example Raney nickel, and $H_2$, a suitable base, such as for example sodium hydroxide, and a suitable solvent, such as for example an alcohol, e.g. ethanol, and tetrahydrofuran;
7: In the presence of a suitable acid, such as for example HCl, and a suitable solvent, such as for example, dioxane;
8: in the presence of a suitable leaving group introducing agent, such as for example phosphoryl chloride, and a suitable solvent, such as for example chloroform.

Some naphthyridines are described in R. Morgentin et al./Tetrahedron 64 (2008) 2772e2782.

Compounds of formula (I-A) wherein $X^2$ is N and $X^1$ is CH; and Y is D (E is a bond) can be prepared according to the reaction schemes described above starting from the corresponding intermediate (1,7-naphthyridine analogue of intermediate of formula (IV)) which can be prepared according to the following reactions in Scheme 2A.

Scheme 2A

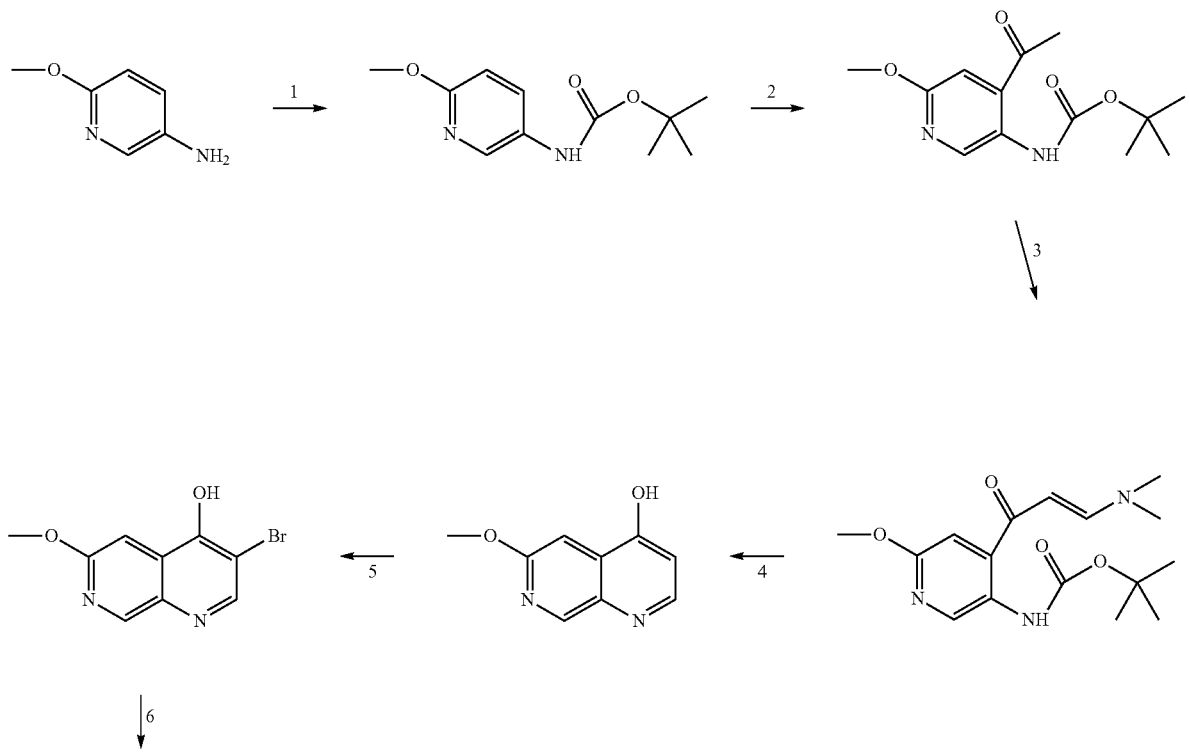

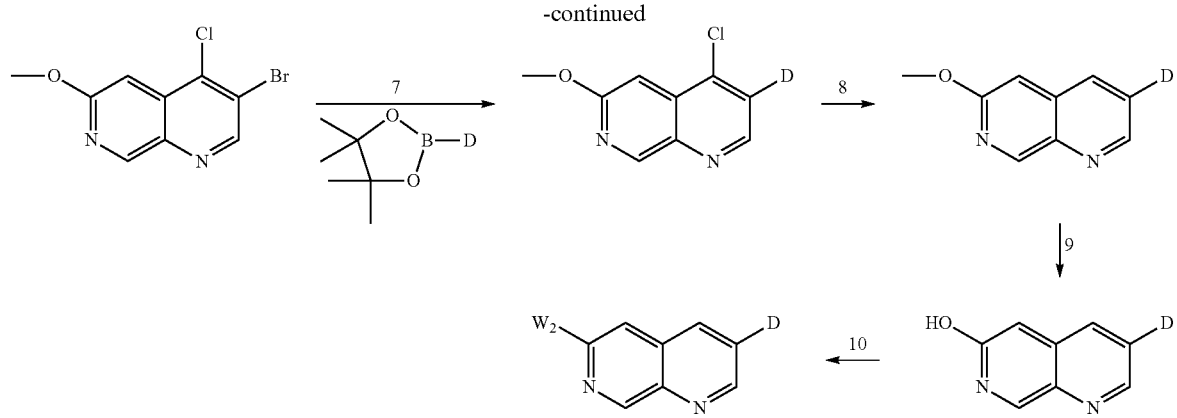

In Scheme 2A, the following reaction conditions apply:
1: in the presence of di-tert-butyl dicarbonate, and a suitable solvent, e.g. dioxane;
2: in the presence of N-methoxy-N-methylacetamide, and tetramethylene diamine used as a base in the presence of BuLi
3: in the presence of N,N-dimethylformamide and N,n-dimethylacetamide
4: in the presence of a suitable acid, such as for example trifluoroacetic acid, and a suitable solvent, such as for example toluene.
5: in the presence of N-bromosuccinimide, and a suitable acid, such as for example acetic acid
6: in the presence of POCl3 and a suitable solvent, such as for example $CHCl_3$
7; in the presence of a suitable base, such as for example sodium carbonate, a suitable catalyst, such as for example $PdCl_2$(pddf).$CH_2Cl_2$, and a suitable solvent, such as for example dioxane and water;
8: in the presence of catalyst, such as for example Raney nickel, and $H_2$, a suitable base, such as for example sodium hydroxide, and a suitable solvent, such as for example an alcohol, e.g. ethanol, and tetrahydrofuran;
9: in the presence of $AlCl_3$, and a suitable solvent, such as for example dichloroethane
10: in the presence of a leaving group introducing agent, such as for example $SOCl_2$ or N-phenyl-bis(trifluoromethanesulfonimide), optionally a suitable base, such as for example triethylamine, and a suitable solvent, such as for example toluene, dichloromethane and N,N-dimethylformamide.

Some of the intermediates are described in R. Morgentin et al./Tetrahedron 64 (2008) 2772e2782.

In general, compounds of formula (I-B) wherein $R^{3a}$ is hydrogen and Y is D (E is a bond), said compounds being represented by formula (I-Ba), can be prepared according to the following reactions in Scheme 3.

Scheme 3

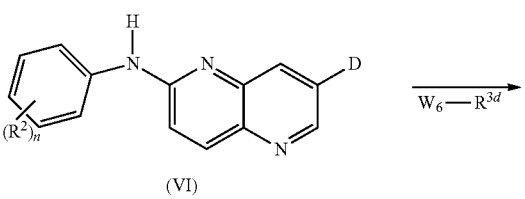

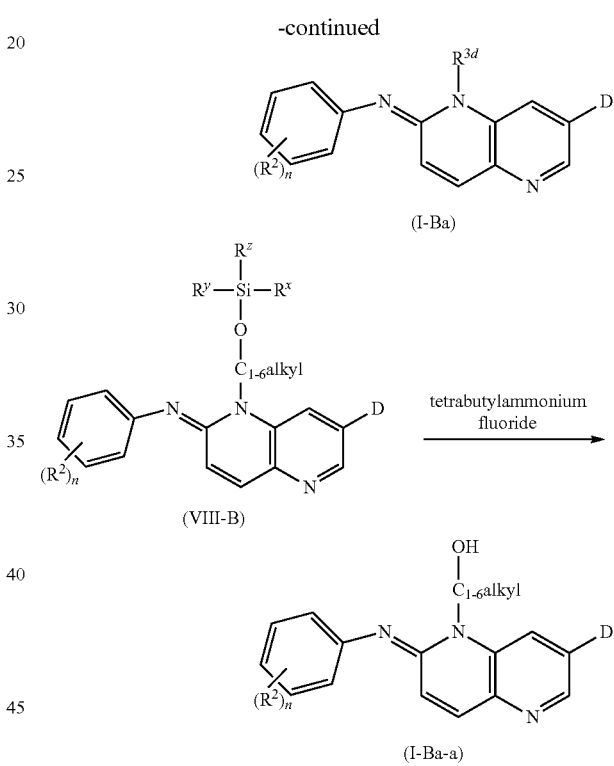

In Scheme 3, an intermediate of formula (VI) can react with $W_6$—$R^{3d}$ wherein $W_6$ represents a suitable leaving group, such as for example halo, e.g. bromo and the like, or —O—S(=O)$_2$—$CH_3$, in the presence of a suitable base, such as for example potassium hydroxide and a suitable phase transfer agent, such as for example tetrabutylammonium bromide and, and a suitable solvent, such as for example 2-methyltetrahydrofuran and water, resulting in a compound of formula (I-Ba).

Intermediates of formula (VIII-B) can react with tetrabutylammonium fluoride, in the presence of a suitable solvent, such as for example tetrahydrofuran, resulting in a compound of formula (I-Ba-a).

In general, compounds of formula (I-A) wherein $X^1$ is N, and $X^2$ is $CR^{3a}$; Y is D (E is a bond), said compounds being represented by formula (I-Ab), can be prepared according to the following reaction Scheme 4.

Scheme 4

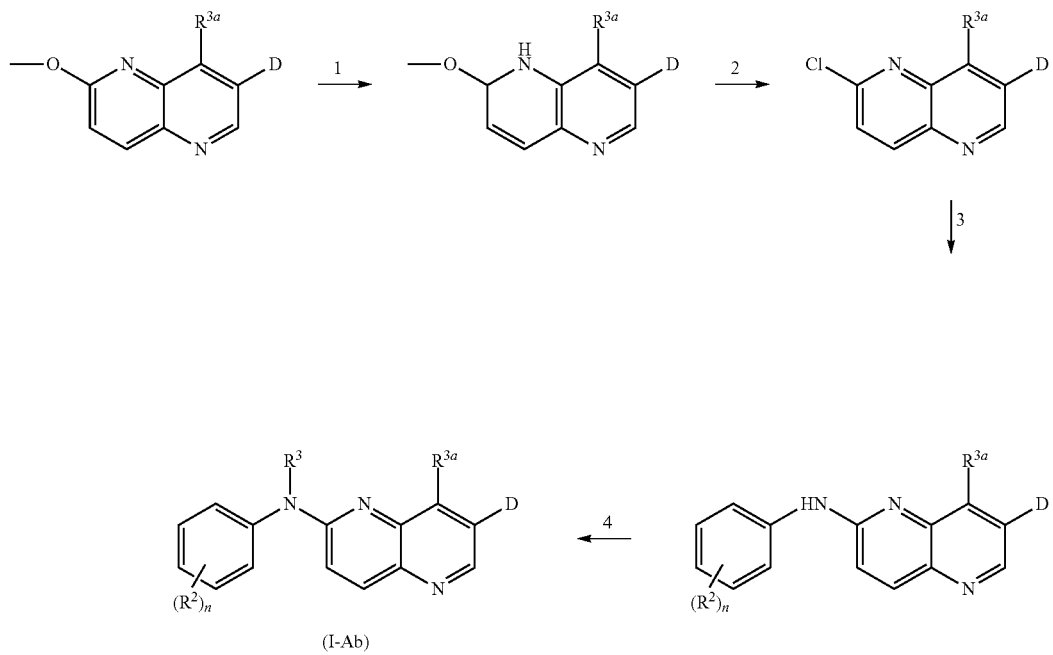

In Scheme 4, the following reaction conditions apply:
1; starting material is prepared according to the reactions described in scheme 2. Said starting material is reacted in the presence of a suitable acid, such as for example HCl, and a suitable solvent, such as for example dioxane.
2; in the presence of POCl3, and a suitable solvent, such as for example chloroform;
3: in the presence of intermediate (V) (see Scheme 1), a suitable base, such as for example diisopropylethylamine, and a suitable solvent, such as for example an alcohol, e.g. 1-propanol;
4: according to the reactions described above.

Intermediates of formula (VIII-a) or (VIII-b) can be prepared according to the following reaction Scheme 4'.

Scheme 4'

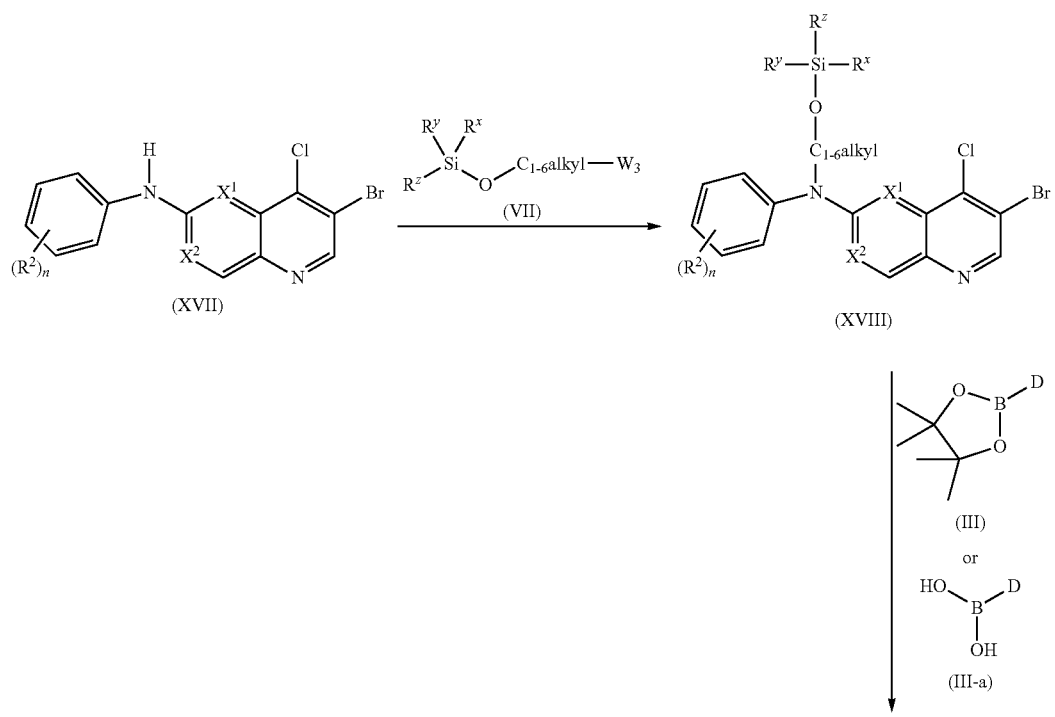

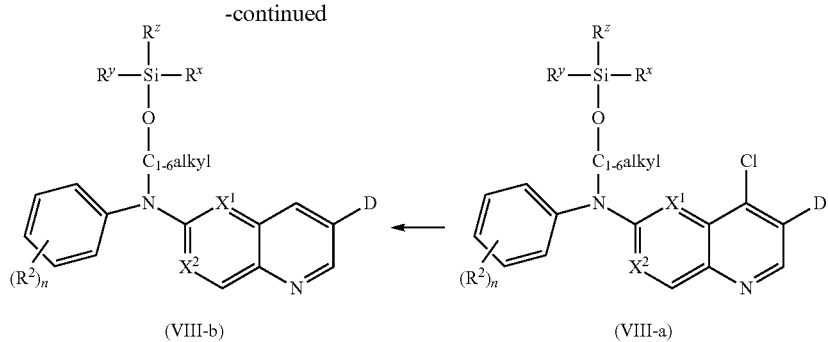

(VIII-b) (VIII-a)

In Scheme 4', an intermediate of formula (XVII) is reacted with an intermediate of formula (VII) in the presence of a suitable base, such as for example sodium hydride, and a suitable solvent, such as for example N,N-dimethylformamide, resulting in an intermediate of formula (XVIII). The intermediate of formula (XVIII) can then be reacted with an intermediate of formula (III) or (III-a) in the presence of a suitable catalyst, such as for example $Pd_2(dba)_3$, a suitable base, such as for example $K_3PO_4$, a suitable ligand, such as for example 2-dicyclohexylphosphino-2',6'-dimethoxy-biphenyl or S-Phos, and a suitable solvent, such as for example dioxane or water or mixtures thereof. Intermediates of formula (VIII-a) can be transformed in an intermediate of formula (VIII-b) in the presence of catalyst, such as for example Raney nickel, and $H_2$, a suitable base, such as for example sodium hydroxide, and a suitable solvent, such as for example an alcohol, e.g. ethanol.

Intermediates of formula (VIII-a) or (VIII-b) can also be prepared according to the following reaction Scheme 4A.

Scheme 4A

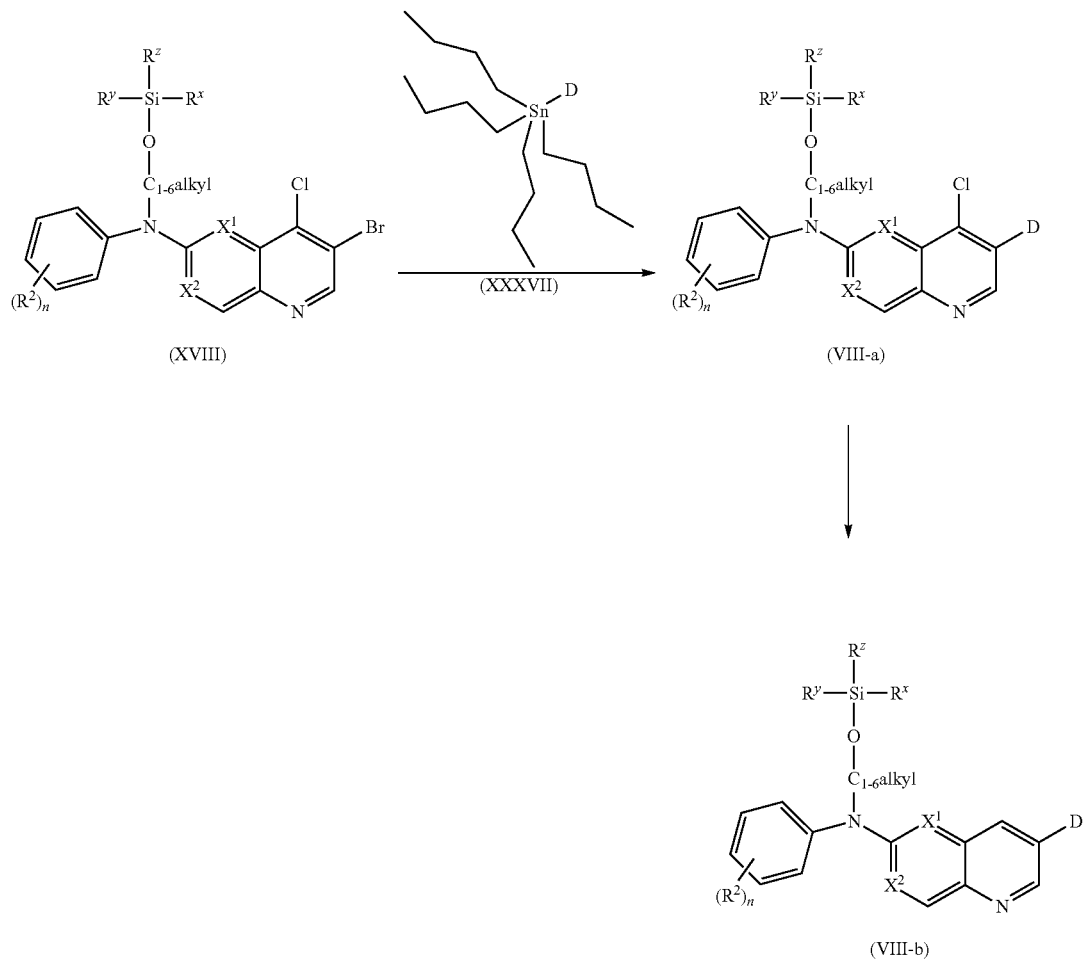

In Scheme 4A, an intermediate of formula (XVIII) is reacted with an intermediate of formula (XXXVII) in the presence of a suitable catalyst, such as for example tetrakis (triphenylphisphine)palladium (0), and a suitable solvent, such as for example toluene.

Intermediates of formula (VIII-a) can be transformed in an intermediate of formula (VIII-b) in the presence of catalyst, such as for example Raney nickel, and H$_2$, a suitable base, such as for example sodium hydroxide, and a suitable solvent, such as for example an alcohol, e.g. ethanol.

Intermediates of formula (XVII) can be prepared according to the following reaction Schemes 5 and 6.

Scheme 5

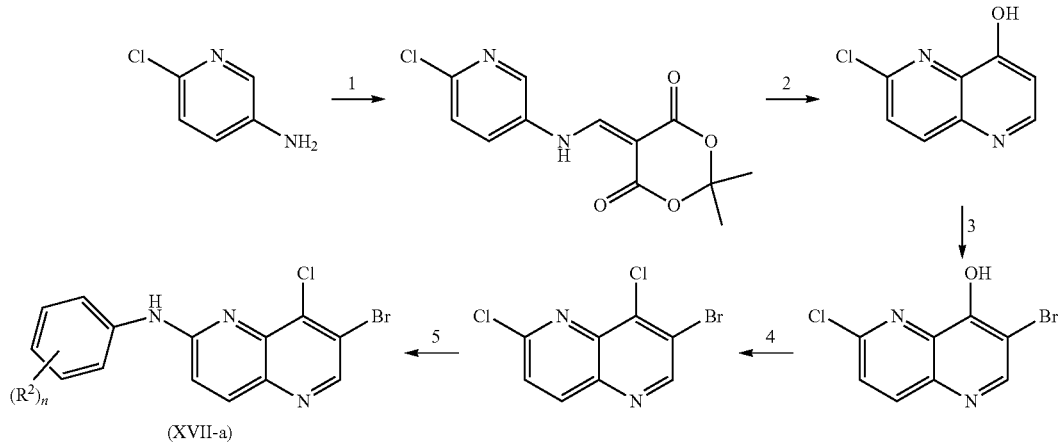

In Scheme 5: the following reaction conditions apply:
1: in the presence of a Meldrum's acid and triethyl orthoformate, and a suitable solvent, such as for example an alcohol, e.g. ethanol;
2: in the presence of diphenyl ether;
3: in the presence of N-bromo-succinimide, and acetic acid;
4: in the presence of phosphoryl chloride, and a suitable solvent, such as for example chloroform;
5: in the presence of a suitable aniline of formula (V) as defined hereinabove, in a suitable solvent, such as for example 1-propanol.

Scheme 6

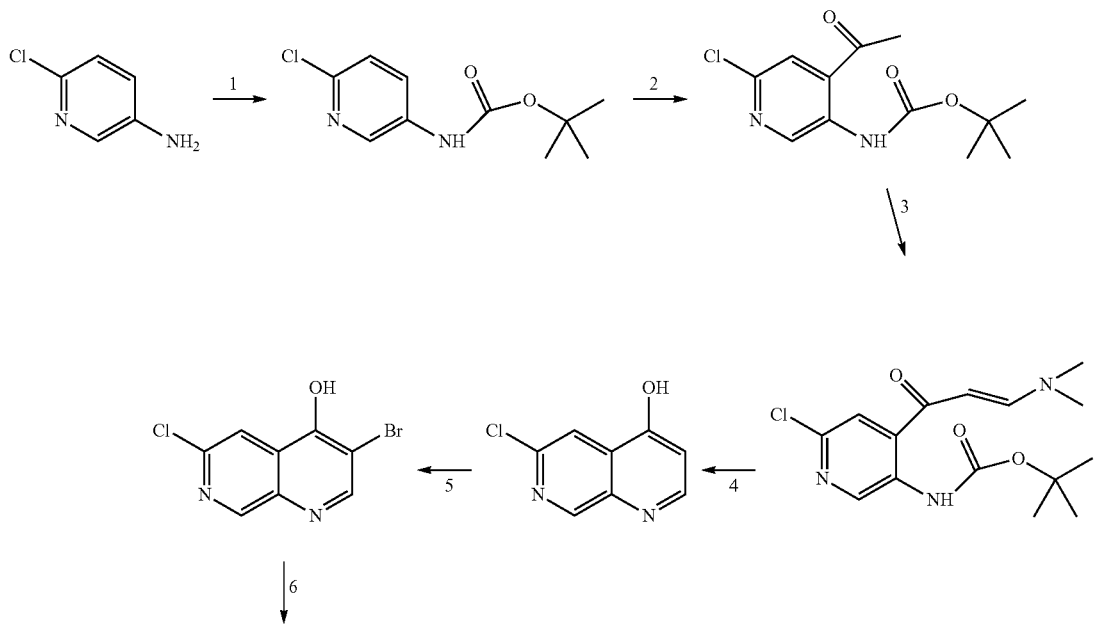

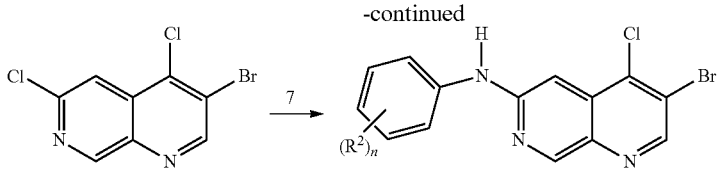

In Scheme 6, the following reaction conditions apply:

1: in the presence of di-tert-butyl dicarbonate, and a suitable solvent, e.g. dioxane;

2: in the presence of N-methoxy-N-methylacetamide, and tetramethylene diamine used as a base and in the presence of BuLi 3: in the presence of N,N-dimethylformamide and NNn-dimethylacetamide 4: in the presence of a suitable acid, such as for example trifluoroacetic acid, and a suitable solvent, such as for example toluene.

5: in the presence of N-bromosuccinimide, and a suitable acid, such as for example acetic acid 6: in the presence of $POCl_3$ and a suitable solvent, such as for example $CHCl_3$ 7; in the presence of a suitable aniline of formula (V) as defined hereinabove, and a suitable solvent, such as for example 1-propanol, resulting in an intermediate of formula (XVII-b)

Intermediates of formula (VIII) wherein D is a ring moiety containing a nitrogen atom, can be further reacted according to the following reaction Scheme 7, depicted for the 1,5-naphthyridine scaffold and for $R^{3a}$ being hydrogen (intermediates of formula (VIII'-b)). It is considered to be within the knowledge of the skilled man to adopt these reactions to the other intermediates of formula (VIII) described hereinabove.

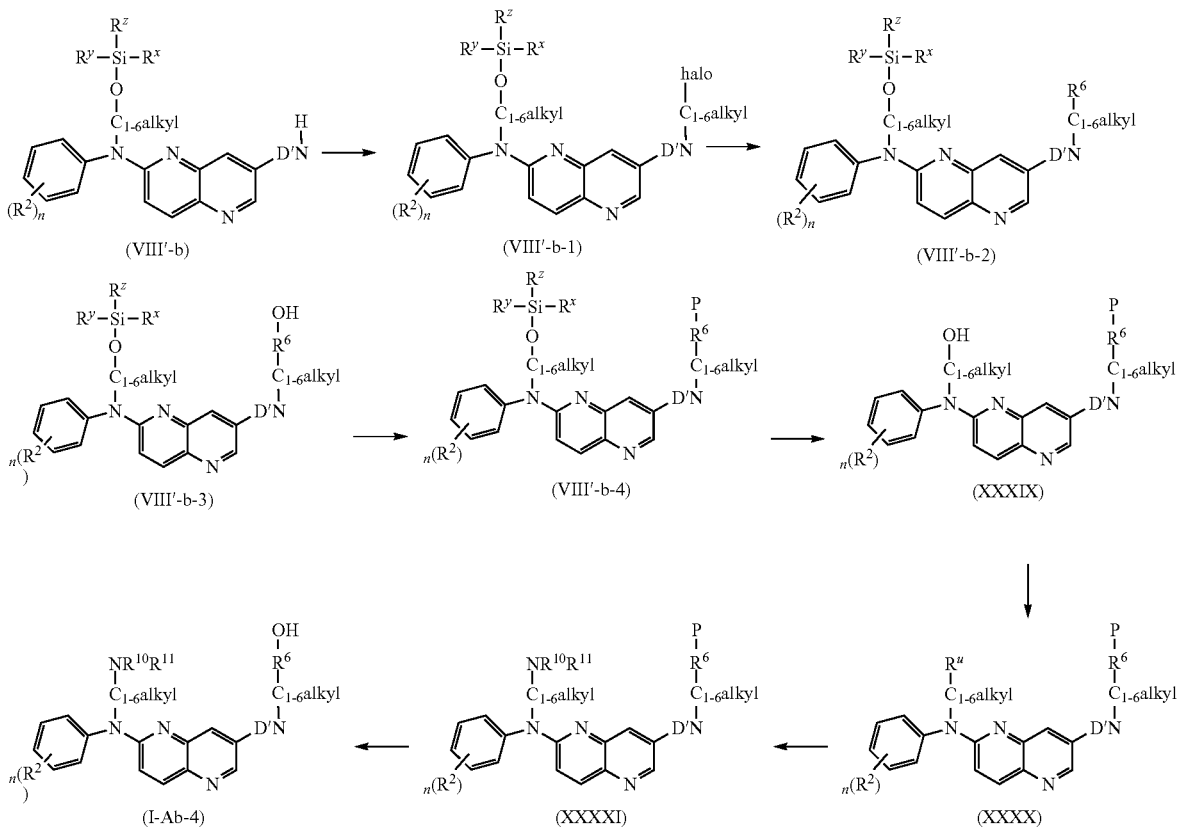

In Scheme 7, the D'N moiety represents a -D moiety wherein the D ring moiety contains a nitrogen atom. Intermediates of formula (VIII'-b) wherein D represents D'NH, can be converted into an intermediate of formula (VIII'-b-2) by reaction with $W_{12}$—$C_{1-6}$alkyl-halo wherein $W_{12}$ represents a suitable leaving group, such as for example halo, e.g. chloro, in the presence of a suitable base, such as for example NaH, and a suitable solvent, such as for example N,N-dimethylformamide. Said intermediates of formula (VIII'-b-1) can be converted into an intermediate of formula (VIII'-b-2) by reaction with $R^6$ in the presence of a suitable base, such as for example $K_2CO_3$, and a suitable solvent, such as for example acetonitrile. When in an intermediate of formula (VIII'-b-2) the $R^6$ carries a hydroxyl group as in an intermediate of formula (VIII'-b-3), then said hydroxyl group can be protected by a suitable protective group P, such as for example —O—C(=O)—$C_{1-6}$alkyl, by reaction with $C_{1-6}$alkyl-C(=O)—$W_{12}$, in the presence of a suitable base, such as for example triethylamine, 4-dimethylaminopyridine, and a suitable solvent, such as for example dichloromethane, resulting in an intermediate of formula (VIII'-b-4) which can be converted into an intermediate of formula (XXXIX) by reaction with tetrabutylammonium fluoride in the presence of a suitable solvent, such as for example tetrahydrofuran. Said intermediate of formula (XXXIX) can be converted into an intermediate of formula (XXXX) wherein $R^u$ represents —$SO_2CH_3$, by reaction with methane sulfonyl chloride in the presence of a suitable base, such as for example triethylamine, and a suitable solvent, such as for example dichloromethane. In particular, this type of reaction is used to prepare intermediates of formula (XXXX) wherein $C_{1-6}$alkyl represents $C_{3-6}$alkyl. For some variants of intermediates of formula (XXXX), e.g. wherein $C_{1-6}$alkyl represents $C_{1-2}$alkyl, it might be preferred to perform the reaction in non basic conditions. Intermediates of formula (XXXX) can be converted into an intermediate of formula (XXXXI) by reaction with an intermediate of formula (X) in a suitable solvent, such as for example acetonitrile. Said intermediate of formula (XXXXI) can then be deprotected into a compound of formula (I-Aa-b-4) in the presence of a suitable base, such as for example $K_2CO_3$, and a suitable solvent, such as for example an alcohol, e.g. methanol and the like. It is considered to be within the knowledge of the person skilled in the art to recognize for which other D ring moieties the described reactions also apply.

Intermediates of formula (VIII'-b) can also be reacted to prepare compounds of the present invention according to the reaction schemes as presented in Scheme 1. It is considered to be within the knowledge of the skilled person to recognize in which condition and for which definitions of $R^1$ on the D ring moiety a protective group may be appropriate for the reactions to be carried out. For instance, a hydroxyl group within the definition of $R^1$ may be protected with a tert. butyldimethylsilyl moiety; a NH group within the definition of $R^1$ may be protected with a —C(=O)—O—C(CH_3)_3 group.

It is also considered to be within the knowledge of the skilled person to recognize appropriate deprotection reactions.

Compounds of formula (I-A) wherein $R^3$ represents optionally substituted $C_{1-6}$alkyl, said compounds being represented by formula (I-Aa-c), can also be prepared according to the below reaction Scheme 8.

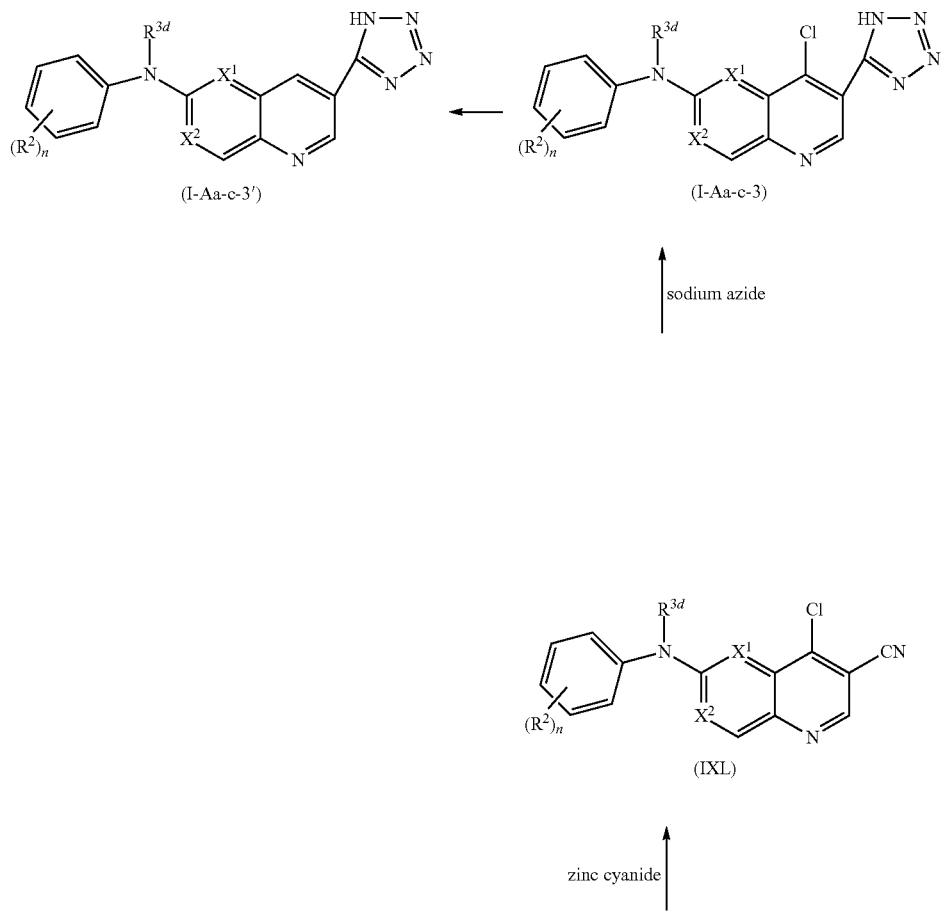

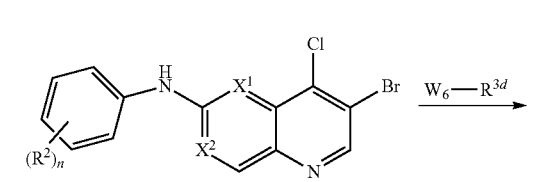
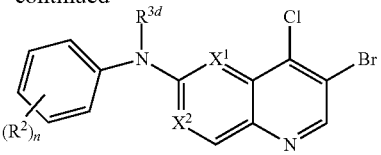
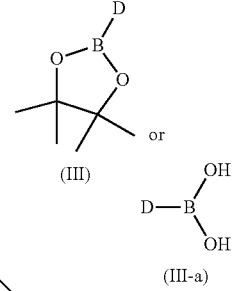
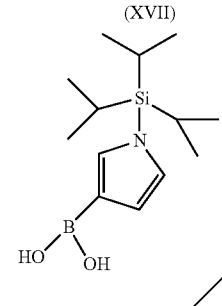
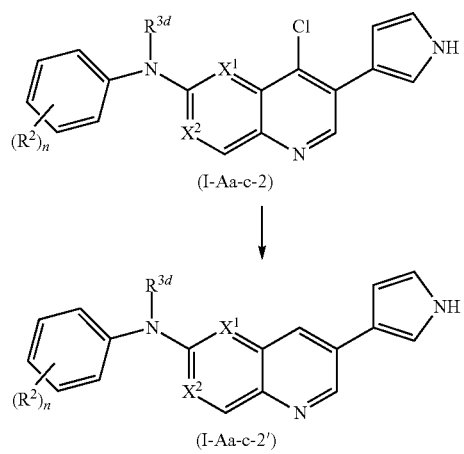
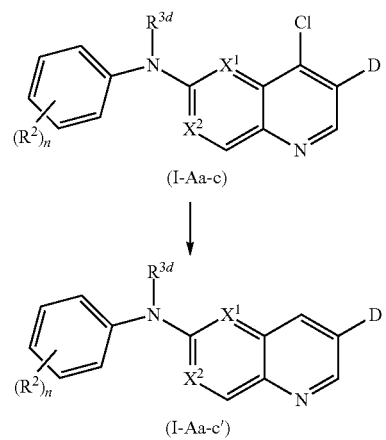

In Scheme 8, an intermediate of formula (XVII) is reacted with $W_6$—$R^{3d}$ wherein $W_6$ represents a suitable leaving group, such as for example halo, e.g. bromo and the like, and $R^{3d}$ represents optionally substituted $C_{1-6}$alkyl, such as for example —$CH_2$—$C_3H_5$, in the presence of a suitable base, such as for example sodium hydride, and a suitable solvent, such as for example N,N-dimethylformamide, resulting in an intermediate of formula (XIX). In a next step, the intermediate of formula (XIX) is reacted with an intermediate of formula (III) or (III-a) in the presence of a suitable catalyst, such as for example tetrakis(triphenyl)phosphine palladium or $Pd_2(dba)_3$ (tris(dibenzylideneacetone) dipalladium (0)), optionally a suitable ligand, such as 2-dicyclohexylphosphino-2',6'-dimethoxybiphenyl, a suitable base, such as for example $Na_2CO_3$ or $K_3PO_4$, and a suitable solvent, such as for example ethylene glycol dimethylether or dioxane or water. Or the intermediate of formula (XIX) is reacted with an intermediate of formula (XXXVII) in the presence of a suitable catalyst, such as for example tetrakis(triphenyl)phosphine palladium, and a suitable solvent, such as for example N,N-dimethylformamide or toluene. Or the intermediate of formula (XIX) is reacted with D-W, wherein W represents a suitable leaving group, such as for example halo, e.g. bromo, iodo and the like, in the presence of a suitable catalyst, such as for example tetrakis(triphenyl) phosphine palladium, zinc chloride and ethylmagnesium chloride to prepare organozincic reacting species, and a suitable solvent, such as for example tetrahydrofuran. An intermediate of formula (XIX) can also react with a suitable ring moiety represented by D, e.g. imidazole or 4-methylimidazole or 3-methylpyrazole or 2-methylimidazole, in the presence of a suitable catalyst, such as for example tris (dibenzylideneacetone) dipalladium (0), a suitable ligand, such as for example Rac-bis (diphenylphosphino)-1,1'-binaphthyl, in the presence of a suitable base, such as for example sodium tert-butoxide, and a suitable solvent, such as for example toluene to obtain the corresponding final compound. Or an intermediate of formula (XIX) can react with e.g. 4-(aminomethyl)piperidine, morpholine, 1,2,4-triazole, ethyl 4-methyl-5-imidazolecarboxylate, piperazine or a derivative thereof, e.g. 1-(2-hydroxyethyl)-piperazine or 1-methyl-piperazine, in the presence of a suitable base, such as for example triethylamine or sodium hydride or cesium carbonate, in the presence of a suitable catalyst, such as for example palladium (II) acetate, a suitable ligand, such as for example Rac-bis (diphenylphosphino)-1,1'-binaphthyl and a suitable solvent, such as for example, tetrahydrofuran, N,N-dimethylformamide, or an alcohol, e.g. 1-butanol, to obtain the corresponding final compound.

An intermediate of formula (XIX) can also react with 1-(triisopropylsilyl)pyrrole-3-boronic acid, in the presence of a suitable catalyst, such as for example tetrakis(triphenyl) phosphine palladium, a suitable base, such as for example sodium carbonate and tetrabutylammonium fluoride, and a suitable solvent, such as for example ethylene glycol dimethylether, to obtain a compound of formula (I-Aa-c-2). An intermediate of formula (XIX) can react with zinc cyanide in the presence of a suitable catalyst, such as for example tetrakis(triphenyl)phosphine palladium, a suitable ligand, such as for example triphenylphosphine, and a suitable solvent, such as for example acetonitrile. The resulting intermediate of formula (IXL) can react with sodium azide and ammonium chloride in the presence of a suitable solvent, such as for example N,N-dimethylformamide, to obtain a compound of formula (I-Aa-c-3).

Compounds of formula (I-Aa-c), (I-Aa-c-2) or compounds of formula (I-Aa-c-3) can be transformed in the corresponding compounds wherein $R^{3a}$ is hydrogen, in the presence of catalyst, such as for example Raney nickel, and $H_2$, a suitable base, such as for example sodium hydroxide, and a suitable solvent, such as for example an alcohol, e.g. ethanol Compounds of formula (I-Aa-c) can alternatively also be prepared according to the below reaction Scheme 9.

In Scheme 9, an intermediate of formula (IV) is reacted with $R^{3d}$—$NH_2$ in the presence of a suitable catalyst, such as for example palladium (II) acetate or $Pd_2dba_3$, a suitable base, such as for example sodium tert-butoxide, and a suitable ligand, such as for example 1,1'-[1,1'-binaphthalene]-2,2'-diylbis[1,1-diphenylphosphine] or xantphos, resulting in an intermediate of formula (XX). This type of reaction can also be performed with $R^{3d}$—$NH_2$ in the presence of a suitable solvent, such as for example an alcohol, e.g. n-propanol. An intermediate of formula (IV) can also react with $R^{3d}$—$NH_2$ in the presence of a suitable deprotonating agent such as for example potassium bis(trimethylsilyl)amide. In a suitable solvent such as for example tetrahydrofuran. Intermediates of formula (XX) are reacted in a next step with an intermediate of formula (XIV) in the presence of a suitable catalyst, such as for example palladium (II) acetate or $Pd_2(dba)_3$ (tris(dibenzylidene acetone) dipalladium (0)), a suitable ligand such as for example 2-dicyclohexylphosphino-tris-isopropyl-biphenyl or 1,1'-[1,1'-binaphthalene]-2,2'-diylbis[1,1-diphenylphosphine], a suitable base, such as for example sodium tert-butoxide, and a suitable solvent, such as for example ethylene glycol dimethylether.

Compounds of formula (I) wherein $R^3$ represents optionally substituted $C_{1-6}$alkyl, and wherein Y is E-D and E is other than a bond, said compounds being represented by formula (I-Ab) can be prepared according to the below reaction Scheme 10.

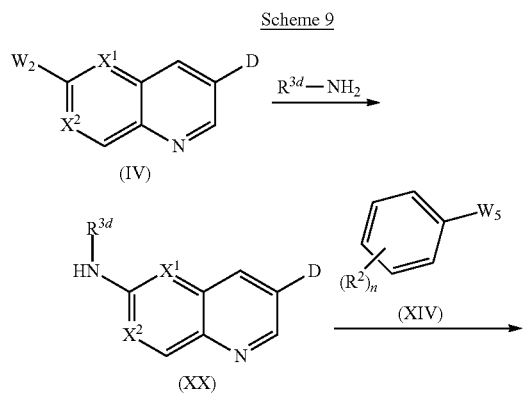

-continued

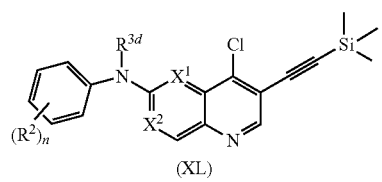
(XL)

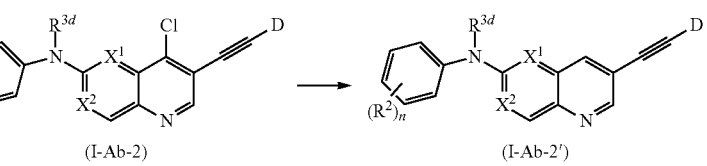
(I-Ab-2)    (I-Ab-2')

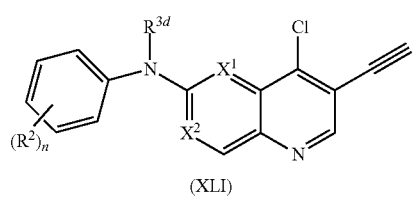
(XLI)

formaldehyde
sodium azide

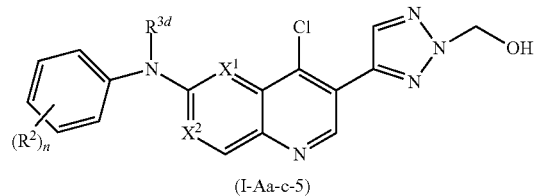
(I-Aa-c-5)

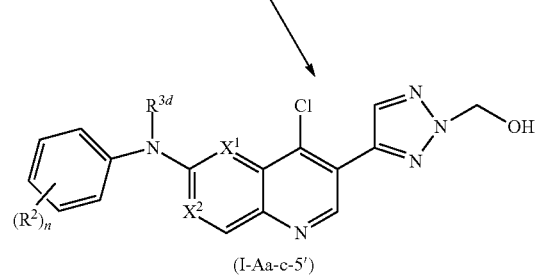
(I-Aa-c-5')

In Scheme 10, an intermediate of formula (XIX) prepared according to the methods described above, is reacted with D-NHR$^{22}$ in the presence of a suitable catalyst, such as for example Pd$_2$(dba)$_3$ (tris(dibenzylideneacetone) dipalladium (0)), a suitable ligand, such as for example 9,9-dimethyl-4,5-bis(diphenylphosphino)xanthenes, a suitable base, such as for example cesium carbonate, and a suitable solvent, such as for example dioxane, resulting in a compound of formula (I-Ab-1). Or an intermediate of formula (XIX) is reacted with

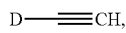
D≡CH, in the presence of a suitable catalyst, such as for example dichlorobis(triphenylphosphine) palladium (II) and copperiodide, a suitable ligand, such as for example triphenylphosphine, a suitable base, such as for example triethylamine, and a suitable solvent, such as for example N,N-dimethylformamide to obtain a compound of formula (I-Ab-2). A compound of formula (I-Ab-2) can also be prepared by reacting an intermediate of formula (XLI) with D-W as defined above, in the presence of a suitable catalyst, such as for example dichlorobis(triphenylphosphine) palladium (II) and copperiodide, a suitable base, such as for example triethylamine, and a suitable solvent, such as for example N,N-dimethylformamide and acetonitrile. The intermediate of formula (XLI) can be prepared by reacting an intermediate of (XIX) with (trimethylsilyl)acetylene in the presence of a suitable catalyst, such as for example dichlorobis (triphenylphosphine) palladium (II) and copperiodide, a suitable ligand, such as for example triphenylphosphine, a suitable base, such as for example triethylamine, and a suitable solvent, such as for example dimethylsulfoxide, followed by reacting the resulting intermediate of formula (XL) with potassium carbonate in a suitable solvent, such as for example an alcohol, e.g. methanol. The intermediate of formula (XLI) can also react with 2-(4-morpholino)-ethyl-azide, in the presence of a suitable catalyst, such as for example copper iodide, a suitable base, such as for example N,N-diisopropylethylamine, and a suitable solvent, such as for example tetrahydrofuran, to obtain a compound wherein E is a bond and D is 2-(4-morpholino)ethyl-1-triazolyl. An intermediate of formula (XLI) can also react with sodium azide and formaldehyde in the presence of a suitable catalyst, such as for example copper sulfate and sodium L ascorbate, and a suitable solvent, such as for example dioxane and acetic acid, to obtain a compound of formula (IAa-c-5). Compounds of formula (I-Ab-1), (I-Ab-2) and (I-Aa-5) can be transformed in corresponding compounds wherein R$^{3a}$ is hydrogen, in the presence of catalyst, such as for example Raney nickel, and H$_2$, a suitable base, such as for example sodium hydroxide, and a suitable solvent, such as for example an alcohol, e.g. ethanol Compounds of formula (I-Ab) can also be prepared according to the below reaction Scheme 10A.
In Scheme 10A, an intermediate of formula (XIX) is reacted with CO gaz, potassium acetate, in the presence of
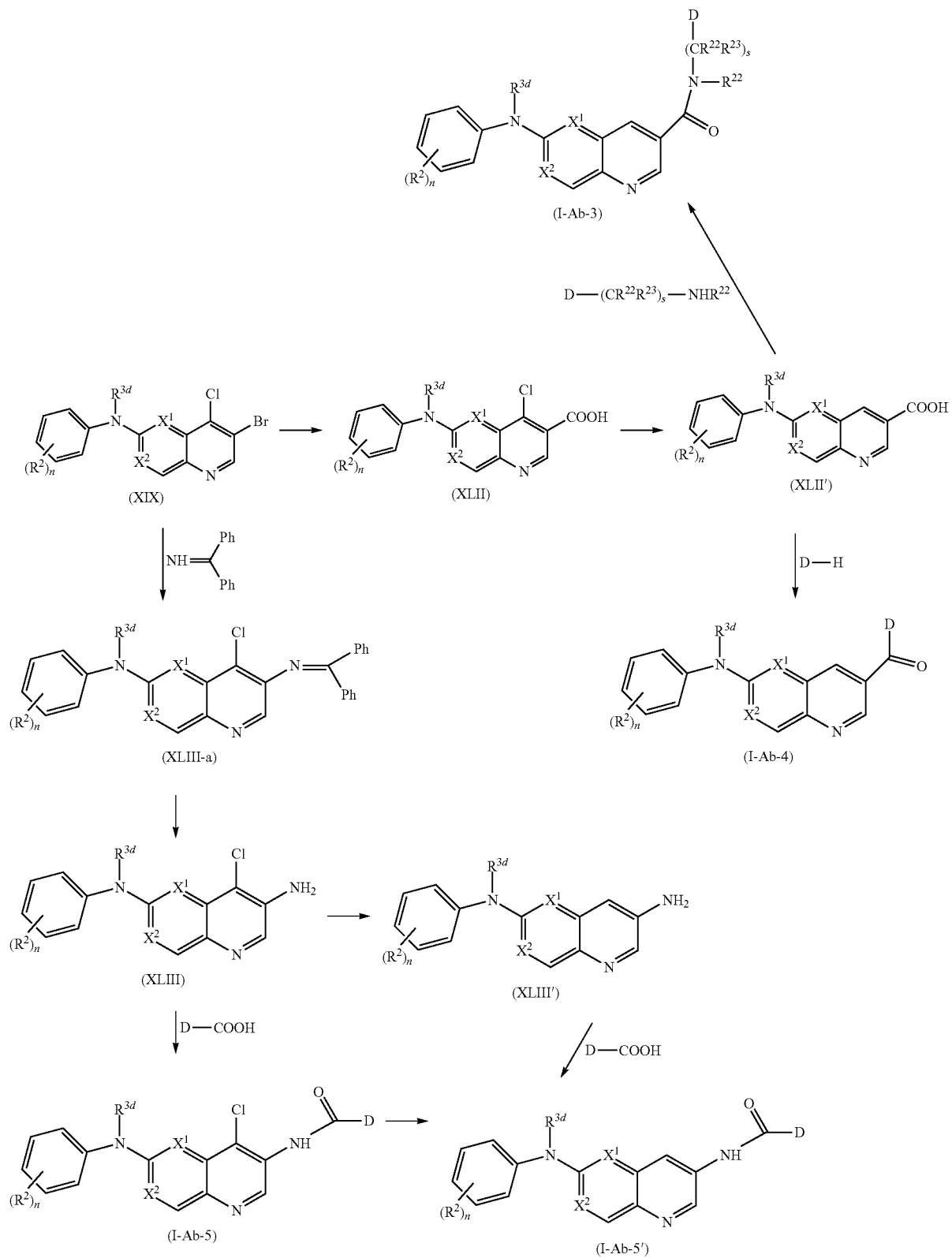

a suitable catalyst, such as for example tetrakis(triphenyl) phosphine palladium, and a suitable solvent, such as for example dioxane resulting in an intermediate of formula (XLII) which can be transformed in an intermediate of formula (XLII') in the presence of catalyst, such as for example Raney nickel, and $H_2$, a suitable base, such as for example sodium hydroxide, and a suitable solvent, such as for example an alcohol, e.g. ethanol. The intermediate of formula (XLII') is reacted with D-$(CR^{22}R^{23})_s$—$NHR^{22}$ in the presence of suitable peptide coupling reagents such as for example 1-(3-dimethylaminopropyl)-3-ethylcarbodiimide hydrochloride and 1-hydroxybenzotriazole, a suitable base, such as for example triethylamine, and a suitable solvent, such as for example methylene chloride, to obtain a compound of formula (I-Ab-3). The intermediate of formula (XLII') can also react with D-H in the presence of suitable peptide coupling reagents such as for example 1-(3-dimethylaminopropyl)-3-ethylcarbodiimide hydrochloride and 1-hydroxy-benzotriazole, a suitable base, such as for example triethylamine, and a suitable solvent, such as for example methylene chloride to obtain a compound of formula (I-Ab-4). An intermediate of formula (XIX) can also react with 1,1-diphenylmethylenimine in the presence of a suitable catalyst such as tris(dibenzylideneacetone)dipalladium, in the presence of a suitable ligand such as for example 9,9-dimethyl-4,5-bis(diphenyl-phosphino)xanthenes, in the presence of a suitable base, such as for example sodium tert-butylate and in the presence of a suitable solvent, such as for example ethylene glycol dimethylether to obtain an intermediate of formula (XLIII-a). Said intermediate can be converted into an amine of formula (XLIII) by hydrolysis in an acidic medium, which can react with D-COOH, in the presence of suitable peptide coupling reagents such as for example 1-(3-dimethylaminopropyl)-3-ethylcarbodiimide hydrochloride and 1-hydroxybenzotriazole, a suitable base, such as for example triethylamine, and a suitable solvent, such as for example methylene chloride to obtain a compound of formula (I-Ab-5). Said compound can be transformed in a compound of formula (I-Ab-5) in the presence of catalyst, such as for example Raney nickel, and $H_2$, and a suitable solvent, such as for example an alcohol, e.g. ethanol Alternatively, the amine of formula (XLIII) can first be concerted into an intermediate of formula (XLIII') according to the method described for (I-Ab-5') and then react with D-COOH to a compound of formula (I-Ab-5')

Compounds of formula (I) wherein $R^3$ is $C_{1-6}$alkyl substituted with 5-amino-1,3,4-oxadiazolyl can be prepared according to the below reaction Scheme 11.

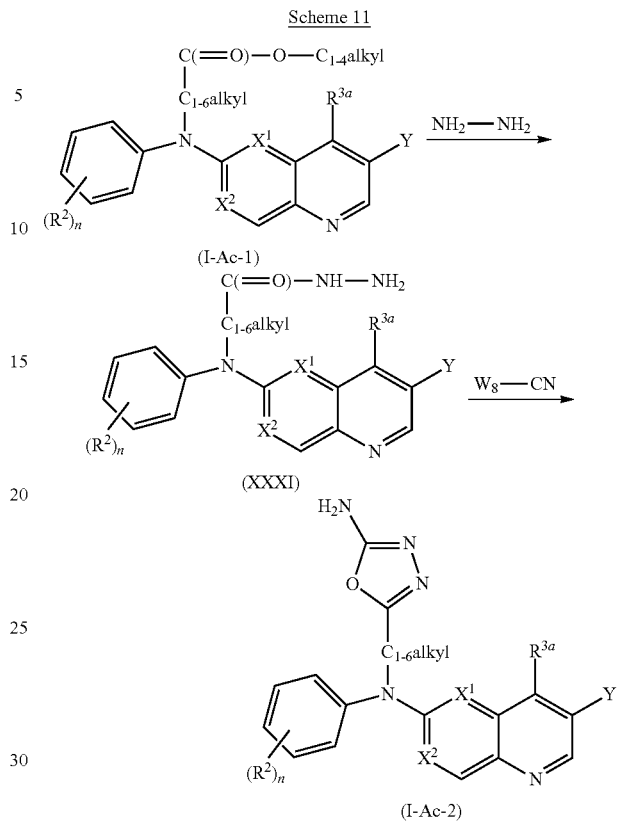

In Scheme 11, a compound of formula (I-Ac-1) is reacted with $NH_2$—$NH_2$ in the presence of a suitable solvent, such as for example an alcohol, e.g. ethanol resulting in an intermediate of formula (XXXI) which is then reacted in a next step with $W_8$—CN, wherein $W_8$ represents a suitable leaving group, such as for example halo, e.g. bromo, in the presence of a suitable base, such as for example $NaHCO_3$, and a suitable solvent, such as for example water or dioxane.

Compounds of formula (I) wherein $R^3$ is $C_{1-6}$alkyl substituted with 3,3-dimethyl-morpholine can be prepared according to the below reaction Scheme 11A

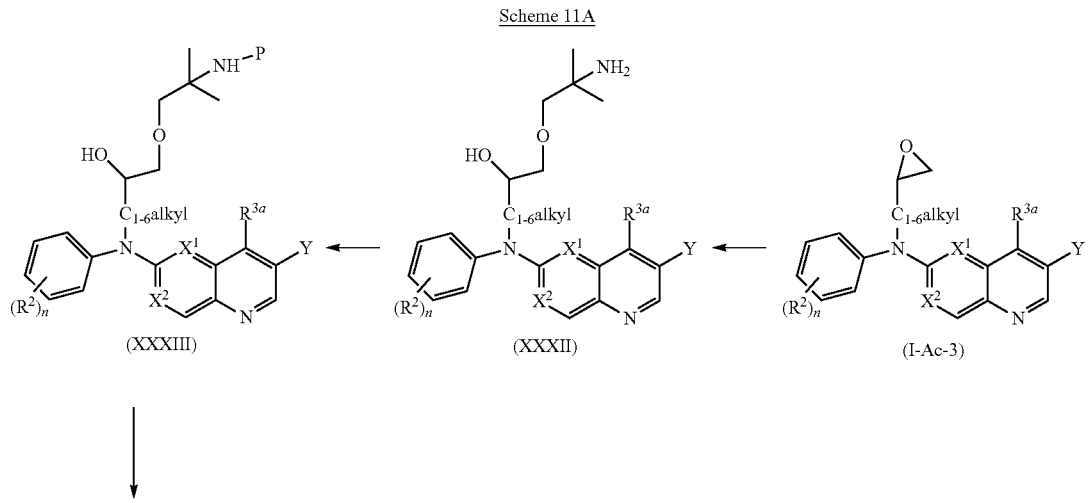

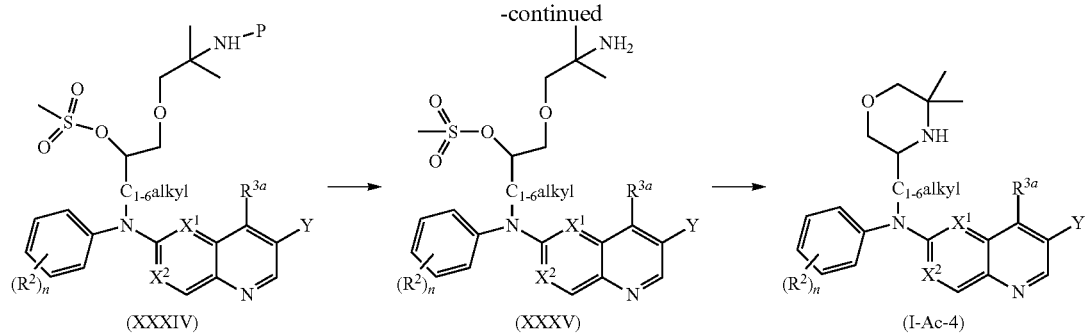

In Scheme 11A, a compound of formula (I-Ac-3) is reacted with 2-amino-2-methyl-1-propanol in the presence of a suitable base, such as for example NaH and in the presence of a suitable solvent, such as for example N,N-dimethylformamide resulting in an intermediate of formula (XXXII) of which the $NH_2$ moiety is protected by a suitable protecting group P, such as for example —C(=O)—O—C$(CH_3)_3$, by reaction with for instance di-tert-butyl dicarbonate in the presence of a suitable solvent, such as for example dioxane, and a suitable base, such as for example $NaHCO_3$, resulting in an intermediate of formula (XXXIII). In a next step, said intermediate is reacted with methanesulfonyl chloride in the presence of a suitable solvent, such as for example dichloromethane, and a suitable base, such as for example triethylamine resulting in an intermediate of formula (XXXIV). In particular, this type of reaction is used to prepare intermediates of formula (XXXIV) wherein $C_{1-6}$alkyl represents $C_{3-6}$alkyl. For some variants of intermediates of formula (XXXIV), e.g. wherein $C_{1-6}$alkyl represents $C_{1-2}$alkyl it might be preferred to perform the reaction in non basic conditions. Intermediates of formula (XXXIV) are converted into an intermediate of formula (XXXV) by reaction with a suitable acid, such as for example trifluoroacetic acid, in the presence of a suitable solvent, such as for example dichloromethane. The intermediate of formula (XXXV) is converted into a compound of formula (I-Ac-4) by reaction with a suitable base, such as for example N,N-diisopropylethylamine and triethylamine in the presence of a suitable solvent, such as for example an alcohol, e.g. methanol.

In general, compounds of formula (I) wherein Y represents —$CCH_3$=N—$OR^{19}$, said compounds being represented by formula (I-Ad), can be prepared as in Scheme 12.

Scheme 12

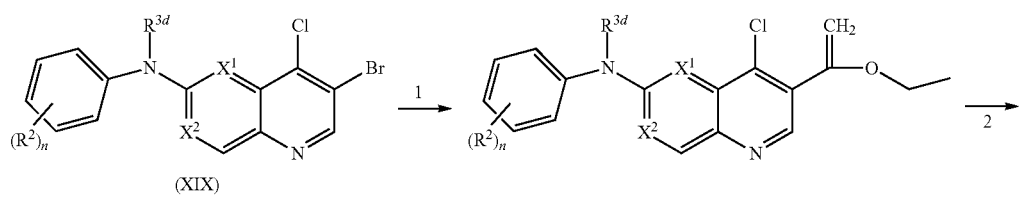

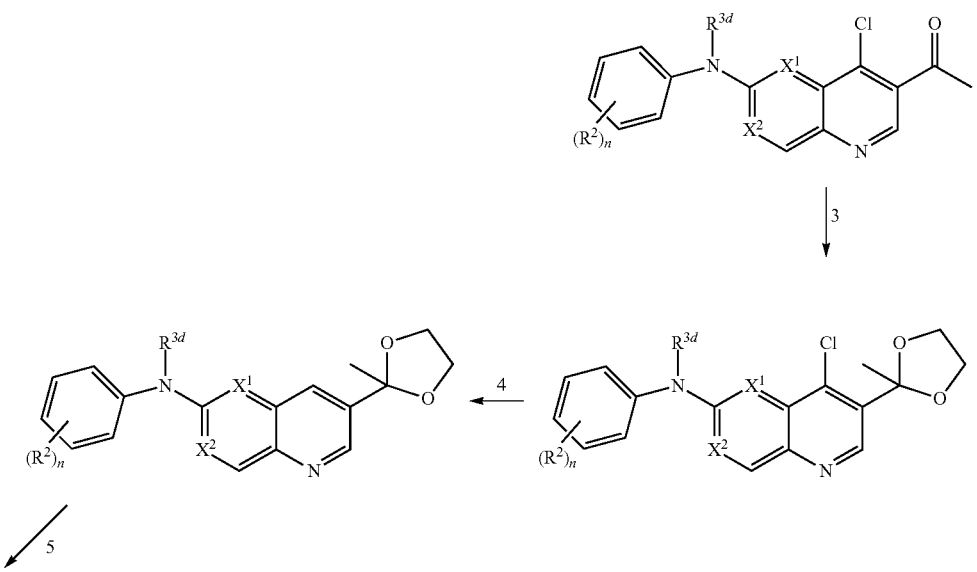

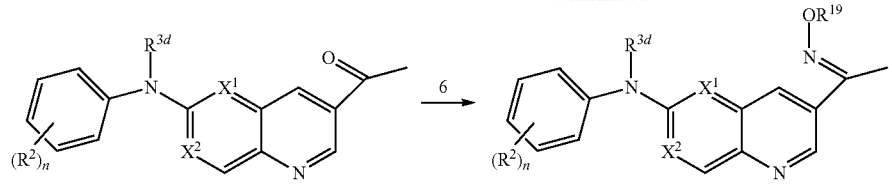

In Scheme 12, the following reaction conditions apply:
1; reaction with tributyl(1-ethoxyvinyl)tin, in the presence of a suitable catalyst, such as for example dichlorobis (triphenylphosphine) palladium (II) and copper iodide, a suitable ligand, such as for example triphenylphosphine, and a suitable solvent, such as for example N,N-dimethylformamide
2: in the presence of a suitable acid, such as for example hydrochloric acid, and a suitable solvent, such as for example acetone. The contained intermediate can also be converted into a compound of formula (I-Aa) wherein E is a direct bond and D is 3-methyl-oxazole or oxazole, by reaction with 1-methyl-1-tosylmethyl isocyanide or tosylmethyl isocyanide, in the presence of a suitable base, such as for example dipotassium carbonate, and a suitable solvent, such as for example an alcohol, e.g. methanol.

3: reaction with ethylene glycol in the presence of an acid to obtain an ketal such as CPD.
4: in the presence of catalyst, such as for example Raney nickel, and $H_2$, in a suitable solvent, such as for example an alcohol, e.g. ethanol.
5: ketal protection can be removed by reaction with an acid such as for example acetic acid in a solvent such as dichloromethane or tetrahydrofuran.
6: reaction with $R^{19}$—O—$NH_2$ in the presence of a suitable base such as for example pyridine, and a suitable solvent, such as for example an alcohol, e.g. ethanol.

As already shown above, the present compounds or some of the above-described intermediates can be prepared by deprotecting the corresponding protected compounds. Other protection-deprotection reactions are shown in the following reaction Scheme 13.

Scheme 13

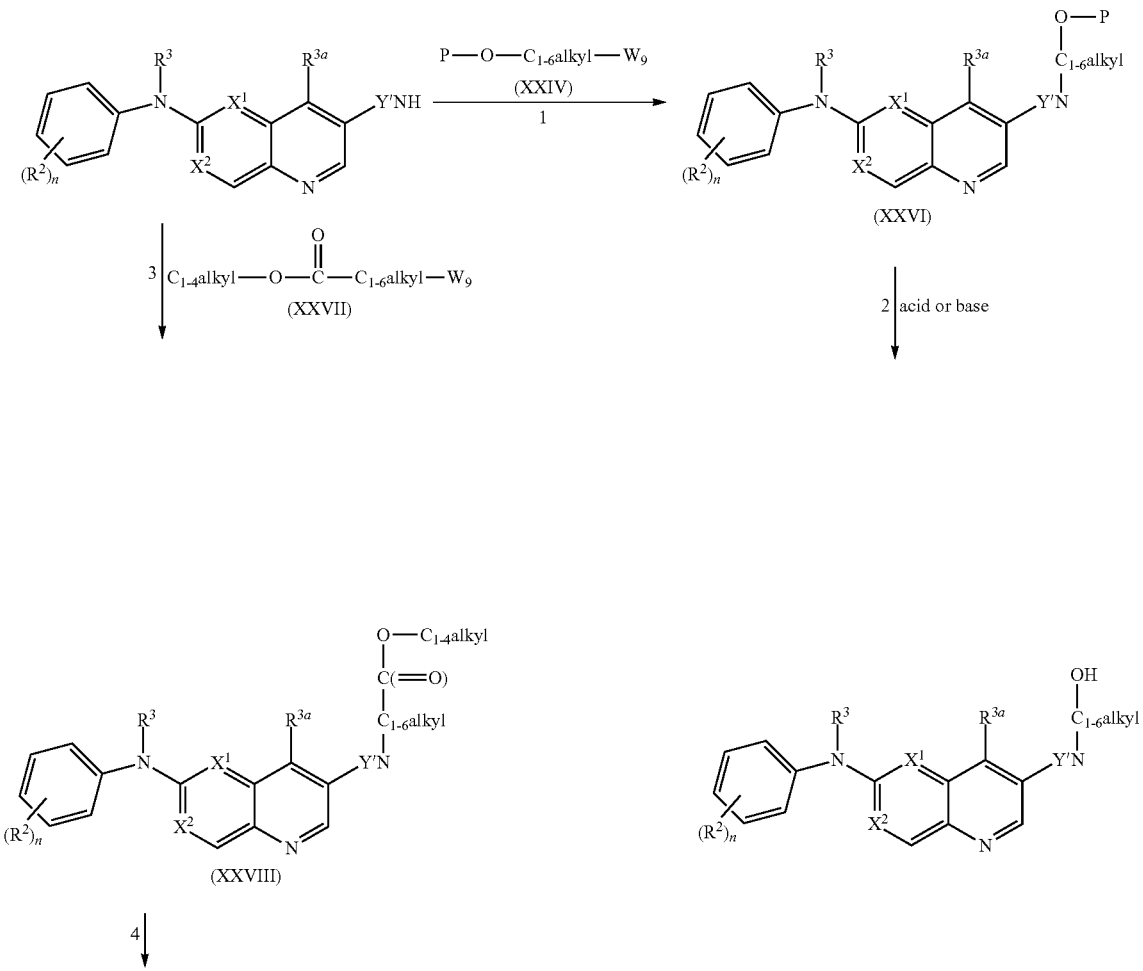

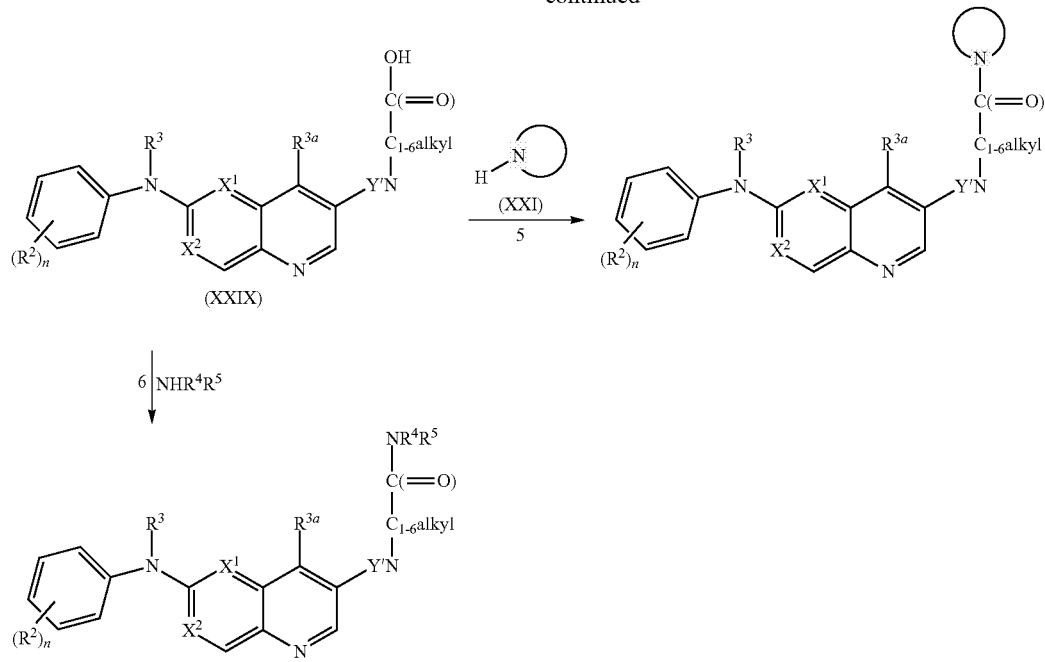

In Scheme 13, the Y'N moiety represents an -E-D moiety wherein the D ring moiety contains a nitrogen atom. Compounds of formula (I-A) wherein $R^1$ represents hydroxy-$C_{1-6}$alkyl can be prepared by deprotecting an intermediate of formula (XXVI) in the presence of a suitable acid, such as for example HCl or trifluoroacetic acid, or a suitable desilylating agent, such as for example tetrabutyl ammonium fluoride, and a suitable solvent, such as an alcohol, e.g. methanol, or tetrahydrofuran (step 2). Intermediates of formula (XXVI) can be prepared by reacting a compound of formula (I-A) wherein $R^1$ is hydrogen with an intermediate of formula (XXIV) wherein $W_9$ represents a suitable leaving group, such as for example halo, e.g. bromo and the like, and P represents a suitable protective group, such as for example —Si(CH$_3$)$_2$(C(CH$_3$)$_3$) or

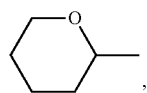, in the presence of a suitable base, such as for example sodium hydride or K$_2$CO$_3$, and a suitable solvent, such as for example N,N-dimethylformamide or acetonitrile (step 1).

Compounds of formula (I-A) wherein $R^1$ represents $C_{1-6}$alkyl substituted with —C(=O)—$R^6$ wherein $R^6$ is an appropriate nitrogen containing ring linked to the C(=O) moiety via the nitrogen atom can be prepared by reacting an intermediate of formula (XXIX) with an intermediate of formula (XXI) in the presence of suitable peptide coupling reagents such as, 1-hydroxy-benzotriazole and 1-(3-dimethylaminopropyl)-3-ethyl carbodiimide HCl (step 5). Intermediates of formula (XXIX) can be prepared by reacting an intermediate of formula (XXVIII) with LiOH in the presence of a suitable solvent, such as for example tetrahydrofuran or water (step 4). Intermediates of formula (XXVIII) can be prepared by as depicted in step 3 with an intermediate of formula (XXVII) wherein $W_9$ is as defined above, in the presence of a suitable base, such as for example sodium hydride, and a suitable solvent, such as for example N,N-dimethylformamide.

Step 6 depicts the preparation of compounds of formula (I-A) starting from an intermediate of formula (XXIX) by reaction with NHR$^4$R$^5$ in the presence of suitable peptide coupling reagents such as 1-hydroxy-benzotriazole and 1-(3-dimethylaminopropyl)-3-ethyl carbodiimide HCl and a suitable base, such as triethylamine, and a suitable solvent, such as for example dichloromethane.

Further protection-deprotection reactions can also be used as outlined in the following reaction Scheme 14.

Scheme 14

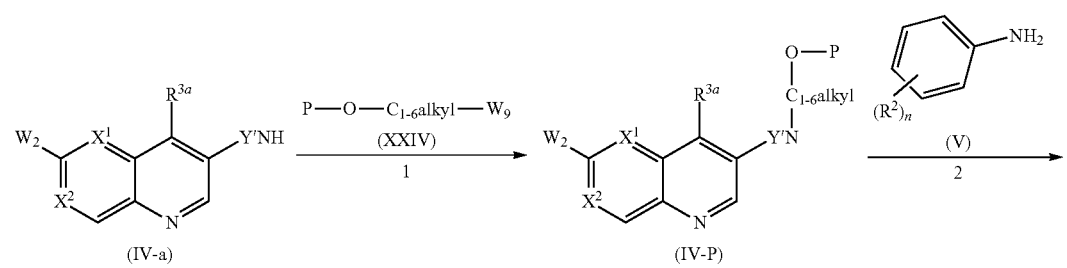

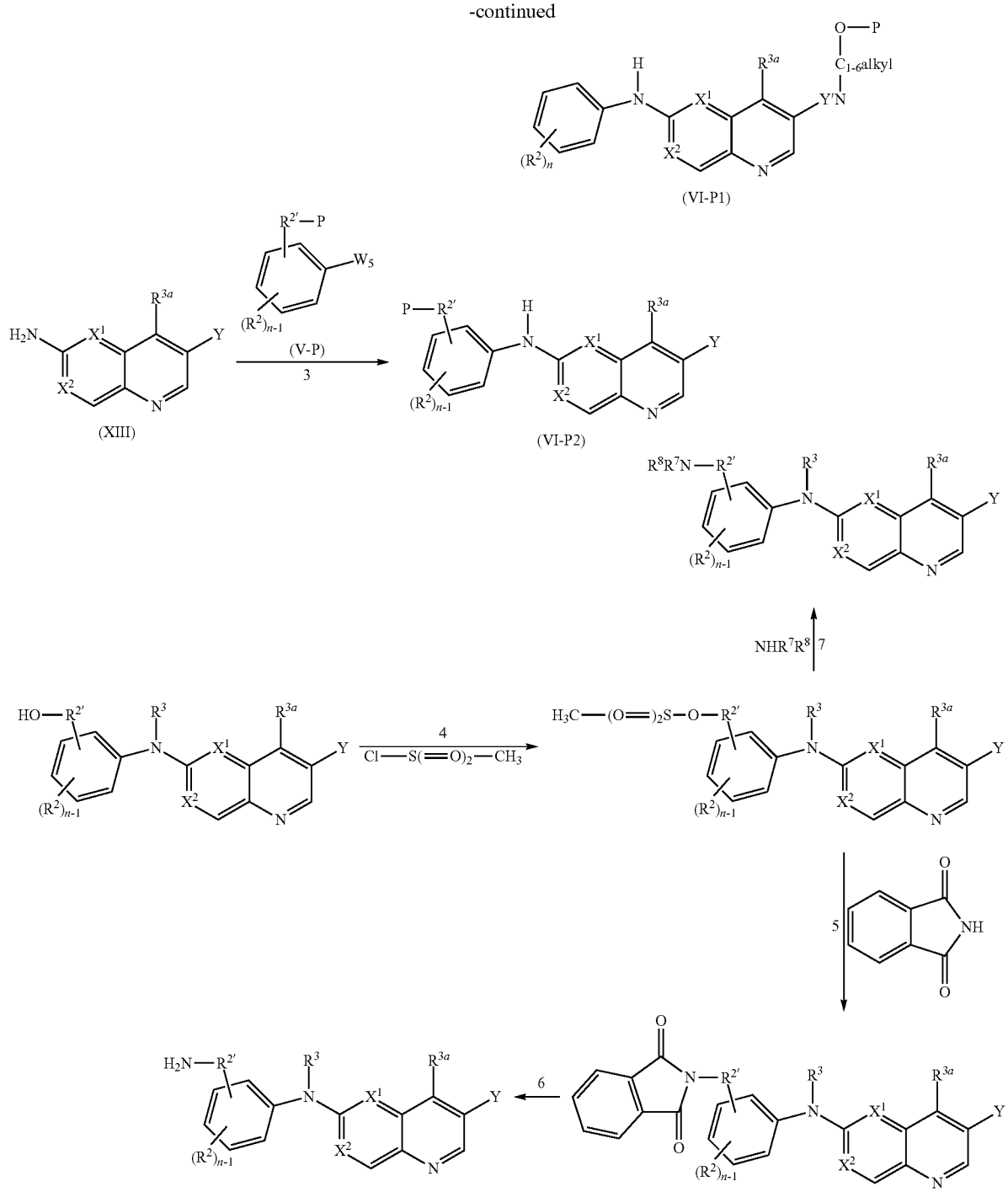

In Scheme 14, the following reaction conditions apply:
1; in the presence of a suitable base, such as for example sodium hydride, and a suitable solvent, such as for example N,N-dimethylformamide.
2: in the presence of a suitable catalyst, such as for example palladium (II)acetate, a suitable base, such as for example sodium tert-butoxide, a suitable ligand, such as for example 1,1'-[1,1'-binaphthalene]-2,2'-diylbis[1,1-diphenylphosphine], and a suitable solvent, such as for example dioxane or ethylene glycol dimethylether. Alternatively, this type of reaction can also be performed in the presence of a suitable deprotonating agent, such as for example potassium bis(trimethylsilyl)amide, in a suitable solvent, such as for example tetrahydrofuran. Or, alternatively this type of reaction can also be performed in the presence of a suitable solvent, such as for example an alcohol, e.g. n-propanol.
3: in the presence of a suitable catalyst, such as for example palladium (II)acetate, a suitable base, such as for example sodium tert-butoxide, a suitable ligand, such as for example 1,1'-[1,1'-binaphthalene]-2,2'-diylbis[1,1-diphenylphosphine], and a suitable solvent, such as for example dioxane or ethylene glycol dimethylether.

4: in the presence of a suitable base, such as for example triethylamine, and a suitable solvent, such as for example dichloromethane.

5: in the presence of a suitable base, such as for example K$_2$CO$_3$, and a suitable solvent, such as for example 1-methyl-2-pyrrolidinone.

6: in the presence of hydrazine monohydrate, and a suitable solvent, such as for example an alcohol, e.g. ethanol.

7: in the presence of a suitable base, such as for example K$_2$CO$_3$, and a suitable solvent, such as for example tetrahydrofuran.

It is to be considered to be within the knowledge of the person skilled in the art to recognize which of the reactions described above for compounds of (I-A) are also applicable for compounds of formula (I-B).

It is considered to be within the knowledge of the person skilled in the art to recognize in which condition and on which part of the molecule a protective group may be appropriate. For instance, protective group on the R$^1$ substituent or on the D moiety, or protective group on the R$^3$ substituent or on the R$^2$ substituent or combinations thereof. The skilled person is also considered to be able to recognize the most feasible protective group, such as for example —C(═O)—O—C$_{1-4}$alkyl or

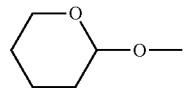

or —O—Si(CH$_3$)$_2$(C(CH$_3$)$_3$) or —CH$_2$—O—CH$_2$CH$_2$—O—CH$_3$ or —CH$_2$—O—CH$_2$—CH$_2$—Si(CH$_3$)$_3$. The skilled person is also considered to be able to recognize the most feasible deprotection reaction conditions, such as for example suitable acids, e.g. trifluoroacetic acid, hydrochloric acid, or suitable salts, such as for example tetrabutylammonium fluoride. Reference herefore is also made to the examples described in the Experimental Part hereinafter.

The skilled person is also considered to be able to recognize that when R$^1$ represents C(═O)-morpholinyl, said R$^1$ can be prepared from —C(═O)—NH—CH$_2$—CH$_2$—O—CH$_2$—CH$_2$—O—SO$_2$-4-methylphenyl, in the presence of sodium hydride, and a suitable solvent, such as for example N,N-dimethylformamide. Or that when R$^1$ represents —NH—C(═O)-morpholinyl, said R$^1$ can be prepared from —NH—C(═O)—O—C(CH$_3$)$_3$ in the presence of morpholine, and a suitable solvent, such as for example 1-methyl-2-pyrrolidinone. Or that when R$^1$ represents hydroxylC$_{1-6}$alkyl, e.g. —CH$_2$—CH$_2$—OH, said R$^1$ can be prepared from the corresponding alkoxycarbonyl intermediate, e.g. —CH$_2$—C(═O)—O—CH$_2$—CH$_3$, in the presence of Dibal-H 1M in hexane, and a suitable solvent, such as for example tetrahydrofuran.

The present invention also comprises deuterated compounds. These deuterated compounds may be prepared by using the appropriate deuterated intermediates during the synthesis process. For instance an intermediate of formula (IV-a)

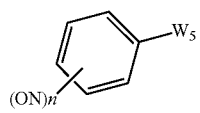

can be converted into an intermediate of formula (IV-b)

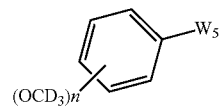

by reaction with iodomethane-D3 in the presence of a suitable base, such as for example cesium carbonate, and a suitable solvent, such as for example acetonitrile.

The compounds of formula (I) may also be converted into each other via art-known reactions or functional group transformations.

For instance, compounds of formula (I) wherein R$^1$ represents tetrahydropyranyl can be converted into a compound of formula (I) wherein R$^1$ represents hydrogen, by reaction with a suitable acid, such as for example HCl or trifluoroacetic acid, in the presence of a suitable solvent, such as for example dichloromethane, dioxane, or an alcohol, e.g. methanol, isopropanol and the like.

Compounds of formula (I) wherein R$^1$ or R$^3$ represent monohaloalkyl, can be converted into a compound of formula (I) wherein R$^1$ or R$^3$ represent C$_{1-6}$alkyl substituted with a ring moiety as defined hereinabove by the intermediate of formula (XXI) and linked to the C$_{1-6}$alkyl moiety by the nitrogen atom, by reaction with an intermediate of formula (XXI) optionally in the presence of a suitable base, such as for example triethylamine or K$_2$CO$_3$ or sodium hydride, and optionally in the presence of a suitable solvent, such as for example acetonitrile, N,N-dimethylformamide or 1-methyl-2-pyrrolidinone. For the R$^3$ moiety, this type of reaction is in particular used to prepare compounds wherein C$_{1-6}$alkyl represents C$_{3-6}$alkyl. For some variants of the compounds, e.g. wherein C$_{1-6}$alkyl represents C$_{1-2}$alkyl, it might be preferred to perform the reaction in non basic conditions.

Compounds of formula (I) wherein R$^1$ or R$^3$ represents C$_{1-6}$alkyl-OH, can be converted into a compound of formula (I) wherein R$^1$ or R$^3$ represent C$_{1-6}$alkyl-F by reaction with diethylaminosulfur trifluoride in the presence of a suitable solvent, such as for example dichloromethane and in the presence of catalytic amounts of an alcohol, such as for example ethanol. Likewise, a compound of formula (I) wherein R$^1$ or R$^3$ represent C$_{1-6}$alkyl substituted with R$^6$ or R$^9$ wherein said R$^6$ or R$^9$ is substituted with OH, can be converted into a compound of formula (I) wherein R$^1$ or R$^3$ represent C$_{1-6}$alkyl substituted with R$^6$ or R$^9$ wherein said R$^6$ or R$^9$ is substituted with F, by reaction with diethylaminosulfur trifluoride in the presence of a suitable solvent, such as for example dichloromethane.

Compounds of formula (I) wherein R$^1$ or R$^3$ represent C$_{1-6}$alkyl substituted with R$^6$ or R$^9$ wherein said R$^6$ or R$^9$ is substituted with —C(═O)—O—C$_{1-6}$alkyl, can be converted into a compound of formula (I) wherein R$^1$ or R$^3$ represent C$_{1-6}$alkyl substituted with R$^6$ or R$^9$ wherein said R$^6$ or R$^9$ is substituted with —CH$_2$—OH, by reaction with LiAlH$_4$ in the presence of a suitable solvent, such as for example tetrahydrofuran.

Compounds of formula (I) wherein R$^3$ represents C$_{1-6}$alkyl substituted with 1,3-dioxo-2H-isoindol-2-yl, can be converted into a compound of formula (I) wherein R$^3$ represents C$_{1-6}$alkyl substituted with amino, by reaction with hydrazine monohydrate in the presence of a suitable solvent, such as for example an alcohol, e.g. ethanol. Compounds of formula (I) wherein R$^1$ or R$^3$ represent C$_{1-6}$alkyl substituted with amino, can be converted into a compound of formula (I) wherein $R^1$ or $R^3$ represents $C_{1-6}$alkyl substituted with —NH—S(=O)$_2$—$C_{1-6}$alkyl, by reaction with Cl—S(=O)$_2$—$C_{1-6}$alkyl in the presence of a suitable base, such as for example triethylamine, and a suitable solvent, such as for example dichloromethane.

Compounds of formula (I) wherein $R^1$ or $R^3$ represents $C_{1-6}$alkyl substituted with halo, can be converted into a compound of formula (I) wherein $R^1$ or $R^3$ represent $C_{1-6}$alkyl substituted with $NR^4R^5$ or $NR^{10}R^{11}$, by reaction with $NHR^4R^5$ or $NHR^{10}R^{11}$, either using such amino in large excess or in the presence of a suitable base, such as for example $K_2CO_3$, and a suitable solvent, such as for example acetonitrile, N,N-dimethylacetamide or 1-methyl-pyrrolidinone. For the $R^3$ moiety, this type of reaction is in particular used to prepare compounds wherein $C_{1-6}$alkyl represents $C_{3-6}$alkyl. For some variants of the compounds, e.g. wherein $C_{1-6}$alkyl represents $C_{1-2}$alkyl, it might be preferred to perform the reaction in non basic conditions.

Compounds of formula (I) wherein $R^1$ represents hydrogen, can be converted into a compound of formula (I) wherein $R^1$ represents polyhalo$C_{1-6}$alkyl or polyhydroxy-$C_{1-6}$alkyl or $C_{1-6}$alkyl or —S(=O)$_2$—$NR^{14}R^{15}$ or —S(=O)$_2$—$C_{1-6}$alkyl, by reaction with polyhalo-$C_{1-6}$alkyl-W or polyhydroxy$C_{1-6}$alkyl-W or $C_{1-6}$alkyl-W or W—S(=O)$_2$—$NR^{14}R^{15}$ or W—S(=O)$_2$—$C_{1-6}$alkyl, wherein W represents a suitable leaving group, such as for example halo, e.g. bromo, iodo and the like, in the presence of a suitable base, such as for example sodium hydride or $K_2CO_3$ or triethylamine or 4-dimethylamino-pyridine or diisopropylamine, and a suitable solvent, such as for example N,N-dimethylformamide or acetonitrile or dichloromethane.

Compounds of formula (I) wherein $R^1$ represents hydrogen can also be converted into a compound of formula (I) wherein $R^1$ represents $C_{1-6}$alkyl-OH, by reaction with W—$C_{1-6}$alkyl-O—Si(CH$_3$)$_2$(C(CH$_3$)$_3$) in the presence of a suitable base, such as for example sodium hydride, and a suitable solvent, such as for example N,N-dimethylformamide and, then followed by a reaction with a suitable desilylating agent such as tetrabutyl ammonium fluoride.

Compounds of formula (I) wherein $R^1$ represents hydrogen, can also be converted into compound of formula (I) wherein $R^1$ represents ethyl substituted with —S(=O)$_2$—$C_{1-6}$alkyl, by reaction with $C_{1-6}$alkyl-vinylsulfone, in the presence of a suitable base, such as for example triethylamine, and a suitable solvent, such as for example an alcohol, e.g. methanol or by reaction with $C_{1-6}$alkyl-2-bromoethylsulfone in the presence of a suitable deprotonating agent, such as for example NaH, and a suitable solvent, such as for example dimethyformamide.

Compounds of formula (I) wherein $R^1$ represents hydrogen can also be converted into a compound of formula (I) wherein $R^1$ represents —CH$_2$—CHOH—CH$_2$

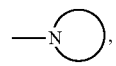, by reaction with

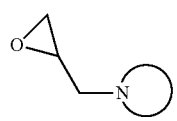

in the presence of a suitable base, such as for example sodium hydride, and a suitable solvent, such as for example N,N-dimethylformamide, wherein

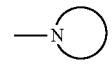

represents a suitable nitrogen containing ring within the definition of $R^6$. Compounds of formula (I) wherein $R^1$ represents $C_{1-6}$alkyl substituted with $R^6$ wherein said $R^6$ is substituted with —C(=O)—O—$C_{1-6}$alkyl or —S(=O)$_2$—$NR^{14}R^{15}$ or wherein $R^3$ represents $C_{1-6}$alkyl substituted with $R^9$ wherein said $R^9$ is substituted with —C(=O)—O—$C_{1-6}$alkyl or —S(=O)$_2$—$NR^{14}R^{15}$, can be converted into a compound of formula (I) wherein the $R^6$ or $R^9$ is unsubstituted, by reaction with a suitable acid, such as for example HCl and a suitable solvent, such as for example dioxane, acetonitrile or an alcohol, e.g. isopropylalcohol. Compounds of formula (I) wherein $R^1$ represents $C_{1-6}$alkyl substituted with $R^6$ wherein said $R^6$ is a ring moiety comprising a nitrogen atom which is substituted with —CH$_2$—OH or wherein $R^3$ represents $C_{1-6}$alkyl substituted with $R^9$ wherein said $R^9$ is a ring moiety comprising a nitrogen atom which is substituted with —CH$_2$—OH, can be converted into a compound of formula (I) wherein the $R^6$ or $R^9$ is unsubstituted, by reaction with sodium hydroxide, in the presence of a suitable solvent, such as for example tetrahydrofuran.

Compounds of formula (I) wherein $R^1$ represents $C_{1-6}$alkyl substituted with $R^6$ or $R^3$ represents $C_{1-6}$alkyl substituted with $R^9$, wherein said $R^6$ or said $R^9$ is unsubstituted, can be converted into a compound of formula (I) wherein said $R^6$ or said $R^9$ is substituted with $C_{1-6}$alkyl, by reaction with W—$C_{1-6}$alkyl wherein W is as defined above, in the presence of a suitable base. Such as for example sodium hydride, and a suitable solvent, such as for example N,N-dimethylformamide.

Compounds of formula (I) wherein $R^1$ or $R^3$ represent hydroxy$C_{1-6}$alkyl, can be converted into the corresponding carbonyl compound, by reaction with dess-Martin-periodinane, in the presence of a suitable solvent, such as for example dichloromethane.

Compounds of formula (I) wherein $R^1$ represents $C_{1-6}$alkyl substituted with $R^6$ or $R^3$ represents $C_{1-6}$alkyl substituted with $R^9$, wherein said $R^6$ or said $R^9$ is substituted with $C_{1-6}$alkyl-halo, can be converted into a compound of formula (I) wherein said $R^6$ or said $R^9$ is substituted with $C_{1-6}$alkyl-CN, by reaction with sodium cyanide, in the presence of a suitable solvent, such as for example water or an alcohol, e.g. ethanol.

Compounds of formula (I) wherein $R^1$ represents $C_{1-6}$alkyl substituted with $R^6$ wherein said $R^6$ is unsubstituted or wherein $R^3$ represents $C_{1-6}$alkyl substituted with $R^9$ wherein said $R^9$ is unsubstituted, can be converted into a compound of formula (I) wherein $R^6$ or $R^9$ is substituted with —CH$_3$ or —CH(CH$_3$)$_2$, by reaction with formaldehyde or acetone and NaBH$_3$CN, in the presence of a suitable solvent, such as for example tetrahydrofuran or an alcohol, e.g. methanol.

Compounds of formula (I) wherein $R^1$ contains a $R^6$ substituent substituted with OH or wherein $R^3$ contains a $R^9$ substituent substituted with OH, can be converted into a compound of formula (I) wherein the $R^6$ or $R^9$ substituent is substituted with $C_{1-6}$alkyloxy, by reaction with W—$C_{1-6}$alkyl, in the presence of a suitable base, such as for example sodium hydride, and a suitable solvent, such as for example N,N-dimethylformamide. Compounds of formula (I) wherein $R^1$ contains a $R^6$ substituent substituted with $C_{1-6}$alkyloxy or wherein $R^3$ contains a $R^9$ substituent substituted with $C_{1-6}$alkyloxy, can be converted into a compound of formula (I) wherein the $R^6$ or $R^9$ substituent is substituted with —OH by reaction with a suitable acid, such as for example hydrochloric acid. Compounds of formula (I) wherein $R^1$ contains a $R^6$ substituent substituted with halo or wherein $R^3$ contains a $R^9$ substituent substituted with halo can be converted into a compound of formula (I) wherein the $R^6$ or $R^9$ substituent is substituted with —$NR^{14}R^{15}$ by reaction with $NHR^{14}R^{15}$ in a suitable solvent, such as for example 1-methyl-pyrrolidinone. Compounds of formula (I) wherein $R^3$ represents $C_{1-6}$alkyl substituted with —C(=O)—O—$C_{1-6}$alkyl, can be converted into a compound of formula (I) wherein $R^3$ represents $C_{1-6}$alkyl substituted with COOH, by reaction with LiOH in the presence of a suitable solvent, such as for example tetrahydrofuran. Said compounds of formula (I) wherein $R^3$ represents $C_{1-6}$alkyl substituted with COOH, can be converted into a compound of formula (I) wherein $R^3$ represents $C_{1-6}$alkyl substituted with —C(=O)—$NH_2$ or —C(=O)—$NHCH_3$ or —C(=O)$NR^{10}R^{11}$, by reaction with $NH(Si(CH_3)_3)_2$ or $MeNH_3^+Cl^-$ or $NHR^{10}R^{11}$ in the presence of suitable peptide coupling reagents such as for example 1-(3-dimethylaminopropyl)-3-ethylcarbodiimide HCl and 1-hydroxybenzotriazole, a suitable base, such as for example triethylamine and a suitable solvent such as for example dichloromethane or N,N-dimethylformamide. Compounds of formula (I) wherein $R^3$ represents $C_{1-6}$alkyl substituted with —C(=O)—O—$C_{1-6}$alkyl, can also be converted into a compound of formula (I) wherein $R^3$ represents $C_{1-6}$alkyl substituted with 4,5-dihydro-imidazol-2-yl, by reaction under $N_2$ with ethylenediamine and trimethylaluminium in the presence of a suitable solvent, such as for example toluene and heptane. This compound of formula (I) wherein $R^3$ represents $C_{1-6}$alkyl substituted with 4,5-dihydro-imidazol-2-yl, can be converted into a compound of formula (I) wherein $R^3$ represents $C_{1-6}$alkyl substituted with —C(=O)—NH—$(CH_2)_2$—$NH_2$ by reaction with sodium hydroxide. Compounds of formula (I) wherein $R^3$ represents $C_{1-6}$alkyl substituted with COOH, can also be converted into a compound of formula (I) wherein $R^3$ represents $C_{1-6}$alkyl substituted with —C(=O)—$N(CH_3)(OCH_3)$ by reaction with dimethylhydroxylamine, in the presence of carbonyldiimidazole and a suitable solvent, such as for example dichloromethane.

Compounds of formula (I) wherein $R^3$ represents $C_{1-6}$alkyl substituted with

can be converted into a compound of formula (I) wherein $R^3$ represents $C_{1-6}$alkyl substituted with 2 OH's, by reaction with a suitable acid, such as for example trifluoroacetic acid, and a suitable solvent, such as for example dioxane or water. These compounds of formula (I) wherein $R^3$ represents $C_{1-6}$alkyl substituted with

can also be converted into a compound of formula (I) wherein $R^3$ represents $C_{1-6}$alkyl substituted with OH and $NR^{10}R^{11}$, by reaction with $NH_2R^{10}R^{11}$ optionally in salt form, such as for example $NHR^{10}R^{11+}Cl^-$, optionally in the presence of a suitable base, such as for example sodium hydride or $Na_2CO_3$ or triethylamine, a suitable additive such as for example KI, and in the presence of a suitable solvent, such as for example N,N-dimethylformamide or an alcohol, e.g. 1-butanol or ethanol.

Compounds of formula (I) wherein $R^3$ represents $C_{1-3}$alkyl substituted with —C(=O)—O—$C_{1-6}$alkyl, can be converted into a compound of formula (I) wherein $R^3$ represents $C_{1-3}$ alkyl substituted with —$C(CH3)_2$—OH, by reaction with iodomethane and Mg powder, in the presence of a suitable solvent, such as for example diethylether or tetrahydrofuran. Compounds of formula (I) wherein $R^3$ represents $C_{1-5}$alkyl substituted with —C(=O)—O—$C_{1-6}$alkyl, can be converted into a compound of formula (I) wherein $R^3$ represents $C_{1-6}$alkyl substituted with —OH, by reaction with $LiAlH_4$ in a suitable solvent, such as for example tetrahydrofuran.

Compounds of formula (I) wherein $R^3$ represents $C_{1-5}$alkyl substituted with —OH, can be converted into a compound of formula (I) wherein $R^3$ represents $C_{1-5}$alkyl substituted with —O—C(=O)—$C_{1-6}$alkyl by reaction with Cl—C(=O)—$C_{1-6}$alkyl in the presence of a suitable base, such as for example NaH, and a suitable solvent, such as for example tetrahydrofuran.

Compounds of formula (I) wherein $R^3$ represents —$CH_2$—CH=$CH_2$, can be converted into a compound of formula (I) wherein $R^3$ represents —$CH_2$—CHOH—$CH_2$—OH, by reaction with potassium permanganate, and a suitable solvent, such as for example acetone or water. Compounds of formula (I) wherein $R^3$ represents $C_{1-6}$alkyl substituted with —C(=O)—$C_{1-4}$alkyl, can be converted into a compound of formula (I) wherein $R^3$ represents $C_{1-6}$alkyl substituted with —C($C_{1-4}$alkyl)=N—OH, by reaction with hydroxylamine, in the presence of a suitable base, such as for example pyridine, and a suitable solvent, such as for example an alcohol, e.g. ethanol.

Compounds of formula (I) wherein $R^3$ represents $C_{1-6}$alkyl substituted with $NH_2$, can be converted into a compound of formula (I) wherein $R^3$ represents $C_{1-6}$alkyl substituted with —NH—C(=O)—$R^6$ or with —NH—C(=O)—$C_{1-6}$alkyl or with —NH—C(=O)-polyhydroxy-$C_{1-6}$alkyl or with —NH—C(=O)-polyhalo$C_{1-6}$alkyl or with —NH—C(=O)-polyhydroxypolyhalo$C_{1-6}$alkyl, by reaction with the corresponding COOH analogue, e.g. $R^6$—COOH or $CF_3$—$C(CH_3)(OH)$—COOH and the like, in the presence of suitable peptide coupling reagents such as 1-hydroxy-benzotriazole and 1-(3-dimethylamino)propyl) carbodiimide optionally in the presence of a suitable base, such as for example triethylamine. Said compounds of formula (I) wherein $R^3$ represents $C_{1-6}$alkyl substituted with $NH_2$, can also be converted into a compound of formula (I) wherein $R^3$ represents $C_{1-6}$alkyl substituted with NH—C(=O)—$CF_3$, by reaction with trifluoroacetic anhydride, in the presence of a suitable base, such as for example triethylamine, and a suitable solvent, such as for example tetrahydrofuran. Said compounds of formula (I) wherein $R^3$ represents $C_{1-6}$alkyl substituted with $NH_2$, can also be converted into a compound of formula (I) wherein $R^3$ represents $C_{1-6}$alkyl substituted with —NH-polyhalo-$C_{1-6}$alkyl, e.g. —NH—$CH_2$—$CH_2$—F, by reaction with polyhalo$C_{1-6}$alkyl-W, with W as defined above, e.g. iodo-2-fluoroethane, in the presence of a suitable base, such as for example $K_2CO_3$, and a suitable solvent, such as for example N,N-dimethylformamide or dioxane. Said compounds of formula (I) wherein $R^3$ represents $C_{1-6}$alkyl substituted with $NH_2$ can also be converted into a compound of formula (I) wherein $R^3$ represents $C_{1-6}$alkyl substituted with —NH—$R^6$ or —N($R^6$)$_2$ wherein $R^6$ represents for example oxetane, by reaction with the appropriate $R^6$ in the presence of a suitable reducing agent, such as for example sodium triacetoxyborohydride, a suitable acid, such as for example acetic acid, and a suitable solvent, such as for example 1,2-dichloroethane.

Compounds of formula (I) wherein $R^3$ represents $C_{1-6}$alkyl substituted with cyano, can be converted into a compound of formula (I) wherein $R^3$ represents $C_{1-6}$alkyl substituted with tetrazolyl by reaction with sodium azide, and $NH_4^+Cl^-$ in the presence of a suitable solvent, such as for example N,N-dimethylformamide.

Compounds of formula (I) wherein $R^3$ represents —CH2-C≡CH, can be converted into a compound of formula (I) wherein $R^3$ represents

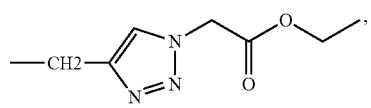

by reaction with ethyl azidoacetate in the presence of CuI and a suitable base, such as for example diisopropylamine, and a suitable solvent, such as for example tetraydrofuran. Compounds of formula (I) wherein $R^3$ represents —CH2-C≡CH, can be converted into a compound of formula (I) wherein $R^3$ represents

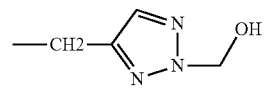

by reaction with sodium azide and formaldehyde, in the presence of a suitable catalyst, such as for example $CuSO_4$ and sodium L ascorbate, a suitable acid, such as for example acetic acid, and a suitable solvent, such as for example dioxane.

Compounds of formula (I) wherein $R^3$ represent $C_{2-6}$alkynyl, can be converted into a compound of formula (I) wherein $R^3$ represents $C_{2-6}$alkynyl substituted with $R^9$, by reaction with W—$R^9$ wherein W is as defined above, in the presence of a suitable catalyst, such as for example dichlorobis(triphenylphosphine)palladium, a suitable co-catalyst such as CuI, a suitable base, such as for example triethylamine, and a suitable solvent, such as for example dimethylsulfoxide.

Compounds of formula (I) wherein $R^3$ comprises $R^9$ substituted with halo, can be converted into a compound of formula (I) wherein $R^3$ comprises $R^9$ substituted with —$NR^{14}R^{15}$ by reaction with $NHR^{14}R^{15}$ in the presence of a suitable solvent, such as for example 1-methyl-2-pyrrolidinone.

Compounds of formula (I) wherein $R^3$ comprises $C_{2-6}$alkynyl, can be hydrogenated into a compound of formula (I) wherein $R^3$ comprises $C_{2-6}$alkyl in the presence of a suitable catalyst, such as for example palladium on charcoal, and a suitable solvent, such as for example ethylacetate.

Compounds of formula (I) wherein $R^3$ comprises $C_{2-6}$alkynyl, can be hydrogenated into a compound of formula (I) wherein $R^3$ comprises $C_{2-6}$alkenyl in the presence of a suitable catalyst, such as for example Lindlar catalyst, and a suitable solvent, such as for example ethylacetate.

Compounds of formula (I) wherein $R^3$ represents $C_{1-6}$alkyl substituted with —P(=O)(O$C_{1-6}$alkyl)$_2$ can be converted into a compound of formula (I) wherein $R^3$ represents $C_{1-6}$alkyl substituted with —P(=O)(OH)$_2$ by reaction with bromotrimethylsilane in the presence of a suitable solvent, such as for example dichloromethane.

Compounds of formula (I) wherein the $R^9$ substituent is substituted with =O, can be converted into the corresponding reduced $R^9$ substituent by reaction with a suitable reducing agent, such as for example $LiAlH_4$ in a suitable solvent, such as for example tetrahydrofuran.

Compounds of formula (I) wherein $R^3$ represents $C_{1-6}$alkyl substituted with —C(=O)—$R^9$ can be converted into a compound of formula (I) wherein $R^3$ represents $C_{1-6}$alkyl substituted with hydroxyl and $R^9$ by reaction with a suitable reducing agent, such as for example sodium borohydride, in the presence of a suitable solvent, such as for example an alcohol, e.g. methanol.

Compounds of formula (I) wherein $R^3$ comprises —$NHR^{10}$ can be converted into a compound of formula (I) wherein $R^3$ comprises —$NR^{10}$—(C=O)-optionally substituted $C_{1-6}$alkyl, by reaction with the corresponding W—(C=O)-optionally substituted $C_{1-6}$alkyl wherein W represents a suitable leaving group, such as for example halo, e.g. chloro and the like, in the presence of a suitable base, such as for example triethylamine, and a suitable solvent, such as for example acetonitrile.

Compounds of formula (I) wherein $R^3$ represents $C_{1-6}$alkyl substituted with $NR^{10}$(benzyl) can be converted into a compound of formula (I) wherein $R^3$ represents $C_{1-6}$alkyl substituted with $NHR^{10}$, by reaction with 1-chloroethylchloroformate in the presence of a suitable solvent, such as for example dichloromethane.

Compounds of formula (I) wherein $R^1$ represents unsubstituted piperidine, can be converted into a compound of formula (I) wherein $R^1$ represents 1-methyl-piperidine, by reaction with iodomethane in the presence of a suitable base, such as for example potassium carbonate, and a suitable solvent, such as for example acetonitrile. Compounds of formula (I) wherein $R^1$ represents hydrogen can be converted into a compound of formula (I) wherein $R^1$ represents optionally substituted $C_{1-6}$alkyl, by reaction with optionally substituted $C_{1-6}$alkyl-W wherein W represents a suitable leaving group, such as for example halo, e.g. bromo and the like, in the presence of a suitable base, such as for example potassium carbonate, and a suitable solvent, such as for example acetonitrile.

Compounds of formula (I) wherein $R^2$ represents halo, e.g. bromo, can be converted into a compound of formula (I) wherein $R^2$ represents cyano, by reaction with zinc cyanide, in the presence of a suitable catalyst, such as for example $Pd_2(dba)_3$ and a suitable ligand, such as for example 1,1-bis(diphenylphosphino)ferrocene, in the presence of a suitable solvent, such as for example N,N-dimethylformamide. Said $R^2$ substituent being cyano can be converted into —$CH_2$—$NH_2$ by hydrogenation in the presence of $NH_3$ and Nickel.

Compounds of formula (I) wherein $R^2$ represents —$OCH_3$ can be converted into a compounds of formula (I) wherein $R^2$ represents —OH by reaction with boron tribromide in the presence of a suitable solvent, such as for example dichloromethane. Compounds of formula (I) wherein $R^2$ represents —OH can be converted into a compounds of formula (I) wherein $R^2$ represents —$OCH_3$ by reaction with methyl iodine in the presence of a suitable base, such as for example potassium carbonate, and a suitable solvent, such as for example N,N-dimethylformamide.

Compounds of formula (I) wherein $R^2$ represents hydrogen, can be converted into a compound of formula (I) wherein $R^2$ represents —CHOH—$CF_3$ by reaction with trifluoroacetaldehyde methyl hemiketal.

For the conversion reactions, reference is also made to the examples described in the Experimental Part hereinafter.

A further aspect of the invention is a process for the preparation of a compound of formula (I) as defined herein, which process comprises:
(i) deprotecting a compound of formula (XXX) wherein P represents a suitable protective group, such as for example a butyloxycarbonyl-group (—$CO_2C(CH_3)_3$) in the presence of a suitable acid, such as for example HCl or trifluoroacetic acid;

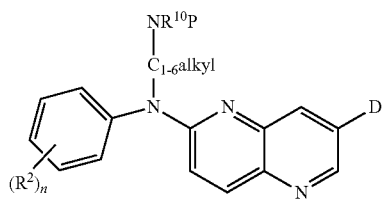

(XXX)

or
(ii) the reaction of a compound of the formula (IX) or (IX'):

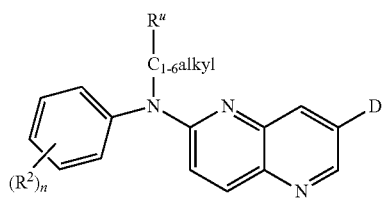

(IX): $R^u$ is —O—(S=O)$_2$—$CH_3$
(IX'): $R^u$ is Cl (IX): $R^u$ is —O—(S=O)$_2$—$CH_3$
(IX'): $R^u$ is Cl
or a protected form thereof, with an appropriately substituted amine or a reactive derivative thereof, such as for example $NHR^{10}R^{11}$ (X), $NHR^{10}P$ (X-a) or H—N (XXI), for example in a sealed vessel, in the presence of a suitable base, such as for example sodium hydride and/or in the presence or absence of a solvent such as acetonitrile, N,N-dimethylformamide or N,N-dimethylacetamide; or
(iii) the reaction of a compound of the formula (VI):

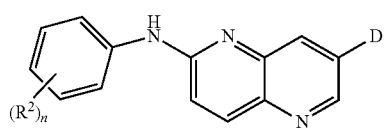

(VI)

or a protected form thereof, with a compound of formula $W_6$—$C_{1-6}$alkyl-$NR^{10}P$ wherein P represents a suitable protective group and $W_6$ represents a suitable leaving group, such as for example halo, e.g. bromo and the like, or —O—S(=O)$_2$—$CH_3$, in the presence of a suitable base, such as for example sodium hydride or potassium hydroxide, and optionally in the presence of a suitable phase transfer agent, such as for example tetrabutylammonium bromide, and a suitable solvent, e.g. N,N-dimethylformamide, N,N-dimethylacetamide, 2-methyltetrahydrofuran, water, followed by removing P and optionally removing any further protecting group present; or
(iv) the reaction of a compound of the formula (VI):

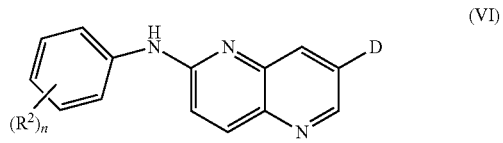

(VI)

or a protected thereof, with a compound of formula $W_6$—$C_{1-6}$alkyl-$NHR^{10}$ wherein We represents a suitable leaving group, such as for example halo, e.g. bromo and the like, or —O—S(=O)$_2$—$CH_3$, in the presence of a suitable base, such as for example sodium hydride or potassium hydroxide, and, optionally, a suitable phase transfer agent, such as for example tetrabutylammonium bromide, and a suitable solvent, e.g. N,N-dimethylformamide, N,N-dimethylacetamide or 2-methyltetrahydrofuran, water;
(v) the reaction of a compound of formula (XXXVI)

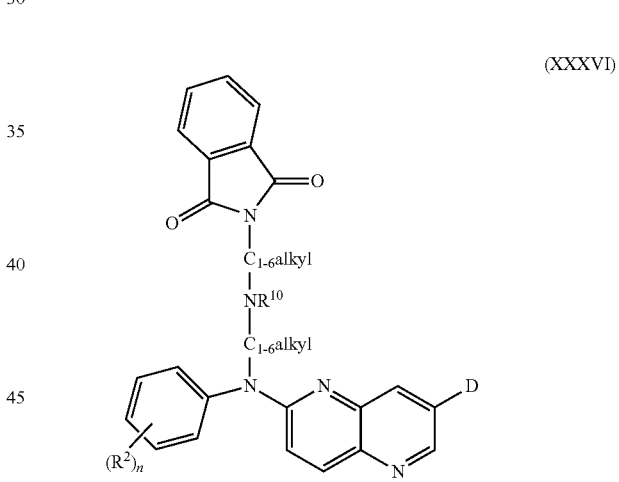

(XXXVI)

with hydrazine in the presence of a suitable solvent, such as for example an alcohol, e.g. ethanol;
(vi) the reaction of a compound of formula (IX-1) wherein $R^u$ represents —O—S(=O)$_2$—$CH_3$,

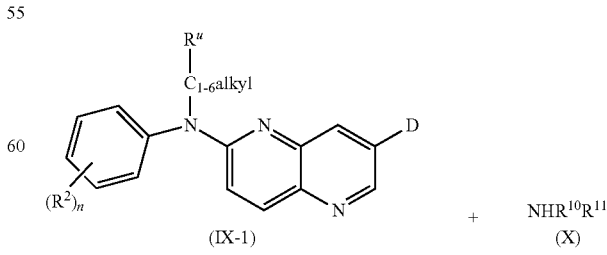

(IX-1)    +    $NHR^{10}R^{11}$
(X)

with an intermediate of formula (X) in the presence of a suitable solvent, such as for example acetonitrile;

(vii) the reaction of a compound of formula (VI)

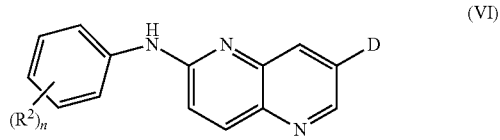
(VI)

with an intermediate of formula $W_{11}$—$R^{3b}$ wherein $R^{3b}$ represents optionally substituted $C_{2-6}$alkynyl and $W_{11}$ represents a suitable leaving group such as for example halo, e.g. chloro, or —O—S(=O)$_2$—CH$_3$, in the presence of a suitable base, such as for example NaH, and a suitable solvent, such as for example N,N-dimethylformamide;

(viii) the reaction of a compound of formula (VIII') wherein $R^x$ and $R^y$ represent $C_{1-4}$alkyl, and $R^z$ represent $C_{1-4}$alkyl or phenyl,

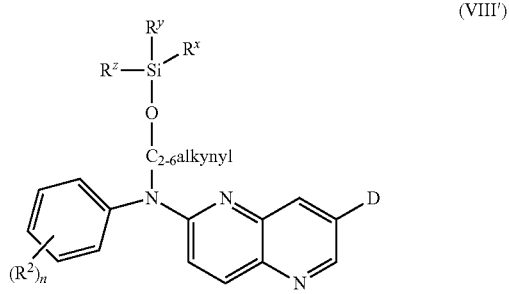
(VIII')

with a suitable acid, such as for example trifluoroacetic acid, in the presence of a suitable solvent, such as for example tetrahydrofuran;

(ix) deprotecting a compound of formula (XXXXII)

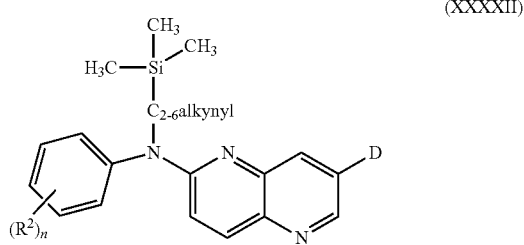
(XXXXII)

in the presence of a suitable base, such as for example K$_2$CO$_3$, and a suitable solvent, such as for example an alcohol, e.g. methanol and the like;

(x) the reaction of a compound of formula (VI)

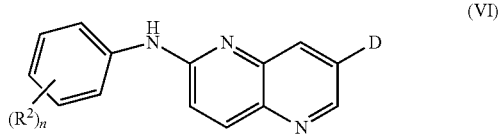
(VI)

with di($C_{1-6}$alkyl)vinylphosphonate in the presence of a suitable catalyst, such as for example tri-N-butylphosphine, and a suitable solvent, such as for example acetonitrile;

(xi) deprotecting a compound of formula (XXXXI) wherein the D'N moiety represents a D moiety wherein the D moiety contains a nitrogen atom

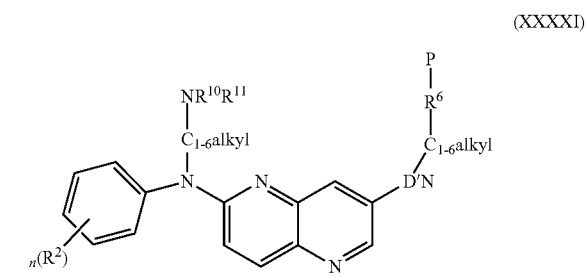
(XXXXI)

in the presence of a suitable base, such as for example K$_2$CO$_3$, and a suitable solvent, such as for example an alcohol, e.g. methanol and the like;

(xii) the reaction of a compound of formula (XXXI)

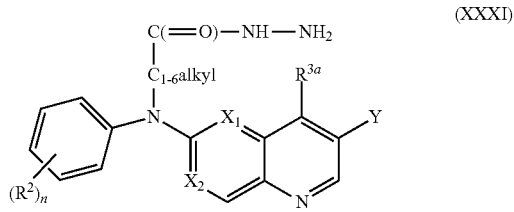
(XXXI)

with $W_8$—CN, wherein $W_8$ represents a suitable leaving group, such as for example halo, e.g. bromo, in the presence of a suitable base, such as for example NaHCO$_3$, and a suitable solvent, such as for example water or dioxane;

(xiii) the reaction of a compound of formula (XXXV)

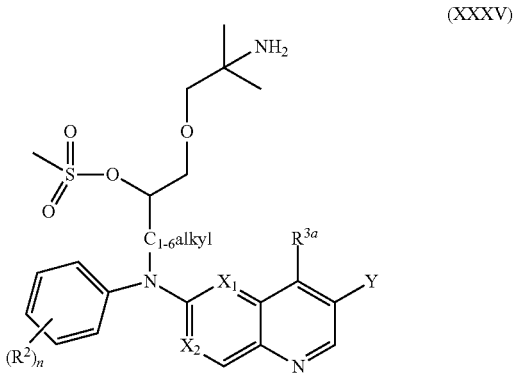
(XXXV)

with a suitable base, such as for example N,N-diisopropylethylamine and triethylamine, in the presence of a suitable solvent, such as for example an alcohol, e.g. methanol;

(xiv) deprotecting a compound of formula (XXVI) wherein P represents a suitable protective group such as for example —Si(CH$_3$)$_2$(C(CH$_3$)$_3$) or

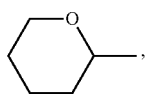

wherein Y'N represents an -E-D moiety wherein the D ring moiety contains a nitrogen atom (XXVI)

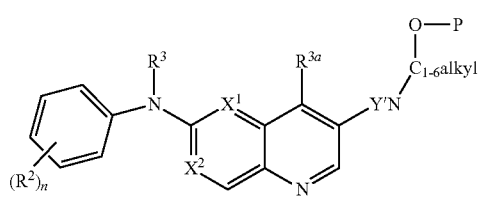

in the presence of a suitable acid, such as for example HCl or trifluoroacetic acid, or a suitable de-silylating agent, such as for example tetrabutyl ammonium fluoride, and a suitable solvent, such as an alcohol, e.g. methanol, or tetrahydrofuran;

(xv) the reaction of a compound of formula (XXIX) wherein Y'N represents an -E-D moiety wherein the D ring moiety contains a nitrogen atom, with a compound of formula (XXI)

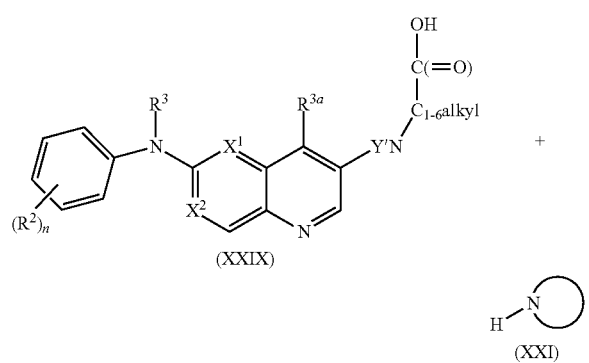

in the presence of suitable peptide coupling reagents such as, 1-hydroxy-benzotriazole and 1-(3-dimethylaminopropyl)-3-ethyl carbodiimide HCl;

(xvi) the reaction of a compound of formula (XXIX) wherein Y'N represents an -E-D moiety wherein the D ring moiety contains a nitrogen atom (XXIX)

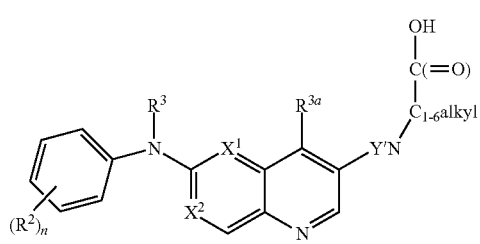

with NHR$^4$R$^5$ in the presence of suitable peptide coupling reagents such as 1-hydroxy-benzotriazole and 1-(3-dimethylaminopropyl)-3-ethyl carbodiimide HCl and a suitable base, such as triethylamine, and a suitable solvent, such as for example dichloromethane;

(xvii) reacting the below compound

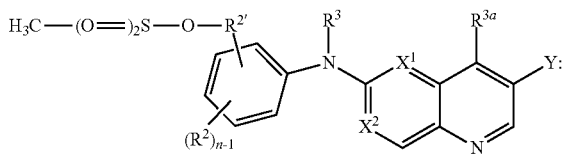

with NHR$^7$R$^8$ in the presence of a suitable base, such as for example K$_2$CO$_3$, and a suitable solvent, such as for example tetrahydrofuran;

(xviii) deprotecting the below compound

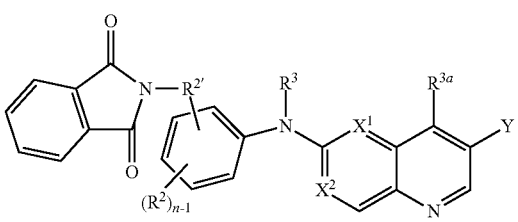

in the presence of hydrazine monohydrate, and a suitable solvent, such as for example an alcohol, e.g. ethanol;
wherein the variables are as defined herein; and optionally thereafter converting one compound of the formula (I) into another compound of the formula (I).

A further embodiment is a process for synthesis of a compound of formula (VI) wherein:

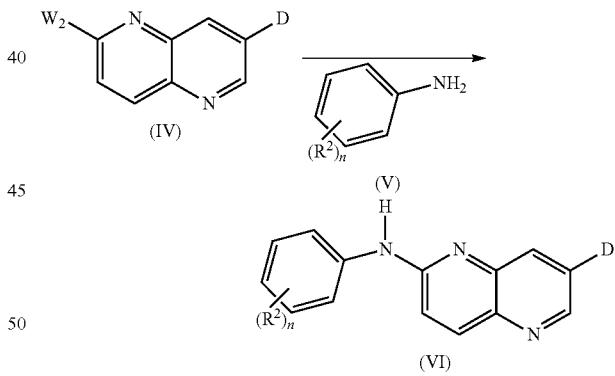

a compound of formula (IV) is reacted with an intermediate of formula (V) in the presence of a suitable catalyst, such as for example palladium (II) acetate, a suitable base, such as sodium tert-butoxide or Cs$_2$CO$_3$, a suitable ligand, such as for example 1,1'-[1,1'-binaphthalene]-2,2'-diylbis[1,1-diphenylphosphine], and a suitable solvent or solvent mixture, such as for example dioxane or ethylene glycol dimethylether and water.

Alternatively a compound of formula (IV) is reacted with an intermediate of formula (V) in the presence of a suitable solvent such as for example an alcohol, e.g. isopropanol, and optionally in the presence of a suitable acid such as for example hydrochloric acid. Alternatively a compound of formula (IV) is reacted with an intermediate of formula (V)

in the presence of a suitable deprotonating agent such as for example potassium bis(trimethylsilyl)amide, in the presence of a suitable solvent such as for example tetrahydrofuran.

In a further embodiment the invention provides a novel intermediate. In one embodiment the invention provides a novel intermediate as described herein. In another embodiment the invention provides a novel intermediate of formula (VI) or formula (IX).

In one embodiment, the present invention also relates to a compound having the following formula:

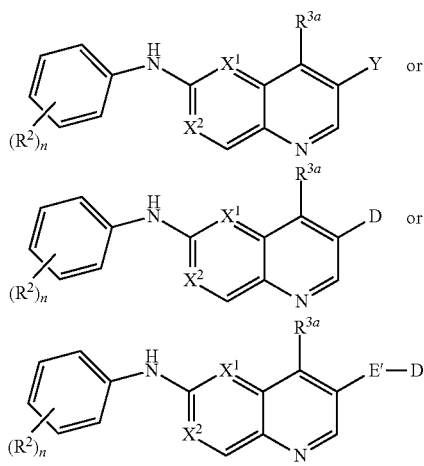

wherein E' represents —$(CR^{22}R^{23})_n$—, $C_{2-4}$alkenediyl optionally substituted with $R^{22}$, $C_{2-4}$alkynediyl optionally substituted with $R^{22}$, —CO—$(CR^{22}R^{23})_s$—, —$(CR^{22}R^{23})_s$—CO—, —$NR^{22}$—$(CR^{22}R^{23})_s$—, —$(CR^{22}R^{23})_s$—$NR^{22}$—, —O—$(CR^{22}R^{23})_s$—, —$(CR^{22}R^{23})_s$—O—, —$S(O)_m$—$(CR^{22}R^{23})_s$—, —$(CR^{22}R^{23})_s$—$S(O)_m$—, —$(CR^{22}R^{23})_s$—CO—$NR^{22}$—$(CR^{22}R^{23})_s$— or —$(CR^{22}R^{23})_s$—$NR^{22}$—CO—$(CR^{22}R^{23})_s$—;
wherein Y, D, $R^2$, $X^1$, $X^2$, $X^3$ and n are as defined for a compound of formula (I-A) above.

Pharmaceutically Acceptable Salts, Solvates or Derivatives Thereof

In this section, as in all other sections of this application, unless the context indicates otherwise, references to formula (I) include references to all other sub-groups, preferences, embodiments and examples thereof as defined herein.

Unless otherwise specified, a reference to a particular compound also includes ionic forms, salts, solvates, isomers, tautomers, N-oxides, esters, prodrugs, isotopes and protected forms thereof, for example, as discussed below; preferably, the ionic forms, or salts or tautomers or isomers or N-oxides or solvates thereof; and more preferably, the ionic forms, or salts or solvates or protected forms thereof, even more preferably the salts or tautomers or solvates thereof. Many compounds of the formula (I) can exist in the form of salts, for example acid addition salts or, in certain cases salts of organic and inorganic bases such as carboxylate, sulphonate and phosphate salts. All such salts are within the scope of this invention, and references to compounds of the formula (I) include the salt forms of the compounds. It will be appreciated that references to "derivatives" include references to ionic forms, salts, solvates, isomers, tautomers, N-oxides, esters, prodrugs, isotopes and protected forms thereof.

According to one aspect of the invention there is provided a compound as defined herein or a salt, tautomer, N-oxide or solvate thereof. According to a further aspect of the invention there is provided a compound as defined herein or a salt or solvate thereof. References to compounds of the formula (I) and sub-groups thereof as defined herein include within their scope the salts or solvates or tautomers or N-oxides of the compounds.

The salt forms of the compounds of the invention are typically pharmaceutically acceptable salts, and examples of pharmaceutically acceptable salts are discussed in Berge et al. (1977) "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used. The compounds of the invention may exist as mono- or di-salts depending upon the pKa of the acid from which the salt is formed.

Acid addition salts may be formed with a wide variety of acids, both inorganic and organic. Examples of acid addition salts include salts formed with an acid selected from the group consisting of acetic, 2,2-dichloroacetic, adipic, alginic, ascorbic (e.g. L-ascorbic), L-aspartic, benzenesulphonic, benzoic, 4-acetamidobenzoic, butanoic, (+) camphoric, camphor-sulphonic, (+)-(1S)-camphor-10-sulphonic, capric, caproic, caprylic, cinnamic, citric, cyclamic, dodecylsulphuric, ethane-1,2-disulphonic, ethanesulphonic, 2-hydroxyethanesulphonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic, (±)-DL-lactic), lactobionic, maleic, malic, (−)-L-malic, malonic, (±)-DL-mandelic, methanesulphonic, naphthalenesulphonic (e.g. naphthalene-2-sulphonic), naphthalene-1,5-disulphonic, 1-hydroxy-2-naphthoic, nicotinic, nitric, oleic, orotic, oxalic, palmitic, pamoic, phosphoric, propionic, L-pyroglutamic, pyruvic, salicylic, 4-amino-salicylic, sebacic, stearic, succinic, sulphuric, tannic, (+)-L-tartaric, thiocyanic, toluenesulphonic (e.g. p-toluenesulphonic), undecylenic and valeric acids, as well as acylated amino acids and cation exchange resins.

One particular group of salts consists of salts formed from acetic, hydrochloric, hydriodic, phosphoric, nitric, sulphuric, citric, lactic, succinic, maleic, malic, isethionic, fumaric, benzenesulphonic, toluenesulphonic, methanesulphonic (mesylate), ethanesulphonic, naphthalenesulphonic, valeric, acetic, propanoic, butanoic, malonic, glucuronic and lactobionic acids. Another group of acid addition salts includes salts formed from acetic, adipic, ascorbic, aspartic, citric, DL-Lactic, fumaric, gluconic, glucuronic, hippuric, hydrochloric, glutamic, DL-malic, methanesulphonic, sebacic, stearic, succinic and tartaric acids.

If the compound is anionic, or has a functional group which may be anionic (e.g., —COOH may be —COO—), then a salt may be formed with a suitable cation. Examples of suitable inorganic cations include, but are not limited to, alkali metal ions such as Na$^+$ and K$^+$, alkaline earth metal cations such as Ca$^{2+}$ and Mg$^{2+}$, and other cations such as Al$^{3+}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$).

Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I). Compounds of the formula (I) containing an amine function may also form N-oxides. A reference herein to a compound of the formula (I) that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* (1977), 7, 509-514) in which the amine compound is reacted with m-chloroperoxybenzoic acid (MCPBA), for example, in an inert solvent such as dichloromethane.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS. Alternatively the skilled person can deliberately form a solvate using crystallisation conditions that include an amount of the solvent required for the particular solvate. Thereafter the standard methods described above, can be used to establish whether solvates had formed. Also encompassed by formula (I) are any complexes (e.g. inclusion complexes or clathrates with compounds such as cyclodextrins, or complexes with metals) of the compounds.

Furthermore, the compounds of the present invention may have one or more polymorph (crystalline) or amorphous forms and as such are intended to be included in the scope of the invention.

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I). Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

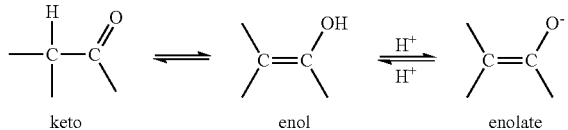

keto  enol  enolate

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) of two or more optical isomers, unless the context requires otherwise. The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog (1966) *Angew. Chem. Int. Ed. Engl.*, 5, 385-415. Optical isomers can be separated by a number of techniques including chiral chromatography (chromatography on a chiral support) and such techniques are well known to the person skilled in the art. As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulphonic, separating the diastereoisomers by preferential crystallisation, and then dissociating the salts to give the individual enantiomer of the free base.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer). When a specific isomeric form is identified (e.g. S configuration, or E isomer), this means that said isomeric form is substantially free of the other isomer(s), i.e. said isomeric form is present in at least 55%, 60%, 65%, 70%, 75%, 80%, 85%, 90%, 95%, 99% or more (e.g. substantially all) of the total amount of the compound of the invention.

The compounds of the invention include compounds with one or more isotopic substitutions, and a reference to a particular element includes within its scope all isotopes of the element. For example, a reference to hydrogen includes within its scope $^1H$, $^2H$ (D), and $^3H$ (T). Similarly, references to carbon and oxygen include within their scope respectively $^{12}C$, $^{13}C$ and $^{14}C$ and $^{16}O$ and $^{18}O$. The isotopes may be radioactive or non-radioactive. In one embodiment of the invention, the compounds contain no radioactive isotopes. Such compounds are preferred for therapeutic use. In another embodiment, however, the compound may contain one or more radioisotopes. Compounds containing such radioisotopes may be useful in a diagnostic context.

Esters such as carboxylic acid esters and acyloxy esters of the compounds of formula (I) bearing a carboxylic acid group or a hydroxyl group are also embraced by formula (I). In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group. Examples of esters are compounds containing the group —C(=O)OR, wherein R is an ester substituent, for example, a $C_{1-6}$ alkyl group, a heterocyclyl group, or a $C_{5-20}$ aryl group, preferably a $C_{1-6}$ alkyl group. Particular examples of ester groups include, but are not limited to, —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

For example, some prodrugs are esters of the active compound (e.g., a physiologically acceptable metabolically labile ester). By "prodrugs" is meant for example any compound that is converted in vivo into a biologically active compound of the formula (I). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is: $C_{1-6}$alkyl (e.g., -Me, -Et, -nPr, -iPr, -nBu, -sBu, -iBu, -tBu); $C_{1-6}$aminoalkyl [e.g., aminoethyl; 2-(N,N-diethylamino)ethyl; 2-(4-morpholino)ethyl]; and acyloxy-$C_{1-7}$alkyl [e.g., acyloxymethyl; acyloxyethyl; pivaloyloxymethyl; acetoxymethyl; 1-acetoxyethyl; 1-(1-methoxy-1-methyl)ethyl-carbonyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxy)carbonyloxyethyl; (4-tetrahydropyranyl)carbonyloxymethyl; and 1-(4-tetrahydropyranyl)carbonyloxyethyl]. Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT) and ligand-directed enzyme pro-drug therapy (LIDEPT) etc.). For example, the prodrug may be a sugar derivative or other glycoside conjugate, or may be an amino acid ester derivative.

Protein Tyrosine Kinases (PTK)

The compounds of the invention described herein inhibit or modulate the activity of certain tyrosine kinases, and thus the compounds will be useful in the treatment or prophylaxis, in particular the treatment, of disease states or conditions mediated by those tyrosine kinases, in particular FGFR.

FGFR

The fibroblast growth factor (FGF) family of protein tyrosine kinase (PTK) receptors regulates a diverse array of physiologic functions including mitogenesis, wound healing, cell differentiation and angiogenesis, and development. Both normal and malignant cell growth as well as proliferation are affected by changes in local concentration of FGFs, extracellular signalling molecules which act as autocrine as well as paracrine factors. Autocrine FGF signalling may be particularly important in the progression of steroid hormone-dependent cancers to a hormone independent state. FGFs and their receptors are expressed at increased levels in several tissues and cell lines and overexpression is believed to contribute to the malignant phenotype. Furthermore, a number of oncogenes are homologues of genes encoding growth factor receptors, and there is a potential for aberrant activation of FGF-dependent signalling in human pancreatic cancer (Knights et al., Pharmacology and Therapeutics 2010 125:1 (105-117); Korc M. et al Current Cancer Drug Targets 2009 9:5 (639-651)).

The two prototypic members are acidic fibroblast growth factor (aFGF or FGF1) and basic fibroblast growth factor (bFGF or FGF2), and to date, at least twenty distinct FGF family members have been identified. The cellular response to FGFs is transmitted via four types of high affinity transmembrane protein tyrosine-kinase fibroblast growth factor receptors (FGFR) numbered 1 to 4 (FGFR1 to FGFR4).

Disruption of the FGFR1 pathway should affect tumor cell proliferation since this kinase is activated in many tumor types in addition to proliferating endothelial cells. The over-expression and activation of FGFR1 in tumor-associated vasculature has suggested a role for these molecules in tumor angiogenesis.

A recent study has shown a link between FGFR1 expression and tumorigenicity in Classic Lobular Carcinomas (CLC). CLCs account for 10-15% of all breast cancers and, in general, lack p53 and Her2 expression whilst retaining expression of the oestrogen receptor. A gene amplification of 8p12-p11.2 was demonstrated in 50% of CLC cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway. Rhabdomyosarcoma (RMS) is the most common pediatric soft tissue sarcoma likely results from abnormal proliferation and differentiation during skeletal myogenesis. FGFR1 is over-expressed in primary rhabdomyosarcoma tumors and is associated with hypomethylation of a 5' CpG island and abnormal expression of the AKT1, NOG, and BMP4 genes. FGFR1 has also been linked to squamous lung cancer, colorectal cancer, glioblastoma, astrocytomas, prostate cancer, small cell lung cancer, melanoma, head and neck cancer, thyroid cancer, uterine cancer.

Fibroblast growth factor receptor 2 has high affinity for the acidic and/or basic fibroblast growth factors, as well as the keratinocyte growth factor ligands. Fibroblast growth factor receptor 2 also propagates the potent osteogenic effects of FGFs during osteoblast growth and differentiation. Mutations in fibroblast growth factor receptor 2, leading to complex functional alterations, were shown to induce abnormal ossification of cranial sutures (craniosynostosis), implying a major role of FGFR signalling in intramembranous bone formation. For example, in Apert (AP) syndrome, characterized by premature cranial suture ossification, most cases are associated with point mutations engendering gain-of-function in fibroblast growth factor receptor 2. In addition, mutation screening in patients with syndromic craniosynostoses indicates that a number of recurrent FGFR2 mutations accounts for severe forms of Pfeiffer syndrome. Particular mutations of FGFR2 include W290C, D321A, Y340C, C342R, C342S, C342W, N549H, K641R in FGFR2.

Several severe abnormalities in human skeletal development, including Apert, Crouzon, Jackson-Weiss, Beare-Stevenson cutis gyrata, and Pfeiffer syndromes are associated with the occurrence of mutations in fibroblast growth factor receptor 2. Most, if not all, cases of Pfeiffer Syndrome (PS) are also caused by de novo mutation of the fibroblast growth factor receptor 2 gene, and it was recently shown that mutations in fibroblast growth factor receptor 2 break one of the cardinal rules governing ligand specificity. Namely, two mutant splice forms of fibroblast growth factor receptor, FGFR2c and FGFR2b, have acquired the ability to bind to and be activated by atypical FGF ligands. This loss of ligand specificity leads to aberrant signalling and suggests that the severe phenotypes of these disease syndromes result from ectopic ligand-dependent activation of fibroblast growth factor receptor 2.

Genetic aberrations of the FGFR3 receptor tyrosine kinase such as chromosomal translocations or point mutations result in ectopically expressed or deregulated, constitutively active, FGFR3 receptors. Such abnormalities are linked to a subset of multiple myelomas and in bladder, hepatocellular, oral squamous cell carcinoma and cervical carcinomas. Accordingly, FGFR3 inhibitors would be useful in the treatment of multiple myeloma, bladder and cervical carcinomas. FGFR3 is also over-expressed in bladder cancer, in particular invasive bladder cancer. FGFR3 is frequently activated by mutation in urothelial carcinoma (UC). Increased expression was associated with mutation (85% of mutant tumors showed high-level expression) but also 42% of tumors with no detectable mutation showed over-expression, including many muscle-invasive tumors. FGFR3 is also linked to endometrial and thyroid cancer.

Over expression of FGFR4 has been linked to poor prognosis in both prostate and thyroid carcinomas. In addition a germline polymorphism (Gly388Arg) is associated with increased incidence of lung, breast, colon, liver (HCC) and prostate cancers. In addition, a truncated form of FGFR4 (including the kinase domain) has also been found to be present in 40% of pituitary tumours but not present in normal tissue. FGFR4 overexpression has been observed in liver, colon and lung tumours. FGFR4 has been implicated in colorectal and liver cancer where expression of its ligand FGF19 is frequently elevated. FGFR4 is also linked to astrocytomas, rhabdomyosarcoma.

Fibrotic conditions are a major medical problem resulting from abnormal or excessive deposition of fibrous tissue. This occurs in many diseases, including liver cirrhosis, glomerulonephritis, pulmonary fibrosis, systemic fibrosis, rheumatoid arthritis, as well as the natural process of wound healing. The mechanisms of pathological fibrosis are not fully understood but are thought to result from the actions of various cytokines (including tumor necrosis factor (TNF), fibroblast growth factors (FGF's), platelet derived growth factor (PDGF) and transforming growth factor beta. (TGFβ) involved in the proliferation of fibroblasts and the deposition of extracellular matrix proteins (including collagen and fibronectin). This results in alteration of tissue structure and function and subsequent pathology.

A number of preclinical studies have demonstrated the up-regulation of fibroblast growth factors in preclinical models of lung fibrosis. TGFβ1 and PDGF have been reported to be involved in the fibrogenic process and further published work suggests the elevation of FGF's and consequent increase in fibroblast proliferation, may be in response to elevated TGFβ1. The potential therapeutic benefit of targeting the fibrotic mechanism in conditions such as idiopathic pulmonary fibrosis (IPF) is suggested by the reported clinical effect of the anti-fibrotic agent pirfenidone. Idiopathic pulmonary fibrosis (also referred to as Cryptogenic fibrosing alveolitis) is a progressive condition involving scarring of the lung. Gradually, the air sacs of the lungs become replaced by fibrotic tissue, which becomes thicker, causing an irreversible loss of the tissue's ability to transfer oxygen into the bloodstream. The symptoms of the condition include shortness of breath, chronic dry coughing, fatigue, chest pain and loss of appetite resulting in rapid weight loss. The condition is extremely serious with approximately 50% mortality after 5 years.

As such, the compounds which inhibit FGFR will be useful in providing a means of preventing the growth or inducing apoptosis in tumours, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors. Patients with activating mutants of any of the isoforms of the specific RTKs discussed herein may also find treatment with RTK inhibitors particularly beneficial.

Vascular Endothelial Growth Factor (VEGFR)

Chronic proliferative diseases are often accompanied by profound angiogenesis, which can contribute to or maintain an inflammatory and/or proliferative state, or which leads to tissue destruction through the invasive proliferation of blood vessels.

Angiogenesis is generally used to describe the development of new or replacement blood vessels, or neovascularisation. It is a necessary and physiological normal process by which vasculature is established in the embryo. Angiogenesis does not occur, in general, in most normal adult tissues, exceptions being sites of ovulation, menses and wound healing. Many diseases, however, are characterized by persistent and unregulated angiogenesis. For instance, in arthritis, new capillary blood vessels invade the joint and destroy cartilage. In diabetes (and in many different eye diseases), new vessels invade the macula or retina or other ocular structures, and may cause blindness. The process of atherosclerosis has been linked to angiogenesis. Tumor growth and metastasis have been found to be angiogenesis-dependent.

The recognition of the involvement of angiogenesis in major diseases has been accompanied by research to identify and develop inhibitors of angiogenesis. These inhibitors are generally classified in response to discrete targets in the angiogenesis cascade, such as activation of endothelial cells by an angiogenic signal; synthesis and release of degradative enzymes; endothelial cell migration; proliferation of endothelial cells; and formation of capillary tubules. Therefore, angiogenesis occurs in many stages and attempts are underway to discover and develop compounds that work to block angiogenesis at these various stages.

There are publications that teach that inhibitors of angiogenesis, working by diverse mechanisms, are beneficial in diseases such as cancer and metastasis, ocular diseases, arthritis and hemangioma.

Vascular endothelial growth factor (VEGF), a polypeptide, is mitogenic for endothelial cells in vitro and stimulates angiogenic responses in vivo. VEGF has also been linked to inappropriate angiogenesis. VEGFR(s) are protein tyrosine kinases (PTKs). PTKs catalyze the phosphorylation of specific tyrosine residues in proteins involved in cell function thus regulating cell growth, survival and differentiation.

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction. Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis.

Inhibition at the kinase domain binding site of VEGFR-2 would block phosphorylation of tyrosine residues and serve to disrupt initiation of angiogenesis.

Angiogenesis is a physiologic process of new blood vessel formation mediated by various cytokines called angiogenic factors. Although its potential pathophysiologic role in solid tumors has been extensively studied for more than 3 decades, enhancement of angiogenesis in chronic lymphocytic leukemia (CLL) and other malignant hematological disorders has been recognized more recently. An increased level of angiogenesis has been documented by various experimental methods both in bone marrow and lymph nodes of patients with CLL. Although the role of angiogenesis in the pathophysiology of this disease remains to be fully elucidated, experimental data suggest that several angiogenic factors play a role in the disease progression. Biologic markers of angiogenesis were also shown to be of prognostic relevance in CLL. This indicates that VEGFR inhibitors may also be of benefit for patients with leukemia's such as CLL.

In order for a tumour mass to get beyond a critical size, it must develop an associated vasculature. It has been proposed that targeting a tumor vasculature would limit tumor expansion and could be a useful cancer therapy. Observations of tumor growth have indicated that small tumour masses can persist in a tissue without any tumour-specific vasculature. The growth arrest of nonvascularized tumors has been attributed to the effects of hypoxia at the center of the tumor. More recently, a variety of proangiogenic and antiangiogenic factors have been identified and have led to the concept of the "angiogenic switch," a process in which disruption of the normal ratio of angiogenic stimuli and inhibitors in a tumor mass allows for autonomous vascularization. The angiogenic switch appears to be governed by the same genetic alterations that drive malignant conversion: the activation of oncogenes and the loss of tumour suppressor genes. Several growth factors act as positive regulators of angiogenesis. Foremost among these are vascular endothelial growth factor (VEGF), basic fibroblast growth factor (bFGF), and angiogenin. Proteins such as thrombospondin (Tsp-1), angiostatin, and endostatin function as negative regulators of angiogenesis.

Inhibition of VEGFR2 but not VEGFR1 markedly disrupts angiogenic switching, persistent angiogenesis, and initial tumor growth in a mouse model. In late-stage tumors, phenotypic resistance to VEGFR2 blockade emerged, as tumors regrew during treatment after an initial period of growth suppression. This resistance to VEGF blockade involves reactivation of tumour angiogenesis, independent of VEGF and associated with hypoxia-mediated induction of other proangiogenic factors, including members of the FGF family. These other proangiogenic signals are functionally implicated in the revascularization and regrowth of tumours in the evasion phase, as FGF blockade impairs progression in the face of VEGF inhibition.

There is evidence for normalization of glioblastoma blood vessels in patients treated with a pan-VEGF receptor tyrosine kinase inhibitor, AZD2171, in a phase 2 study. MRI determination of vessel normalization in combination with circulating biomarkers provides for an effective means to assess response to antiangiogenic agents.

PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. A growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation.

Advantages of a Selective Inhibitor

Development of FGFR kinase inhibitors with a differentiated selectivity profile provides a new opportunity to use these targeted agents in patient sub-groups whose disease is driven by FGFR deregulation. Compounds that exhibit reduced inhibitory action on additional kinases, particularly VEGFR2 and PDGFR-beta, offer the opportunity to have a differentiated side-effect or toxicity profile and as such allow for a more effective treatment of these indications. Inhibitors of VEGFR2 and PDGFR-beta are associated with toxicities such as hypertension or oedema respectively. In the case of VEGFR2 inhibitors this hypertensive effect is often dose limiting, may be contraindicated in certain patient populations and requires clinical management.

Biological Activity and Therapeutic Uses

The compounds of the invention, and subgroups thereof, have fibroblast growth factor receptor (FGFR) inhibiting or modulating activity and/or vascular endothelial growth factor receptor (VEGFR) inhibiting or modulating activity, and/or platelet derived growth factor receptor (PDGFR) inhibiting or modulating activity, and which will be useful in preventing or treating disease states or conditions described herein. In addition the compounds of the invention, and subgroups thereof, will be useful in preventing or treating diseases or condition mediated by the kinases. References to the preventing or prophylaxis or treatment of a disease state or condition such as cancer include within their scope alleviating or reducing the incidence of cancer.

As used herein, the term "modulation", as applied to the activity of a kinase, is intended to define a change in the level of biological activity of the protein kinase. Thus, modulation encompasses physiological changes which effect an increase or decrease in the relevant protein kinase activity. In the latter case, the modulation may be described as "inhibition". The modulation may arise directly or indirectly, and may be mediated by any mechanism and at any physiological level, including for example at the level of gene expression (including for example transcription, translation and/or post-translational modification), at the level of expression of genes encoding regulatory elements which act directly or indirectly on the levels of kinase activity. Thus, modulation may imply elevated/suppressed expression or over- or under-expression of a kinase, including gene amplification (i.e. multiple gene copies) and/or increased or decreased expression by a transcriptional effect, as well as hyper- (or hypo-)activity and (de)activation of the protein kinase(s) (including (de)activation) by mutation(s). The terms "modulated", "modulating" and "modulate" are to be interpreted accordingly.

As used herein, the term "mediated", as used e.g. in conjunction with a kinase as described herein (and applied for example to various physiological processes, diseases, states, conditions, therapies, treatments or interventions) is intended to operate limitatively so that the various processes, diseases, states, conditions, treatments and interventions to which the term is applied are those in which the kinase plays a biological role. In cases where the term is applied to a disease, state or condition, the biological role played by a kinase may be direct or indirect and may be necessary and/or sufficient for the manifestation of the symptoms of the disease, state or condition (or its aetiology or progression). Thus, kinase activity (and in particular aberrant levels of kinase activity, e.g. kinase over-expression) need not necessarily be the proximal cause of the disease, state or condition: rather, it is contemplated that the kinase mediated diseases, states or conditions include those having multifactorial aetiologies and complex progressions in which the kinase in question is only partially involved. In cases where the term is applied to treatment, prophylaxis or intervention, the role played by the kinase may be direct or indirect and may be necessary and/or sufficient for the operation of the treatment, prophylaxis or outcome of the intervention. Thus, a disease state or condition mediated by a kinase includes the development of resistance to any particular cancer drug or treatment.

Thus, for example, the compounds of the invention may be useful in alleviating or reducing the incidence of cancer.

More particularly, the compounds of the formulae (I) and sub-groups thereof are inhibitors of FGFRs. For example, compounds of the invention have activity against FGFR1, FGFR2, FGFR3, and/or FGFR4, and in particular FGFRs selected from FGFR1, FGFR2 and FGFR3; or in particular the compounds of formula (I) and sub-groups thereof are inhibitors of FGFR4.

Preferred compounds are compounds that inhibit one or more FGFR selected from FGFR1, FGFR2, FGFR3, and FGFR4. Preferred compounds of the invention are those having $IC_{50}$ values of less than 0.1 µM.

Compounds of the invention also have activity against VEGFR.

In addition many of the compounds of the invention exhibit selectivity for the FGFR 1, 2, and/or 3, and/or 4 compared to VEGFR (in particular VEGFR2) and/or PDGFR and such compounds represent one preferred embodiment of the invention. In particular, the compounds exhibit selectivity over VEGFR2. For example, many compounds of the invention have $IC_{50}$ values against FGFR1, 2 and/or 3 and/or 4 that are between a tenth and a hundredth of the $IC_{50}$ against VEGFR (in particular VEGFR2) and/or PDGFR B. In particular preferred compounds of the invention have at least 10 times greater activity against or inhibition of FGFR in particular FGFR1, FGFR2, FGFR3 and/or FGFR4 than VEGFR2. More preferably the compounds of the invention have at least 100 times greater activity against or inhibition of FGFR in particular FGFR1, FGFR2, FGFR3 and/or FGFR4 than VEGFR2. This can be determined using the methods described herein.

As a consequence of their activity in modulating or inhibiting FGFR, and/or VEGFR kinases, the compounds will be useful in providing a means of preventing the growth or inducing apoptosis of neoplasias, particularly by inhibiting angiogenesis. It is therefore anticipated that the compounds will prove useful in treating or preventing proliferative disorders such as cancers. In addition, the compounds of the invention could be useful in the treatment of diseases in which there is a disorder of proliferation, apoptosis or differentiation.

In particular tumours with activating mutants of VEGFR or upregulation of VEGFR and patients with elevated levels of serum lactate dehydrogenase may be particularly sensitive to the compounds of the invention. Patients with activating mutants of any of the isoforms of the specific RTKs discussed herein may also find treatment with the compounds of the invention particularly beneficial. For example, VEGFR overexpression in acute leukemia cells where the clonal progenitor may express VEGFR. Also, particular tumours with activating mutants or upregulation or overexpression of any of the isoforms of FGFR such as FGFR1, FGFR2 or FGFR3 or FGFR4 may be particularly sensitive to the compounds of the invention and thus patients as discussed herein with such particular tumours may also find treatment with the compounds of the invention particularly beneficial. It may be preferred that the treatment is related to or directed at a mutated form of one of the receptor tyrosine kinases, such as discussed herein. Diagnosis of tumours with such mutations could be performed using techniques known to a person skilled in the art and as described herein such as RTPCR and FISH.

Examples of cancers which may be treated (or inhibited) include, but are not limited to, a carcinoma, for example a carcinoma of the bladder, breast, colon (e.g. colorectal carcinomas such as colon adenocarcinoma and colon adenoma), kidney, urothelial, uterus, epidermis, liver, lung (for example adenocarcinoma, small cell lung cancer and non-small cell lung carcinomas, squamous lung cancer), oesophagus, head and neck, gall bladder, ovary, pancreas (e.g. exocrine pancreatic carcinoma), stomach, gastrointestinal (also known as gastric) cancer (e.g. gastrointestinal stromal tumours), cervix, endometrium, thyroid, prostate, or skin (for example squamous cell carcinoma or dermatofibrosarcoma protuberans); pituitary cancer, a hematopoietic tumour of lymphoid lineage, for example leukemia, acute lymphocytic leukemia, chronic lymphocytic leukemia, B-cell lymphoma (e.g. diffuse large B-cell lymphoma), T-cell lymphoma, Hodgkin's lymphoma, non-Hodgkin's lymphoma, hairy cell lymphoma, or Burkett's lymphoma; a hematopoietic tumour of myeloid lineage, for example leukemias, acute and chronic myelogenous leukemias, chronic myelomonocytic leukemia (CMML), myeloproliferative disorder, myeloproliferative syndrome, myelodysplastic syndrome, or promyelocytic leukemia; multiple myeloma; thyroid follicular cancer; hepatocellular cancer, a tumour of mesenchymal origin (e.g. Ewing's sarcoma), for example fibrosarcoma or rhabdomyosarcoma; a tumour of the central or peripheral nervous system, for example astrocytoma, neuroblastoma, glioma (such as glioblastoma multiforme) or schwannoma; melanoma; seminoma; teratocarcinoma; osteosarcoma; xeroderma pigmentosum; keratoctanthoma; thyroid follicular cancer; or Kaposi's sarcoma. In particular, squamous lung cancer, breast cancer, colorectal cancer, glioblastoma, astrocytomas, prostate cancer, small cell lung cancer, melanoma, head and neck cancer, thyroid cancer, uterine cancer, gastric cancer, hepatocellular cancer, cervix cancer, multiple myeloma, bladder cancer, endometrial cancer, urothelial cancer, colon cancer, rhabdomyosarcoma, pituitary gland cancer.

Certain cancers are resistant to treatment with particular drugs. This can be due to the type of the tumour or can arise due to treatment with the compound. In this regard, references to multiple myeloma includes bortezomib sensitive multiple myeloma or refractory multiple myeloma. Similarly, references to chronic myelogenous leukemia includes imitanib sensitive chronic myelogenous leukemia and refractory chronic myelogenous leukemia. Chronic myelogenous leukemia is also known as chronic myeloid leukemia, chronic granulocytic leukemia or CML. Likewise, acute myelogenous leukemia, is also called acute myeloblastic leukemia, acute granulocytic leukemia, acute nonlymphocytic leukaemia or AML.

The compounds of the invention can also be used in the treatment of hematopoetic diseases of abnormal cell proliferation whether pre-malignant or stable such as myeloproliferative diseases. Myeloproliferative diseases ("MPD"s) are a group of diseases of the bone marrow in which excess cells are produced. They are related to, and may evolve into, myelodysplastic syndrome. Myeloproliferative diseases include polycythemia vera, essential thrombocythemia and primary myelofibrosis. A further haematological disorder is hypereosinophilic syndrome. T-cell lymphoproliferative diseases include those derived from natural Killer cells.

In addition the compounds of the invention can be used to gastrointestinal (also known as gastric) cancer e.g. gastrointestinal stromal tumours. Gastrointestinal cancer refers to malignant conditions of the gastrointestinal tract, including the esophagus, stomach, liver, biliary system, pancreas, bowels, and anus.

Thus, in the pharmaceutical compositions, uses or methods of this invention for treating a disease or condition comprising abnormal cell growth, the disease or condition comprising abnormal cell growth in one embodiment is a cancer.

Particular subsets of cancers include multiple myeloma, bladder, cervical, prostate and thyroid carcinomas, lung, breast, and colon cancers.

A further subset of cancers includes multiple myeloma, bladder, hepatocellular, oral squamous cell carcinoma and cervical carcinomas.

The compound of the invention, having FGFR such as FGFR1 inhibitory activity, may be particularly useful in the treatment or prevention of breast cancer in particular Classic Lobular Carcinomas (CLC).

As the compounds of the invention have FGFR4 activity they will also be useful in the treatment of prostate or pituitary cancers, or they will be useful in the treatment of breast cancer, lung cancer, prostate cancer, liver cancer (HCC) or lung cancer.

In particular the compounds of the invention as FGFR inhibitors, are useful in the treatment of multiple myeloma, myeloproliferatoive disorders, endometrial cancer, prostate cancer, bladder cancer, lung cancer, ovarian cancer, breast cancer, gastric cancer, colorectal cancer, and oral squamous cell carcinoma.

Further subsets of cancer are multiple myeloma, endometrial cancer, bladder cancer, cervical cancer, prostate cancer, lung cancer, breast cancer, colorectal cancer and thyroid carcinomas.

In particular the compounds of the invention are useful in the treatment of multiple myeloma (in particular multiple myeloma with t(4;14) translocation or overexpressing FGFR3), prostate cancer (hormone refractory prostate carcinomas), endometrial cancer (in particular endometrial tumours with activating mutations in FGFR2) and breast cancer (in particular lobular breast cancer).

In particular the compounds are useful in the treatment of lobular carcinomas such as CLC (Classic lobular carcinoma).

As the compounds have activity against FGFR3 they will be useful in the treatment of multiple myeloma and bladder cancer.

In particular the compounds are useful for the treatment of t(4;14) translocation positive multiple myeloma.

In one embodiment the compounds may be useful for the treatment of sarcoma. In one embodiment the compounds may be useful for the treatment of lung cancer, e.g. squamous cell carcinoma.

As the compounds have activity against FGFR2 they will be useful in the treatment of endometrial, ovarian, gastric, hepatocellular, uterine, cervix and colorectal cancers. FGFR2 is also overexpressed in epithelial ovarian cancer, therefore the compounds of the invention may be specifically useful in treating ovarian cancer such as epithelial ovarian cancer.

In one embodiment, the compounds may be useful for the treatment of lung cancer, in particular NSCLC, squamous cell carcinoma, liver cancer, kidney cancer, breast cancer, colon cancer, colorectal cancer, prostate cancer.

Compounds of the invention may also be useful in the treatment of tumours pre-treated with VEGFR2 inhibitor or VEGFR2 antibody (e.g. Avastin).

In particular the compounds of the invention may be useful in the treatment of VEGFR2-resistant tumours. VEGFR2 inhibitors and antibodies are used in the treatment of thyroid and renal cell carcinomas, therefore the compounds of the invention may be useful in the treatment of VEGFR2-resistant thyroid and renal cell carcinomas.

The cancers may be cancers which are sensitive to inhibition of any one or more FGFRs selected from FGFR1, FGFR2, FGFR3, FGFR4, for example, one or more FGFRs selected from FGFR1, FGFR2 or FGFR3.

Whether or not a particular cancer is one which is sensitive to inhibition of FGFR or VEGFR signalling may be determined by means of a cell growth assay as set out below or by a method as set out in the section headed "Methods of Diagnosis".

The compounds of the invention, and in particular those compounds having FGFR, or VEGFR inhibitory activity, may be particularly useful in the treatment or prevention of cancers of a type associated with or characterised by the presence of elevated levels of FGFR, or VEGFR, for example the cancers referred to in this context in the introductory section of this application.

The compounds of the present invention may be useful for the treatment of the adult population. The compounds of the present invention may be useful for the treatment of the pediatric population.

It has been discovered that some FGFR inhibitors can be used in combination with other anticancer agents. For example, it may be beneficial to combine an inhibitor that induces apoptosis with another agent which acts via a different mechanism to regulate cell growth thus treating two of the characteristic features of cancer development. Examples of such combinations are set out below.

The compounds of the invention may be useful in treating other conditions which result from disorders in proliferation such as type II or non-insulin dependent diabetes mellitus, autoimmune diseases, head trauma, stroke, epilepsy, neurodegenerative diseases such as Alzheimer's, motor neurone disease, progressive supranuclear palsy, corticobasal degeneration and Pick's disease for example autoimmune diseases and neurodegenerative diseases.

One sub-group of disease states and conditions that the compounds of the invention may be useful consists of inflammatory diseases, cardiovascular diseases and wound healing.

FGFR, and VEGFR are also known to play a role in apoptosis, angiogenesis, proliferation, differentiation and transcription and therefore the compounds of the invention could also be useful in the treatment of the following diseases other than cancer; chronic inflammatory diseases, for example systemic lupus erythematosus, autoimmune mediated glomerulonephritis, rheumatoid arthritis, psoriasis, inflammatory bowel disease, autoimmune diabetes mellitus, Eczema hypersensitivity reactions, asthma, COPD, rhinitis, and upper respiratory tract disease; cardiovascular diseases for example cardiac hypertrophy, restenosis, atherosclerosis; neurodegenerative disorders, for example Alzheimer's disease, AIDS-related dementia, Parkinson's disease, amyotropic lateral sclerosis, retinitis pigmentosa, spinal muscular atropy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases and cancer pain.

In addition, mutations of FGFR2 are associated with several severe abnormalities in human skeletal development and thus the compounds of invention could be useful in the treatment of abnormalities in human skeletal development, including abnormal ossification of cranial sutures (craniosynostosis), Apert (AP) syndrome, Crouzon syndrome, Jackson-Weiss syndrome, Beare-Stevenson cutis gyrate syndrome, and Pfeiffer syndrome.

The compound of the invention, having FGFR such as FGFR2 or FGFR3 inhibitory activity, may be particularly useful in the treatment or prevention of the skeletal diseases. Particular skeletal diseases are achondroplasia or thanatophoric dwarfism (also known as thanatophoric dysplasia).

The compound of the invention, having FGFR such as FGFR1, FGFR2 or FGFR3 inhibitory activity, may be particularly useful in the treatment or prevention in pathologies in which progressive fibrosis is a symptom. Fibrotic conditions in which the compounds of the inventions may be useful in the treatment of include diseases exhibiting abnormal or excessive deposition of fibrous tissue for example in liver cirrhosis, glomerulonephritis, pulmonary fibrosis, systemic fibrosis, rheumatoid arthritis, as well as the natural process of wound healing. In particular the compounds of the inventions may also be useful in the treatment of lung fibrosis in particular in idiopathic pulmonary fibrosis.

The over-expression and activation of FGFR and VEGFR in tumor-associated vasculature has also suggested a role for compounds of the invention in preventing and disrupting initiation of tumor angiogenesis. In particular the compounds of the invention may be useful in the treatment of cancer, metastasis, leukemia's such as CLL, ocular diseases such as age-related macular degeneration in particular wet form of age-related macular degeneration, ischemic proliferative retinopathies such as retinopathy of prematurity (ROP) and diabetic retinopathy, rheumatoid arthritis and hemangioma.

The activity of the compounds of the invention as inhibitors of FGFR1-4, VEGFR and/or PDGFR A/B can be measured using the assays set forth in the examples below and the level of activity exhibited by a given compound can be defined in terms of the $IC_{50}$ value. Preferred compounds of the present invention are compounds having an $IC_{50}$ value of less than 1 µM, more preferably less than 0.1 µM.

The invention provides compounds that have FGFR inhibiting or modulating activity, and which may be useful in preventing or treating disease states or conditions mediated by FGFR kinases.

In one embodiment, there is provided a compound as defined herein for use in therapy, for use as a medicine. In a further embodiment, there is provided a compound as defined herein for use in the prophylaxis or treatment, in particular in the treatment, of a disease state or condition mediated by a FGFR kinase.

Thus, for example, the compounds of the invention may be useful in alleviating or reducing the incidence of cancer. Therefore, in a further embodiment, there is provided a compound as defined herein for use in the prophylaxis or treatment, in particular the treatment, of cancer. In one embodiment, the compound as defined herein is for use in the prophylaxis or treatment of FGFR-dependent cancer. In one embodiment, the compound as defined herein is for use in the prophylaxis or treatment of cancer mediated by FGFR kinases.

Accordingly, the invention provides inter alia:

A method for the prophylaxis or treatment of a disease state or condition mediated by a FGFR kinase, which method comprises administering to a subject in need thereof a compound of the formula (I) as defined herein.

A method for the prophylaxis or treatment of a disease state or condition as described herein, which method comprises administering to a subject in need thereof a compound of the formula (I) as defined herein.

A method for the prophylaxis or treatment of cancer, which method comprises administering to a subject in need thereof a compound of the formula (I) as defined herein.

A method for alleviating or reducing the incidence of a disease state or condition mediated by a FGFR kinase, which method comprises administering to a subject in need thereof a compound of the formula (I) as defined herein.

A method of inhibiting a FGFR kinase, which method comprises contacting the kinase with a kinase-inhibiting compound of the formula (I) as defined herein.

A method of modulating a cellular process (for example cell division) by inhibiting the activity of a FGFR kinase using a compound of the formula (I) as defined herein.

A compound of formula (I) as defined herein for use as a modulator of a cellular process (for example cell division) by inhibiting the activity of a FGFR kinase.

A compound of formula (I) as defined herein for use in the prophylaxis or treatment of cancer, in particular the treatment of cancer.

A compound of formula (I) as defined herein for use as a modulator (e.g. inhibitor) of FGFR.

The use of a compound of formula (I) as defined herein for the manufacture of a medicament for the prophylaxis or treatment of a disease state or condition mediated by a FGFR kinase, the compound having the formula (I) as defined herein.

The use of a compound of formula (I) as defined herein for the manufacture of a medicament for the prophylaxis or treatment of a disease state or condition as described herein.

The use of a compound of formula (I) as defined herein for the manufacture of a medicament for the prophylaxis or treatment, in particular the treatment, of cancer.

The use of a compound of formula (I) as defined herein for the manufacture of a medicament for modulating (e.g. inhibiting) the activity of FGFR.

Use of a compound of formula (I) as defined herein in the manufacture of a medicament for modulating a cellular process (for example cell division) by inhibiting the activity of a FGFR kinase.

The use of a compound of the formula (I) as defined herein for the manufacture of a medicament for prophylaxis or treatment of a disease or condition characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of a cancer, the cancer being one which is characterised by up-regulation of a FGFR kinase (e.g. FGFR1 or FGFR2 or FGFR3 or FGFR4).

The use of a compound of the formula (I) as defined herein for the manufacture of a medicament for the prophylaxis or treatment of cancer in a patient selected from a sub-population possessing a genetic aberrations of FGFR3 kinase.

The use of a compound of the formula (I) as defined herein for the manufacture of a medicament for the prophylaxis or treatment of cancer in a patient who has been diagnosed as forming part of a sub-population possessing a genetic aberrations of FGFR3 kinase.

A method for the prophylaxis or treatment of a disease or condition characterised by up-regulation of a FGFR kinase (e.g. FGFR1 or FGFR2 or FGFR3 or FGFR4), the method comprising administering a compound of the formula (I) as defined herein.

A method for alleviating or reducing the incidence of a disease or condition characterised by up-regulation of a FGFR kinase (e.g. FGFR1 or FGFR2 or FGFR3 or FGFR4), the method comprising administering a compound of the formula (I) as defined herein.

A method for the prophylaxis or treatment of (or alleviating or reducing the incidence of) cancer in a patient suffering from or suspected of suffering from cancer; which method comprises (i) subjecting a patient to a diagnostic test to determine whether the patient possesses a genetic aberrations of FGFR3 gene; and (ii) where the patient does possess the said variant, thereafter administering to the patient a compound of the formula (I) as defined herein having FGFR3 kinase inhibiting activity.

A method for the prophylaxis or treatment of (or alleviating or reducing the incidence of) a disease state or condition characterised by up-regulation of an FGFR kinase (e.g. FGFR1 or FGFR2 or FGFR3 or FGFR4); which method comprises (i) subjecting a patient to a diagnostic test to detect a marker characteristic of up-regulation of a FGFR kinase (e.g. FGFR1 or FGFR2 or FGFR3 or FGFR4) and (ii) where the diagnostic test is indicative of up-regulation of a FGFR kinase, thereafter administering to the patient a compound of the formula (I) as defined herein having FGFR kinase inhibiting activity.

In one embodiment, the disease mediated by FGFR kinases is a oncology related disease (e.g. cancer). In one embodiment, the disease mediated by FGFR kinases is a non-oncology related disease (e.g. any disease disclosed herein excluding cancer). In one embodiment the disease mediated by FGFR kinases is a condition described herein. In one embodiment the disease mediated by FGFR kinases is a skeletal condition described herein. Particular abnormalities in human skeletal development, include abnormal ossification of cranial sutures (craniosynostosis), Apert (AP) syndrome, Crouzon syndrome, Jackson-Weiss syndrome, Beare-Stevenson cutis gyrate syndrome, Pfeiffer syndrome, achondroplasia and thanatophoric dwarfism (also known as thanatophoric dysplasia).

Mutated Kinases

Drug resistant kinase mutations can arise in patient populations treated with kinase inhibitors. These occur, in part, in the regions of the protein that bind to or interact with the particular inhibitor used in therapy. Such mutations reduce or increase the capacity of the inhibitor to bind to and inhibit the kinase in question. This can occur at any of the amino acid residues which interact with the inhibitor or are important for supporting the binding of said inhibitor to the target. An inhibitor that binds to a target kinase without requiring the interaction with the mutated amino acid residue will likely be unaffected by the mutation and will remain an effective inhibitor of the enzyme.

A study in gastric cancer patient samples showed the presence of two mutations in FGFR2, Ser167Pro in exon IIIa and a splice site mutation 940-2A-G in exon IIIc. These mutations are identical to the germline activating mutations that cause craniosynotosis syndromes and were observed in 13% of primary gastric cancer tissues studied. In addition activating mutations in FGFR3 were observed in 5% of the patient samples tested and overexpression of FGFRs has been correlated with a poor prognosis in this patient group.

In addition there are chromosomal translocations or point mutations that have been observed in FGFR which give rise to gain-of-function, over-expressed, or constitutively active biological states.

The compounds of the invention would therefore find particular application in relation to cancers which express a mutated molecular target such as FGFR. Diagnosis of tumours with such mutations could be performed using techniques known to a person skilled in the art and as described herein such as RTPCR and FISH.

It has been suggested that mutations of a conserved threonine residue at the ATP binding site of FGFR would result in inhibitor resistance. The amino acid valine 561 has been mutated to a methionine in FGFR1 which corresponds to previously reported mutations found in Abl (T315) and EGFR (T766) that have been shown to confer resistance to selective inhibitors. Assay data for FGFR1 V561M showed that this mutation conferred resistance to a tyrosine kinase inhibitor compared to that of the wild type.

Methods of Diagnosis

Prior to administration of a compound of the formula (I), a patient may be screened to determine whether a disease or condition from which the patient is or may be suffering is one which would be susceptible to treatment with a compound having activity against FGFR, and/or VEGFR.

For example, a biological sample taken from a patient may be analysed to determine whether a condition or disease, such as cancer, that the patient is or may be suffering from is one which is characterised by a genetic abnormality or abnormal protein expression which leads to up-regulation of the levels or activity of FGFR, and/or VEGFR or to sensitisation of a pathway to normal FGFR, and/or VEGFR activity, or to upregulation of these growth factor signalling pathways such as growth factor ligand levels or growth factor ligand activity or to upregulation of a biochemical pathway downstream of FGFR, and/or VEGFR activation.

Examples of such abnormalities that result in activation or sensitisation of the FGFR, and/or VEGFR signal include loss of, or inhibition of apoptotic pathways, up-regulation of the receptors or ligands, or presence of mutant variants of the receptors or ligands e.g PTK variants. Tumours with mutants of FGFR1, FGFR2 or FGFR3 or FGFR4 or up-regulation, in particular over-expression of FGFR1, or gain-of-function mutants of FGFR2 or FGFR3 may be particularly sensitive to FGFR inhibitors.

For example, point mutations engendering gain-of-function in FGFR2 have been identified in a number of conditions. In particular activating mutations in FGFR2 have been identified in 10% of endometrial tumours.

In addition, genetic aberrations of the FGFR3 receptor tyrosine kinase such as chromosomal translocations or point mutations resulting in ectopically expressed or deregulated, constitutively active, FGFR3 receptors have been identified and are linked to a subset of multiple myelomas, bladder and cervical carcinomas. A particular mutation T6741 of the PDGF receptor has been identified in imatinib-treated patients. In addition, a gene amplification of 8p12-p11.2 was demonstrated in 50% of lobular breast cancer (CLC) cases and this was shown to be linked with an increased expression of FGFR1. Preliminary studies with siRNA directed against FGFR1, or a small molecule inhibitor of the receptor, showed cell lines harbouring this amplification to be particularly sensitive to inhibition of this signalling pathway.

Alternatively, a biological sample taken from a patient may be analysed for loss of a negative regulator or suppressor of FGFR or VEGFR. In the present context, the term "loss" embraces the deletion of a gene encoding the regulator or suppressor, the truncation of the gene (for example by mutation), the truncation of the transcribed product of the gene, or the inactivation of the transcribed product (e.g. by point mutation) or sequestration by another gene product.

The term up-regulation includes elevated expression or over-expression, including gene amplification (i.e. multiple gene copies) and increased expression by a transcriptional effect, and hyperactivity and activation, including activation by mutations. Thus, the patient may be subjected to a diagnostic test to detect a marker characteristic of up-regulation of FGFR, and/or VEGFR. The term diagnosis includes screening. By marker we include genetic markers including, for example, the measurement of DNA composition to identify mutations of FGFR, and/or VEGFR. The term marker also includes markers which are characteristic of up regulation of FGFR and/or VEGFR, including enzyme activity, enzyme levels, enzyme state (e.g. phosphorylated or not) and mRNA levels of the aforementioned proteins.

The diagnostic tests and screens are typically conducted on a biological sample selected from tumour biopsy samples, blood samples (isolation and enrichment of shed tumour cells), stool biopsies, sputum, chromosome analysis, pleural fluid, peritoneal fluid, buccal spears, biopsy or urine.

Methods of identification and analysis of mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

Identification of an individual carrying a mutation in FGFR, and/or VEGFR may mean that the patient would be particularly suitable for treatment with a FGFR, and/or VEGFR inhibitor. Tumours may preferentially be screened for presence of a FGFR, and/or VEGFR variant prior to treatment. The screening process will typically involve direct sequencing, oligonucleotide microarray analysis, or a mutant specific antibody. In addition, diagnosis of tumours with such mutations could be performed using techniques known to a person skilled in the art and as described herein such as RT-PCR and FISH.

In addition, mutant forms of, for example FGFR or VEGFR2, can be identified by direct sequencing of, for example, tumour biopsies using PCR and methods to sequence PCR products directly as hereinbefore described. The skilled artisan will recognize that all such well-known techniques for detection of the over expression, activation or mutations of the aforementioned proteins could be applicable in the present case.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference. An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), *BMC Cancer,* 3:3). Briefly, the protocol is as follows: double-stranded cDNA is synthesized from total RNA Using a (dT)24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of FGFR, and/or VEGFR, or detection of FGFR, and/or VEGFR variants or mutants could be applicable in the present case.

Abnormal levels of proteins such as FGFR or VEGFR can be measured using standard enzyme assays, for example, those assays described herein. Activation or overexpression could also be detected in a tissue sample, for example, a tumour tissue. By measuring the tyrosine kinase activity with an assay such as that from Chemicon International. The tyrosine kinase of interest would be immunoprecipitated from the sample lysate and its activity measured.

Alternative methods for the measurement of the over expression or activation of FGFR or VEGFR including the isoforms thereof, include the measurement of microvessel density. This can for example be measured using methods described by Orre and Rogers (Int J Cancer (1999), 84(2) 101-8). Assay methods also include the use of markers, for example, in the case of VEGFR these include CD31, CD34 and CD105. Therefore all of these techniques could also be used to identify tumours particularly suitable for treatment with the compounds of the invention.

The compounds of the invention are particular useful in treatment of a patient having a mutated FGFR. The G697C mutation in FGFR3 is observed in 62% of oral squamous cell carcmonas and causes constitutive activation of the kinase activity. Activating mutations of FGFR3 have also been identified in bladder carcinoma cases. These mutations were of 6 kinds with varying degrees of prevelence: R248C, S249C, G372C, S373C, Y375C, K652Q. In addition, a Gly388Arg polymorphism in FGFR4 has been found to be associated with increased incidence and aggressiveness of prostate, colon, lung, liver (HCC) and breast cancer.

Therefore in a further aspect the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having activity against FGFR.

Particular mutations a patient is screened for include G697C, R248C, S249C, G372C, S373C, Y375C, K652Q mutations in FGFR3 and Gly388Arg polymorphism in FGFR4.

In another aspect the invention includes a compound of the invention for use in the prophylaxis or treatment of cancer in a patient selected from a sub-population possessing a variant of the FGFR gene (for example G697C mutation in FGFR3 and Gly388Arg polymorphism in FGFR4).

MRI determination of vessel normalization (e.g. using MRI gradient echo, spin echo, and contrast enhancement to measure blood volume, relative vessel size, and vascular permeability) in combination with circulating biomarkers (circulating progenitor cells (CPCs), CECs, SDF1, and FGF2) may also be used to identify VEGFR2-resistant tumours for treatment with a compound of the invention.

Pharmaceutical Compositions and Combinations

In view of their useful pharmacological properties, the subject compounds may be formulated into various pharmaceutical forms for administration purposes.

In one embodiment the pharmaceutical composition (e.g. formulation) comprises at least one active compound of the invention together with one or more pharmaceutically acceptable carriers, adjuvants, excipients, diluents, fillers, buffers, stabilisers, preservatives, lubricants, or other materials well known to those skilled in the art and optionally other therapeutic or prophylactic agents.

To prepare the pharmaceutical compositions of this invention, an effective amount of a compound of the present invention, as the active ingredient is combined in intimate admixture with a pharmaceutically acceptable carrier, which carrier may take a wide variety of forms depending on the form of preparation desired for administration. The pharmaceutical compositions can be in any form suitable for oral, parenteral, topical, intranasal, ophthalmic, otic, rectal, intravaginal, or transdermal administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets.

Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, to aid solubility for example, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient, calculated to produce the desired therapeutic effect, in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The compound of the invention is administered in an amount sufficient to exert its anti-tumour activity.

Those skilled in the art could easily determine the effective amount from the test results presented hereinafter. In general it is contemplated that a therapeutically effective amount would be from 0.005 mg/kg to 100 mg/kg body weight, and in particular from 0.005 mg/kg to 10 mg/kg body weight. It may be appropriate to administer the required dose as single, two, three, four or more sub-doses at appropriate intervals throughout the day. Said sub-doses may be formulated as unit dosage forms, for example, containing 0.5 to 500 mg, in particular 1 mg to 500 mg, more in particular 10 mg to 500 mg of active ingredient per unit dosage form.

Depending on the mode of administration, the pharmaceutical composition will preferably comprise from 0.05 to 99% by weight, more preferably from 0.1 to 70% by weight, even more preferably from 0.1 to 50% by weight of the compound of the present invention, and, from 1 to 99.95% by weight, more preferably from 30 to 99.9% by weight, even more preferably from 50 to 99.9% by weight of a pharmaceutically acceptable carrier, all percentages being based on the total weight of the composition.

As another aspect of the present invention, a combination of a compound of the present invention with another anti-cancer agent is envisaged, especially for use as a medicine, more specifically for use in the treatment of cancer or related diseases.

For the treatment of the above conditions, the compounds of the invention may be advantageously employed in combination with one or more other medicinal agents, more particularly, with other anti-cancer agents or adjuvants in cancer therapy. Examples of anti-cancer agents or adjuvants (supporting agents in the therapy) include but are not limited to:

platinum coordination compounds for example cisplatin optionally combined with amifostine, carboplatin or oxaliplatin;

taxane compounds for example paclitaxel, paclitaxel protein bound particles (Abraxane™) or docetaxel;

topoisomerase I inhibitors such as camptothecin compounds for example irinotecan, SN-38, topotecan, topotecan hcl;

topoisomerase II inhibitors such as anti-tumour epipodophyllotoxins or podophyllotoxin derivatives for example etoposide, etoposide phosphate or teniposide;

anti-tumour vinca alkaloids for example vinblastine, vincristine or vinorelbine;

anti-tumour nucleoside derivatives for example 5-fluorouracil, leucovorin, gemcitabine, gemcitabine hcl, capecitabine, cladribine, fludarabine, nelarabine;

alkylating agents such as nitrogen mustard or nitrosourea for example cyclophosphamide, chlorambucil, carmustine, thiotepa, mephalan (melphalan), lomustine, altretamine, busulfan, dacarbazine, estramustine, ifosfamide optionally in combination with mesna, pipobroman, procarbazine, streptozocin, telozolomide, uracil;

anti-tumour anthracycline derivatives for example daunorubicin, doxorubicin optionally in combination with dexrazoxane, doxil, idarubicin, mitoxantrone, epirubicin, epirubicin hcl, valrubicin;

molecules that target the IGF-1 receptor for example picropodophilin;

tetracarcin derivatives for example tetrocarcin A;

glucocorticoiden for example prednisone;

antibodies for example trastuzumab (HER2 antibody), rituximab (CD20 antibody), gemtuzumab, gemtuzumab ozogamicin, cetuximab, pertuzumab, bevacizumab, alemtuzumab, eculizumab, ibritumomab tiuxetan, nofetumomab, panitumumab, tositumomab, CNTO 328;

estrogen receptor antagonists or selective estrogen receptor modulators or inhibitors of estrogen synthesis for example tamoxifen, fulvestrant, toremifene, droloxifene, faslodex, raloxifene or letrozole;

aromatase inhibitors such as exemestane, anastrozole, letrazole, testolactone and vorozole;

differentiating agents such as retinoids, vitamin D or retinoic acid and retinoic acid metabolism blocking agents (RAMBA) for example accutane;

DNA methyl transferase inhibitors for example azacytidine or decitabine;

antifolates for example premetrexed disodium;

antibiotics for example antinomycin D, bleomycin, mitomycin C, dactinomycin, carminomycin, daunomycin, levamisole, plicamycin, mithramycin;

antimetabolites for example clofarabine, aminopterin, cytosine arabinoside or methotrexate, azacitidine, cytarabine, floxuridine, pentostatin, thioguanine;

apoptosis inducing agents and antiangiogenic agents such as Bcl-2 inhibitors for example YC 137, BH 312, ABT 737, gossypol, HA 14-1, TW 37 or decanoic acid;

tubuline-binding agents for example combrestatin, colchicines or nocodazole;

kinase inhibitors (e.g. EGFR (epithelial growth factor receptor) inhibitors, MTKI (multi target kinase inhibitors), mTOR inhibitors) for example flavoperidol, imatinib mesylate, erlotinib, gefitinib, dasatinib, lapatinib, lapatinib ditosylate, sorafenib, sunitinib, sunitinib maleate, temsirolimus;

farnesyltransferase inhibitors for example tipifarnib;

histone deacetylase (HDAC) inhibitors for example sodium butyrate, suberoylanilide hydroxamide acid (SAHA), depsipeptide (FR 901228), NVP-LAQ824, R306465, JNJ-26481585, trichostatin A, vorinostat;

Inhibitors of the ubiquitin-proteasome pathway for example PS-341, MLN 0.41 or bortezomib;

Yondelis;

Telomerase inhibitors for example telomestatin;

Matrix metalloproteinase inhibitors for example batimastat, marimastat, prinostat or metastat.

Recombinant interleukins for example aldesleukin, denileukin diftitox, interferon alfa 2a, interferon alfa 2b, peginterferon alfa 2b MAPK inhibitors Retinoids for example alitretinoin, bexarotene, tretinoin Arsenic trioxide Asparaginase Steroids for example dromostanolone propionate, megestrol acetate, nandrolone (decanoate, phenpropionate), dexamethasone Gonadotropin releasing hormone agonists or antagonists for example abarelix, goserelin acetate, histrelin acetate, leuprolide acetate Thalidomide, lenalidomide Mercaptopurine, mitotane, pamidronate, pegademase, pegaspargase, rasburicase BH3 mimetics for example ABT-737

MEK inhibitors for example PD98059, AZD6244, CI-1040 colony-stimulating factor analogs for example filgrastim, pegfilgrastim, sargramostim; erythropoietin or analogues thereof (e.g. darbepoetin alfa); interleukin 11; oprelvekin; zoledronate, zoledronic acid; fentanyl; bisphosphonate; palifermin.

a steroidal cytochrome P450 17alpha-hydroxylase-17,20-lyase inhibitor (CYP17), e.g. abiraterone, abiraterone acetate.

The compounds of the present invention also have therapeutic applications in sensitising tumour cells for radiotherapy and chemotherapy.

Hence the compounds of the present invention can be used as "radiosensitizer" and/or "chemosensitizer" or can be given in combination with another "radiosensitizer" and/or "chemosensitizer".

The term "radiosensitizer", as used herein, is defined as a molecule, preferably a low molecular weight molecule, administered to animals in therapeutically effective amounts to increase the sensitivity of the cells to ionizing radiation and/or to promote the treatment of diseases which are treatable with ionizing radiation.

The term "chemosensitizer", as used herein, is defined as a molecule, preferably a low molecular weight molecule, administered to animals in therapeutically effective amounts to increase the sensitivity of cells to chemotherapy and/or promote the treatment of diseases which are treatable with chemotherapeutics.

Several mechanisms for the mode of action of radiosensitizers have been suggested in the literature including: hypoxic cell radiosensitizers (e.g., 2-nitroimidazole compounds, and benzotriazine dioxide compounds) mimicking oxygen or alternatively behave like bioreductive agents under hypoxia; non-hypoxic cell radiosensitizers (e.g., halogenated pyrimidines) can be analogues of DNA bases and preferentially incorporate into the DNA of cancer cells and thereby promote the radiation-induced breaking of DNA molecules and/or prevent the normal DNA repair mechanisms; and various other potential mechanisms of action have been hypothesized for radiosensitizers in the treatment of disease.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

In view of their useful pharmacological properties, the components of the combinations according to the invention, i.e. the one or more other medicinal agent and the compound according to the present invention may be formulated into various pharmaceutical forms for administration purposes. The components may be formulated separately in individual pharmaceutical compositions or in a unitary pharmaceutical composition containing all components.

The present invention therefore also relates to a pharmaceutical composition comprising the one or more other medicinal agent and the compound according to the present invention together with a pharmaceutical carrier.

The present invention further relates to the use of a combination according to the invention in the manufacture of a pharmaceutical composition for inhibiting the growth of tumour cells.

The present invention further relates to a product containing as first active ingredient a compound according to the invention and as further active ingredient one or more anticancer agent, as a combined preparation for simultaneous, separate or sequential use in the treatment of patients suffering from cancer.

The one or more other medicinal agents and the compound according to the present invention may be administered simultaneously (e.g. in separate or unitary compositions) or sequentially in either order. In the latter case, the two or more compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The platinum coordination compound is advantageously administered in a dosage of 1 to 500 mg per square meter $(mg/m^2)$ of body surface area, for example 50 to 400 $mg/m^2$, particularly for cisplatin in a dosage of about 75 $mg/m^2$ and for carboplatin in about 300 $mg/m^2$ per course of treatment.

The taxane compound is advantageously administered in a dosage of 50 to 400 mg per square meter $(mg/m^2)$ of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

The camptothecin compound is advantageously administered in a dosage of 0.1 to 400 mg per square meter $(mg/m^2)$ of body surface area, for example 1 to 300 $mg/m^2$, particularly for irinotecan in a dosage of about 100 to 350 $mg/m^2$ and for topotecan in about 1 to 2 $mg/m^2$ per course of treatment.

The anti-tumour podophyllotoxin derivative is advantageously administered in a dosage of 30 to 300 mg per square meter $(mg/m^2)$ of body surface area, for example 50 to 250 $mg/m^2$, particularly for etoposide in a dosage of about 35 to 100 $mg/m^2$ and for teniposide in about 50 to 250 $mg/m^2$ per course of treatment.

The anti-tumour vinca alkaloid is advantageously administered in a dosage of 2 to 30 mg per square meter $(mg/m^2)$ of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

The anti-tumour nucleoside derivative is advantageously administered in a dosage of 200 to 2500 mg per square meter $(mg/m^2)$ of body surface area, for example 700 to 1500 $mg/m^2$, particularly for 5-FU in a dosage of 200 to 500 $mg/m^2$, for gemcitabine in a dosage of about 800 to 1200 $mg/m^2$ and for capecitabine in about 1000 to 2500 $mg/m^2$ per course of treatment.

The alkylating agents such as nitrogen mustard or nitrosourea is advantageously administered in a dosage of 100 to 500 mg per square meter $(mg/m^2)$ of body surface area, for example 120 to 200 $mg/m^2$, particularly for cyclophosphamide in a dosage of about 100 to 500 $mg/m^2$, for chlorambucil in a dosage of about 0.1 to 0.2 mg/kg, for carmustine in a dosage of about 150 to 200 $mg/m^2$, and for lomustine in a dosage of about 100 to 150 $mg/m^2$ per course of treatment.

The anti-tumour anthracycline derivative is advantageously administered in a dosage of to 75 mg per square meter $(mg/m^2)$ of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter $(mg/m^2)$ of body surface area, or as known in the art, if different. Trastuzumab is advantageously administered in a dosage of 1 to 5 mg per square meter $(mg/m^2)$ of body surface area, particularly 2 to 4 $mg/m^2$ per course of treatment.

These dosages may be administered for example once, twice or more per course of treatment, which may be repeated for example every 7, 14, 21 or 28 days.

The compounds of formula (I), the pharmaceutically acceptable addition salts, in particular pharmaceutically acceptable acid addition salts, and stereoisomeric forms thereof can have valuable diagnostic properties in that they can be used for detecting or identifying the formation of a complex between a labelled compound and other molecules, peptides, proteins, enzymes or receptors.

The detecting or identifying methods can use compounds that are labelled with labelling agents such as radioisotopes, enzymes, fluorescent substances, luminous substances, etc. Examples of the radioisotopes include $^{125}I$, $^{131}I$, $^{3}H$ and $^{14}C$. Enzymes are usually made detectable by conjugation of an appropriate substrate which, in turn catalyses a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase.

Biological samples can be defined as body tissue or body fluids. Examples of body fluids are cerebrospinal fluid, blood, plasma, serum, urine, sputum, saliva and the like.

General Synthetic Routes

The following examples illustrate the present invention but are examples only and are not intended to limit the scope of the claims in any way.

Experimental Part

Hereinafter, the term 'ACN' or $CH_3CN$ means acetonitrile, 'DCM' means dichloromethane, '$K_2CO_3$' means potassium carbonate, '$Cs_2CO_3$' means cesium carbonate, '$Na_2CO_3$' means sodium carbonate, '$MgSO_4$' means magnesium sulphate, '$Na_2SO_4$' means sodium sulphate, 'MeOH' or '$CH_3OH$' means methanol, 'EtOH' means ethanol, 'EtOAc' means ethyl acetate, '$Et_3N$' means triethylamine, 'THF' means tetrahydrofuran, '$NH_4Cl$' means ammonium chloride, 'NaI' means sodium iodide, 'NaOH' means sodium hydroxide, 'NaCl' means sodium chloride, 'DMF' means N,N-dimethylformamide, 'NaH' means sodium hydride, 60% dispersion in mineral oil, '$Pd(OAc)_2$' means palladium(II) acetate (47% Pd), '$PdCl_2(dppf).CH_2Cl_2$' means 1,1'-Bis(diphenylphosphino)ferrocene-palladium(II) dichloride dichloromethane complex, 'KOH' means potassium hydroxide, '$CO_2$' means carbon dioxide, '$Et_2O$' means diethyl ether, 'DMSO' means dimethyl sulfoxide, 'HCl' means hydrochloric acid, '$SiO_2$' or 'SiOH' means silica, '$N_2$' means nitrogen, 'MP' means melting point 'rt' means room temperature, '$CHCl_3$' means chloroform, '$POCl_3$' means phosphorus oxychloride, 'DiPEA' means N,N-diisopropylethylamine, 'Ni' means Raney Nickel, 50% slurry in water '$NaHCO_3$' means sodium hydrogen carbonate, 'TFA' means trifluoroacetic acid, 'DMAP' means 4-dimethylaminopyridine, '$NaBH_4$' means sodium borohydride, 'LiCl' means lithium chloride, 'Ruphos' means 2-Dicyclohexylphosphino-2',6'-diisopropoxybiphenyl, 'pH' means potential hydrogen, '$H_2$' means hydrogen, 'AlCl3' means aluminium trichloride, 'h' means hour; 'mn' means minute; 'Xantphos' means 4,5-Bis(diphenylphosphino)-9,9-dimethylxanthene, 'M.P.' means melting point; 'DSC' means differential scanning calorimetry.

Some compounds of the present invention were obtained as salt forms or hydrates or contain some amounts of solvent. Hereinafter, these compounds are reported as determined based on elemental analysis.

A. Preparation of the Intermediates

Example A1 a) Preparation of Intermediate 1

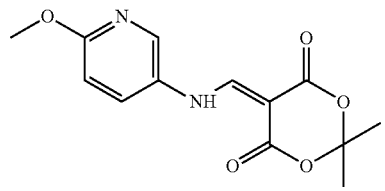

Under argon atmosphere, meldrum's acid (108 g, 752 mmol) and triethyl orthoformate (108 ml, 651 mmol) were added to a solution of 5-amino-2-methoxypyridine (62.2 g, 501 mmol) in ethanol (210 ml). The mixture was stirred at 80° C. for 3 hours and then cooled to room temperature and stirred overnight. The precipitate was filtered off, washed with ethanol (2×200 ml) and then was dried to afford 138 g (99%) of intermediate 1, that was used without further purification for the next step.

b) Preparation of Intermediate 2

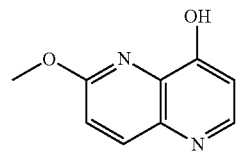

Intermediate 1 (13.6 g, 49.6 mmol) was added portionwise to diphenyl ether (100 ml, 630 mmol) at 220° C. The solution was stirred at reflux for 10 minutes and then cooled to room temperature. The combined precipitated solid were filtered off and washed with diethyl ether (2×500 ml) to give 45.6 g of a pale brown solid. The solid was triturated in diethyl ether (2×500 ml), filtered off and dried under vacuum to give 44 g (50%) of intermediate 2, that was used without further purification for the next step.

c) Preparation of Intermediate 3

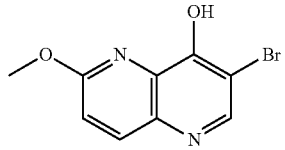

N-bromosuccinimide (57.8 g, 325 mmol) was added to a solution of intermediate 2 (44 g, 250 mmol) in acetic acid (800 ml) at room temperature. The mixture was stirred for 2 hours, was filtered off and washed successively with acetic acid (100 ml) and diethyl ether (2×500 ml), then dried to give 58.2 g (91%, beige solid) of intermediate 3, that was used without further purification for the next step.

d) Preparation of Intermediate 4

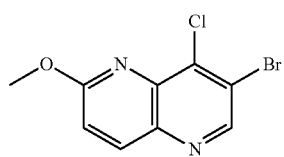

Phosphoryl chloride (213 ml, 2282 mmol) was added to a mixture of intermediate 3 (58.2 g, 228 mmol) in chloroform (213 ml). The solution was refluxed for 3 hours, concentrated till dryness and dried under vacuum. The residual solid was carefully basified with a 1M aqueous solution of sodium hydroxide (300 ml), diluted with water (300 ml) and extracted with ethyl acetate (6×500 ml). The combined organic layers were dried over sodium sulfate, filtered and concentrated, yielding 54.0 g (87%) of intermediate 4 that was used without further purification for the next step.

e) Preparation of Intermediate 5

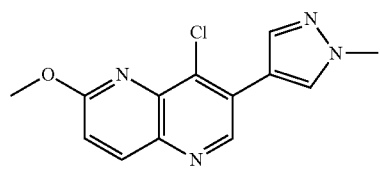

A solution of intermediate 4 (31.4 g, 115 mmol), 1-Methylpyrazole-4-boronic acid pinacol ester (25.1 g, 121 mmol), sodium carbonate (36.5 g, 344 mmol) in a mixture of 1,4-dioxane (400 ml) and water (120 ml) was degassed and filled with argon (operation repeated 3 times). $PdCl_2$ (dppf).$CH_2Cl_2$ (4.68 g, 5.74 mmol) was added and the resulting mixture was degassed and filled with argon (operation repeated twice) and stirred at 110° C. for 16 hours. After cooling to room temperature, ethyl acetate (500 ml) and water (500 ml) were added to the reaction mixture. The layers were separated and the aqueous layer was extracted with ethyl acetate (2×400 ml). The combined organic layers were dried over sodium sulfate, filtered and evaporated to dryness. The residue was sonicated in diethyl ether (500 ml), filtered on glass-frit, washed with diethyl ether (2×200 ml) and dried under vacuum, yielding 29.2 g (93%) of intermediate 5.

Analogous preparation of intermediate 22 starting from intermediate 24

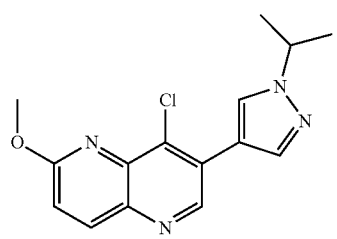 [SMILES: COc1ccc2ncc(-c3cnn(C(C)C)c3)c(Cl)c2n1]

Analogous preparation of intermediate 27 starting from intermediate 4

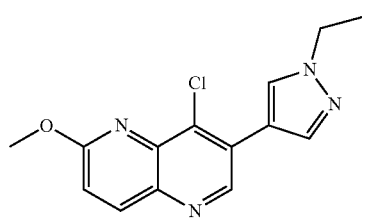 [SMILES: CCn1cc(-c2cnc3ccc(OC)nc3c2Cl)cn1]

Analogous preparation of intermediate 50 starting from intermediate 4

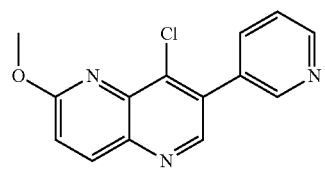 [SMILES: COc1ccc2ncc(-c3cccnc3)c(Cl)c2n1]

Analogous preparation of intermediate 56 starting from intermediate 4

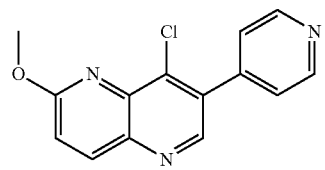 [SMILES: COc1ccc2ncc(-c3ccncc3)c(Cl)c2n1]

Analogous preparation of intermediate 70 starting from intermediate 4

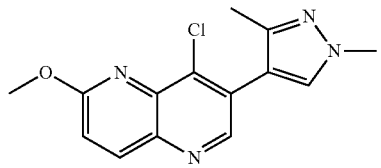

f) Preparation of Intermediate 6

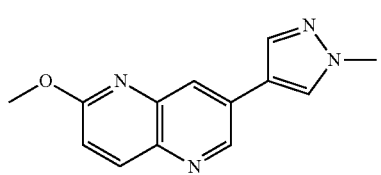

A catalytic amount of Raney Nickel (50% slurry in water, 1.68 g, 28.6 mmol) was washed twice with ethanol and collected after decantation. This catalytic amount was added to a solution of intermediate 5 (26.2 g, 95.4 mmol) in a mixture of ethanol (700 ml), tetrahydrofuran (500 ml) and 1M in NaOH (114 ml, 114 mmol). The mixture was purged and stirred under hydrogen atmosphere (1 bar) at 50° C. for 16 hours. An additional amount of Raney Nickel (50% slurry in water, 1.68 g, 28.6 mmol) was added and the reaction mixture was purged and stirred under hydrogen atmosphere (1 bar) at 50° C. for 24 hours. The mixture was cooled to room temperature, filtered through celite, washed with tetrahydrofuran (500 ml) and concentrated. The residue was triturated in diethyl ether (500 ml), the precipitate was filtered off and washed with diethyl ether (100 ml). The obtained product was adsorbed on silica gel and purified by chromatography over silica gel (mobile phase, gradient from 96% DCM, 4% MeOH to 94% DCM, 6% MeOH). The product fractions were collected and the solvent was evaporated, yielding 9.05 g (39%) of intermediate 6.

Analogous preparation of intermediate 21 starting from intermediate 22

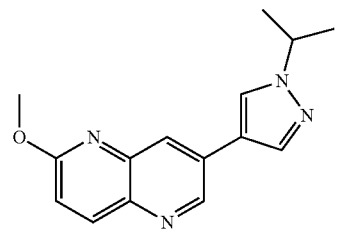 [SMILES: COc1ccc2ncc(-c3cnn(C(C)C)c3)cc2n1]

Analogous preparation of intermediate 26 starting from intermediate 27

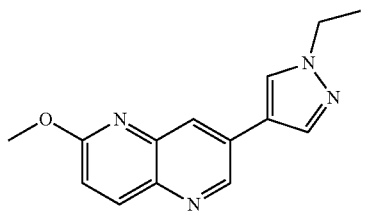 [SMILES: CCn1cc(-c2cnc3ccc(OC)nc3c2)cn1]

Analogous preparation of intermediate 49 starting from intermediate 50

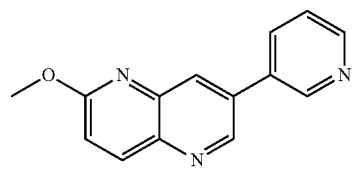 [SMILES: COc1ccc2ncc(-c3cccnc3)cc2n1]

Analogous preparation of intermediate 55 starting from intermediate 56

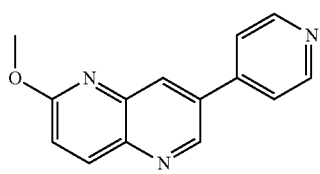 [SMILES: COc1ccc2ncc(-c3ccncc3)cc2n1]

Analogous preparation of intermediate 69 starting from intermediate 70

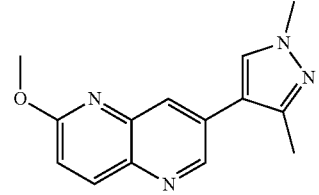 [SMILES: COc1ccc2ncc(-c3cn(C)nc3C)cc2n1]

Intermediate 6 was also prepared as follows:

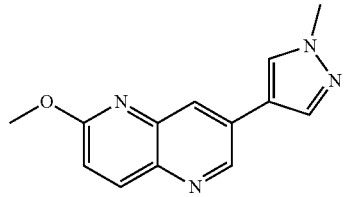 [SMILES: COc1ccc2ncc(-c3cnn(C)c3)cc2n1]

The reaction was performed in parallel in 3 batches (3×21.2 g).

A catalytic amount of Raney Nickel, 50% slurry in water (2.72 g; 46.3 mmol) was washed twice with ethanol and collected after decantation. This catalytic amount was added to a solution of intermediate 5 (21.2 g; 77.3 mmol) in a mixture of EtOH (400 mL), THF (400 mL) and NaOH 1M (81.3 mL; 81.3 mmol). The mixture was purged and stirred under hydrogen atmosphere (1 bar) at 50° C. for 90 hours. The 3 reactions were combined and the resulting mixture was cooled to room temperature, filtered through a pad of Celite®, washed with EtOH (1000 mL), then with THF (300 mL) and concentrated. The residue (63.9 g, brown solid) was purified several times by column chromatography over silica gel (eluent: petroleum ether/ethyl acetate 50/50 to 0/100). The product fractions were collected and the solvent was evaporated to give 31.2 g (56%, beige solid) of intermediate 6.

g) Preparation of Intermediate 7

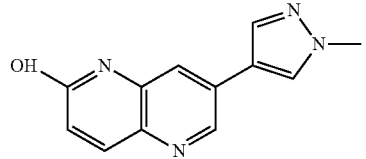 [SMILES: Cn1cc(-c2cnc3ccc(O)nc3c2)cn1]

6M aqueous HCl (94 ml, 564 mmol) was added to a solution of intermediate 6 (9.0 g, 37.6 mmol) in 1,4-dioxane (200 ml). The mixture was stirred at 80° C. for 3 hours, cooled down to room temperature and concentrated. The residue was suspended in a mixture of water, dichloromethane and methanol (300 ml; 3/2/1). The mixture was basified with a 3N aqueous solution of NaOH until pH=9 and the resulting solution was concentrated, yielding 13.7 g (161%) of intermediate 7, which was used without further purification for the next step.

Analogous preparation of intermediate 20 starting from intermediate 21

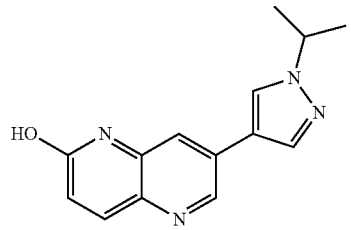 [SMILES: CC(C)n1cc(-c2cnc3ccc(O)nc3c2)cn1]

Analogous preparation of intermediate 25 starting from intermediate 26

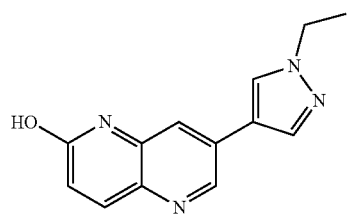 [SMILES: CCn1cc(-c2cnc3ccc(O)nc3c2)cn1]

Analogous preparation of intermediate 48 starting from intermediate 49

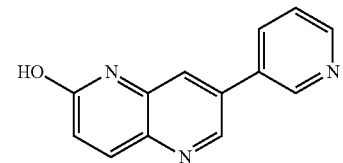 [SMILES: Oc1ccc2ncc(-c3cccnc3)cc2n1]

Analogous preparation of intermediate 54 starting from intermediate 55

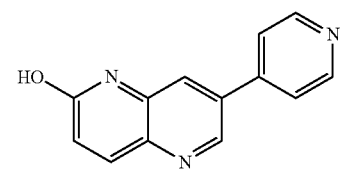 [SMILES: Oc1ccc2ncc(-c3ccncc3)cc2n1]

Analogous preparation of intermediate 68 starting from intermediate 69

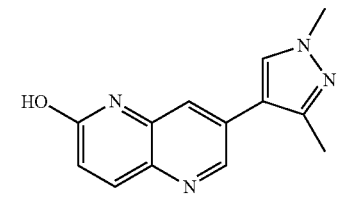 [SMILES: Cc1nn(C)cc1-c1cnc2ccc(O)nc2c1]

Intermediate 7 was also prepared as follows;

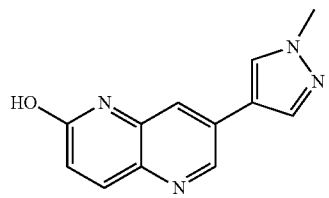 [SMILES: Cn1cc(-c2cnc3ccc(O)nc3c2)cn1]

Aqueous HCl 6M (44 mL; 266 mmol) was added to a solution of intermediate 6 (4.26 g; 17.7 mmol) in dioxane (85 mL). The mixture was stirred at 80° C. for 3 hours, cooled to room temperature and quenched with an aqueous saturated solution of potassium carbonate (300 mL). The precipitated solid was filtered off, washed with water (400 mL) and Et$_2$O (200 mL) affording fraction A (hydrated intermediate 7). The filtrate was extracted with a 9/1 mixture of CH$_2$Cl$_2$/MeOH (4×1 L). Fraction A was added to the combined organic layers. The resulting mixture was evaporated. The residual solid was suspended in methanol and concentrated to afford 5.22 g of intermediate 7 which was used as such in the next step.

h) Preparation of Intermediate 8

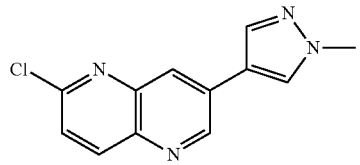 [SMILES: Cn1cc(-c2cnc3ccc(Cl)nc3c2)cn1]

The reaction was performed under argon.

Phosphoryl chloride (200 ml, 2146 mmol) was added to a suspension of intermediate 7 (crude 13.7 g, maximum 37.6 mmol) in chloroform (200 ml). The reaction mixture was refluxed for 16 hours, cooled to room temperature and concentrated. The residual solid was taken up in a mixture of dichloromethane/methanol 95/5 (300 ml), slowly basified at 0° C. with a 3M aqueous solution of sodium hydroxide (60 ml) and diluted with water (100 ml). The aqueous layer was extracted with a mixture of dichloromethane/methanol 95/5 (2×150 ml). The combined organic layers were dried over sodium sulfate, filtered and concentrated. The obtained residue was dissolved in a mixture of dichloromethane and methanol (400 ml; 3/1), adsorbed on silica gel and purified by chromatography over silica gel (mobile phase, gradient from 97% DCM, 3% MeOH to 95% DCM, 5% MeOH). The product fractions were collected and the solvent was evaporated, yielding 6.15 g (67%) of intermediate 8, which was used without further purification for the next step.

Analogous preparation of intermediate 19 starting from intermediate 20

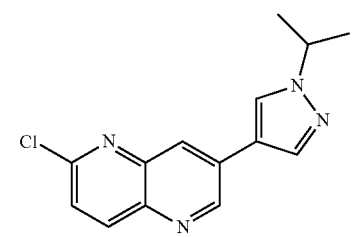 [SMILES: CC(C)n1cc(-c2cnc3ccc(Cl)nc3c2)cn1]

Analogous preparation of intermediate 24 starting from intermediate 25

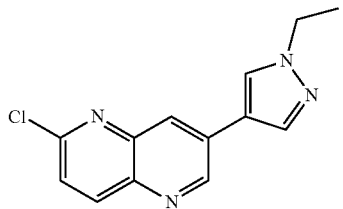 [SMILES: CCn1cc(-c2cnc3ccc(Cl)nc3c2)cn1]

Analogous preparation of intermediate 47 starting from intermediate 48

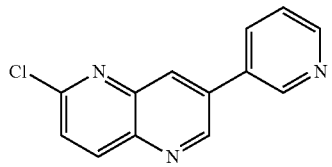 [SMILES: Clc1ccc2ncc(-c3cccnc3)cc2n1]

Analogous preparation of intermediate 53 starting from intermediate 54

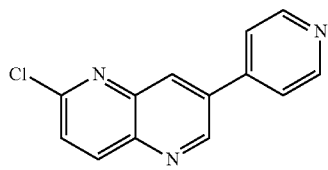 [SMILES: Clc1ccc2ncc(-c3ccncc3)cc2n1]

Analogous preparation of intermediate 67 starting from intermediate 68

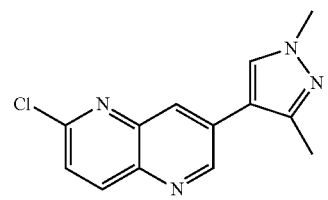 [SMILES: Cc1nn(C)cc1-c1cnc2ccc(Cl)nc2c1]

Intermediate 8 was also prepared as follows:

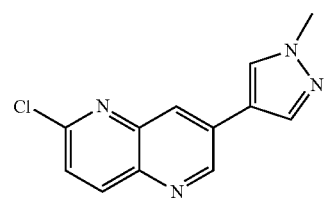 [SMILES: Cn1cc(-c2cnc3ccc(Cl)nc3c2)cn1]

POCl$_3$ (18.5 mL; 199 mmol) was added to a suspension of intermediate 7 (4.5 g; 19.9 mmol) in CHCl$_3$ (19 mL). The reaction mixture was refluxed for 3 hours, cooled to room temperature and concentrated. The residual solid was taken up in a mixture of DCM/MeOH 97/3 (500 mL) and washed with a 1M aqueous solution of sodium hydroxide (500 mL). The aqueous layer was extracted with a mixture of DCM/MeOH 97/3 (2×250 mL). The combined organic layers were washed with brine, dried over Na$_2$SO$_4$, filtered and concentrated to give 3.61 g (74%, yellow solid) of intermediate 8.

i) Preparation of Intermediate 9

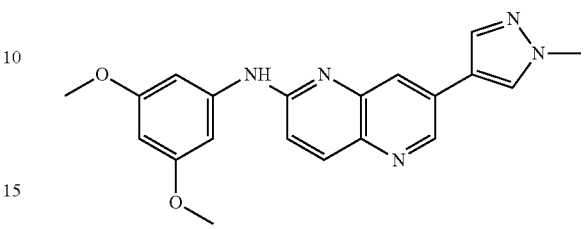

3,5-Dimethoxyaniline (1.25 g, 8.2 mmol) was added to a solution of intermediate 8 (1.0 g, 4.1 mmol) in 1-propanol (70 ml). The reaction mixture was refluxed for 16 hours. The resulting precipitate was filtered off, rinsed with 1-propanol (15 ml), diethylether (20 ml) and dried under vacuum, yielding 1.02 g (69%) of intermediate 9.

The filtrate was concentrated under reduced pressure till dryness. The residue was dissolved in a mixture of dichloromethane and methanol (50 ml; 4/1) and purified by chromatography over silica gel (mobile phase, gradient from 96% DCM, 4% MeOH to 94% DCM, 6% MeOH). The product fractions were collected and the solvent was evaporated yielding 0.456 g (31%) of intermediate 9.

Analogous preparation of intermediate 18 starting from intermediate 19

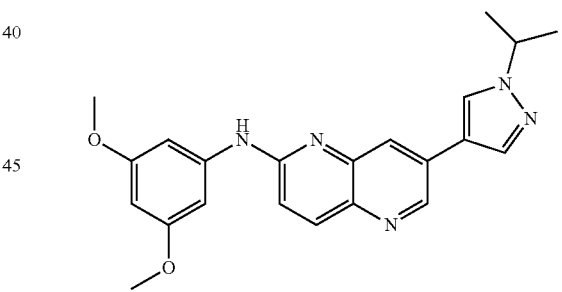

Analogous preparation of intermediate 23 starting from intermediate 24

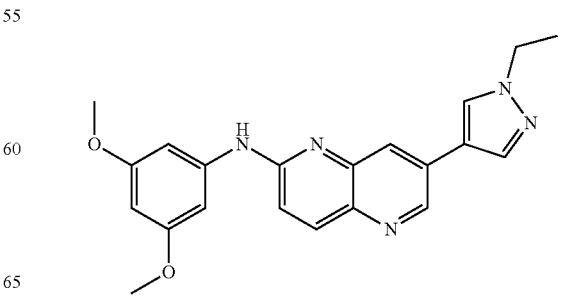

Analogous preparation of intermediate 32 starting from intermediate 8

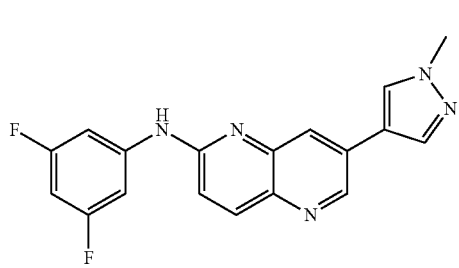 [SMILES: Cn1cc(-c2cnc3ccc(Nc4cc(F)cc(F)c4)nc3c2)cn1]

Analogous preparation of intermediate 33 starting from intermediate 8

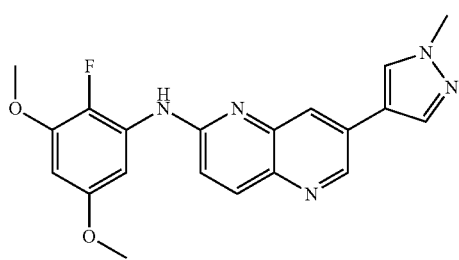 [SMILES: COc1cc(Nc2ccc3ncc(-c4cnn(C)c4)cc3n2)c(F)c(OC)c1]

Analogous preparation of intermediate 46 starting from intermediate 47

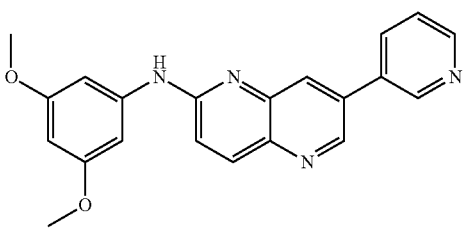 [SMILES: COc1cc(Nc2ccc3ncc(-c4cccnc4)cc3n2)cc(OC)c1]

Analogous preparation of intermediate 52 starting from intermediate 53

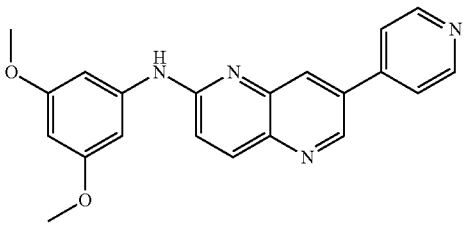 [SMILES: COc1cc(Nc2ccc3ncc(-c4ccncc4)cc3n2)cc(OC)c1]

Analogous preparation of intermediate 66 starting from intermediate 67

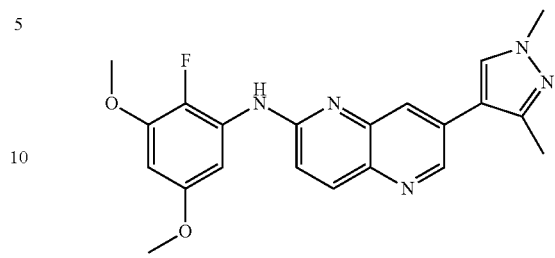

Alternative preparation of intermediate 9

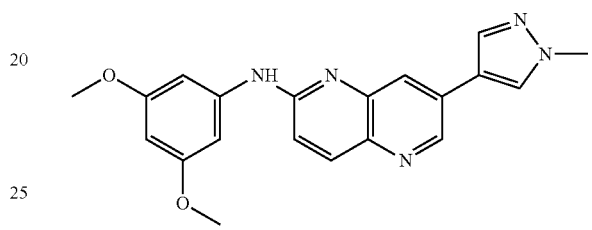

The reaction was performed 5 time on same amounts in parallel.

Palladium (II) acetate (0.069 g, 0.1 mmol) was added to a mixture of intermediate 8 (0.72 g, 2.9 mmol), 3,5-dimethoxyaniline (0.9 g, 5.9 mmol), cesium carbonate (4.8 g, 14.7 mmol) and 2,2'-bis(diphenylphosphino)-1,1'-binaphthyl (0.366 g, 0.59 mmol) in a 50/50 (v/v) mixture of NMP and 1,4-dioxane (15.0 ml). The mixture was stirred at 150° C. for 30 minutes under microwave irradiation and was concentrated. The combined residues of 5 experiments were purified by chromatography over silica gel (mobile phase: gradient from 100% DCM to 96% DCM, 4% MeOH). The product fractions were collected and the solvent was evaporated yielding 4.57 g (86%) of crude intermediate 9. A sample (0.4 g) was purified by chromatography over silica gel (mobile phase: gradient from 100% DCM to 98% DCM, 2% MeOH). The desired fractions were collected and the solvent was evaporated. to afford 0.187 g green solid (MP: 229-230° C.)

Example A2

Preparation of Intermediate 10

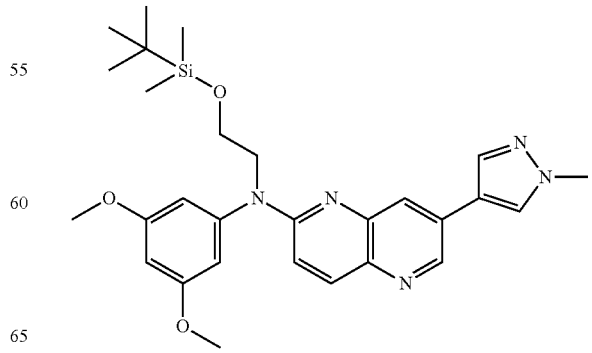

The reaction was performed in anhydrous conditions under argon atmosphere. NaH (60% in mineral oil, 0.332 g, 8.30 mmol) was added to a solution of intermediate 9 (2.0 g, 5.5 mmol) in dimethylformamide (50 ml) at 0° C. The mixture was stirred at 0° C. for 40 minutes, then (2-bromoethoxy)-tert-butyl-dimethylsilane (1.78 ml, 8.3 mmol) was added at 0° C. The mixture was stirred at 0° C. for 1 hour and at room temperature overnight. Ice water (800 g) was added and the mixture was extracted with ethyl acetate (1×800 ml and 2×400 ml). The combined organic layers were washed with brine (3×400 ml), dried over sodium sulfate, filtered and concentrated, yielding 3.17 g (110%) of intermediate 10, which was used without further purification for the next step.

Analogous Preparation of Intermediate 11

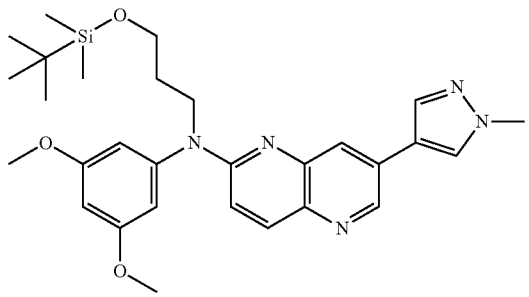

Analogous preparation of intermediate 31 starting from intermediate 28

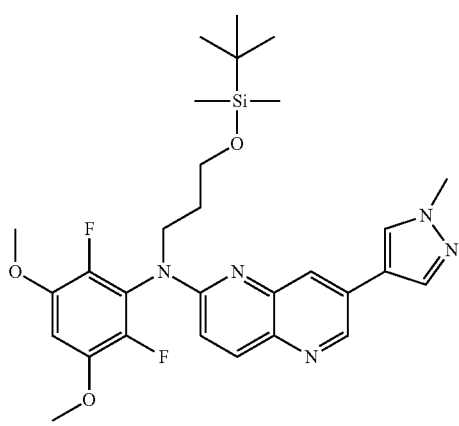 [SMILES: COc1cc(OC)c(F)c(N(CCCO[Si](C)(C)C(C)(C)C)c2ccc3ncc(-c4cnn(C)c4)cc3n2)c1F]

Example A2a

Preparation of Intermediate 51

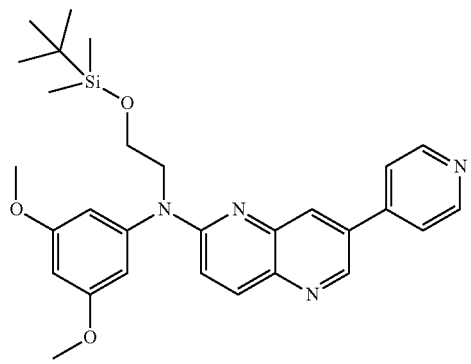 [SMILES: COc1cc(OC)cc(N(CCO[Si](C)(C)C(C)(C)C)c2ccc3ncc(-c4ccncc4)cc3n2)c1]

NaH (11.2 mg; 0.279 mmol) was added to a mixture of intermediate 52 (0.050 g; 0.140 mmol) in DMF (2 mL) at 0° C. The mixture was stirred at 0° C. for 30 minutes, then (2-bromoethoxy)-tert-butyldimethylsilane (6 μL; 0.279 mmol) was added at 0° C. The mixture was stirred at 0° C. for 30 minutes and at room temperature for 72 hours. Additional NaH (11.2 mg; 0.279 mmol) was added at 0° C. The mixture was stirred at 0° C. for 30 minutes and (2-bromoethoxy)-tert-butyldimethylsilane (6 μL; 0.279 mmol) was added. The mixture was stirred at 00° C. for 30 minutes and 65 hours at room temperature. Ice water (5 mL) was added and the mixture was extracted with EtOAc (3×10 mL). The combined organic layers were washed with brine (3×10 mL), dried over Na$_2$SO$_4$, filtered and concentrated. The residue (0.118 g) was purified by column chromatography over silica gel (eluent: DCM/MeOH: from 99/1 to 98/2). The product fractions were collected and the solvent was evaporated to give 0.04 g (56%, yellow solid) of intermediate 51.

Example A3

Preparation of Intermediate 12

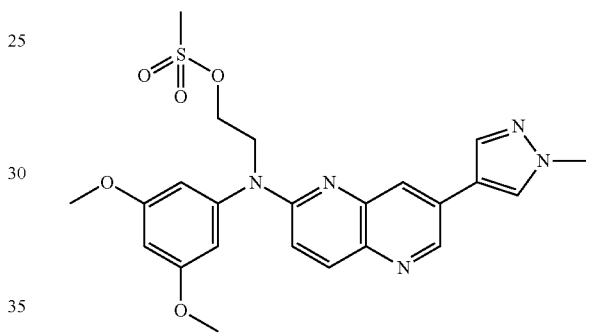

The reaction was performed in anhydrous conditions under argon atmosphere. Methanesulfonyl chloride (0.04 ml, 0.51 mmol) was added dropwise to a mixture of compound 1 (0.104 g, 0.26 mmol), triethylamine (0.083 ml, 0.59 mmol) and 4-dimethyl-aminopyridin (0.004 g, 0.031 mmol) in dichloromethane (2.10 ml) at 00° C. The mixture was stirred at 0° C. for 10 minutes and at room temperature overnight. Ice water (25 ml) was added and the mixture was extracted with dichloromethane (4×25 ml). The combined organic layers were dried over sodium sulfate, filtered and concentrated. The aqueous layer was concentrated to dryness, yielding 0.153 g (123%) of intermediate 12, which was used without further purification for the next step.

Example A4

Preparation of Intermediate 12

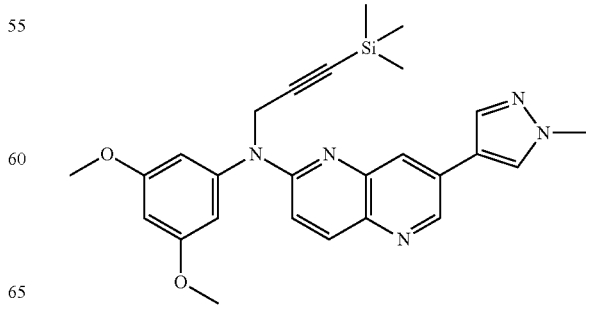

The reaction was performed in anhydrous conditions under argon atmosphere. NaH (60% in mineral oil, 0.355 g, 8.86 mmol) was added portionwise to a solution of intermediate 9 (1.60 g, 4.43 mmol) in N,N-dimethylformamide (12.7 ml) at 0° C. The mixture was stirred at 0° C. for 30 minutes and 3-bromo-1-trimethylsilyl-1-propyne (2.03 ml, 12.4 mmol) was added dropwise. The mixture was stirred at 0° C. for 3 hours. Water (450 ml) was added and the mixture was extracted with ethyl acetate (4×200 ml). The combined organic layers were dried over sodium sulfate, filtered and concentrated. The residue (6.12 g) was purified by chromatography over silica gel (mobile phase, gradient from 100% DCM to 95% DCM, 5% MeOH). The product fractions were collected and the solvent was evaporated, yielding 1.60 g (77%) of intermediate 13.

Example A5 a) Preparation of Intermediate 14

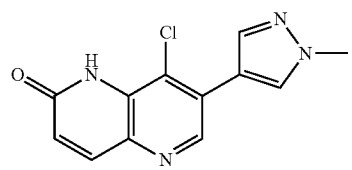 [SMILES: Cn1cc(-c2cnc3ccc(=O)[nH]c3c2Cl)cn1]

A 6M HCl solution (16.4 ml, 98.3 mmol) was added to a solution of intermediate 5 (1.8 g, 6.55 mmol) in 1,4-dioxane (30 ml) at room temperature. The reaction mixture was heated at 80° C. for 16 hours. The reaction mixture was basified (pH=8) with a 3M NaOH solution (35 ml) and extracted with a 9/1 mixture of DCM and MeOH. The organic layers were dried over $Na_2SO_4$, filtered and concentrated to dryness. The residue was purified by chromatography over silica gel (40-63 μm, mobile phase, gradient from 100% DCM to 85% DCM, 15% MeOH). The product fractions were evaporated to dryness, yielding 1.17 g (68%) of intermediate 14.

b) Preparation of Intermediate 15

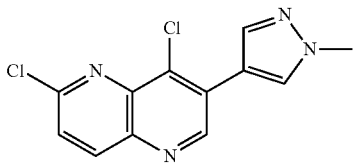 [SMILES: Cn1cc(-c2cnc3ccc(Cl)nc3c2Cl)cn1]

Phosphoryl chloride (16 ml, 172 mmol) was added to a solution of intermediate 14 (1.2 g, 4.6 mmol) in chloroform (16 ml) at room temperature. The reaction mixture was refluxed for 16 hours, cooled down to room temperature and concentrated to dryness. The residue was taken up in a 95/5 mixture of DCM and MeOH (30 ml), cooled to 0° C. and carefully basified with a 3M NaOH solution (10 ml). The mixture was diluted with water (10 ml) and extracted twice with a 95/5 mixture of DCM and MeOH. The combined organic layers were dried over $Na_2SO_4$, filtered and concentrated to dryness. The residual solid was triturated in $Et_2O$ (50 ml), filtered, rinsed with $Et_2O$ and dried under vacuum yielding 1.15 g (89%) of intermediate shown.

c) Preparation of Intermediate 16

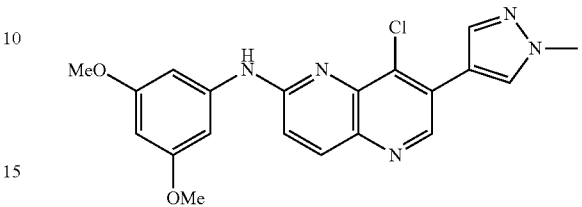

3,5-Dimethoxyaniline (587 mg, 3.83 mmol) and N,N-diisopropylethylamine (1.34 ml, 7.67 mmol) were added to a suspension of 2,8-dichloro-7-(1-methyl-1H-pyrazol-4-yl)-1,5-naphthyridine (1.07 g, 3.83 mmol) in 1-propanol (30 ml). The mixture was refluxed for 16 hours. 3,5-Dimethoxyaniline (176 mg, 1.15 mmol) and N,N-diisopropylethylamine (1.34 ml, 7.67 mmol) were added again, and the mixture was refluxed for 4 hours. 3,5-Dimethoxyaniline (176 mg, 1.15 mmol) was added, the mixture was refluxed for 16 hours and cooled down to room temperature. The precipitate was filtered off, washed with EtOH and dried under vacuum. The solid was taken up with a saturated aqueous solution of $NaHCO_3$ (100 ml) and extracted with a 9/1 mixture of DCM and MeOH. The combined organic layers were dried over $Na_2SO_4$, filtered, concentrated to dryness and dried under vacuum for 16 hours yielding 840 mg (55%) of intermediate 16 which was used without further purification for the next step.

d) Preparation of Intermediate 17

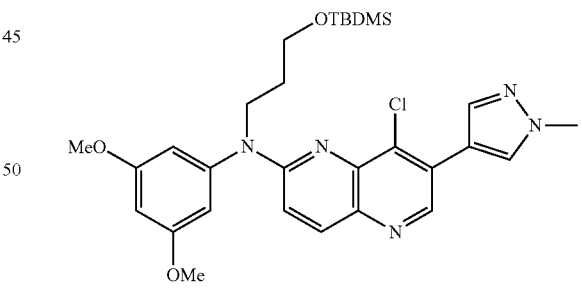

Sodium hydride (60% in mineral oil, 91 mg, 2.3 mmol) was added to a solution of intermediate 16 (300 mg, 0.76 mmol) in DMF (7.5 ml) at 0° C. The mixture was stirred at 0° C. for 45 minutes and (3-bromopropoxy)-tert-butyldimethylsilane (0.264 ml, 1.14 mmol) was added. The mixture was stirred at 0° C. for 2 hours and at room temperature overnight. Water was added and the mixture was extracted with DCM. The combined organic layers were washed with brine, dried over $Na_2SO_4$, filtered and concentrated to dryness yielding 616 mg of intermediate 17 which was used without further purification for the next step.

Analogous preparation of intermediate 29 starting from intermediate 16

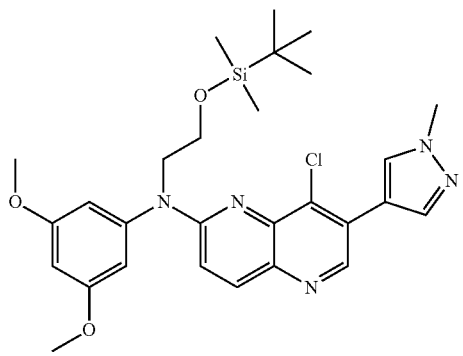 [SMILES: COc1cc(OC)cc(N(CCO[Si](C)(C)C(C)(C)C)c2ccc3ncc(-c4cnn(C)c4)c(Cl)c3n2)c1]

Example A6

Preparation of Intermediate 30

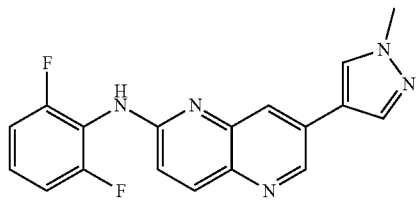 [SMILES: Cn1cc(-c2cnc3ccc(Nc4c(F)cccc4F)nc3c2)cn1]

Potassium bis(trimethylsilyl)amide 1M in THF (6.29 mL; 6.29 mmol) was added to a solution of 2,6-difluoroaniline (0.369 mL; 3.43 mmol) in THF (8 mL) at 00° C. The mixture was stirred at 0° C. for 1 hour and intermediate 8 (0.700 g; 2.86 mmol) was added. The mixture was stirred at 0° C. for 2 hours and at room temperature overnight. Water (200 mL) was added and the mixture was extracted with EtOAc (3×100 mL). The organic layer was dried over $Na_2SO_4$, filtered and concentrated. The residue (1 g, brown solid) was purified by column chromatography over silica gel (eluent: from 100% DCM to 99% DCM, 1% MeOH). The product fractions were collected and the solvent was evaporated to give 0.901 g (93%) of intermediate 30. MP: 209° C. (DSC).

Analogous preparation of intermediate 28 starting from intermediate 8

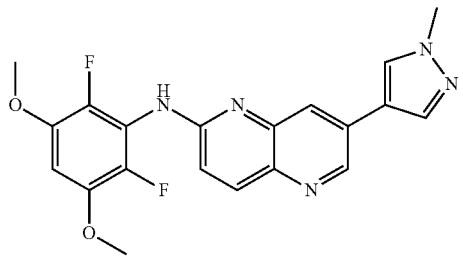 [SMILES: COc1cc(OC)c(F)c(Nc2ccc3ncc(-c4cnn(C)c4)cc3n2)c1F]

Analogous preparation of intermediate 36 starting from intermediate 8

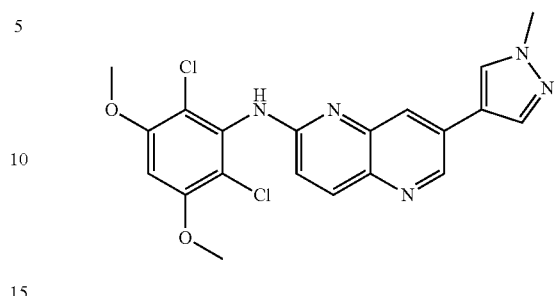

Example A7 a) Preparation of Intermediate 35

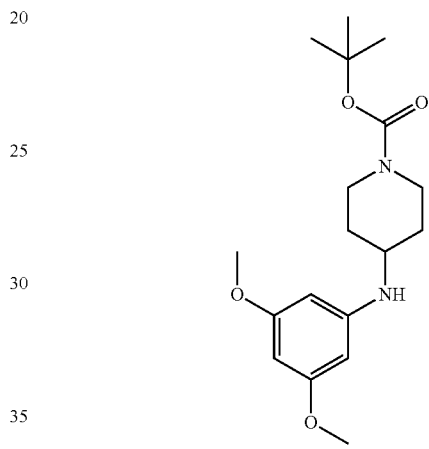

Sodium triacetoxyborohydride (6.82 g; 32.2 mmol) and acetic acid (0.6 mL) were added to a mixture of 3,5-dimethoxyaniline (3.08 g; 20.1 mmol) and 1-boc-4-piperidone (4.00 g; 20.1 mmol) in dichloroethane (150 mL) at 0° C. The mixture was stirred at room temperature for 65 hours. Ice water (150 mL) and an aqueous saturated solution of $K_2CO_3$ (400 mL) were added and the mixture was extracted with DCM (4×200 mL). The combined organic layers were dried over $Na_2SO_4$, filtered and concentrated to give 6.80 g (100%, white solid) of intermediate 35. The product was used as such in the next step.

b) Preparation of Intermediate 34

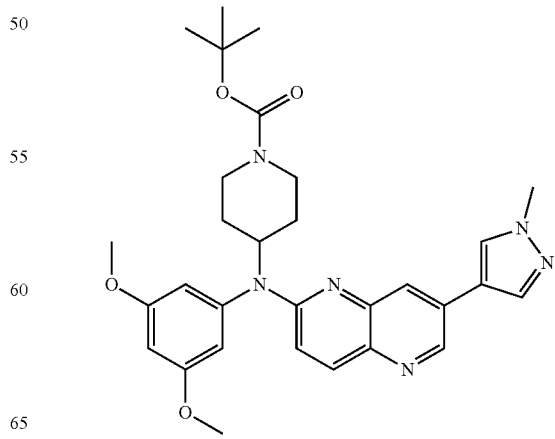

Pd(OAc)$_2$ (0.02 g; 0.08 mmol) was added to a mixture of intermediate 8 (0.40 g; 1.63 mmol), intermediate 35 (0.77 g; 2.28 mmol), Cs$_2$CO$_3$ (1.59 g; 4.89 mmol) and Ruphos (0.01 g; 0.02 mmol) in dioxane (6 mL). The mixture was heated at 100° C. overnight. Water (200 mL) was added and the mixture was extracted with DCM (4×150 mL). The combined organic layers were dried over Na$_2$SO$_4$, filtered and concentrated. The residue was purified by column chromatography over silica gel (eluent: DCM/MeOH 100/0 to 95/5). The product fractions were collected and concentrated to give 0.30 g of intermediate 34 (purity 12%, contaminated by 88% of intermediate 8).

Example A8 a) Preparation of Intermediate 38

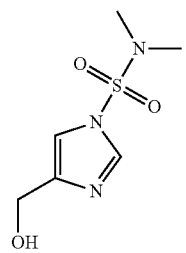

Sodium borohydride (0.994 g; 26.28 mmol) was added portion wise to a solution of 4-formyl-N, N-dimethyl-1H-imidazole-1-sulfonamide (CAS 140174-48-7) (4.45 g; 21.9 mmol) in MeOH (45 mL) at 5° C. under N$_2$ flow. The reaction mixture was then stirred at room temperature for 2 hours, poured onto ice water, extracted with DCM, dried over MgSO$_4$, filtered and evaporated to dryness. The residue was crystallized from Et$_2$O. The precipitate was filtered and dried yielding 2.5 g (56%) of intermediate 38 M.P.: 99° C. (Kofler).

b) Preparation of Intermediate 37

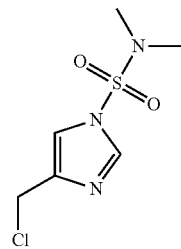

Methanesulfonyl chloride (0.249 mL; 3.22 mmol) and LiCl (0.341 g; 8.04 mmol) were added to a solution of intermediate 38 (0.550 g; 2.68 mmol) and Et$_3$N (0.747 mL; 5.36 mmol) in THF (6 mL) at 0° C. The mixture was stirred at 0° C. for 1 hour and at room temperature for 3 hours. Water (100 mL) was added and the mixture was extracted with EtOAc (3×50 mL). The combined organic layers were washed with brine (75 mL), dried over Na$_2$SO$_4$, filtered and concentrated to give 0.597 g (100%, yellow oil with tendency to crystallize) (stored at 4° C.) of intermediate 37. The product was used as such in the next step.

Example A9

Preparation of Intermediate 39

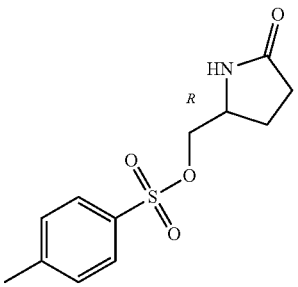

Et$_3$N (7.46 mL; 52.11 mmol), p-toluenesulfonyl chloride (9.94 g; 52.11 mmol) and DMAP (531 mg; 4.34 mmol) were added successively to a solution of (R)-(−)5-(hydroxymethyl)-2-pyrrolidinone (CAS 66673-40-3) (5 g; 43.43 mmol) in DCM (75 mL) at 5° C. under N$_2$ flow. The reaction mixture was stirred at room temperature for 2 hours. An aqueous solution of HCl 1N was added. The mixture was extracted with DCM (3 times). The organic layer was dried over MgSO$_4$, filtered and the solvent was evaporated to dryness. The residue was taken up in ACN, filtered, washed with Et$_2$O and dried yielding 8.44 g (72%) of intermediate 39.

Example A10

Preparation of Intermediate 41

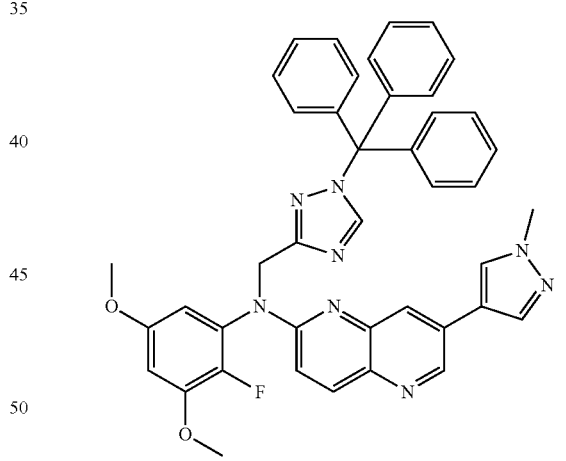

NaH (0.105 g; 2.64 mmol) was added to a solution of intermediate 33 (0.5 g; 1.32 mmol) in DMF (13 mL) at 0° C. The mixture was stirred at 0° C. for 45 minutes and 1H-1,2,4-Triazole-3-methanol, 1-(triphenylmethyl)-,3-methanesulfonate (CAS: 163009-16-3) (1.11 g; 2.64 mmol) was added portion wise. The mixture was stirred at 0° C. for 30 minutes and at room temperature for 16 hours. EtOAc (100 mL) was added and the mixture was washed with brine (3×100 mL). The organic layer was dried over Na$_2$SO$_4$, filtered and concentrated. The residue (1.54 g, orange foam) was purified by column chromatography over silica gel (eluent: DCM/MeOH 99/1 to 95/5). The product fractions were collected and the solvent was evaporated to give 0.785 g (85%, yellow foam) of intermediate 41.

Analogous preparation of intermediate 40 starting from intermediate 9

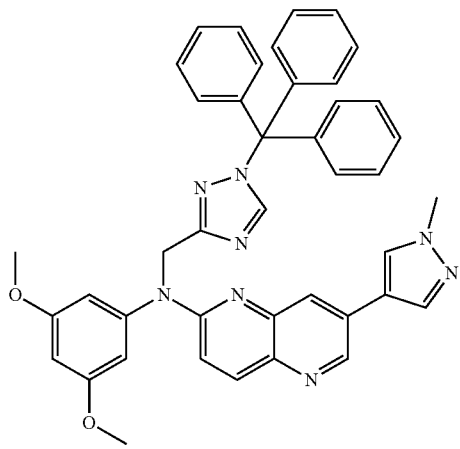 [SMILES: COc1cc(OC)cc(N(Cc2ncn(C(c3ccccc3)(c3ccccc3)c3ccccc3)n2)c2ccc3ncc(-c4cnn(C)c4)cc3n2)c1]

Analogous preparation of intermediate 42 starting from intermediate 28

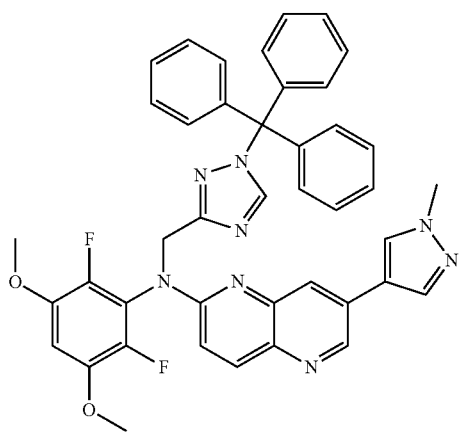 [SMILES: COc1cc(OC)c(F)c(N(Cc2ncn(C(c3ccccc3)(c3ccccc3)c3ccccc3)n2)c2ccc3ncc(-c4cnn(C)c4)cc3n2)c1F]

Example A11 a) Preparation of Intermediate 43

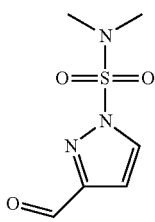

Dimethylsulfamoyl chloride (3.09 mL; 28.62 mmol) was added to a solution of 1-H-pyrazole-3-carbaldehyde (2.5 g; 26.02 mmol) and triethylamine (5.96 mL; 41.63 mmol) in ACN (25 mL) and the reaction mixture was stirred at 50° C. overnight. The reaction mixture was poured into ice water and extracted with EtOAc. The organic layer was washed with brine and dried over MgSO₄, filtered and evaporated to dryness. The residue was purified by chromatography over silica gel (Irregular SiOH, 15-45 µm, 80 g; mobile phase: 99% DCM, 1% MeOH). The product fractions were collected and evaporated to dryness yielding 4.42 g of intermediate 43 (84%).

b) Preparation of Intermediate 44

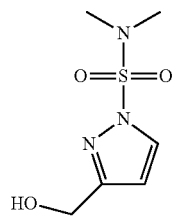

Sodium borohydride (987.41 mg; 26.1 mmol) was added portionwise to a solution of intermediate 43 (4.42 g; 21.75 mmol) in MeOH (50 mL) at 5° C. The reaction mixture was then stirred at room temperature 2 hours, poured onto ice water, extracted with DCM, dried over MgSO₄, filtered and evaporated to dryness. The crude product was taken up with Et₂O. The precipitate was filtered and dried yielding 3.04 g of intermediate 44 (73%).

c) Preparation of Intermediate 45

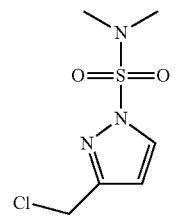

Triethylamine (4.24 mL; 29.63 mmol), methanesulfonyl chloride (1.38 mL; 17.78 mmol) and lithium chloride (1.88 g; 44.45 mmol) were added successively to a solution of intermediate 44 (3.04 g; 14.82 mmol) in THF (75 mL) at 5° C. under N₂ flow and the reaction mixture was stirred at room temperature for 4 hours. The reaction mixture was poured into ice water and extracted with EtOAc. The organic layer was washed with brine, dried over MgSO₄, filtered and evaporated to dryness yielding 3.82 g of intermediate 45 which was used in the next step without any further purification.

Example A12 a) Preparation of Intermediate 57

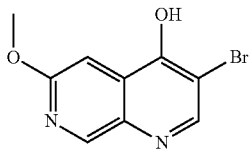

6-methoxy-1,7-naphthyridin-4(1H)-one (CAS 952059-64-2) (19.2 g; 66.2 mmol) was solubilized by heating in acetic acid (300 mL) and N-bromosuccinimide (17.7 g; 99.2 mmol) was added. The mixture was stirred at room temperature for 1 hour. The resulting yellow precipitate was filtered off and successively washed with acetic acid (2×100 mL) and Et$_2$O (2×200 mL) to give 16.3 g (96%, pale yellow solid) of intermediate 57 which was used as such in the next step.

b) Preparation of Intermediate 58

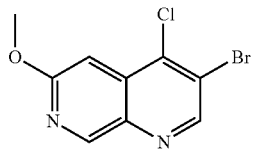

The reaction was performed on 2 batches of intermediate 57 (16.3 g; 63.9 mmol) and (10.1 g; 39.6 mmol):

POCl$_3$ (160 mL; 1.72 mol) was added to a mixture of intermediate 57 (16.3 g; 63.9 mmol) in chloroform (160 mL). The solution was stirred at reflux for 2 hours, concentrated and dried under vacuum. The residual solid was taken up with EtOAc (300 mL), cooled to 0° C. and carefully basified with a 3M aqueous solution of NaOH (250 mL). Then, the resulting mixture was diluted with water (200 mL) and extracted with EtOAc (3×400 mL). The combined organic layers were dried over Na$_2$SO$_4$, filtered, combined with the other batch (from 10.1 g of intermediate 57) and concentrated to give 26.5 g (overall yield 94%, pale yellow solid) of intermediate 58 which was used as such in the next step.

c) Preparation of Intermediate 59

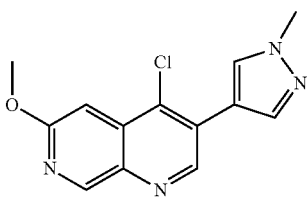 [SMILES: COc1cc2c(Cl)c(-c3cnn(C)c3)cnc2cn1]

The reaction was performed on 2 batches of intermediate 58 (21.5 g; 78.6 mmol) and (9.8 g; 358 mmol):

A solution of intermediate 58 (21.5 g; 78.6 mmol), 1-methylpyrazole-4-boronic acid pinacol ester (17.2 g; 82.5 mmol), Na$_2$CO$_3$ (25 g; 236 mmol) in a mixture of dioxane (510 mL) and water (210 mL) was degassed and backfilled with argon (operation repeated 3 times). PdCl$_2$(dppf).CH$_2$Cl$_2$ (3.21 g; 3.93 mmol) was added and the resulting mixture was degassed and backfilled with argon (operation repeated twice) and stirred at 110° C. for 16 hours. After cooling to room temperature and concentration of the solution, the residue was combined with the other batch (from 9.8 g). A mixture of EtOAc (800 mL) and MeOH (100 mL) was added. The organic layer was washed with a saturated aqueous solution of NaHCO$_3$ (500 mL) and water (300 mL). The layers were separated and the aqueous layer was extracted with a mixture of EtOAc and MeOH (9/1; 3×300 mL). The combined organic layers were dried over Na$_2$SO$_4$, filtered and evaporated to dryness. The resulting solid was triturated in Et$_2$O (500 mL), filtered off and rinsed with Et$_2$O (200 mL) to give 29.3 g (overall yield 93%, red-brown solid) of intermediate 59 M.P.: 180° C. (DSC).

d) Preparation of Intermediate 60

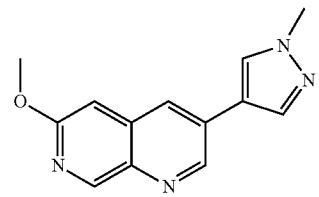 [SMILES: COc1cc2cc(-c3cnn(C)c3)cnc2cn1]

A catalytic amount of Raney Nickel, 50% slurry in water (1.88 g; 32.0 mmol) was washed twice with EtOH and collected after decantation. This catalytic amount was added to a solution of intermediate 59 (29.3 g; 107 mmol) in a mixture of EtOH (500 mL), THF (500 mL) and NaOH 1N (112 mL; 112 mmol). The mixture was purged and stirred under hydrogen atmosphere (1 bar) at 50° C. for 65 hours. The mixture was cooled to room temperature, filtered through a pad of Celite® which was washed with a mixture of THF and EtOH (1/1; 400 mL) and concentrated. The residue (brown solid) was adsorbed on silica gel and purified by column chromatography over silica gel (eluent: from 98% DCM, 2% MeOH to 95% DCM, 5% MeOH). The product fractions were collected and the solvent was evaporated. The resulting solid (16.5 g, orange solid) was triturated in Et$_2$O (300 mL), filtered off and washed with Et$_2$O (100 mL) to give 13.15 g (51%, beige solid) of intermediate 60. M.P.: 161° C. (DSC).

e) Preparation of Intermediate 61

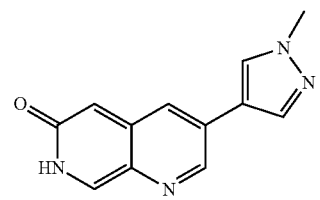 [SMILES: Cn1cc(-c2cnc3c[nH]c(=O)cc3c2)cn1]

AlCl$_3$ (16.6 g; 125 mmol) was added in one portion to a solution of intermediate 60 (5 g; 20.8 mmol) in 1,2-dichloroethane (300 mL) at room temperature. The reaction mixture was stirred at reflux for 1 hour and cooled to room temperature. MeOH (500 mL) was added. The mixture was concentrated under reduced pressure, taken up in a mixture of MeOH and DCM (8/2; 1 L), adsorbed on silica gel and purified by column chromatography over silica gel (eluent: from 95% DCM, 5% MeOH to 80% DCM, 20% MeOH). The product fractions were collected and the solvent was evaporated to give 13.8 g (brown solid) of intermediate 61 which was used as such in the next step.

f) Preparation of Intermediate 62

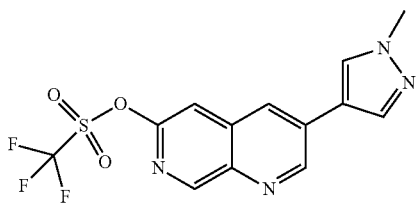 [SMILES: Cn1cc(-c2cnc3cnc(OS(=O)(=O)C(F)(F)F)cc3c2)cn1]

N-Phenyl-bis(trifluoromethanesulfonimide) (14.9 g; 41.6 mmol) was added portion wise to a suspension of intermediate 61 (13.8 g; 20.8 mmol) and Et₃N (43.5 mL; 312 mmol) in a mixture of DCM (400 mL) and DMF (100 mL) at room temperature. The reaction mixture was stirred at room temperature for 65 hours and concentrated under reduced pressure. The residue was taken up in a mixture of EtOAc (500 mL) and brine (500 mL), filtered through a pad of Celite® which was rinsed with EtOAc (200 mL) and brine (200 mL). The layers were separated and the aqueous layer was extracted with EtOAc (2×200 mL). The combined organic layers were dried over Na₂SO₄, filtered and concentrated. The residue (25.2 g, brown oil) was purified by column chromatography over silica gel (eluent: from 100% DCM to 96% DCM, 4% MeOH). The fractions containing the product were collected and the solvent was evaporated. The resulting residue (3.5 g, pale brown oil) was purified by column chromatography over silica gel (eluent: from 100% DCM to 98% DCM, 2% MeOH). The product fractions were collected and the solvent was evaporated to give 1.02 g (14% over 2 steps from intermediate 60, beige solid) of intermediate 62.

g) Preparation of Intermediate 63

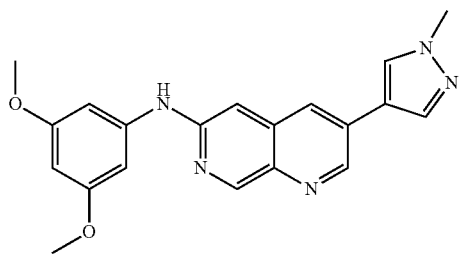 [SMILES: COc1cc(Nc2cc3cc(-c4cnn(C)c4)cnc3cn2)cc(OC)c1]

The reaction was performed on 2 batches of intermediate 62 (0.57 g; 1.58 mmol) and (0.42 g; 1.17 mmol):

A solution of intermediate 62 (0.57 g; 1.58 mmol), 3,5-dimethoxyaniline (0.29 g; 1.89 mmol), Cs₂CO₃ (1.54 g; 4.73 mmol) and xantphos (0.05 g; 0.08 mmol) in toluene (40 mL) was degassed and backfilled with argon (operation repeated 3 times). Pd₂dba₃ (0.04 g; 0.047 mmol) was added. The resulting mixture was degassed and backfilled with argon (operation repeated twice), stirred at 110° C. for 16 hours and concentrated under reduced pressure. The residue was taken up in a mixture of water (100 mL) and DCM (100 mL). The layers were separated and the aqueous layer was extracted with DCM (2×50 mL). The combined organic layers were dried over Na₂SO₄ and concentrated. The residues coming from the 2 batches were combined and the resulting residue was purified by column chromatography over silica gel (eluent: DCM/MeOH 99/1 to 97/3). The product fractions were collected and concentrated. The resulting solid was triturated in Et₂O (30 mL), filtered off, rinsed with Et₂O (10 mL) and dried under vacuum to give 0.66 g (overall yield 63%) of intermediate 63 (M.P.: 208° C. (DSC).

Example A13 a) Preparation of Intermediate 64

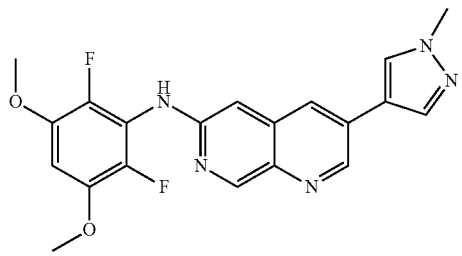 [SMILES: COc1cc(OC)c(F)c(Nc2cc3cc(-c4cnn(C)c4)cnc3cn2)c1F]

Two reactions, performed on intermediate 62 respectively on 0.938 g and 0.100 g, were combined for the work up. The synthesis is described below:

A solution of intermediate 62 (0.938 g; 2.62 mmol), 2,6-difluoro-3,5-dimethoxyaniline (0.990 g; 5.24 mmol), Cs₂CO₃ (4.26 g; 13.1 mmol) and xantphos (0.151 g; 0.26 mmol) in a mixture of toluene (65 mL) and dioxane (20 mL) was degassed and backfilled with argon (operation repeated 3 times). Pd₂dba₃ (0.144 g; 0.16 mmol) was added. The resulting mixture was degassed and backfilled with argon (operation repeated twice), stirred at 110° C. for 65 hours and concentrated under reduced pressure. The residue was pooled with the reaction mixture performed on 0.1 g of intermediate 62 in a mixture of DCM (200 mL) and MeOH (50 mL), adsorbed on silica gel and purified by column chromatography over silica gel (eluent: DCM/MeOH 99/1 to 97/3). The fractions containing the product were collected and the solvent was evaporated. The residue (0.578 g, orange solid) was triturated in Et₂O (30 mL), filtered off, rinsed with Et₂O (10 mL) and dried under vacuum at 80° C. overnight to give 0.431 g (37%, yellow solid) of intermediate 64. M.P.: 228° C. (DSC).

Analogous preparation of intermediate 65 starting from intermediate 62

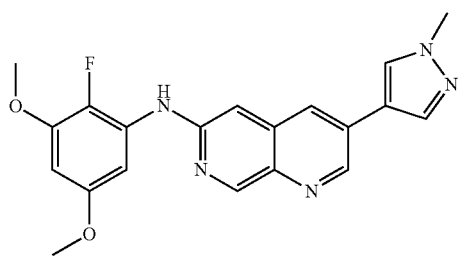 [SMILES: COc1cc(Nc2cc3cc(-c4cnn(C)c4)cnc3cn2)c(F)c(OC)c1]

B. Preparation of the compounds

Example B1

Preparation of Compound 1

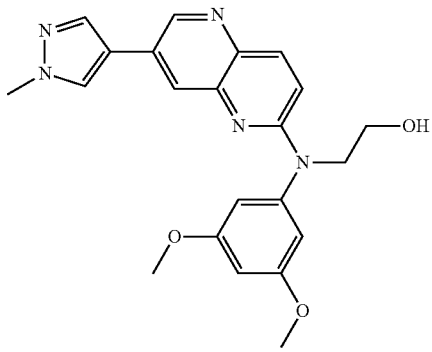 [SMILES: COc1cc(OC)cc(N(CCO)c2ccc3ncc(-c4cnn(C)c4)cc3n2)c1]

The reaction was performed in anhydrous conditions under argon atmosphere. Tetrabutylammonium fluoride (1M in THF; 7.3 ml, 7.3 mmol) was added to a solution of intermediate 10 (crude 3.17 g, maximum 5.53 mmol) in THF (120 ml) and the mixture was stirred at room temperature overnight. Ice water (400 ml) and an aqueous saturated solution of potassium carbonate (600 ml) were added. The mixture was extracted with ethyl acetate (1×800 ml and 2×300 ml). The combined organic layers were washed with brine (400 ml), dried over sodium sulfate, filtered and concentrated. The residue was purified by chromatography over silica gel (mobile phase, gradient from 100% DCM to 98% DCM, 2% MeOH). The desired fractions were collected and the solvent was evaporated, yielding 1.51 g (67% over 2 steps) of compound 1.

Analogous preparation of compound 2

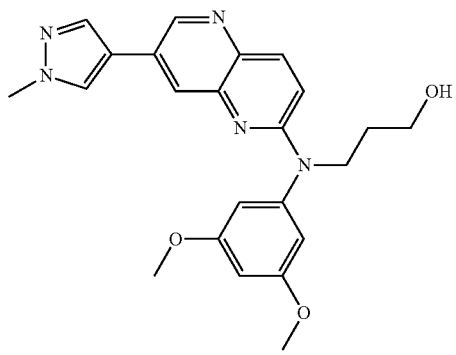 [SMILES: COc1cc(OC)cc(N(CCCO)c2ccc3ncc(-c4cnn(C)c4)cc3n2)c1]

starting from intermediate 11

Analogous preparation of compound 22 starting from intermediate 31

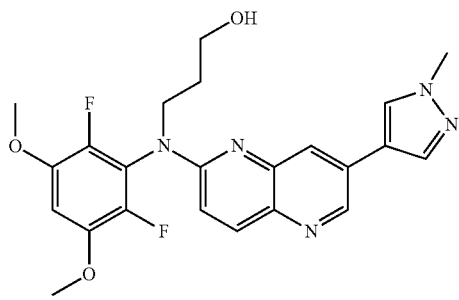 [SMILES: COc1cc(OC)c(F)c(N(CCCO)c2ccc3ncc(-c4cnn(C)c4)cc3n2)c1F]

Example B1-a

Preparation of Compound 61

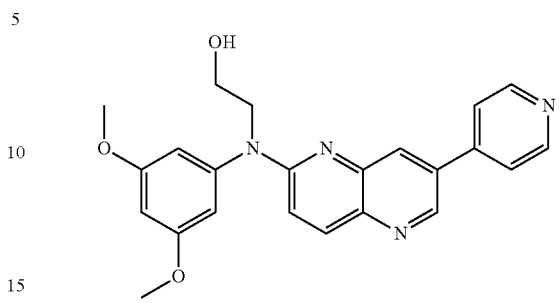

Intermediate 51 (0.04 g; 0.077 mmol) was dissolved in a mixture of aqueous HCl 3N (2 mL) and THF (3 mL). The reaction mixture was stirred at room temperature for 16 hours. The mixture was quenched with a 3M solution of NaOH (4 mL) and extracted with EtOAc (3×10 mL). The organic layer were dried over $Na_2SO_4$, filtered and concentrated. The residue (yellow gum) was purified by column chromatography over silica gel (eluent: DCM/MeOH 98/2). The product fractions were collected and the solvent was evaporated. The yellow solid was triturated in $Et_2O$ (15 mL). The supernatant liquid was removed and the resulting solid was dried under vacuum (70° C., 5 h) to give 0.022 g (71%, pale yellow solid) of compound 61. MP: 209° C. (Buchi M-560).

Example B2

Preparation of Compound 3

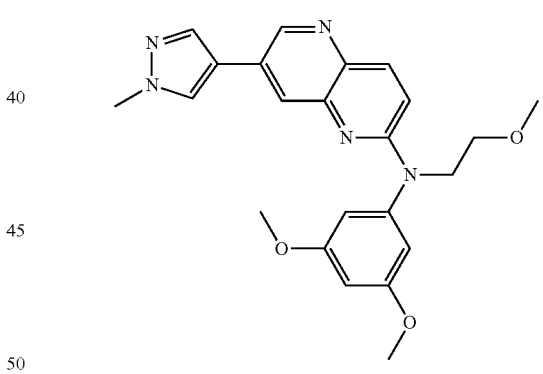

The reaction was performed in anhydrous conditions under argon atmosphere. NaH (60% in mineral oil, 0.1 g, 2.5 mmol) was added to a mixture of intermediate 9 (0.3 g, 0.83 mmol) in N,N-dimethylformamide (7 ml) at 0° C. The mixture was stirred at 0° C. for 45 minutes and bromo-ethyl methyl ether (0.31 ml, 3.32 mmol) was added. The mixture was stirred at 0° C. for 1 hour and at room temperature overnight. Ice water (100 ml) was added and the mixture was extracted with ethyl acetate (3×100 ml). The combined organic layers were dried over sodium sulfate, filtered and concentrated. The residue was purified by chromatography over silica gel (mobile phase, gradient from 100% DCM to 90% DCM, 10% MeOH). The product fractions were collected and the solvent was evaporated. The residue was dissolved in ethyl acetate (100 ml) and washed with water (3×60 ml). The organic layer was dried over sodium sulfate, filtered and concentrated. The residue was triturated in diethyl ether (4×5 ml) and dried under vacuum, yielding 0.222 g (64%) of compound 3 (MP: 138° C. (DSC)).

Analogous preparation of compound 35 starting from intermediate 28

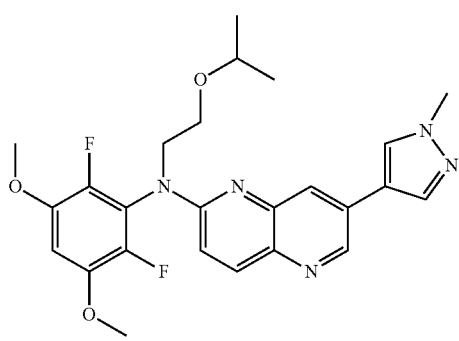 [SMILES: COc1cc(OC)c(F)c(N(CCOC(C)C)c2ccc3ncc(-c4cnn(C)c4)cc3n2)c1F]

Analogous preparation of compound 36 starting from intermediate 33

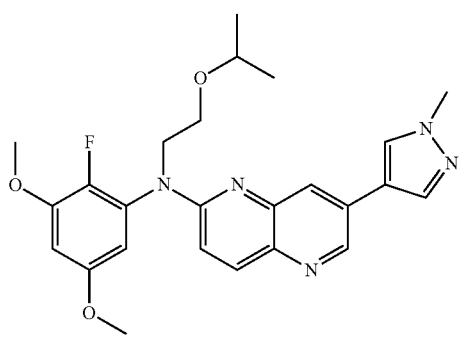 [SMILES: COc1cc(OC)c(F)c(N(CCOC(C)C)c2ccc3ncc(-c4cnn(C)c4)cc3n2)c1]

Analogous preparation of compound 45 starting from intermediate 28

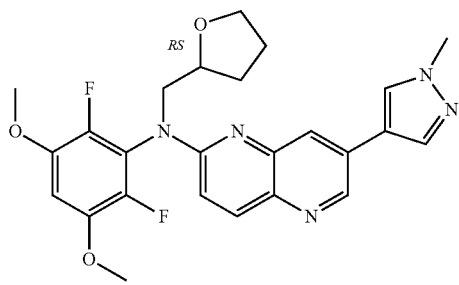 [SMILES: COc1cc(OC)c(F)c(N(CC2CCCO2)c2ccc3ncc(-c4cnn(C)c4)cc3n2)c1F]

Analogous preparation of compound 50 starting from intermediate 9

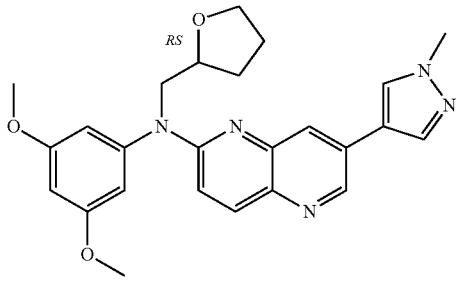 [SMILES: COc1cc(OC)cc(N(CC2CCCO2)c2ccc3ncc(-c4cnn(C)c4)cc3n2)c1]

Analogous preparation of compound 51 starting from intermediate 33

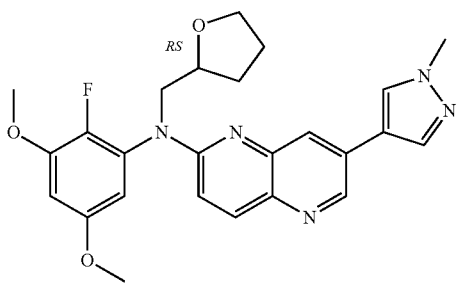 [SMILES: COc1cc(OC)c(F)c(N(CC2CCCO2)c2ccc3ncc(-c4cnn(C)c4)cc3n2)c1]

Analogous preparation of compound 54 starting from intermediate 33

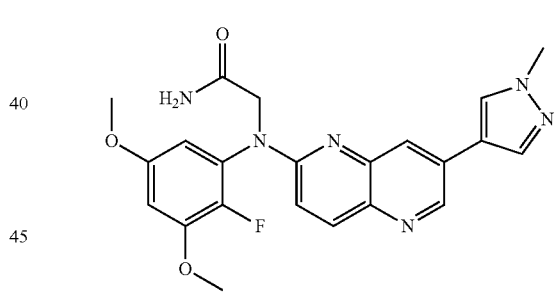

Analogous preparation of compound 57 starting from intermediate 33

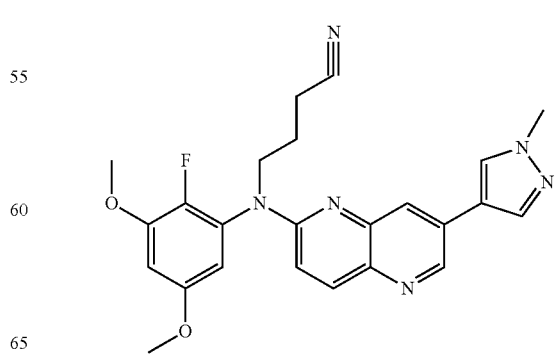

Analogous preparation of compound 69 starting from intermediate 63

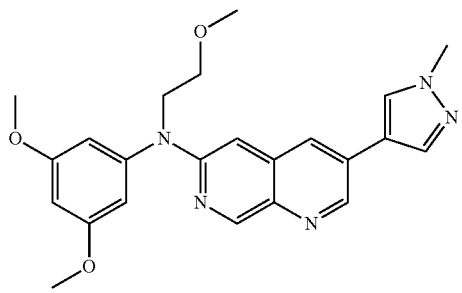 [SMILES: COCCN(c1cc(OC)cc(OC)c1)c1cc2cc(-c3cnn(C)c3)cnc2cn1]

Example B2a-1

Preparation of Compound 40

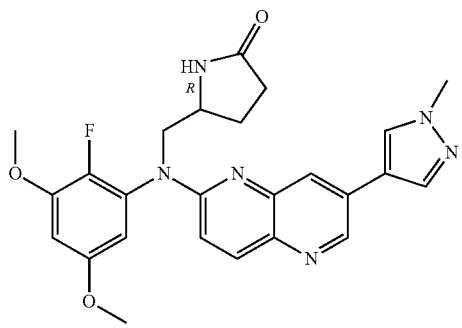

NaH (0.380 g; 9.49 mmol) was added to a solution of intermediate 33 (0.900 g; 2.37 mmol) in DMF (18 mL) at 0° C. The mixture was stirred at 0° C. for 45 minutes and intermediate 39 (0.958 g; 3.56 mmol) was added. The mixture was stirred at 00° C. for 1 hour and at room temperature overnight. Water (100 mL) and brine (150 mL) were added and the mixture was extracted with EtOAc (3×150 mL). The combined organic layers were dried over $Na_2SO_4$, filtered and concentrated. The residue (1.96 g, brown oil) was purified by column chromatography over silica gel (eluent: DCM/MeOH 100/0 to 95/5). The product fractions were collected and the solvent was evaporated. The resulting solid was triturated in $Et_2O$ and dried under vacuum to give 0.354 g (31%, yellow solid) of the expected compound which was purified again by column chromatography over silica gel (eluent: DCM/MeOH 98/2 to 96/4). The product fractions were collected and the solvent was evaporated affording 2 fractions which were triturated in $Et_2O$. The precipitates were filtered and dried under vacuum to give 0.071 g (6%, yellow solid) of compound 40 and 0.207 g (18%, yellow solid) of compound 40 M.P.: decomposition starting from 211° C., DSC).

Example B2a-2

Preparation of Compound 41

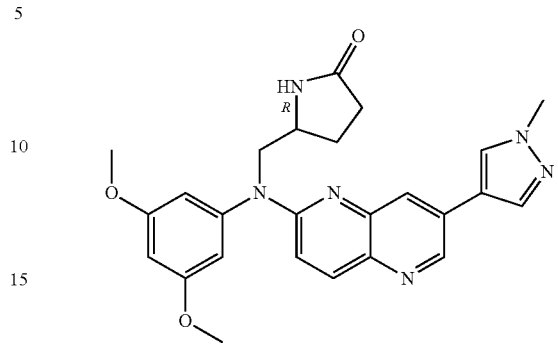

NaH (0.443 g; 11.1 mmol) was added to a solution of intermediate 9 (1.00 g; 2.77 mmol) in DMF (20 mL) at 0° C. The mixture was stirred at 0° C. for 45 minutes and intermediate 39 (CAS 128899-31-0) (1.12 g; 4.16 mmol) was added. The mixture was stirred at 0° C. for 1 hour and at room temperature overnight. Water (250 mL) and brine (100 mL) were added and the mixture was extracted with EtOAc (3×150 mL). The combined organic layers were dried over $Na_2SO_4$, filtered and concentrated. The residue (2.47 g, brown oil) was purified by column chromatography over silica gel (eluent: DCM/MeOH 100/0 to 95/5). The product fractions were collected and the solvent was evaporated to give 0.289 g (yellow solid) of the expected compound which was purified again by column chromatography over silica gel (eluent: DCM/methanol 98/2 to 95/5). The product fractions were collected and the solvent was evaporated to give 0.235 g (19%, beige solid) of compound 41. M.P.: decomposition starting from 276° C., DSC).

Example B2a-3

Preparation of Compound 42

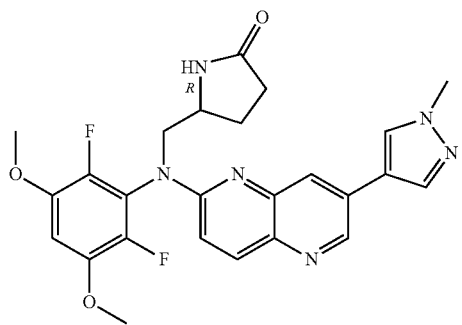

NaH (0.362 g; 9.04 mmol) was added to a solution of intermediate 28 (0.900 g; 2.26 mmol) in DMF (20 mL) at 0° C. The mixture was stirred at 0° C. for 45 minutes and intermediate 39 (0.913 g; 3.39 mmol) was added. The mixture was stirred at 0° C. for 1 hour and at room temperature for 72 hours. Water (100 mL) and brine (150 mL) were added and the mixture was extracted with EtOAc (3×150 mL). The combined organic layers were dried over $Na_2SO_4$, filtered and concentrated. The residue (2.42 g, brown oil) was purified by column chromatography over silica gel (eluent: EtOAc/MeOH 100/0 to 98/2). The product fractions were collected and the solvent was evaporated to give 0.502 g (yellow gum) of expected product which was purified again by column chromatography over silica gel (15-40 µm, eluent: DCM/MeOH 99/1 to 97/3). The product fractions were collected and the solvent was evaporated. The resulting residue was triturated in Et₂O. The precipitate was filtered and dried under vacuum to give 0.239 g (21%, yellow solid) of compound 42. M.P.: decomposition starting from 233° C. (DSC).

Example B2a-4

Preparation of Compound 43

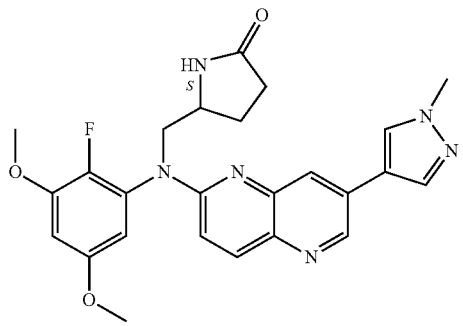

NaH (0.380 g; 9.49 mmol) was added to a solution of intermediate 33 (0.900 g; 2.37 mmol) in DMF (18 mL) at 0° C. The mixture was stirred at 00° C. for 45 minutes and (S)-(+)-5-(hydroxy-methyl)-2-pyrrolidinone p-toluenesulfonate (CAS 51693-17-5) (0.958 g; 3.56 mmol) was added. The mixture was stirred at 0° C. for 1 hour and at room temperature overnight. Water (100 mL) and brine (150 mL) were added and the mixture was extracted with EtOAc (3×150 mL). The combined organic layers were dried over Na₂SO₄, filtered and concentrated. The residue (3.34 g, brown oil) was purified by column chromatography over silica gel (eluent: DCM/MeOH 100/0 to 96/4). The product fractions were collected and the solvent was evaporated. The resulting residue was triturated in Et₂O and dried under vacuum to give 0.277 g (25%, brown solid) of compound 43. M.P.: decomposition starting from 221° C. (DSC).

Analogous preparation of compound 37 starting from intermediate 9

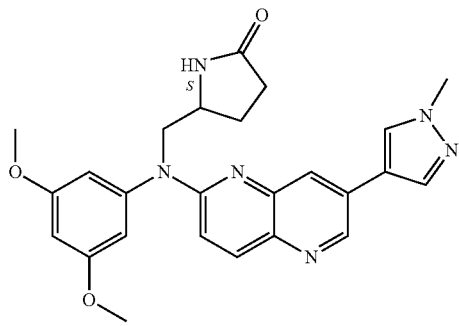

Analogous preparation of compound 44 starting from intermediate 28

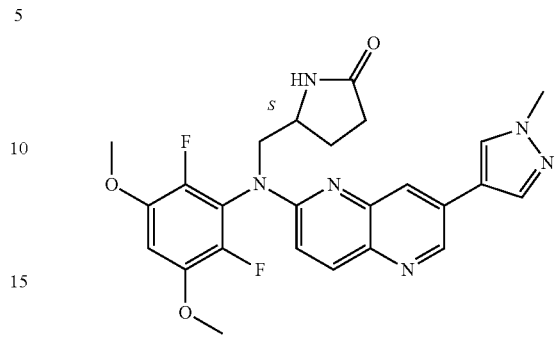

Example B2a-5

Preparation of Compound 70

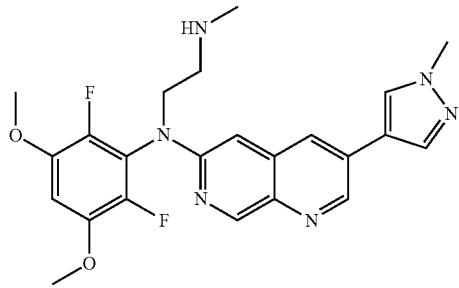 [SMILES: CNCCN(c1cc2cc(-c3cnn(C)c3)cnc2cn1)c1c(F)c(OC)cc(OC)c1F]

NaH (0.160 g; 4.00 mmol) was added to a solution of intermediate 64 (0.397 g; 1.00 mmol) in DMF (10 mL) at 0° C. The reaction mixture was stirred at 0° C. for 45 minutes and (2-chloroethyl)-methylamine hydrochloride (CAS 4535-90-4) (0.195 g; 1.50 mmol) was added. The reaction mixture was stirred at 0° C. for 1 hour then, at room temperature for 65 hours. Water (30 mL) and brine (70 mL) were added and the mixture was extracted with EtOAc (3×50 mL). The combined organic layers were washed with brine (3×50 mL), dried over Na₂SO₄, filtered and the solvent was evaporated. The residue (0.85 g, red-brown solid) was purified by column chromatography over silica gel (eluent: DCM/MeOH/NH₄OH: from 95/5/0 to 90/10/0 to 90/10/1). The product fractions were collected and the solvent was evaporated to give 230 mg of an intermediate residue which was triturated in Et₂O (20 mL). The precipitate was filtered off, washed with Et₂O and dried under vacuum at 80° C. for 16 hours to give 210 mg (47%) of compound 70. M.P.: 148° C. (DSC).

Example B2a-6

Preparation of Compound 46

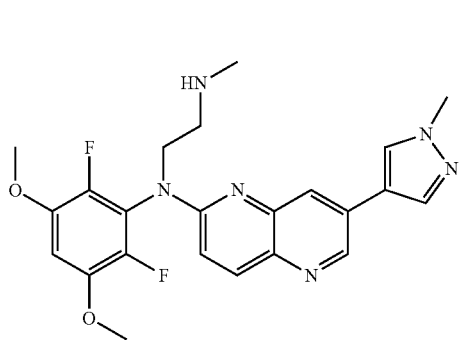 [SMILES: CNCCN(c1ccc2ncc(-c3cnn(C)c3)cc2n1)c1c(F)c(OC)cc(OC)c1F]

Two reactions performed on intermediate 28 respectively on 1.00 g and 0.050 g were combined for the work up. The synthesis is described below: NaH (0.403 g; 10.1 mmol) was added to a solution of intermediate 28 (1.00 g; 2.52 mmol) in DMF (25 mL) at 0° C. The mixture was stirred at 0° C. for 45 minutes and methylaminoethyl chloride hydrochloride (0.491 g; 3.78 mmol) was added. The mixture was stirred at 0° C. for 1 hour and at room temperature overnight. The reaction mixture and the reaction mixture (from 0.05 g of intermediate 28) were combined. Water (100 mL) and brine (150 mL) were added. The mixture was extracted with EtOAc (3×150 mL). The combined organic layers were dried over $Na_2SO_4$, filtered and concentrated. The residue (4.43 g, brown oil) was purified by column chromatography over silica gel (eluent: DCM/MeOH 100/0 to 93/7). The product fractions were collected and the solvent was evaporated. The resulting fraction was triturated in $Et_2O$ (4×5 mL) and dried under vacuum to give 0.208 g (18%, yellow solid) of compound 46. 0.184 g of this fraction were purified by achiral SFC on (AMINO 6 μm 150×21.2 mm; mobile phase: 0.3% isopropylamine, 75% $CO_2$, 25% MeOH). The product fractions were collected and the solvent was evaporated. The residue (145 mg) was crystallized from $Et_2O$ to give, after filtration, 124 mg (11%) of compound 46. M.P.: 157° C. (DSC).

Analogous preparation of compound 52 starting from intermediate 36

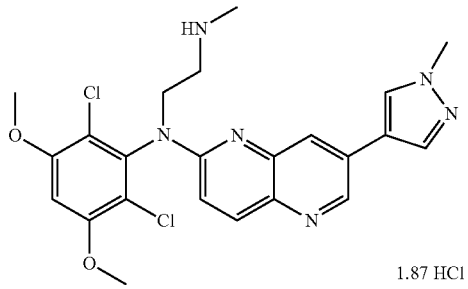 [SMILES: CNCCN(c1ccc2ncc(-c3cnn(C)c3)cc2n1)c1c(Cl)c(OC)cc(OC)c1Cl]

1.87 HCl

Analogous preparation of compound 73 starting from intermediate 65

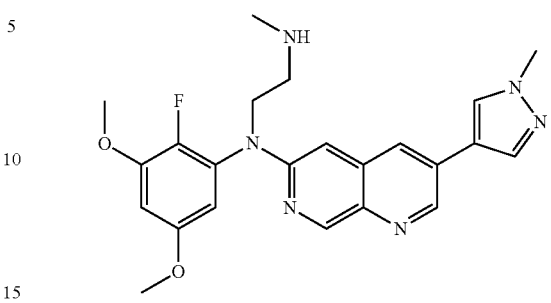

Example B3

Preparation of

Compound 4

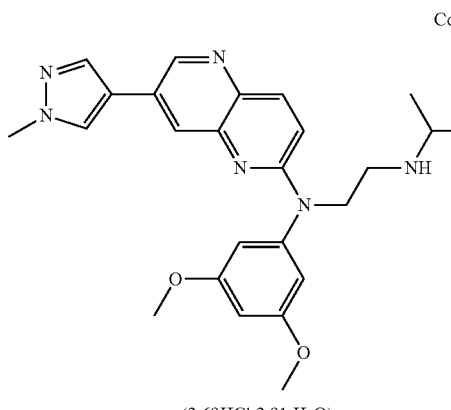

(2.69HCl 2.91 $H_2O$)

Compound 5

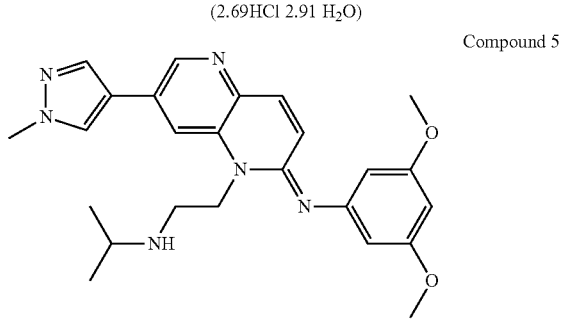

Compound 6

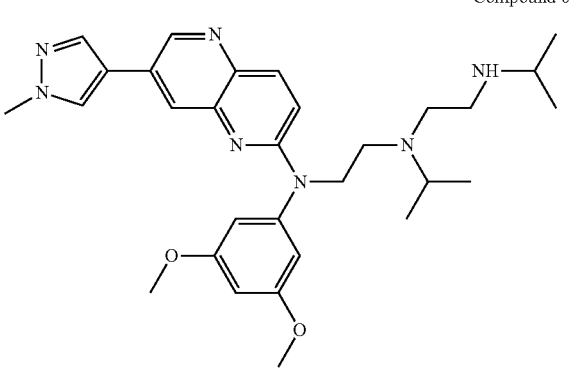

A mixture of intermediate 9 (0.5 g, 1.4 mmol), tetrabutyl ammonium bromide (0.11 g, 0.35 mmol) and Potassium hydroxide (1.16 g, 20.8 mmol) in 2-methyltetrahydrofuran (7.5 ml) and water (0.6 ml) was heated at 50° C. for 1 hour. Isopropylaminoethyl chloride hydrochloride (0.39 g, 2.5 mmol) was added and the mixture was heated at 50° C. overnight. Water (25 ml) was added and the mixture was extracted with a mixture of dichloromethane/methanol 95/5 (3×25 ml). The combined organic layers were dried over sodium sulfate, filtered and concentrated. The residue was purified by chromatography over silica gel (mobile phase, gradient from 98% DCM, 2% MeOH to 90% DCM, 10% MeOH). The desired fractions were collected and the solvent was evaporated, yielding 0.233 g of a residue that was further submitted for purification by chromatography over silica gel (mobile phase, gradient from 95% DCM, 5% MeOH to 95% DCM, 5% MeOH, 0.1% NH$_4$OH). The desired fractions were collected and the solvent was evaporated, yielding 0.13 g of Fraction 1 consisting of a mixture of compound 4 and compound 5.

Alternatively a mixture of compound 4 and 6 can be obtained using the following conditions:

In anhydrous conditions under argon atmosphere, NaH (60% in mineral oil, 0.232 g, 5.8 mmol) was added slowly to a suspension of intermediate 9 (0.35 g, 0.97 mmol) in N,N-dimethylformamide (10 ml) at 0° C. and the mixture was stirred at 0° C. for 10 minutes. Isopropylaminoethyl chloride hydrochloride (0.459 g, 2.9 mmol) was added portionwise and the reaction mixture was stirred at room temperature for 48 h ours. The reaction mixture was quenched with a saturated solution of ammonium chloride (15 ml) and the mixture was extracted with ethyl acetate (3×50 ml). The combined organic layers were washed with a saturated solution of sodium chloride (2×50 ml), dried over sodium sulfate, filtered and concentrated to dryness. The residue was purified by chromatography over silica gel (mobile phase, gradient from 95% DCM, 5% MeOH to 90% DCM, 10%). The fractions were collected and the solvent was evaporated yielding 0.22 g of fraction 2 composed of a mixture of compound 4 and compound 6.

Fraction 1 and Fraction 2 were combined and purified by achiral SFC (mobile phase, 0.3% isopropylamine, 86% CO$_2$, 14% MeOH). The desired fractions were collected and concentrated, yielding 17 mg of compound 5, 168 mg of compound 4 and 60 mg of product fraction 3 containing compound 4 and compound 6.

Compound 4 was converted into the HCl salt (3 eq. 1M solution in water) in Et$_2$O and triturated. The precipitate was filtered off, washed with Et$_2$O and dried under vacuum, yielding 153 mg of compound 4 (mp=175° C. Kofler).

Product fraction 3 was purified by chiral SFC on (5 μm mobile phase, 0.3% isopropylamine, 85% CO$_2$, 15% MeOH), yielding 22 mg of compound 6.

Example B3a

Preparation of Compound 30

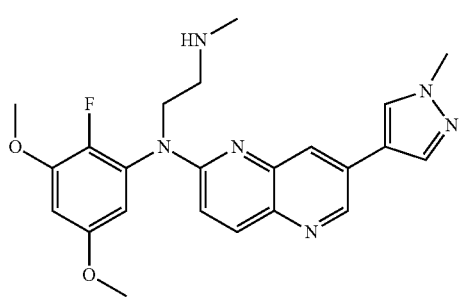 [SMILES: CNCCN(c1ccc2ncc(-c3cnn(C)c3)cc2n1)c1cc(OC)cc(OC)c1F]

A mixture of intermediate 33 (0.56 g; 1.46 mmol), tetrabutylammonium bromide (0.12 g; 0.37 mmol) and KOH (1.23 g; 21.9 mmol) in 2-methyltetrahydrofuran (8.5 mL) and water (1 mL) was heated at 50° C. for 1 hour. Methylaminoethyl chloride hydrochloride (0.34 g; 2.63 mmol) was added and the mixture was heated at 50° C. overnight. Water (200 mL) was added and the mixture was extracted with DCM (3×150 mL). The combined organic layers were dried over Na$_2$SO$_4$, filtered and concentrated. The residue was purified by column chromatography over silica gel (eluent: DCM/MeOH 98/2 to 85/15). The fractions containing the product were collected and concentrated to afford after trituration in Et$_2$O and drying under vacuum to give 0.408 g of the expected compound. This solid was purified by achiral SFC on (AMINO 6 μm 150×21.2 mm; mobile phase: 0.3% isopropylamine, 75% CO$_2$, 25% MeOH) to give 308 mg of an intermediate residue which was crystallized from Et$_2$O to afford 256 mg (40%) of compound 30. MP: 120° C. (gum) (Kofler).

Analogous preparation of compound 12 starting from intermediate 18

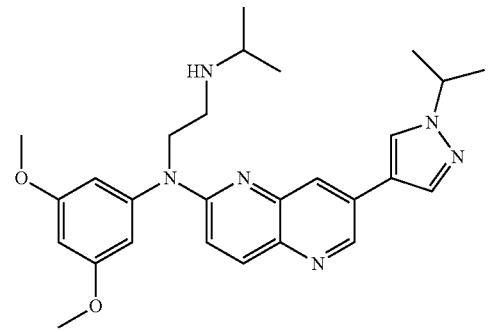 [SMILES: COc1cc(OC)cc(N(CCNC(C)C)c2ccc3ncc(-c4cnn(C(C)C)c4)cc3n2)c1]

Analogous preparation of compound 13 starting from intermediate 23

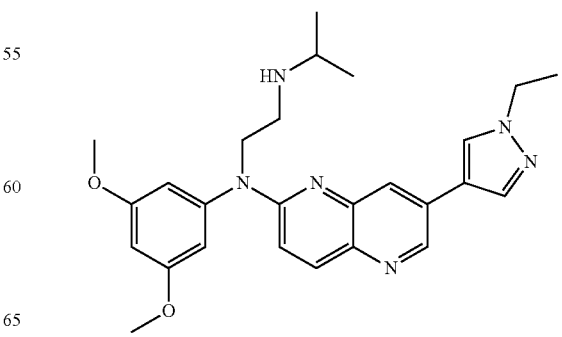

Analogous preparation of compound 23 starting from intermediate 32

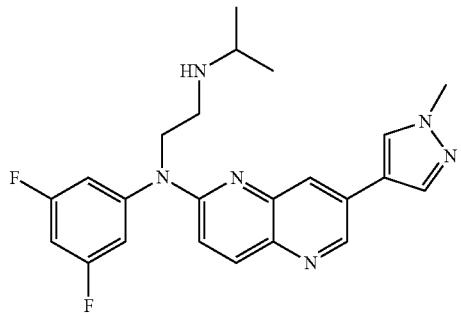 [SMILES: CC(C)NCCN(c1cc(F)cc(F)c1)c1ccc2ncc(-c3cnn(C)c3)cc2n1]

Analogous preparation of compound 26 starting from intermediate 28

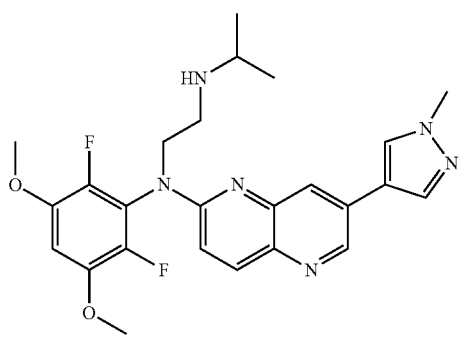 [SMILES: COc1cc(OC)c(F)c(N(CCNC(C)C)c2ccc3ncc(-c4cnn(C)c4)cc3n2)c1F]

Analogous preparation of compound 68 starting from intermediate 63

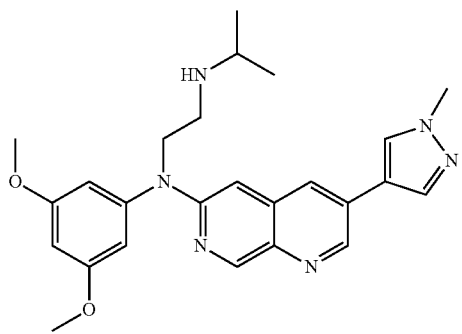 [SMILES: COc1cc(OC)cc(N(CCNC(C)C)c2cc3cc(-c4cnn(C)c4)cnc3cn2)c1]

Example B3b

Preparation of Compound 21

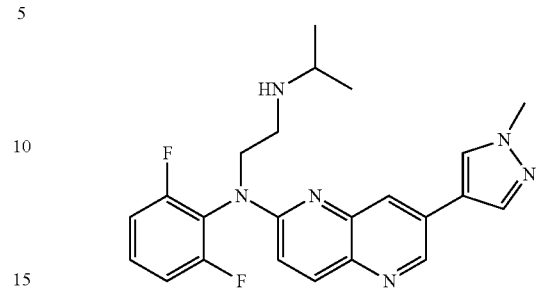

and compound 20

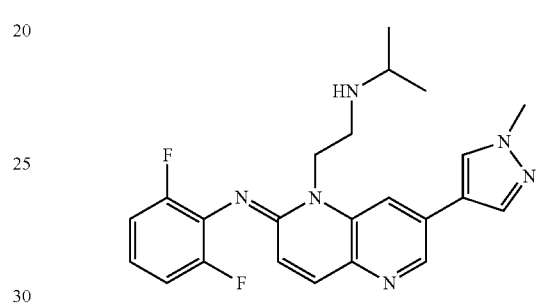

A mixture of intermediate 30 (0.66 g; 1.94 mmol), tetrabutylammonium bromide (0.16 g; 0.49 mmol) and KOH (1.63 g; 29.1 mmol) in 2-methyltetrahydrofuran (11 mL) and water (1.6 mL) was heated at 50° C. for 1 hour. Isopropylaminoethyl chloride hydrochloride (0.55 g; 3.49 mmol) was added and the mixture was heated at 50° C. overnight. Water (400 mL) was added and the mixture was extracted with DCM (3×200 mL). The combined organic layers were washed with brine (300 mL), dried over $Na_2SO_4$, filtered and concentrated. The residue was purified by column chromatography over silica gel (eluent: DCM/MeOH 100/0 to 85/15). The fractions containing the product were collected and concentrated to give 0.485 g of a mixture of compound 20 and 21. This solid was purified by achiral SFC on (CYANO 6 μm 150×21.2 mm; mobile phase: 0.3% isopropylamine, 80% $CO_2$, 20% MeOH) to give 40 mg of compound 20 (5%), M.P.: 130-134° C. (Kofler), and 360 mg of an intermediate compound which was crystallized from $Et_2O$ to give 330 mg (40%) of compound 21. M.P.: 78° C. (DSC).

Analogous preparation of compound 29

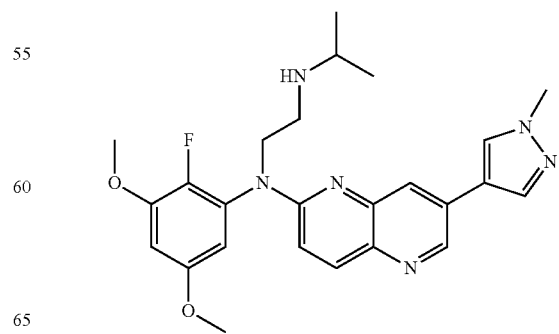

and compound 28

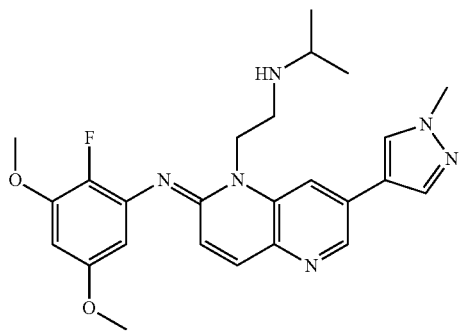 [SMILES: COc1cc(/N=c2\ccc3ncc(-c4cnn(C)c4)cc3n2CCNC(C)C)c(F)c(OC)c1]

starting from intermediate 33

Example B4

Preparation of Compound 7

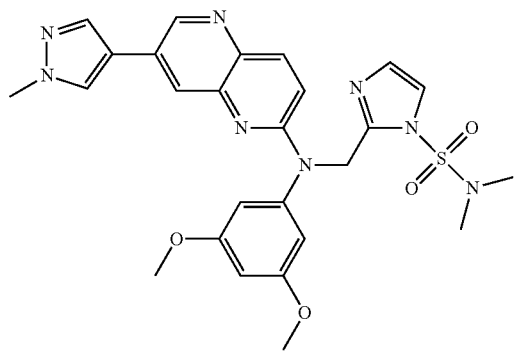

The reaction was performed in anhydrous conditions under argon. NaH (60% in mineral oil; 0.083 g, 2.1 mmol) was added portionwise to a solution of intermediate 9 (0.5 g, 1.4 mmol) in DMF (7 ml) at 0° C. The reaction mixture was stirred at 0° C. for 30 minutes and 2-(chloromethyl)-N,N-dimethyl-1H-imidazole-1-sulfonamide, (0.371 g, 1.7 mmol) was added. The mixture was warmed up to room temperature overnight. The mixture was diluted with water (25 ml) and extracted with ethyl acetate (3×40 ml). The combined organic layers were washed with a saturated aqueous solution of NaCl (3×40 ml), dried over sodium sulfate, filtered and concentrated. The residue was purified by chromatography over silica gel (mobile phase, gradient from 99% DCM, 1% MeOH to 95% DCM, 5% MeOH). The desired fractions were collected and the solvent was evaporated to give 0.55 g (72%) of compound 7 which was used without further purification for the next step.

Analogous preparation of compound 17 starting from intermediate 16

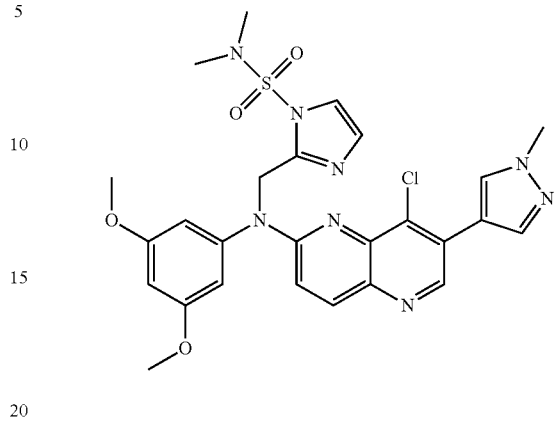

Analogous preparation of compound 18 starting from intermediate 30

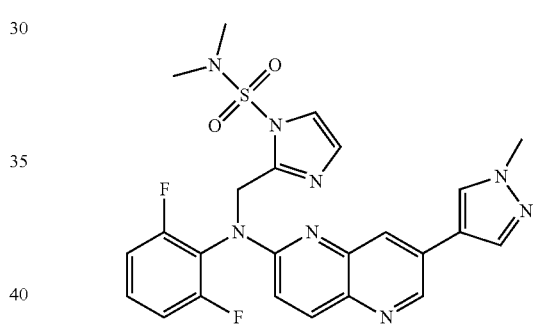

Analogous preparation of compound 25 starting from intermediate 32

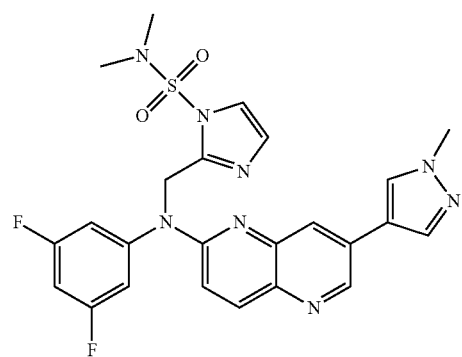 [SMILES: CN(C)S(=O)(=O)n1ccnc1CN(c1cc(F)cc(F)c1)c1ccc2ncc(-c3cnn(C)c3)cc2n1]

Analogous preparation of compound 27 starting from intermediate 33

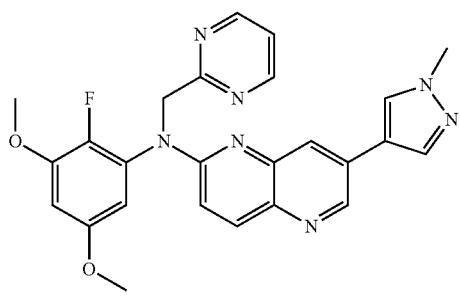 [SMILES: COc1cc(OC)c(F)c(N(Cc2ncccn2)c2ccc3ncc(-c4cnn(C)c4)cc3n2)c1]

Analogous preparation of compound 32 starting from intermediate 9

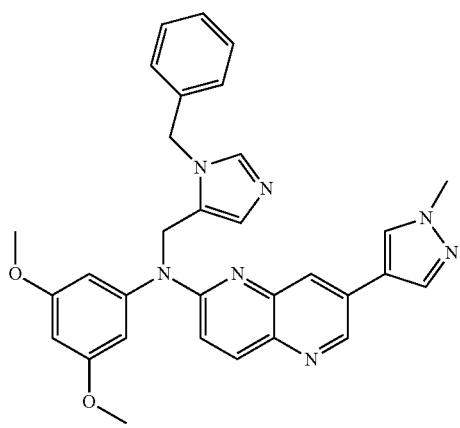 [SMILES: COc1cc(OC)cc(N(Cc2cncn2Cc2ccccc2)c2ccc3ncc(-c4cnn(C)c4)cc3n2)c1]

Analogous preparation of compound 33 starting from intermediate 36

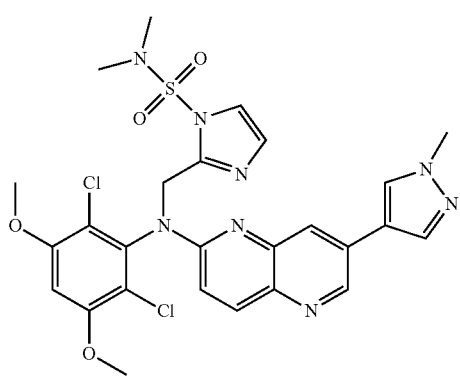 [SMILES: COc1cc(OC)c(Cl)c(N(Cc2nccn2S(=O)(=O)N(C)C)c2ccc3ncc(-c4cnn(C)c4)cc3n2)c1Cl]

Analogous preparation of compound 38 starting from intermediate 9 and intermediate 37

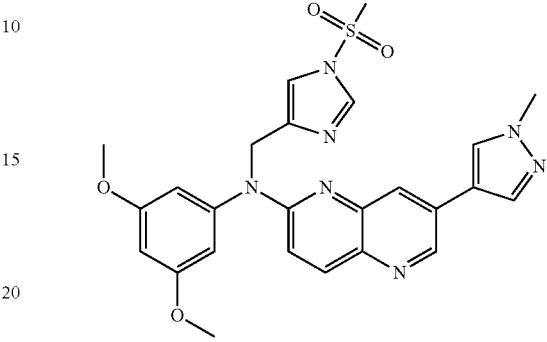

Analogous preparation of compound 56 starting from intermediate 33 and intermediate 45

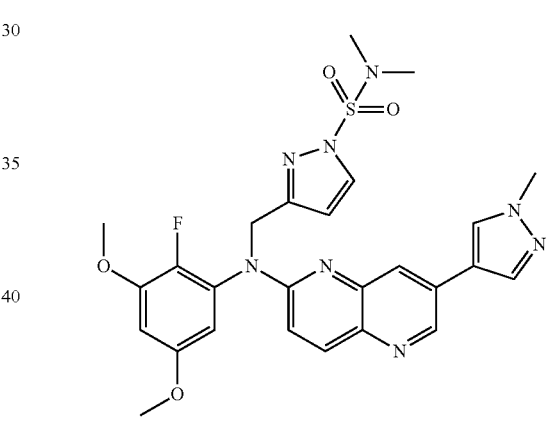

Analogous preparation of compound 58 starting from intermediate 33 and 1,3-oxazole-2-ylmethylmethanesulfonate (CAS 916810-51-0)

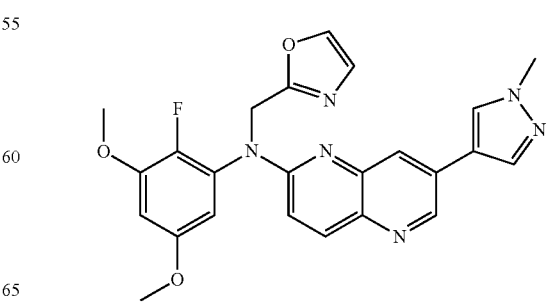

Analogous preparation of compound 60 starting from intermediate 46

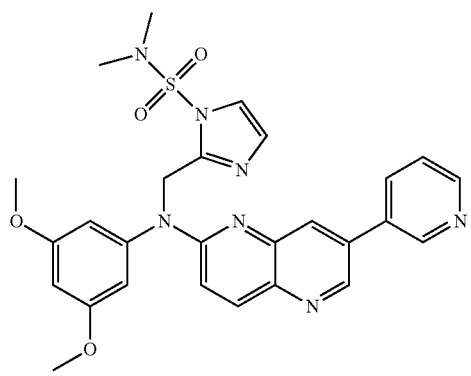 [SMILES: COc1cc(OC)cc(N(Cc2nccn2S(=O)(=O)N(C)C)c2ccc3ncc(-c4cccnc4)cc3n2)c1]

Analogous preparation of compound 63 starting from intermediate 52

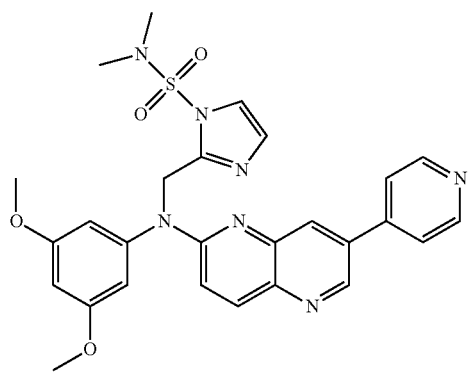 [SMILES: COc1cc(OC)cc(N(Cc2nccn2S(=O)(=O)N(C)C)c2ccc3ncc(-c4ccncc4)cc3n2)c1]

Analogous preparation of compound 64 starting from intermediate 28

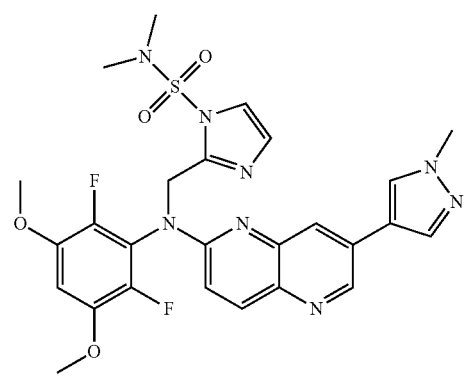 [SMILES: COc1cc(OC)c(F)c(N(Cc2nccn2S(=O)(=O)N(C)C)c2ccc3ncc(-c4cnn(C)c4)cc3n2)c1F]

Analogous preparation of compound 66 starting from intermediate 63

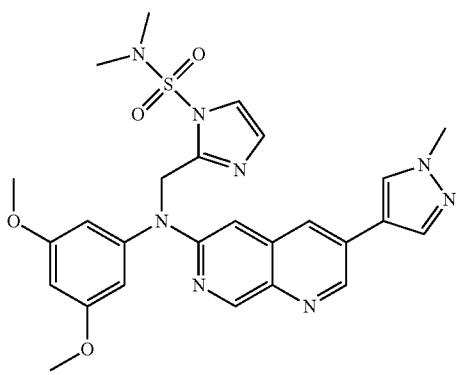 [SMILES: COc1cc(OC)cc(N(Cc2nccn2S(=O)(=O)N(C)C)c2cc3cc(-c4cnn(C)c4)cnc3cn2)c1]

Analogous preparation of compound 71 starting from intermediate 64

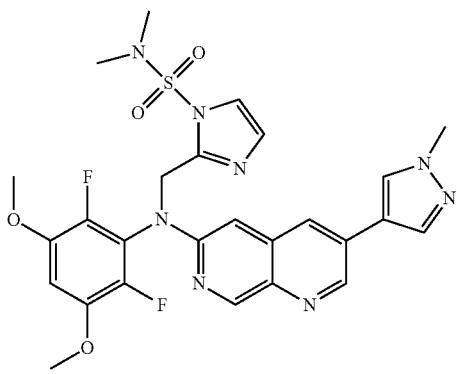 [SMILES: COc1cc(OC)c(F)c(N(Cc2nccn2S(=O)(=O)N(C)C)c2cc3cc(-c4cnn(C)c4)cnc3cn2)c1F]

Analogous preparation of compound 76 starting from intermediate 65

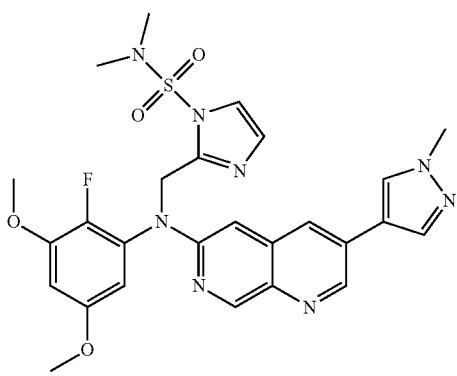 [SMILES: COc1cc(OC)c(F)c(N(Cc2nccn2S(=O)(=O)N(C)C)c2cc3cc(-c4cnn(C)c4)cnc3cn2)c1]

Example B4a

Preparation of Compound 14

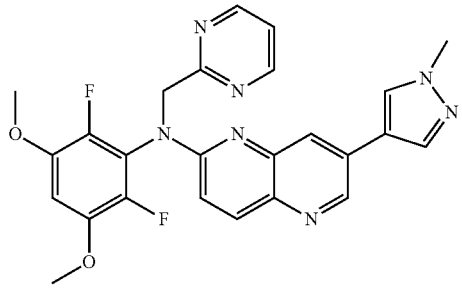

The reaction was performed on 2 batches of intermediate 28 (0.057 g; 0.14 mmol) and (0.23 g; 0.58 mmol):

NaH (0.07 g; 1.74 mmol) was added to a solution of intermediate 28 (0.230 g; 0.58 mmol) in DMF (8 mL) at 0° C. The mixture was stirred at 0° C. for 45 minutes and 2-(chloromethyl)pyrimidine hydrochloride (0.143 g; 0.87 mmol) was added. The mixture was stirred at 0° C. for 3 hours. Water (200 mL) was added and the reaction mixture (from 0.057 g of intermediate 28) was combined to the mixture. The mixture was extracted with EtOAc (3×200 mL). The combined organic layers were dried over $Na_2SO_4$, filtered and concentrated. The residue (1.73 g, brown oil) was purified by column chromatography over silica gel (eluent: DCM/MeOH from 100/0 to 95/5). The product fractions were collected and the solvent was evaporated to give 0.295 g which was triturated in $Et_2O$ (4×5 mL). The solid was filtered and dried under vacuum to give 0.286 g (overall yield 81%, yellow solid) of compound 14 M.P.: 183° C. (DSC).

Example B5

Preparation of Compound 8

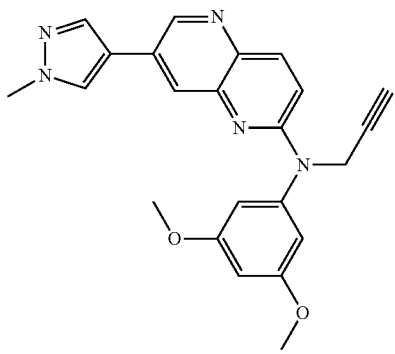 [SMILES: C#CCN(c1cc(OC)cc(OC)c1)c1ccc2ncc(-c3cnn(C)c3)cc2n1]

Potassium carbonate (0.45 g, 3.4 mmol) was added to a mixture of intermediate 13 (1.6 g, 3.4 mmol) in MeOH (34 ml) and the mixture was stirred at room temperature overnight. The mixture was concentrated to dryness and purified by chromatography over silica gel (mobile phase, 98% DCM, 2%). The desired fractions were collected and the solvent was evaporated, yielding 0.665 g (49%) of compound 8.

Example B6

Preparation of Compound 11

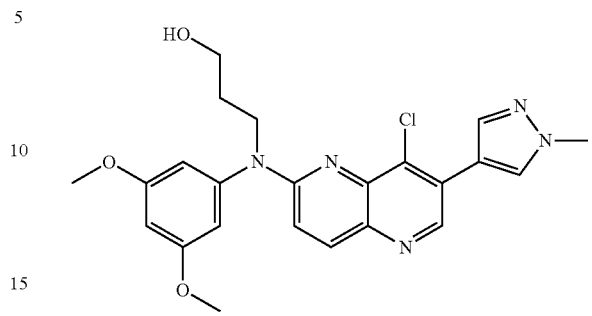

A 1M tetrabutylammonium solution in THF (1.13 ml, 1.13 mmol) was added to a solution of intermediate 17 (0.76 mmol) in THF (38 ml). The reaction mixture was stirred at room temperature for 2 hours. Water and a saturated solution of $K_2CO_3$ were added and the mixture was extracted with AcOEt. The combined organic layers were washed with brine, dried over $Na_2SO_4$, filtered and concentrated to dryness. The residue was purified by chromatography over silica gel (40-63 μm, mobile phase, gradient from 98% DCM, % MeOH to 96% DCM, 4% MeOH). The product fractions were collected and evaporated to dryness, yielding 190 mg (55%) of compound 11 (MP: 167° C., DSC).

Analogous preparation of compound 15 starting from intermediate 29

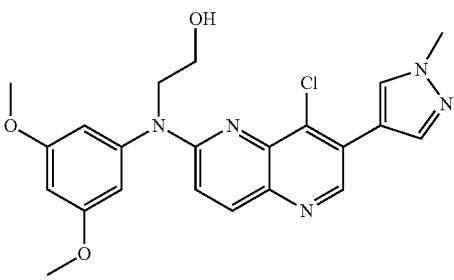 [SMILES: COc1cc(OC)cc(N(CCO)c2ccc3ncc(-c4cnn(C)c4)c(Cl)c3n2)c1]

Example B7

Preparation of Compound 48

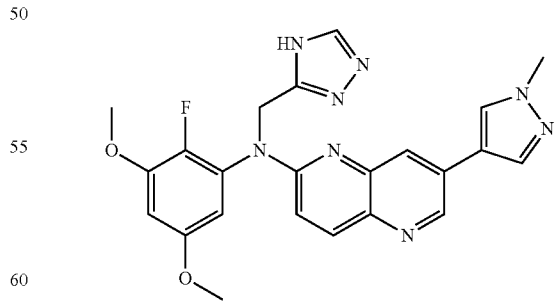

Two reactions performed on intermediate 41 respectively on 0.735 g and 0.05 g were combined for the work up. The synthesis is described below:

HCl 12M (0.436 mL; 5.23 mmol) was added to a solution of intermediate 41 (0.735 g; 1.05 mmol) in MeOH (15 mL)

at 0° C. The mixture was warmed to room temperature and stirred at room temperature for 16 hours. The reaction mixture and the reaction mixture (from 0.05 g of intermediate 41) were poured into a mixture of ice water (100 mL) and solid NaHCO₃ (about 20 g). The aqueous layer was extracted with a mixture of EtOAc/MeOH (9/1; 3×40 mL). The combined organic layers were dried over Na₂SO₄, filtered and concentrated. The residue (1.32 g, yellow solid) was adsorbed on silica gel and purified by column chromatography over silica gel (eluent: DCM/MeOH 97/3 to 93/7). The product fractions were collected and the solvent was evaporated. The residue (0.500 g) was triturated in Et₂O (30 mL). The precipitate was filtered off, washed with Et₂O (10 mL) and dried under vacuum at 80° C. for 16 hours to give 0.420 g (overall yield 82%, yellow solid) of compound 48. M.P.: 216° C. (DSC).

Analogous preparation of compound 47 starting from intermediate 40

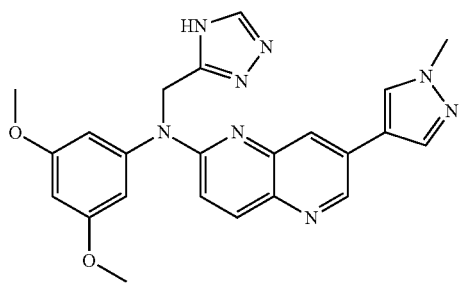 [SMILES: COc1cc(OC)cc(N(Cc2nnc[nH]2)c2ccc3ncc(-c4cnn(C)c4)cc3n2)c1]

Analogous preparation of compound 49 starting from intermediate 42

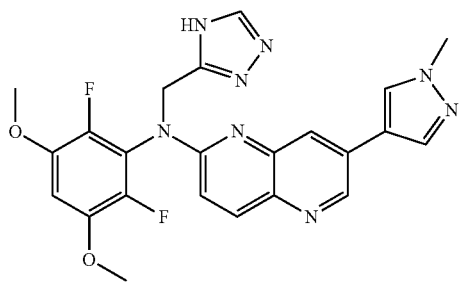 [SMILES: COc1cc(OC)c(F)c(N(Cc2nnc[nH]2)c2ccc3ncc(-c4cnn(C)c4)cc3n2)c1F]

Example B8

Preparation of Compound 31

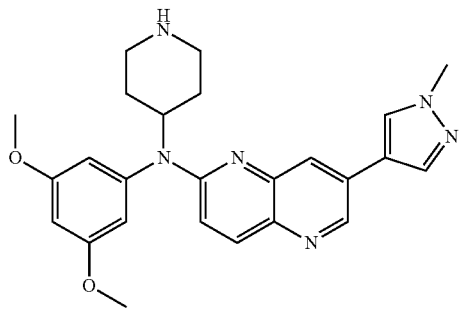 [SMILES: COc1cc(OC)cc(N(c2ccc3ncc(-c4cnn(C)c4)cc3n2)C2CCNCC2)c1]

HCl 4M in dioxane (6.9 mL; 27.7 mmol) was added to a mixture of intermediate 34 (0.30 g; 0.55 mmol) in DCM (1.5 mL) and the mixture was stirred at room temperature overnight. A 2M aqueous solution of NaOH (15 mL) and water (130 mL) were added (pH=14). The mixture was extracted with DCM (3×100 mL). The combined organic layers were washed with brine (150 mL), dried over Na₂SO₄, filtered and concentrated. The residue was purified by column chromatography over silica gel (eluent: DCM/MeOH 95/5 to 90/10, then DCM/MeOH/NH₄OH 90/10/0.1 to 90/10/0.4).

The fractions containing the product were collected and concentrated to give 0.084 g of the expected compound. This solid was purified by preparative TLC (SiOH, eluent: DCM/MeOH/NH₄OH 90/10/0.1) to give an intermediate residue which was triturated in Et₂O and dried under vacuum to give 68 mg of expected compound. This fraction was purified by reverse phase chromatography (C18 Luna 10 μm, eluent: MeOH/water/trifluoroacetic acid 40/60/0.1). The resulting fraction was triturated in Et₂O. The precipitate was filtered and dried under vacuum to give 0.025 g (10%) of compound 31. MP: 150° C. (DSC).

Example B9

Preparation of Compound 74

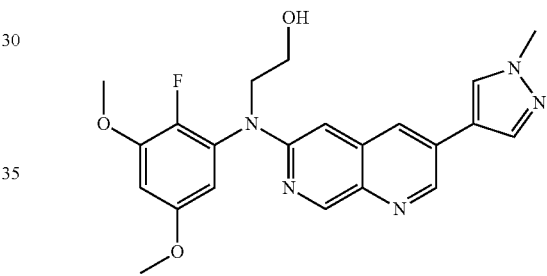

NaH (8 mg; 0.198 mmol) was added to a mixture of intermediate 65 (50 mg; 0.132 mmol) in DMF (2 mL) at 0° C. The mixture was stirred at 0° C. for 30 minutes, then (2-bromoethoxy)-tert-butyldimethylsilane (CAS 86864-60-1) (0.042 mL; 0.198 mmol) was added at 0° C. The mixture was stirred at 0° C. for 1 hour and at room temperature for 65 hours. The reaction mixture was cooled to 0° C. and additional NaH (8 mg; 0.198 mmol) was added The mixture was stirred at 0° C. for 30 minutes, then (2-bromoethoxy)-tert-butyldimethylsilane (CAS 86864-60-1) (0.042 mL; 0.198 mmol) was added. The mixture was stirred at 0° C. for 1 hour and at room temperature for 2 hours.

Ice water (5 mL) was added and the mixture was extracted with EtOAc (3×10 mL). The combined organic layers were washed with brine (3×10 mL), dried over Na₂SO₄, filtered and concentrated. The residue was taken-up with THF (2 mL) and aqueous 3M HCl (2 mL) and stirred at room temperature for 16 hours. The reaction mixture was basified with an aqueous 3M solution of NaOH (2.5 mL), diluted with water (20 mL) and extracted with a mixture of DCM/MeOH (9/1; 3×15 mL). The organic layers were dried over Na₂SO₄, filtered and the solvent was evaporated. The residue (0.067 g) was purified by column chromatography over silica gel (eluent: DCM/MeOH: from 98/2 to 97/3). The product fractions were collected and the solvent was evaporated to give 24 mg of an intermediate residue which was triturated in Et₂O (2 mL). The precipitate was filtered off rinsed with Et₂O (10 mL) and dried under vacuum at 80° C. for 16 hours to give 20 mg (36%, yellow solid) of compound 74. M.P.: 200° C. (DSC).

Analogous preparation of compound 75 starting from intermediate 65

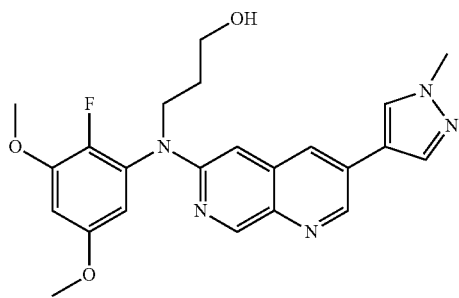 [SMILES: COc1cc(OC)c(F)c(N(CCCO)c2cc3cc(-c4cnn(C)c4)cnc3cn2)c1]

Analogous preparation of compound 78 starting from intermediate 66

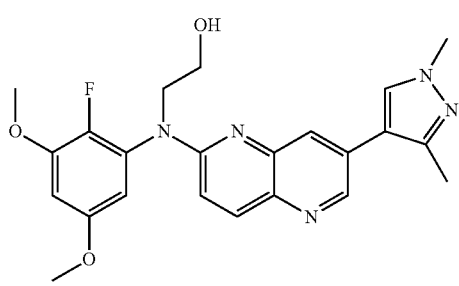 [SMILES: COc1cc(OC)c(F)c(N(CCO)c2ccc3ncc(-c4cn(C)nc4C)cc3n2)c1]

C. Conversion of compounds

Example C1

Preparation of Compound 9

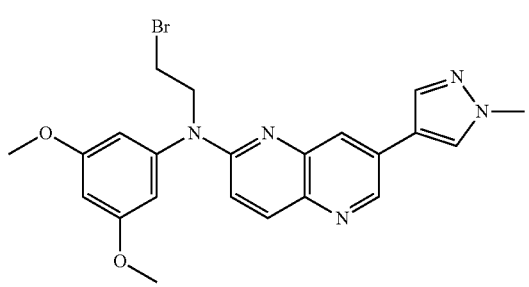

Compound 1 (1.0 g, 2.5 mmol) was added to a mixture of triphenyl phosphine (0.776 g, 3.0 mmol), 2,3-dichloro-5,6-dicyanobenzoquinone (0.672 g, 3.0 mmol) and tetrabutylammonium bromide (0.954 g, 3.0 mmol) in dichloromethane (22 ml). The mixture was stirred at room temperature for 30 minutes and concentrated to dryness. The residual brown solid was purified by chromatography over silica gel (mobile phase, gradient from 100% DCM to 80% DCM, 20%). The product fractions were collected and the solvent was evaporated, yielding 0.720 g (62%) of compound 9.

Example C2

Preparation of Compound 10

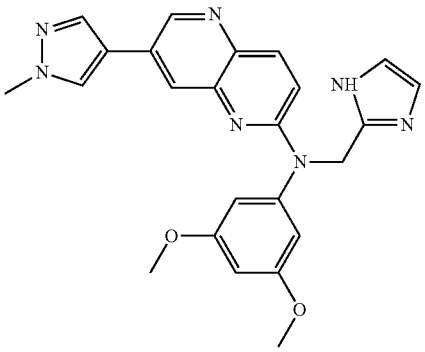 [SMILES: COc1cc(OC)cc(N(Cc2ncc[nH]2)c2ccc3ncc(-c4cnn(C)c4)cc3n2)c1]

A 4N hydrochloric acid solution in dioxane (2.5 ml, 10 mmol) was added to a solution of compound 7 (0.55 g, 1.0 mmol) in acetonitrile (10 ml). The reaction mixture was heated at 50° C. for 16 hours. After cooling to room temperature, the mixture was basified with a 1M aqueous solution of sodium hydroxide (20 ml), diluted with water (100 ml) and extracted with dichloromethane (3×100 ml). The combined organic layers were dried over sodium sulfate, filtered and concentrated. The desired residue was purified by chromatography over silica gel (mobile phase, gradient from 97% DCM, 3% MeOH to 85% DCM, 15% MeOH). Two product fractions were collected and the solvent was evaporated, yielding 0.233 g (42%) of unreacted started material (compound 7) and 0.204 g of fraction 2.

Fraction 2 was purified again by chromatography over silica gel (mobile phase, gradient from 98% DCM, 2% MeOH to 90% DCM, 10% MeOH). The desired fractions were collected and the solvent was evaporated. The residue was triturated in diethylether, filtered off and dried under vacuum, yielding 0.137 g of compound 10 (MP: 195° C., DSC).

Analogous preparation of compound 16 starting from compound 17

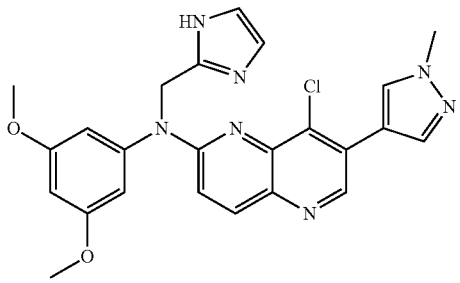 [SMILES: COc1cc(OC)cc(N(Cc2ncc[nH]2)c2ccc3ncc(-c4cnn(C)c4)c(Cl)c3n2)c1]

Analogous preparation of compound 19 starting from compound 18

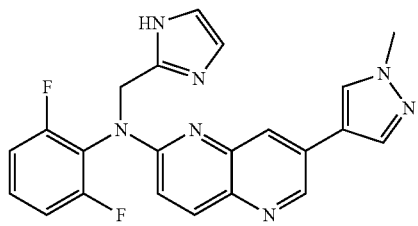 [SMILES: Cn1cc(-c2cnc3ccc(N(Cc4ncc[nH]4)c4c(F)cccc4F)nc3c2)cn1]

Analogous preparation of compound 24 starting from compound 25

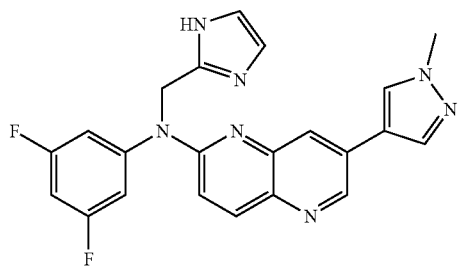 [SMILES: Cn1cc(-c2cnc3ccc(N(Cc4ncc[nH]4)c4cc(F)cc(F)c4)nc3c2)cn1]

Analogous preparation of compound 34 starting from compound 33

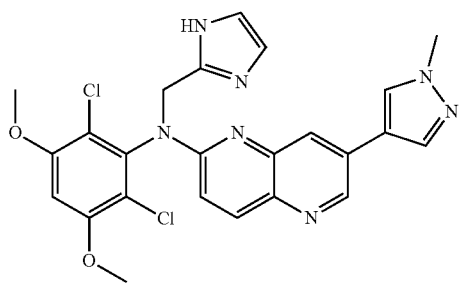 [SMILES: COc1cc(OC)c(Cl)c(N(Cc2ncc[nH]2)c2ccc3ncc(-c4cnn(C)c4)cc3n2)c1Cl]

Analogous preparation of compound 55 starting from compound 56

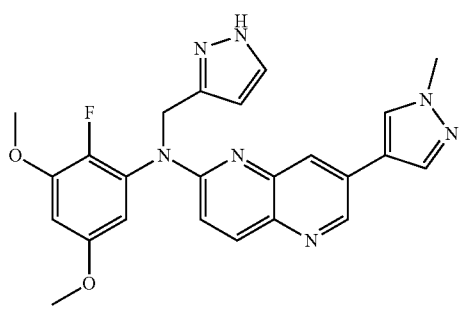 [SMILES: COc1cc(OC)c(F)c(N(Cc2cc[nH]n2)c2ccc3ncc(-c4cnn(C)c4)cc3n2)c1]

Analogous preparation of compound 59 starting from compound 60

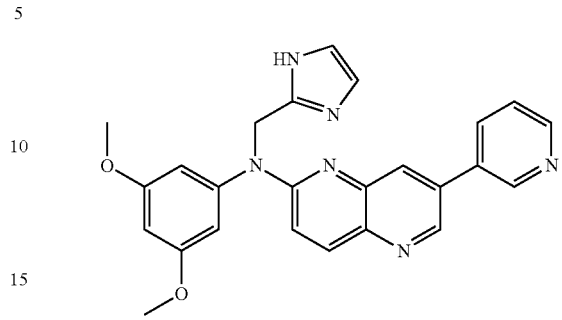

Analogous preparation of compound 62 starting from compound 63

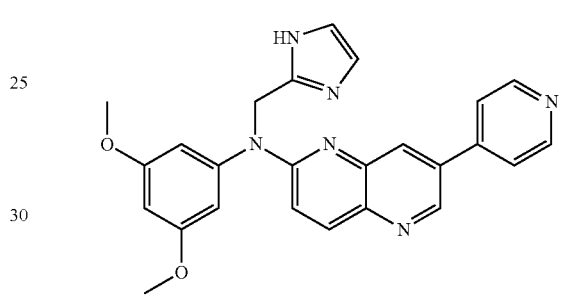

Analogous preparation of compound 65 starting from compound 64

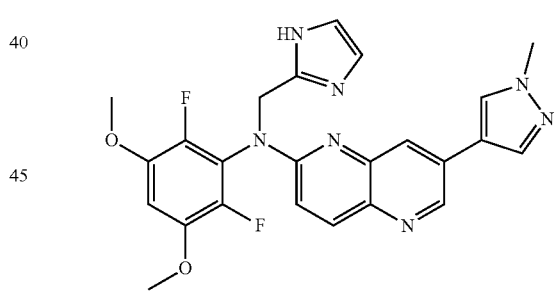

Analogous preparation of compound 67 starting from compound 66

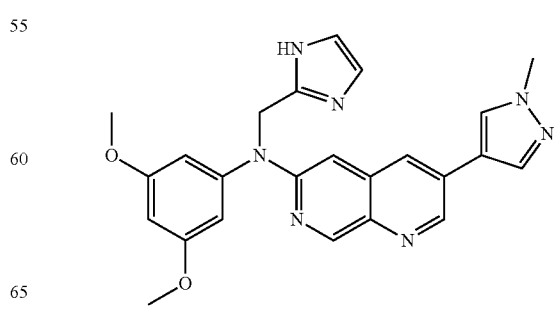

Analogous preparation of compound 72 starting from compound 71

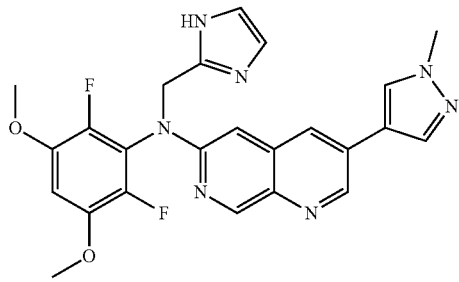 [SMILES: COc1cc(OC)c(F)c(N(Cc2ncc[nH]2)c2cc3cc(-c4cnn(C)c4)cnc3cn2)c1F]

Analogous preparation of compound 77 starting from compound 76

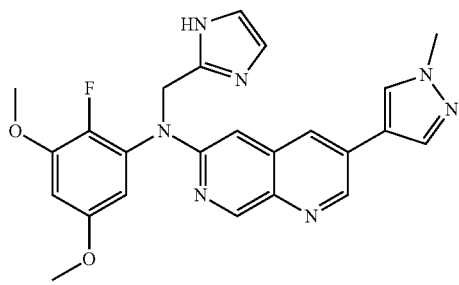 [SMILES: COc1cc(OC)c(F)c(N(Cc2ncc[nH]2)c2cc3cc(-c4cnn(C)c4)cnc3cn2)c1]

Example C2a

Preparation of Compound 39

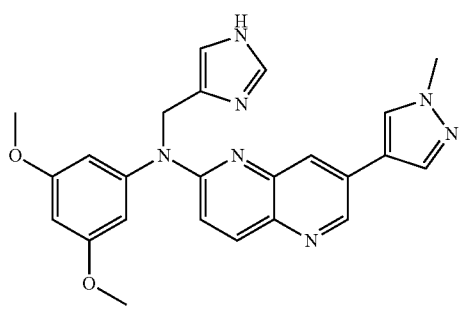 [SMILES: COc1cc(OC)cc(N(Cc2c[nH]cn2)c2ccc3ncc(-c4cnn(C)c4)cc3n2)c1]

HCl 4M in dioxane (4.3 mL; 17.2 mmol) was added dropwise to a solution of compound 38 (0.473 g; 0.86 mmol) in ACN (8.6 mL). The mixture was stirred at room temperature for 1 hour, at 50° C. overnight and was allowed to cool to room temperature. A 1M aqueous solution of NaOH (80 mL) and water (80 mL) were added (pH=14). The mixture was extracted with DCM (3×100 mL). The combined organic layers were washed with brine (100 mL), dried over $Na_2SO_4$, filtered and concentrated. The residue (0.410 g, yellow gum) was purified by column chromatography over silica gel (eluent: EtOAc/MeOH 95/5 to 90/10). The product fractions were collected and the solvent was evaporated. The resulting residue was triturated in $Et_2O$ (4×5 mL) and dried under vacuum to give 0.254 g (67%, yellow solid) of compound 39 M.P.: 188° C. (DSC).

Example C3

Preparation of Compound 53

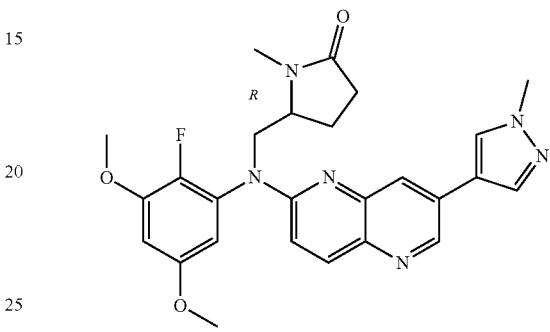

NaH (0.038 g; 0.94 mmol) was added to a suspension of compound 40 (0.287 g; 0.63 mmol) in DMF (3 mL) at 0° C. The reaction mixture was stirred at 0° C. for 1 hour, then iodomethane (0.058 mL; 0.94 mmol) was added at 0° C. The reaction mixture was stirred at 0° C. for 1 h and at room temperature overnight. Water (50 mL) and brine (50 mL) were added and the mixture was extracted with EtOAc (3×50 mL). The combined organic layers were dried over $Na_2SO_4$, filtered and concentrated. The residue (0.600 g, yellow oil) was purified by column chromatography over silica gel (eluent: DCM/MeOH from 100/0 to 95/5). The fractions containing product were collected and the solvent was evaporated. The residue was triturated in $Et_2O$. The precipitate was filtered and dried under vacuum to give 41 mg (14%, yellow solid) of compound 53. M.P.: 192° C. (DSC).

The following compounds were prepared according to reaction protocols of one of the above Examples using alternative starting materials as appropriate.

In the tables A1 and A1a=CX (or =BX) indicates that the preparation of this compound is described in Conversion X (or Method BX).

In the tables A1 and A1a~CX (or ~BX) indicates that this compound is prepared according to Conversion X (or Method BX).

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

TABLE A1

| Comp. No. | Compound Struct. | Method | Melting Point (° C.) | (Kofler (K) or DSC or Buchi) | HPLC Rt (min) | MS M+ (H⁺) | LC/GC/MS method |
|---|---|---|---|---|---|---|---|
| 1 | | =B1 | 166-167° C. | Buchi | 12.57 | 406 | 2 |
| 3 | | =B2 | 138° C. | DSC | 10.92 | 420 | 3 |
| 6 | | =B3 | – | – | 2.58 | 532 | 1 |
| 4 | | =B3 | 217° C. | DSC | 9.91 | 447 | 3 | as a HCl salt

TABLE A1-continued compounds and physico-chemical data

| Comp. No. | Compound Struct. | Method | Melting Point (° C.) | (Kofler (K) or DSC or Buchi) | HPLC Rt (min) | MS M+ (H+) | LC/GC/ MS method |
|---|---|---|---|---|---|---|---|
| 5 | | =B3 | 112° C. | Kofler | 2.36 | 447 | 1 |
| 10 | | =C2 | 195° C. | DSC | 11.9 | 442 | 2 |
| 7 | | =B4 | 80-86° C. | Buchi | 13.84 | 549 | 2 |
| 2 | | ~B1 | 154° C. | DSC | 12.83 | 420 | 2 |

TABLE A1-continued compounds and physico-chemical data

| Comp. No. | Compound Struct. | Method | Melting Point (°C.) | (Kofler (K) or DSC or Buchi) | HPLC Rt (min) | MS M+ (H+) | LC/GC/ MS method |
|---|---|---|---|---|---|---|---|
| 8 | | =B5 | 188-189° C. | Buchi | 13.97 | 400 | 2 |
| 11 | | =B6 | 167° C. | DSC | 11.85 | 454 | 3 |
| 9 | | =C1 | — | — | — | — | — |

TABLE A1a compounds and physico-chemical data

| Compound No. | Compound | Method | Melting Point (°C.) | (Kofler (K) or DSC) | HPLC RT (min) | MS M+ (H+) | LC/GC/ MS method |
|---|---|---|---|---|---|---|---|
| 14 | | =B4a | 183 | DSC | 10.59 | 490 | 3 |

TABLE A1a-continued compounds and physico-chemical data

| Compound No. | Compound | Method | Melting Point (° C.) | (Kofler (K) or DSC) | HPLC RT (min) | MS M+ (H+) | LC/GC/MS method |
|---|---|---|---|---|---|---|---|
| 22 | | B1 | 173 | DSC | 10.54 | 456 | 3 |
| 65 | | C2 | 237 | DSC | 9.60 | 478 | 3 |
| 32 | | B4 | 176 | DSC | 10.65 | 532 | 3 |
| 35 | | B2 | 127° C. | DSC | 12.03 | 484 | 3 |

TABLE A1a-continued compounds and physico-chemical data

| Compound No. | Compound | Method | Melting Point (° C.) | (Kofler (K) or DSC) | HPLC RT (min) | MS M+ (H+) | LC/GC/MS method |
|---|---|---|---|---|---|---|---|
| 33 | | B3 | 204 | DSC | 11.17 | 617 | 3 |
| 29 | | B3b | 105 | K | 2.29 | 465 | 1 |
| 30 | | =B3a | 120 | K | 2.15 | 437 | 1 |
| 31 | | =B8 | 150 | DSC | 11.79 | 445 | 4 |

TABLE A1a-continued compounds and physico-chemical data

| Compound No. | Compound | Method | Melting Point (° C.) | (Kofler (K) or DSC) | HPLC RT (min) | MS M+ (H+) | LC/GC/MS method |
|---|---|---|---|---|---|---|---|
| 27 | | B4 | 182 | DSC | 10.63 | 472 | 3 |
| 16 | | C2 | 208 | DSC | 10.30 | 476 | 3 |
| 15 | | B6 | 165 | DSC | 10.47 | 440 | 3 |
| 23 | | B3a | Gum at 60 | K | 2.31 | 423 | 1 |
| 13 | | B3a | — | — | 2.4 | 461 | 1 |

TABLE A1a-continued
compounds and physico-chemical data
| Compound No. | Compound | Method | Melting Point (° C.) | (Kofler (K) or DSC) | HPLC RT (min) | MS M+ (H+) | LC/GC/ MS method |
|---|---|---|---|---|---|---|---|
| 12 | 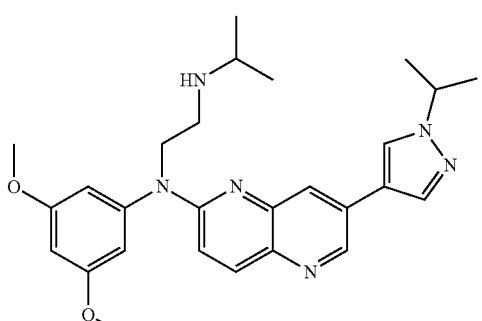 | B3a | — | — | 2.52 | 475 | 1 |
| 21 | 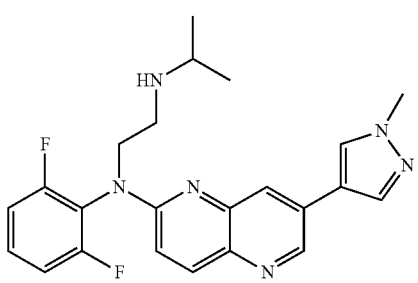 [SMILES: CC(C)NCCN(c1ccc2ncc(-c3cnn(C)c3)cc2n1)c1c(F)cccc1F] | =B3b | 78 | DSC | 2.18 | 423 | 1 |
| 19 | 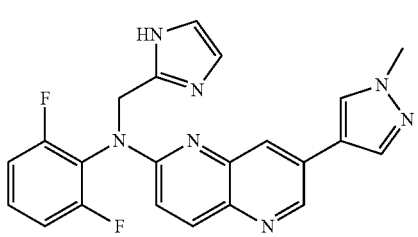 [SMILES: Cn1cc(-c2cnc3ccc(N(Cc4ncc[nH]4)c4c(F)cccc4F)nc3c2)cn1] | C2 | 246 | DSC | 9.13 | 418 | 3 |
| 24 | 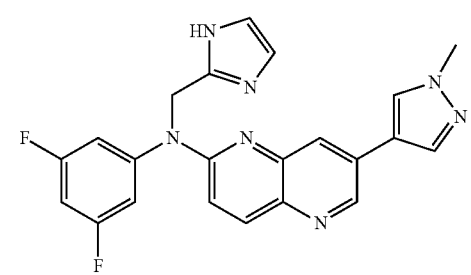 [SMILES: Cn1cc(-c2cnc3ccc(N(Cc4ncc[nH]4)c4cc(F)cc(F)c4)nc3c2)cn1] | C2 | 232 | DSC | 9.41 | 418 | 3 |
| 18 | 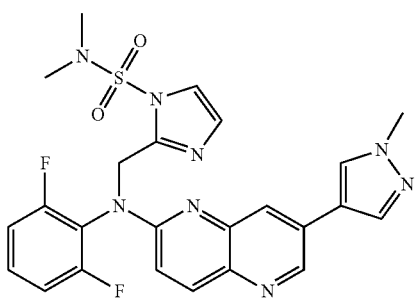 [SMILES: CN(C)S(=O)(=O)n1ccnc1CN(c1ccc2ncc(-c3cnn(C)c3)cc2n1)c1c(F)cccc1F] | B4 | 164 | DSC | 10.87 | 525 | 3 |

TABLE A1a-continued compounds and physico-chemical data

| Compound No. | Compound | Method | Melting Point (° C.) | (Kofler (K) or DSC) | HPLC RT (min) | MS M+ (H⁺) | LC/GC/MS method |
|---|---|---|---|---|---|---|---|
| 26 | | B3a | 130 | K | 2.27 | 483 | 1 |
| 34 | | C2 | 237 | DSC | 10.01 | 510 | 3 |
| 36 | | B2 | 120 | DSC | 11.78 | 466 | 3 |
| 37 | | B2a-4 | >300 | DSC | 10.21 | 459 | 3 |

TABLE A1a-continued compounds and physico-chemical data

| Compound No. | Compound | Method | Melting Point (°C.) | (Kofler (K) or DSC) | HPLC RT (min) | MS M+ (H+) | LC/GC/MS method |
|---|---|---|---|---|---|---|---|
| 38 | | B4 | 192 | DSC | 13.77 | 549 | 4 |
| 39 | | =C2a | 188 | DSC | 9.51 | 442 | 3 |
| 40 | | B2a-1 | Decomposition from 211 | DSC | 10.32 | 477 | 3 |
| 41 | | =B2a-2 | Decomposition from 276 | DSC | 10.24 | 459 | 3 |

TABLE A1a-continued compounds and physico-chemical data

| Compound No. | Compound | Method | Melting Point (° C.) | (Kofler (K) or DSC) | HPLC RT (min) | MS M+ (H+) | LC/GC/ MS method |
|---|---|---|---|---|---|---|---|
| 42 | | =B2a-3 | Decomposition from 233 | DSC | 10.39 | 495 | 3 |
| 43 | | =B2a-4 | Decomposition from 221 | DSC | 10.32 | 477 | 3 |
| 44 | | B2a-4 | Decomposition from 205 | DSC | 10.39 | 495 | 3 |
| 45 | | B2 | 179 | DSC | 11.46 | 482 | 3 |

TABLE A1a-continued compounds and physico-chemical data

| Compound No. | Compound | Method | Melting Point (° C.) | (Kofler (K) or DSC) | HPLC RT (min) | MS M+ (H+) | LC/GC/ MS method |
|---|---|---|---|---|---|---|---|
| 46 | | =B2a-6 | 157 | DSC | 2.11 | 455 | 1 |
| 47 | | B7 | 212-214 | Buchi | 9.17 | 443 | 3 |
| 48 | | =B7 | 216 | DSC | 9.21 | 461 | 3 |
| 49 | | B7 | 235 | DSC | 9.19 | 479 | 3 |
| 50 | | B2 | 139 | DSC | 10.98 | 446 | 3 |

TABLE A1a-continued compounds and physico-chemical data

| Compound No. | Compound | Method | Melting Point (° C.) | (Kofler (K) or DSC) | HPLC RT (min) | MS M+ (H+) | LC/GC/MS method |
|---|---|---|---|---|---|---|---|
| 51 | | B2 | 141 | DSC | 11.20 | 464 | 3 |
| 52 | as a hydrochloric acid salt | B2a-6 | 80, gum | K | 2.22 | 487 | 1 |
| 53 | | =C3 | 192 | DSC | 10.25 | 491 | 3 |
| 54 | | B2 | 230 | DSC | 9.62 | 437 | 3 |

TABLE A1a-continued compounds and physico-chemical data

| Compound No. | Compound | Method | Melting Point (° C.) | (Kofler (K) or DSC) | HPLC RT (min) | MS M+ (H+) | LC/GC/MS method |
|---|---|---|---|---|---|---|---|
| 55 | | C2 | 195 | DSC | 10.09 | 460 | 3 |
| 56 | | B4 | Decomposition at 300 | DSC | 11.66 | 567 | 3 |
| 57 | | B2 | 155 | DSC | 11.01 | 447 | 3 |
| 58 | | B4 | 149 | DSC | 10.80 | 461 | 3 |

TABLE A1a-continued compounds and physico-chemical data

| Compound No. | Compound | Method | Melting Point (° C.) | (Kofler (K) or DSC) | HPLC RT (min) | MS M+ (H+) | LC/GC/ MS method |
|---|---|---|---|---|---|---|---|
| 59 | | C2 | 242 | DSC | 8.84 | 439 | 3 |
| 60 | | B4 | 201 | DSC | 10.48 | 546 | 3 |
| 61 | | =B1a | 209 | Buchi-M-550 | 9.03 | 403 | 3 |
| 62 | | C2 | 222 | DSC | 8.99 | 439 | 3 |

TABLE A1a-continued compounds and physico-chemical data

| Compound No. | Compound | Method | Melting Point (° C.) | (Kofler (K) or DSC) | HPLC RT (min) | MS M+ (H⁺) | LC/GC/ MS method |
|---|---|---|---|---|---|---|---|
| 63 | | B4 | 215 | DSC | 10.61 | 546 | 3 |
| 69 | | B2 | 198 | DSC | 11.65 | 420 | 3 |
| 68 | | B3a | 163 | DSC | 10.62 | 447 | 3 |
| 66 | | B4 | 182 | DSC | 11.73 | 549 | 3 |

TABLE A1a-continued compounds and physico-chemical data

| Compound No. | Compound | Method | Melting Point (° C.) | (Kofler (K) or DSC) | HPLC RT (min) | MS M+ (H+) | LC/GC/ MS method |
|---|---|---|---|---|---|---|---|
| 67 | | C2 | 210 | DSC | 10.10 | 442 | 3 |
| 70 | | =B2a-5 | 148 | DSC | 9.76 | 455 | 3 |
| 72 | | C2 | 234 | DSC | 9.80 | 478 | 3 |
| 71 | | B4 | 127 | DSC | 11.23 | 585 | 3 |
| 77 | | C2 | 230 | DSC | 9.99 | 460 | 3 |

TABLE A1a-continued compounds and physico-chemical data

| Compound No. | Compound | Method | Melting Point (° C.) | (Kofler (K) or DSC) | HPLC RT (min) | MS M+ (H+) | LC/GC/ MS method |
|---|---|---|---|---|---|---|---|
| 76 | | B4 | 132 | DSC | 11.52 | 567 | 3 |
| 75 | | B9 | 151 | DSC | 10.80 | 438 | 3 |
| 74 | | =B9 | 200 | DSC | 10.54 | 424 | 3 |
| 73 | | B2a-6 | 172 | DSC | 9.90 | 437 | 3 |

TABLE A1a-continued compounds and physico-chemical data

| Compound No. | Compound | Method | Melting Point (° C.) | (Kofler (K) or DSC) | HPLC RT (min) | MS M+ (H⁺) | LC/GC/MS method |
|---|---|---|---|---|---|---|---|
| 20 | | =B3b | 130-134 | K | 2.38 | 423 | 1 |
| 28 | | B3b | Gum at 70 | K | 2.37 | 465 | 1 |
| 64 | | B4 | 144 | DSC | 11.15 | 585 | 3 |
| 17 | | B4 | | | | | |

TABLE A1a-continued compounds and physico-chemical data

| Compound No. | Compound | Method | Melting Point (° C.) | (Kofler (K) or DSC) | HPLC RT (min) | MS M+ (H+) | LC/GC/ MS method |
|---|---|---|---|---|---|---|---|
| 25 | (structure) | B4 | | | | | |
| 78 | (structure) | B9 | 153 | DSC | 10.05 | 438 | 3 |

Analytical Part
LC/GC/NMR

The LC/GC data reported in Table A1 were determined as follows.

General Procedure A

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method I

In addition to the general procedure A: Reversed phase UPLC was carried out on a Waters Acquity BEH (bridged ethylsiloxane/silica hybrid) C18 column (1.7 μm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 μl was used. Cone voltage was 20V for positive and negative ionization mode. Mass spectra were acquired by scanning from 100 to 1000 in 0.2 seconds using an interscan delay of 0.1 seconds.

General Procedure B

The HPLC measurement was performed using an HPLC 1100/1200 (Agilent) system comprising a quaternary pump with degasser, an autosampler, a diode-array detector (DAD) and a column as specified in the respective methods below, the column is held at a room temperature. The MS detector (MS-Agilent simple quadripole) was configured with an electrospray-APCI ionization source. Nitrogen was used as the nebulizer gas. Data acquisition was performed with a Chemstation data system.

Method 2

In addition to the general procedure B: Reversed phase HPLC was carried out on a Nucleosil C18 column (3 μm, 3×150 mm) with a flow rate of 0.42 ml/min. Two mobile phases (mobile phase A: Water TFA 0.1%; mobile phase B: 100% acetonitrile) were employed to run a gradient condition from 98% A for 3 minutes, to 100% B in 12 minutes, 100% B for 5 minutes, then back to 98% A in 2 minutes, and reequilibrated with 98% A for 6 minutes. An injection volume of 2 μl was used. The capillary voltage was 2 kV, the corona discharge was held at 1 μA and the source temperature was maintained at 250° C. A variable voltage was used for the fragmentor. Mass spectra were acquired in electrospray ionization and APCI in positive mode, by scanning from 100 to 1100 amu.

Method 3

In addition to the general procedure B: Reversed phase HPLC was carried out on a Agilent Eclipse C18 column (5 μm, 4.6×150 mm) with a flow rate of 1 ml/min. Two mobile phases (mobile phase A: Water TFA 0.1%; mobile phase B: 100% acetonitrile) were employed to run a gradient condition from 98% A for 3 minutes, to 100% B in 12 minutes, 100% B for 5 minutes, then back to 98% A in 2 minutes, and reequilibrated with 98% A for 6 minutes. An injection volume of 2 μl was used. The capillary voltage was 2 kV, the corona discharge was held at 1 μA and the source temperature was maintained at 250° C. A variable voltage was used for the fragmentor. Mass spectra were acquired in electrospray ionization and APCI in positive mode, by scanning from 80 to 1000 amu.

Method 4

In addition to the general procedure NOVA: Reversed phase HPLC was carried out on a Agilent Eclipse C18 column (5 μm, 4.6×150 mm) with a flow rate of 1.0 ml/min. Two mobile phases (mobile phase A: Water with 0.1% TFA; mobile phase B: 100% methanol) were employed to run a gradient condition from 98% A held for 3 minutes to 100% B in 12 minutes, 100% B for 5 minutes, then back to 98% A in 2 minutes, and reequilibrated with 98% A for 5 minutes. An injection volume of 2 μl was used. The capillary voltage was 2 kV, the corona discharge was held at 1 μA and the source temperature was maintained at 250° C. A variable voltage was used for the fragmentor. Mass spectra were acquired in electrospray ionization and APCI in positive mode, by scanning from 100 to 1000 amu.

Melting point (M.P.) were taken with a Kofler hot bar or a Büchi Melting Point M-560 but also, for a number of compounds, they were determined with a DSC1 Star$^e$ System (Mettler-Toledo). In this case, melting points were measured with a temperature gradient of 5 or 10° C./minute. Maximum temperature was 350° C. Values are peak values."

NMR Data

The below NMR experiments were carried out using a Bruker Avance 500 and a Bruker Avance DRX 400 spectrometers at ambient temperature, using internal deuterium lock and equipped with reverse triple-resonance ($^1$H, $^{13}$C, $^{15}$N TXI) probe head for the 500 MHz and with reverse double-resonance ($^1$H, $^{13}$C, SEI) probe head for the 400 MHz. Chemical shifts (δ) are reported in parts per million (ppm).

Compound 11

$^1$H NMR (400 MHz, DMSO-$d_6$): δ 8.80 (1H, s), 8.47 (1H, s), 8.13 (1H, s), 7.95 (1H, d, J=9.4 Hz), 6.87 (d, 1H, J=9.4 Hz), 6.55-6.53 (3H, m), 4.50 (1H, t, J=5.2 Hz), 4.17 (2H, t, J=7.2 Hz), 3.96 (3H, s), 3.77 (6H, s), 3.53 (2H, q, J=6.0 Hz), 1.87 (2H, qt, J=6.7 Hz).

Compound 4

$^1$H NMR (500 MHz, DMSO-d6) δ 9.07 (br.s, 1H), 8.91 (br.s, 2H), 8.48 (s, 1H), 8.43 (br.s, 1H), 8.15 (s, 1H), 8.10 (d, J=9.4 Hz, 1H), 6.92 (d, J=9.4 Hz, 1H), 6.72 (d, J=2.2 Hz, 2H), 6.59 (t, J=2.2 Hz, 1H), 4.35 (t, J=6.6 Hz, 2H), 3.94 (s, 3H), 3.78 (s, 6H), 3.45 (spt, J=6.2 Hz, 1H), 3.26 (quin, J=6.6 Hz, 2H), 1.28 (d, J=6.2 Hz, 6H).

Compound 30

$^1$H NMR (500 MHz, DMSO-$d_6$) δ (ppm) 8.91 (d, J=1.9 Hz, 1H), 8.46 (s, 1H), 8.15 (s, 1H), 8.11 (d, J=1.9 Hz, 1H), 7.95 (d, J=9.5 Hz, 1H), 6.76-6.82 (m, 1H), 6.66-6.72 (m, 2H), 4.09 (t, J=6.8 Hz, 2H), 3.90 (s, 1H), 3.88 (s, 1H), 3.78 (s, 3H), 2.78 (t, J=6.8 Hz, 2H), 2.31 (s, 3H)

Compound 31

$^1$H NMR (400 MHz, DMSO-$d_6$) δ 8.86 (s, 1H), 8.47 (s, 1H), 8.16 (s, 1H), 8.09 (s, 1H), 7.85 (d, J=9.3 Hz, 1H), 6.64 (br. s., 1H), 6.32-6.45 (m, 3H), 5.01-5.21 (m, 1H), 3.91 (s, 3H), 3.78 (s, 6H), 3.01 (d, J=11.9 Hz, 2H), 2.66 (d, J=13.4 Hz, 2H), 1.90 (d, J=11.9 Hz, 2H), 1.20-1.39 (m, 3H)

Compound 39

$^1$H NMR (400 MHz, DMSO-$d_6$) δ 11.46-11.97 (m, 1H), 8.80-9.04 (m, 1H), 8.47 (s, 1H), 8.07-8.29 (m, 2H), 7.78-8.00 (m, 1H), 7.43-7.60 (m, 1H), 7.05 (s, 1H), 6.80-6.99 (m, 1H), 6.60-6.79 (m, 2H), 6.34-6.52 (m, 1H), 5.09-5.30 (m, 2H), 3.91 (s, 3H), 3.74 (s, 6H)

Compound 40

$^1$H NMR (400 MHz, DMSO-$d_6$) δ 8.94 (s, 1H), 8.47 (s, 1H), 8.16 (br. s., 2H), 7.98 (d, J=9.1 Hz, 1H), 7.78 (s, 1H), 6.81 (br. s., 2H), 6.69 (d, J=9.1 Hz, 1H), 4.11 (br. s., 2H), 3.85-3.96 (m, 7H), 3.79 (s, 3H), 2.21-2.32 (m, 1H), 2.03-2.17 (m, 2H), 1.85 (br. s., 1H)

Compound 41

$^1$H NMR (400 MHz, DMSO-$d_6$) δ 8.90 (s, 1H), 8.45 (s, 1H), 8.19-8.08 (m, 2H), 7.92 (d, J=9.3 Hz, 1H), 7.81 (s, 1H), 6.77 (d, J=9.3 Hz, 1H), 6.66 (s, 2H), 6.53 (br. s., 1H), 4.17-4.29 (m, 1H), 4.06-4.16 (m, 1H), 3.87-3.98 (m, 4H), 3.78 (s, 6H), 2.21-2.32 (m, 1H), 2.04-2.18 (m, 2H), 1.73-1.89 (m, 1H)

Compound 42

$^1$H NMR (400 MHz, DMSO-$d_6$) δ 8.98 (s, 1H), 8.48 (s, 1H), 8.17 (s, 2H), 8.05 (d, J=9.1 Hz, 1H), 7.56 (s, 1H), 7.07-7.20 (m, 1H), 6.51-6.91 (m, 1H), 4.11-4.26 (m, 1H), 3.99-4.06 (m, 1H), 3.88-3.97 (m, 9H), 3.79-3.87 (m, 1H), 2.20-2.32 (m, 1H), 2.01-2.18 (m, 2H), 1.84-1.99 (m, 1H)

Compound 43

$^1$H NMR (400 MHz, DMSO-$d_6$) δ 8.94 (s, 1H), 8.47 (s, 1H), 8.16 (s, 2H), 7.98 (d, J=9.1 Hz, 1H), 7.78 (s, 1H), 6.81 (br. s., 2H), 6.69 (d, J=9.1 Hz, 1H), 4.04-4.25 (m, 2H), 3.85-3.97 (m, 7H), 3.79 (s, 3H), 2.19-2.31 (m, 1H), 2.03-2.16 (m, 2H), 1.76-1.93 (m, 1H)

Compound 48

$^1$H NMR (400 MHz, DMSO-$d_6$) δ 13.82 (br. s., 1H), 8.95 (s, 1H), 8.46 (s, 1H), 8.21-8.34 (m, 1H), 8.15 (s, 2H), 8.02 (d, J=9.3 Hz, 1H), 6.82 (d, J=9.3 Hz, 1H), 6.68-6.78 (m, 2H), 5.35 (br. s., 2H), 3.91 (s, 3H), 3.88 (s, 3H), 3.73 (s, 3H)

Compound 70

$^1$H NMR (400 MHz, DMSO-$d_6$) δ 9.03-8.87 (m, 2H), 8.43 (br. s., 1H), 8.24 (br. s., 1H), 8.10 (br. s., 1H), 6.93-7.17 (m, 1H), 6.67 (br. s., 1H), 3.71-4.06 (m, 12H), 2.84 (br. s., 2H), 2.37 (s, 3H)

Pharmacological Part

Biological Assays a

FGFR1 (Enzymatic Assay)

In a final reaction volume of 30 μL, FGFR1 (h) (25 ng/ml) was incubated with 50 mM HEPES pH 7.5, 6 mM MnCl$_2$, 1 mM DTT, 0.1 mM Na$_3$VO$_4$, 0.01% Triton-X-100, 500 nM Btn-Flt3 and 5 μM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 μM to 0.1 nM) was determined and used to calculate an IC$_{50}$ (M) and pIC$_{50}$ (−log IC$_{50}$) value.

FGFR2 (Enzymatic Assay)

In a final reaction volume of 30 μL, FGFR2 (h) (150 ng/ml) was incubated with 50 mM HEPES pH 7.5, 6 mM MnCl$_2$, 1 mM DTT, 0.1 mM Na$_3$VO$_4$, 0.01% Triton-X-100, 500 nM Btn-Flt3 and 0.4 μM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in (Relative Fluorescence Units). In this assay, the inhibitory effect of different compound concentrations (range 10 µM to 0.1 nM) was determined and used to calculate an $IC_{50}$ (M) and $pIC_{50}$ (−log $IC_{50}$) value.

FGFR3 (Enzymatic Assay)

In a final reaction volume of 30 µL, FGFR3 (h) (40 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 25 µM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 µM to 0.1 nM) was determined and used to calculate an $IC_{50}$ (M) and $pIC_{50}$ (−log $IC_{50}$) value.

FGFR4 (Enzymatic Assay)

In a final reaction volume of 30 µL, FGFR4 (h) (60 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 5 µM ATP in the presence of compound (1% DMSO final). After incubation for 60 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 µM to 0.1 nM) was determined and used to calculate an $IC_{50}$ (M) and $pIC_{50}$ (−log $IC_{50}$) value.

KDR (VEGFR2) (Enzymatic Assay)

In a final reaction volume of 30 µL, KDR (h) (150 ng/ml) was incubated with 50 mM HEPES pH 7.5, 6 mM $MnCl_2$, 1 mM DTT, 0.1 mM $Na_3VO_4$, 0.01% Triton-X-100, 500 nM Btn-Flt3 and 3 µM ATP in the presence of compound (1% DMSO final). After incubation for 120 minutes at room temperature the reaction was stopped with 2.27 nM EU-anti P-Tyr, 7 mM EDTA, 31.25 nM SA-XL-665 and 0.02% BSA which was present for 60 minutes at room temperature. Time-Resolved Fluorescence Resonance Energy Transfer (TR-FRET) signal (ex340 nm. Em 620 nm, em 655 nm) was measured afterwards and results are expressed in RFU (Relative Fluorescence Units). In this assay, the inhibitory effect of different compound concentrations (range 10 µM to 0.1 nM) was determined and used to calculate an $IC_{50}$ (M) and $pIC_{50}$ (−log $IC_{50}$) value.

Ba/F3-FGFR1 (Minus IL3 or Plus IL3) (Cellular Proliferation Assay)

In a 384 well plate, 100 nl of compound dilution in DMSO was sprayed before adding 50 µl cell culture medium (phenol red free RPMI-1640, 10% FBS, 2 mM L-Glutamine and 50 µg/ml Gentamycin) containing 20000 cells per well of Ba/F3-FGFR1-transfected cells. Cells were put in an incubator at 37° C. and 5% $CO_2$. After 24 hours, 10 µl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a flurorescence plate reader.

In this assay, the inhibitory effect of different compound concentrations (range 10 µM to 0.1 nM) was determined and used to calculate an $IC_{50}$ (M) and $pIC_{50}$ (−log $IC_{50}$) value. As a counterscreen the same experiment was performed in the presence of 10 ng/ml murine IL3.

Ba/F3-FGFR3 (Minus IL3 or Plus IL3) (Cellular Proliferation Assay)

In a 384 well plate, 100 nl of compound dilution in DMSO was sprayed before adding 50 µl cell culture medium (phenol red free RPMI-1640, 10% FBS, 2 mM L-Glutamine and 50 µg/ml Gentamycin) containing 20000 cells per well of Ba/F3-FGFR3-transfected cells. Cells were put in an incubator at 37° C. and 5% $CO_2$. After 24 hours, 10 µl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a flurorescence plate reader.

In this assay, the inhibitory effect of different compound concentrations (range 10 µM to 0.1 nM) was determined and used to calculate an $IC_{50}$ (M) and $pIC_{50}$ (−log $IC_{50}$) value. As a counterscreen the same experiment was performed in the presence of 10 ng/ml murine IL3.

Ba/F3-KDR (Minus IL3 or Plus IL3) (Cellular Proliferation Assay)

In a 384 well plate, 100 nl of compound dilution in DMSO was sprayed before adding 50 µl cell culture medium (phenol red free RPMI-1640, 10% FBS, 2 mM L-Glutamine and 50 µg/ml Gentamycin) containing 20000 cells per well of Ba/F3-KDR-transfected cells. Cells were put in an incubator at 37° C. and 5% $CO_2$. After 24 hours, 10 µl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a flurorescence plate reader.

In this assay, the inhibitory effect of different compound concentrations (range 10 µM to 0.1 nM) was determined and used to calculate an $IC_{50}$ (M) and $pIC_{50}$ (−log $IC_{50}$) value. As a counterscreen the same experiment was performed in the presence of 10 ng/ml murine IL3.

Ba/F3-Flt3 (Minus IL3 or Plus IL3) (Cellular Proliferation Assay)

In a 384 well plate, 100 nl of compound dilution in DMSO was sprayed before adding 50 µl cell culture medium (phenol red free RPMI-1640, 10% FBS, 2 mM L-Glutamine and 50 µg/ml Gentamycin) containing 20000 cells per well of Ba/F3-Flt3-transfected cells. Cells were put in an incubator at 37° C. and 5% $CO_2$. After 24 hours, 10 µl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a flurorescence plate reader.

In this assay, the inhibitory effect of different compound concentrations (range 10 µM to 0.1 nM) was determined and used to calculate an $IC_{50}$ (M) and $pIC_{50}$ (−log $IC_{50}$) value. As a counterscreen the same experiment was performed in the presence of 10 ng/ml murine IL3.

Ba/F3-FGFR4 (Cellular Proliferation Assay)

In a 384 well plate, 100 nl of compound dilution in DMSO was sprayed before adding 50 µl cell culture medium (phenol red free RPMI-1640, 10% FBS, 2 mM L-Glutamine and 50 µg/ml Gentamycin) containing 20000 cells per well of Ba/F3-FGFR4-transfected cells. Cells were put in an incubator at 37° C. and 5% $CO_2$. After 24 hours, 10 µl of Alamar Blue solution (0.5 mM $K_3Fe(CN)_6$, 0.5 mM $K_4Fe(CN)_6$, 0.15 mM Resazurin and 100 mM Phosphate Buffer) was added to the wells, incubated for 4 hours at 37° C. and 5% $CO_2$ before RFU's (Relative Fluorescence Units) (ex. 540 nm., em. 590 nm.) were measured in a flurorescence plate reader.

In this assay, the inhibitory effect of different compound concentrations (range 10 µM to 0.1 nM) was determined and used to calculate an $IC_{50}$ (M) and $pIC_{50}$ ($-\log IC_{50}$) value.

Data for the compounds of the invention in the above assays are provided in Table A2 and A2a.

TABLE A2

(If data were generated multiple times for a compound or different batches were tested, average values are reported)

| Co. No. | FGFR 1 $pIC_{50}$ | FGFR 2 $pIC_{50}$ | FGFR 3 $pIC_{50}$ | FGFR 4 $pIC_{50}$ | VEGFR 2 (KDR) $pIC_{50}$ | BAF3-FGFR1 (MIN IL3) $pIC_{50}$ | BAF3-FGFR1 (PLUS IL3) $pIC_{50}$ | BAF3-FGFR3 (MIN IL3) $pIC_{50}$ | BAF3-FGFR3 (PLUS IL3) $pIC_{50}$ | BAF3-KDR (MIN IL3) $pIC_{50}$ | BAF3-KDR (PLUS IL3) $pIC_{50}$ | BAF3-FLT3 (MIN IL3) $pIC_{50}$ | BAF3-FLT3 (PLUS IL3) $pIC_{50}$ | BAF3-FGFR4 $pIC_{50}$ |
|---|---|---|---|---|---|---|---|---|---|---|---|---|---|---|
| 1 | 8.6 | 8.5 | 9.0 | 8.1 | 7.5 | 7.4 | <5 | ~7.7 | <5 | 5.9 | <5 | 5.05 | <5 | 7.1 |
| 3 | 8.7 | 8.6 | 8.8 | 8.2 | 7.3 | 6.9 | <5 | 7.0 | <5 | 5.3 | <5 | <5 | <5 | 6.4 |
| 6 | 8.7 | 8.3 | 8.4 | 8.1 | 7.3 | 7.1 | 5.2 | 7.0 | 5.2 | 5.9 | 5.1 | 5.3 | 5.0 | 6.8 |
| 4 | 8.9 | 8.4 | 8.5 | 8.3 | 7.5 | 8.25 | <5 | 8.0 | <5 | 5.9 | <5 | 5.1 | <5 | 7.6~7.7 |
| 5 | 8.7 | 8.3 | 8.2 | 7.9 | 7.2 | 7.3 | <5 | 7.2 | <5 | 5.6 | <5 | <5 | <5 | 6.6 |
| 10 | 9.3 | 8.8 | 9.2 | 9.0 | 7.7 | 8.2 | <5 | 8.2 | <5 | 5.8 | <5 | <5 | <5 | ~7.5 |
| 2 | 8.9 | 8.5 | 9.2 | 8.7 | 7.7 | 7.4 | <5 | 7.4 | <5 | 5.8 | <5 | <5 | <5 | 6.9 |
| 7 | 9.0 | 8.4 | 8.7 | 8.0 | 7.3 | 7.0 | <5 | 6.7 | <5 | <5 | <5 | <5 | <5 | 5.9 |
| 8 | 8.5 | 8.4 | 8.8 | 8.0 | 7.1 | 6.5 | <5 |  | <5 | 5.1 | <5 | <5 | <5 | 5.9 |
| 11 | 9.1 | 9.9 | 9.3 | 8.7 | 7.8 |  |  |  |  |  |  |  |  | 6.7 |

TABLE A2a (If data were generated multiple times for a compound or different batches were tested, average values are reported)

| Co. No. | FGFR 1 $pIC_{50}$ | FGFR 2 $pIC_{50}$ | FGFR 3 $pIC_{50}$ | FGFR 4 $pIC_{50}$ | VEGFR 2 (KDR) $pIC_{50}$ | BAF3-FGFR1 (MIN IL3) $pIC_{50}$ | BAF3-FGFR1 (PLUS IL3) $pIC_{50}$ | BAF3-FGFR3 (MIN IL3) $pIC_{50}$ | BAF3-FGFR3 (PLUS IL3) $pIC_{50}$ | BAF3-KDR (MIN IL3) $pIC_{50}$ | BAF3-KDR (PLUS IL3) $pIC_{50}$ | BAF3-FLT3 (MIN IL3) $pIC_{50}$ | BAF3-FLT3 (PLUS IL3) $pIC_{50}$ | BAF3-FGFR 4 $pIC_{50}$ |
|---|---|---|---|---|---|---|---|---|---|---|---|---|---|---|
| 64 | 8.53 | 8.11 | 8.45 | 8.54 | 7.46 | ~8.2 | 6.09 | 7.86 | 5.62 | 6.53 | 5.75 | 5.61 | 5.54 | ~7.55 |
| 14 | 7.77 | 7.71 | 8.27 | 7.96 | 6.96 | 7.77 | 5.32 | 7.66 | 5.03 | 5.83 | 5.05 | 5.11 | <5 | 7.13 |
| 22 | 8.31 | 8.14 | 8.78 | 8.84 | 7.49 | 8.61 | <5 | 8.36 | <5 | 6.87 | <5 | 5.41 | <5 | 8.03 |
| 65 | 8.74 | 8.43 | 8.89 | 8.94 | 7.76 | 8.75 | 5.35 | ~8.49 | <5 | 6.37 | 5.02 | 5.45 | 5.11 | ~8.2 |
| 26 | 9.01 | 8.43 | 8.63 | 8.52 | 7.76 | >9.27 | 5.26 | 8.54 | <5 | 7.05 | <5 | — | — | 8.36 |
| 18 | 7.55 | 7.89 | 6.98 | 6.82 | 6.81 | 6.59 | 5.53 | 5.89 | 5.26 | 5.08 | 5.06 | — | — | 5.72 |
| 24 | 7.64 | 8.05 | 8.02 | 7.54 | 6.73 | 6.13 | <5 | ~6.17 | <5 | 5.04 | <5 | — | — | 5.80 |
| 19 | 7.65 | 7.88 | 7.78 | 7.36 | 6.83 | 6.39 | 5.19 | 6.10 | <5 | 5.16 | <5 | — | — | 5.93 |
| 20 | 7.41 | 7.51 | 7.32 | 6.92 | 6.48 | 6.46 | 5.22 | 6.22 | <5 | 5.04 | <5 | — | — | 6.00 |
| 21 | 8.53 | 8.47 | 8.30 | 7.95 | 6.91 | 7.28 | 5.14 | ~7.16 | <5 | 5.56 | <5 | — | — | 6.71 |
| 12 | 8.72 | 8.43 | 8.47 | 8.30 | 7.78 | 8.22 | <5 | 7.89 | <5 | 6.43 | <5 | — | — | 7.53 |
| 13 | 8.89 | 8.49 | 8.45 | 8.20 | 7.74 | 8.29 | <5 | 7.82 | <5 | 6.36 | <5 | — | — | 7.54 |
| 23 | 7.60 | 8.02 | 7.67 | 7.27 | 6.21 | 6.36 | <5 | 6.15 | <5 | 5.08 | <5 | — | — | 6.22 |
| 15 | 9.14 | 9.12 | 9.26 | 8.61 | 8.05 | 7.48 | <5 | 5.80 | <5 | 5.67 | <5 | — | — | 6.60 |
| 16 | 9.35 | 8.89 | 9.24 | 8.99 | 8.23 | 7.75 | <5 | 7.35 | <5 | 5.87 | <5 | — | — | 7.20 |
| 27 | 8.87 | 8.52 | 8.73 | 8.41 | 7.50 | 7.66 | <5 | 6.90 | <5 | 5.71 | <5 | <5 | <5 | 6.77 |
| 31 | 9.17 | 8.66 | 8.57 | 8.48 | 7.92 | 8.60 | <5 | 8.35 | <5 | 7.16 | <5 | — | — | 8.10 |
| 67 | 6.64 | 7.11 | 7.49 | 6.61 | <6 | 5.05 | <5 | 5.22 | <5 | <5 | <5 | — | — | <5 |
| 66 | 6.86 | 6.39 | 6.31 | ~5.35 | <6 | <5 | <5 | <5 | <5 | <5 | <5 | — | — | <5 |
| 30 | 8.92 | 8.44 | 8.46 | 8.30 | 7.64 | 7.93 | <5 | 7.78 | <5 | 6.56 | <5 | — | — | 7.44 |
| 29 | 8.96 | 8.47 | 8.42 | 8.34 | 7.72 | 8.56 | <5 | 8.62 | <5 | 6.82 | <5 | — | — | 8.10 |
| 28 | 8.57 | 8.09 | 8.04 | 8.18 | 7.34 | 7.81 | <5 | 7.77 | <5 | 6.20 | <5 | — | — | 7.23 |
| 69 | <6 | <6 | ~6.04 | 5.35 | <6 | 5.09 | <5 | <5 | <5 | <5 | <5 | — | — | <5 |
| 68 | 6.89 | 6.93 | 6.76 | 6.11 | <6 | 5.33 | <5 | 5.47 | <5 | <5 | <5 | — | — | 5.15 |
| 33 | 8.65 | 8.06 | 8.14 | 7.44 | 7.31 | 7.38 | <5 | 7.12 | <5 | 5.77 | <5 | — | — | 5.94 |
| 35 | 8.81 | 8.36 | 8.56 | 8.72 | 7.91 | 7.63 | <5 | ~8 | <5 | 5.98 | <5 | — | — | 6.90 |
| 32 | 8.30 | 8.30 | 8.38 | 7.80 | 7.45 | 6.25 | <5 | 6.14 | <5 | 5.33 | <5 | — | — | 5.60 |
| 34 | 8.89 | 8.43 | 8.68 | 8.08 | 7.84 | 7.40 | <5 | 7.42 | <5 | 6.16 | <5 | — | — | 6.42 |
| 40 | 8.84 | 8.67 | 8.76 | 8.64 | 8.10 | 7.55 | <5 | ~7.6 | <5 | 6.31 | <5 | — | — | 7.00 |
| 39 | 9.45 | 9.22 | 9.14 | 9.04 | 8.27 | 8.00 | <5 | ~8.08 | <5 | 5.82 | ~5.09 | — | — | 7.31 |
| 38 | 8.37 | 8.65 | 8.47 | 8.24 | 7.35 | 6.65 | <5 | ~6.58 | <5 | 5.41 | <5 | — | — | 6.30 |
| 37 | 8.63 | 8.54 | 8.74 | 8.31 | 7.43 | 7.10 | <5 | ~7.15 | <5 | 5.47 | <5 | — | — | ~6.49 |
| 36 | 8.70 | 8.52 | 8.55 | 8.45 | 7.74 | 7.06 | <5 | 7.20 | <5 | 5.50 | <5 | — | — | 6.45 |
| 41 | 8.57 | 8.73 | 8.87 | 8.36 | 7.82 | 7.13 | <5 | ~7.22 | <5 | 5.60 | <5 | — | — | 6.35 |
| 44 | 9.01 | 8.68 | 8.85 | 9.00 | 8.05 | 8.22 | <5 | ~8.08 | <5 | 6.31 | <5 | — | — | 7.59 |
| 43 | 8.97 | 8.73 | 8.83 | 8.73 | 7.67 | 7.59 | <5 | 7.77 | <5 | 5.71 | <5 | — | — | 6.94 |
| 42 | 9.02 | 8.71 | 8.80 | 8.92 | 8.23 | 8.12 | <5 | ~8.11 | <5 | 6.91 | <5 | — | — | 7.74 |

TABLE A2a-continued (If data were generated multiple times for a compound or different batches were tested, average values are reported)

| Co. No. | FGFR 1 pIC$_{50}$ | FGFR 2 pIC$_{50}$ | FGFR 3 pIC$_{50}$ | FGFR 4 pIC$_{50}$ | VEGFR 2 (KDR) pIC$_{50}$ | BAF3-FGFR1 (MIN IL3) pIC$_{50}$ | BAF3-FGFR1 (PLUS IL3) pIC$_{50}$ | BAF3-FGFR3 (MIN IL3) pIC$_{50}$ | BAF3-FGFR3 (PLUS IL3) pIC$_{50}$ | BAF3-KDR (MIN IL3) pIC$_{50}$ | BAF3-KDR (PLUS IL3) pIC$_{50}$ | BAF3-FLT3 (MIN IL3) pIC$_{50}$ | BAF3-FLT3 (PLUS IL3) pIC$_{50}$ | BAF3-FGFR 4 pIC$_{50}$ |
|---|---|---|---|---|---|---|---|---|---|---|---|---|---|---|
| 46 | 9.04 | 8.74 | 8.81 | 8.65 | 7.97 | 8.50 | <5 | ~8.55 | <5 | 6.84 | <5 | — | — | 7.99 |
| 45 | 8.94 | 8.55 | 8.70 | 8.65 | 7.99 | 7.64 | <5 | 7.67 | <5 | 6.64 | <5 | — | — | 7.13 |
| 47 | 8.84 | 8.84 | 9.16 | 8.82 | 7.70 | 7.16 | <5 | ~7.63 | <5 | ~6.01 | <5 | — | — | 6.81 |
| 48 | 8.87 | 8.68 | 8.95 | 8.96 | 7.87 | 7.71 | <5 | ~7.9 | <5 | 6.13 | <5 | — | — | 7.06 |
| 49 | 8.68 | 8.50 | 8.84 | 9.03 | 7.99 | 8.18 | <5 | 8.15 | <5 | 6.65 | <5 | — | — | 7.66 |
| 50 | 8.56 | 8.54 | 8.59 | 8.06 | 7.40 | 6.69 | <5 | 6.54 | <5 | 5.23 | <5 | — | — | 5.96 |
| 51 | 8.30 | 8.33 | 8.59 | 8.24 | 7.41 | 7.12 | <5 | ~7.13 | <5 | 5.48 | <5 | — | — | ~6.54 |
| 70 | 7.90 | 7.95 | 7.77 | 7.38 | 6.74 | 7.10 | <5 | ~7.06 | <5 | 5.29 | <5 | — | — | 6.36 |
| 53 | 8.20 | 8.42 | 8.39 | 7.88 | 7.72 | 6.77 | <5 | 6.80 | <5 | 5.70 | <5 | — | — | 6.30 |
| 71 | 7.84 | 7.82 | 7.59 | 7.08 | 6.77 | 6.34 | <5 | 6.27 | <5 | <5 | <5 | — | — | 5.71 |
| 72 | 8.28 | 8.45 | 8.60 | 8.09 | 6.71 | 6.21 | <5 | 6.39 | <5 | <5 | <5 | — | — | 5.95 |
| 52 | 8.60 | 8.10 | 8.17 | 7.35 | 6.98 | 7.26 | <5 | 6.85 | <5 | 5.71 | <5 | — | — | 6.36 |
| 73 | 7.26 | 7.30 | 7.14 | 6.45 | <6 | 6.10 | <5 | ~6.14 | <5 | <5 | <5 | — | — | 5.56 |
| 74 | 7.21 | 7.25 | 7.44 | 6.56 | ~6.04 | 5.62 | <5 | 5.60 | <5 | <5 | <5 | — | — | 5.17 |
| 75 | 7.09 | 7.13 | 7.44 | 6.66 | <6 | 5.62 | <5 | 5.39 | <5 | <5 | <5 | — | — | 5.01 |
| 76 | 7.46 | 7.24 | 6.88 | 6.06 | <6 | 5.46 | <5 | 5.54 | <5 | <5 | <5 | — | — | <5 |
| 77 | 7.56 | 7.86 | 8.01 | 7.25 | <6 | 5.55 | <5 | 5.67 | <5 | <5 | <5 | — | — | 5.11 |
| 54 | 8.44 | 8.15 | 8.55 | 7.82 | 7.27 | 6.03 | <5 | ~6.8 | <5 | 5.63 | <5 | — | — | 6.09 |
| 56 | 8.67 | 8.25 | 8.15 | 8.21 | 7.31 | 6.96 | <5 | ~7.11 | <5 | 5.97 | <5 | — | — | 6.91 |
| 58 | 9.07 | 8.66 | 8.63 | 8.20 | 7.66 | 7.35 | ~5 | 7.61 | <5 | 5.71 | <5 | — | — | 6.76 |
| 63 | 8.58 | 8.41 | 7.94 | 7.34 | 6.85 | 6.23 | <5 | 6.11 | <5 | <5 | <5 | — | — | 5.48 |
| 62 | 9.07 | 8.84 | 8.81 | 8.44 | 7.30 | 7.47 | <5 | 7.69 | <5 | 5.20 | <5 | — | — | 6.84 |
| 57 | 9.26 | 8.84 | 8.92 | 8.92 | 8.14 | 7.77 | <5 | ~8.16 | <5 | 6.21 | <5 | — | — | 7.30 |
| 61 | 8.45 | 8.53 | 8.84 | 7.93 | 7.11 | 6.53 | <5 | ~7.05 | <5 | 5.16 | <5 | — | — | 6.18 |
| 55 | 9.38 | 8.85 | 8.93 | 8.83 | 8.24 | 7.76 | ~5 | ~8.06 | <5 | 6.21 | <5 | — | — | 7.37 |
| 60 | 8.51 | 8.31 | 8.09 | 7.13 | 6.80 | 5.63 | <5 | 5.72 | <5 | <5 | <5 | — | — | 5.05 |
| 59 | 8.87 | 8.81 | 8.74 | 8.40 | 7.09 | 7.55 | <5 | ~7.53 | <5 | 5.37 | <5 | — | — | 6.64 |

The invention claimed is:

1. A method for treating a subject suffering from or being at risk of suffering from a disease state or condition selected from: a carcinoma of the bladder, breast, colon, kidney, epidermis, liver, lung, oesophagus, head and neck, gall bladder, ovary, pancreas, stomach, cervix, endometrium, thyroid, prostate, or skin; gastrointestinal cancer: a hematopoietic tumour of lymphoid lineage; a hematopoietic tumour of myeloid lineage; multiple myeloma; thyroid follicular cancer; a tumour of mesenchymal origin; a tumour of the central or peripheral nervous system: melanoma; seminoma; teratocarcinoma; osteosarcoma; xeroderma pigmentosum; keratoctanthoma; Kaposi's sarcoma: myeloproliferative disorders; colorectal cancer; squamous cell carcinoma; and oral squamous cell carcinoma, said method comprising administering to the subject a compound selected from the group consisting of a compound of formula (I-A) or (I-B)

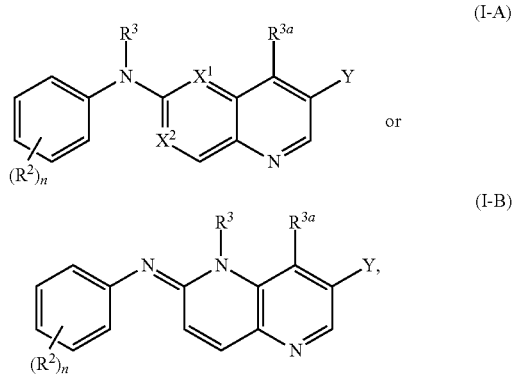

a tautomeric form, stereochemically isomeric form, and isotopic form thereof, wherein $X^1$ is N and $X^2$ is $CR^{3a}$, or $X^2$ is N and $X^1$ is $CR^{3a}$;

each $R^2$ is independently selected from hydroxyl, halogen, cyano, $C_{1-4}$alkyl, $C_{2-4}$alkenyl, $C_{2-4}$alkynyl, $C_{1-4}$alkoxy, hydroxy$C_{1-4}$alkyl, hydroxy$C_{1-4}$alkoxy, halo$C_{1-4}$alkyl, halo$C_{1-4}$alkoxy, hydroxyhalo$C_{1-4}$alkyl, hydroxyhalo$C_{1-4}$alkoxy, $C_{1-4}$alkoxy$C_{1-4}$alkyl, halo-$C_{1-4}$alkoxy$C_{1-4}$alkyl, $C_{1-4}$alkoxy$C_{1-4}$alkyl wherein each $C_{1-4}$alkyl may optionally be substituted with one or two hydroxyl groups, hydroxyhalo$C_{1-4}$alkoxy-$C_{1-4}$alkyl, $R^{13}$, $C_{1-4}$alkyl substituted with $R^{13}$, $C_{1-4}$alkyl substituted with —C(=O)—$R^{13}$, $C_{1-4}$alkoxy substituted with $R^{13}$, $C_{1-4}$alkoxy substituted with —C(=O)—$R^{13}$, —C(=O)—$R^{13}$, $C_{1-4}$alkyl substituted with —NR$^7$R$^8$, $C_{1-4}$alkyl substituted with —C(=O)—NR$^7$R$^8$, $C_{1-4}$alkoxy substituted with —NR$^7$R$^8$, $C_{1-4}$alkoxy substituted with —C(=O)—NR$^7$R$^8$, —NR$^7$R$^8$ and —C(=O)—NR$^7$R$^8$; or when two $R^2$ groups are attached to adjacent carbon atoms they may be taken together to form a radical of formula:

—O—(C($R^{17}$)$_2$)$_p$—O—;
—X—CH=CH—; or
—X—CH=N—; wherein $R^{17}$ represents hydrogen or fluorine, p represents 1 or 2 and X represents O or S;

Y represents —C$R^{18}$=N—O$R^{19}$ or -E-D;

D represents a 3 to 12 ring membered monocyclic or bicyclic carbocyclyl or a 3 to 12 ring membered monocyclic or bicyclic heterocyclyl containing at least one heteroatom selected from N, O and S, wherein said carbocyclyl and heterocyclyl may each be optionally substituted by one or more (e.g. 1, 2 or 3) $R^1$ groups;

E represents a bond, —(C$R^{22}R^{23}$)$_n$—, $C_{2-4}$alkenediyl optionally substituted with $R^{22}$, $C_{2-4}$alkynediyl optionally substituted with $R^{22}$, —CO—$(CR^{22}R^{23})_s$—, —$(CR^{22}R^{23})_s$—CO—, —$NR^{22}$—$(CR^{22}R^{23})_s$—, —$(CR^{22}R^{23})_s$—$NR^{22}$—, —O—$(CR^{22}R^{23})_s$—, —$(CR^{22}R^{23})_s$—O—, —S(O)$_m$—$(CR^{22}R^{23})_s$, —$(CR^{22}R^{23})_s$—S(O)$_m$—, —$(CR^{22}R^{23})_s$—CO—$NR^{22}$—$(CR^{22}R^{23})_s$— or —$(CR^{22}R^{23})_s$—$NR^{22}$—CO—$(CR^{22}R^{23})_s$—;

$R^1$ represents hydrogen, halo, cyano, $C_{1-6}$alkyl, $C_{1-6}$alkoxy, —C(=O)—O—$C_{1-6}$alkyl, $C_{2-4}$alkenyl, hydroxy$C_{1-6}$alkyl, halo$C_{1-6}$alkyl, hydroxyhalo-$C_{1-6}$alkyl, cyano$C_{1-4}$alkyl, $C_{1-6}$alkoxy$C_{1-6}$alkyl wherein each $C_{1-6}$alkyl may optionally be substituted with one or two hydroxyl groups, —$NR^4R^5$, $C_{1-6}$alkyl substituted with —O—C(=O)—$C_{1-6}$alkyl, $C_{1-6}$alkyl substituted with —$NR^4R^5$, —C(=O)—$NR^4R^5$, —C(=O)—$C_{1-6}$alkyl-$NR^4R^5$, $C_{1-6}$alkyl substituted with —C(=O)—$NR^4R^5$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^{12}$—S(=O)$_2$—$NR^{14}R^{15}$, $R^6$, $C_{1-6}$alkyl substituted with $R^6$, —C(=O)—$R^6$, $C_{1-6}$alkyl substituted with —C(=O)—$R^6$, hydroxy$C_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(O$C_{1-6}$alkyl)$_2$;

$R^{3a}$ represents hydrogen, chlorine, hydroxyl, or $C_{1-6}$alkoxy;

$R^3$ represents hydroxyl, $C_{1-6}$alkoxy, hydroxy$C_{1-6}$alkoxy, $C_{1-6}$alkoxy substituted with —$NR^{10}R^{11}$, $C_{1-6}$alkyl, $C_{2-6}$alkenyl, $C_{2-6}$alkynyl, halo$C_{1-6}$alkyl optionally substituted with —O—C(=O)—$C_{1-6}$alkyl, hydroxy-$C_{1-6}$alkyl optionally substituted with —O—C(=O)—$C_{1-6}$alkyl, hydroxy$C_{2-6}$alkenyl, hydroxy$C_{2-6}$alkynyl, hydroxyhalo$C_{1-6}$alkyl, cyano$C_{1-6}$alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxy$C_{1-6}$alkyl-O—C(=O)—, $C_{1-6}$alkyl substituted with $C_{1-6}$alkoxy$C_{1-6}$alkyl-C(=O)—, $C_{1-6}$alkyl substituted with —O—$C_{1-6}$alkoxy$C_{1-6}$alkyl wherein each $C_{1-6}$alkyl may optionally be substituted with one or two hydroxyl groups or with —O—C(=O)—$C_{1-6}$alkyl, $C_{2-6}$alkenyl substituted with $C_{1-6}$alkoxy, $C_{2-6}$alkynyl substituted with $C_{1-6}$alkoxy, $C_{1-6}$alkyl substituted with $R^9$ and optionally substituted with —O—C(=O)—$C_{1-6}$alkyl, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —$NR^{10}R^{11}$, $C_{2-6}$alkenyl substituted with —$NR^{10}R^{11}$, $C_{2-6}$alkynyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —O—C(=O)—$NR^{10}R^{11}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —$NR^{12}$—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —$NR^2$—S(=O)$_2$—$NR^{14}R^{15}$, $R^{13}$, $C_{1-6}$alkyl substituted with —P(=O)(OH)$_2$ or $C_{1-6}$alkyl substituted with —P(=O)(O$C_{1-6}$alkyl)$_2$;

$R^4$ and $R^5$ each independently represent hydrogen, $C_{1-6}$alkyl, $C_{1-6}$alkyl substituted with —$NR^{14}R^{15}$ hydroxy$C_{1-6}$alkyl, halo$C_{1-6}$alkyl, hydroxyhalo$C_{1-6}$alkyl, $C_{1-6}$alkoxy$C_{1-6}$alkyl wherein each $C_{1-6}$alkyl may optionally be substituted with one or two hydroxyl groups, —S(=O)$_2$—$C_{1-6}$alkyl, —S(=O)$_2$-halo-$C_{1-6}$alkyl, —S(=O)$_2$—$NR^{14}R^{15}$, —C(=O)—$NR^{14}R^{15}$, —C(=O)—O—$C_{1-6}$alkyl, —C(=O)—$R^3$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NH—S(=O)$_2$—$NR^{14}R^{15}$, $R^{13}$ or $C_{1-6}$alkyl substituted with $R^{13}$;

$R^6$ represents $C_{3-8}$cycloalkyl, $C_{3-8}$cycloalkenyl, phenyl, 4 to 7-membered monocyclic heterocyclyl containing at least one heteroatom selected from N, O and S; said $C_{3-8}$cycloalkyl, $C_{3-8}$cycloalkenyl, phenyl, 4 to 7-membered monocyclic heterocyclyl, optionally and each independently being substituted by 1, 2, 3, 4 or 5 substituents, each substituent independently being selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O—C(=O)—, —$NR^{14}R^{15}$, —C(=O)—$NR^{14}R^{15}$, $C_{1-6}$alkyl substituted with —$NR^{14}R^{15}$, $C_{1-6}$alkyl substituted with —C(=O)—$NR^{14}R^{15}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl and $C_{1-6}$alkyl substituted with —NH—S(=O)$_2$—$NR^{14}R^{15}$;

$R^7$ and $R^8$ each independently represent hydrogen, $C_{1-6}$alkyl, hydroxy$C_{1-6}$alkyl, halo$C_{1-6}$alkyl, hydroxyhalo$C_{1-6}$alkyl or $C_{1-6}$alkoxy$C_{1-6}$alkyl;

$R^9$ represents $C_{3-8}$cycloalkyl, $C_{3-8}$cycloalkenyl, phenyl, naphthyl, or 3 to 12 membered monocyclic or bicyclic heterocyclyl containing at least one heteroatom selected from N, O and S, said $C_{3-8}$cycloalkyl, $C_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl-O—C(=O)—, $C_{1-4}$alkyl substituted with $C_{1-4}$alkyl-O—C(=O)—, $C_{1-4}$alkyl-C(=O)—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —$NR^{14}R^{15}$, —C(=O)—$NR^{14}R^{15}$, $C_{1-4}$alkyl substituted with —$NR^{14}R^{15}$, $C_{1-4}$alkyl substituted with —C(=O)—$NR^{14}R^{15}$, $C_{1-4}$alkoxy, —S(=O)$_2$—$C_{1-4}$alkyl, —S(=O)$_2$-halo$C_{1-4}$alkyl, —S(=O)$_2$—$NR^{14}R^{15}$, $C_{1-4}$alkyl substituted with —S(=O)$_2$—$NR^{14}R^{15}$, $C_{1-4}$alkyl substituted with —NH—S(=O)$_2$—$C_{1-4}$alkyl, $C_{1-4}$alkyl substituted with —NH—S(=O)$_2$-halo$C_{1-4}$alkyl, $C_{1-4}$alkyl substituted with —NH—S(=O)$_2$—NR$^{14}$R$^{15}$, R$^{13}$, —C(=O)—R$^{13}$, C$_{1-4}$alkyl substituted with R$^{13}$, phenyl optionally substituted with R$^{16}$, phenylC$_{1-6}$alkyl wherein the phenyl is optionally substituted with R$^{16}$, a 5 or 6-membered aromatic monocyclic heterocyclyl containing at least one heteroatom selected from N, O and S wherein said heterocyclyl is optionally substituted with R$^{16}$;

or when two of the substituents of R$^9$ are attached to the same atom, they may be taken together to form a 4 to 7-membered saturated monocyclic heterocyclyl containing at least one heteroatom selected from N, O and S;

R$^{10}$ and R$^{11}$ each independently represent hydrogen, carboxyl, C$_{1-6}$alkyl, cyanoC$_{1-6}$alkyl, C$_{1-6}$alkyl substituted with —NR$^{14}$R$^{15}$, C$_{1-6}$alkyl substituted with —C(=O)—NR$^{14}$R$^{15}$, haloC$_{1-6}$alkyl, hydroxyC$_{1-6}$alkyl, hydroxyhaloC$_{1-6}$alkyl, C$_{1-6}$alkoxy, C$_{1-6}$alkoxyC$_{1-6}$alkyl wherein each C$_{1-6}$alkyl may optionally be substituted with one or two hydroxyl groups, R$^6$, C$_{1-6}$alkyl substituted with R$^6$, —C(=O)—R$^6$, —C(=O)—C$_{1-6}$alkyl, —C(=O)-hydroxyC$_{1-6}$alkyl, —C(=O)-haloC$_{1-6}$alkyl, —C(=O)-hydroxyhaloC$_{1-6}$alkyl, C$_{1-6}$alkyl substituted with —Si(CH$_3$)$_3$, —S(=O)$_2$—C$_{1-6}$alkyl, —S(=O)$_2$-haloC$_{1-6}$alkyl, —S(=O)$_2$—NR$^{14}$R$^{15}$, C$_{1-6}$alkyl substituted with —S(=O)$_2$—C$_{1-6}$alkyl, C$_{1-6}$alkyl substituted with —S(=O)$_2$-haloC$_{1-6}$alkyl, C$_{1-6}$alkyl substituted with —S(=O)$_2$—NR$^{14}$R$^{15}$, C$_{1-6}$alkyl substituted with —NH—S(=O)$_2$—C$_{1-6}$alkyl, C$_{1-6}$alkyl substituted with —NH—S(=O)$_2$-haloC$_{1-6}$alkyl, C$_{1-6}$alkyl substituted with carboxyl, or C$_{1-6}$alkyl substituted with —NH—S(=O)$_2$—NR$^{14}$R$^{15}$;

R$^{12}$ represents hydrogen or C$_{1-4}$alkyl optionally substituted with C$_{1-4}$alkoxy;

R$^{13}$ represents C$_{3-8}$cycloalkyl or a saturated 4 to 6-membered monocyclic heterocyclyl containing at least one heteroatom selected from N, O and S, wherein said C$_{3-8}$cycloalkyl or monocyclic heterocyclyl is optionally substituted with 1, 2 or 3 substituents each independently selected from halogen, hydroxyl, C$_{1-6}$alkyl, haloC$_{1-6}$alkyl, =O, cyano, —C(=O)—C$_{1-6}$alkyl, C$_{1-6}$alkoxy, and —NR$^{14}$R$^{15}$;

R$^{14}$ and R$^{15}$ each independently represent hydrogen, or haloC$_{1-4}$alkyl, or C$_{1-4}$alkyl optionally substituted with a substituent selected from hydroxyl, C$_{1-4}$alkoxy, amino and mono- or di(C$_{1-4}$alkyl)amino;

R$^{16}$ represents hydroxyl, halogen, cyano, C$_{1-4}$alkyl, C$_{1-4}$alkoxy, —NR$^{14}$R$^{15}$ or —C(=O)NR$^{14}$R$^{15}$;

R$^{18}$ represents hydrogen, C$_{1-6}$ alkyl, C$_{3-8}$ cycloalkyl, C$_{1-4}$alkyl substituted with C$_{3-8}$ cycloalkyl;

R$^{19}$ represents hydrogen; C$_{1-6}$alkyl; C$_{3-8}$ cycloalkyl; C$_{1-6}$alkyl substituted with —O—R$^{20}$; —(CH$_2$)$_r$—CN; —(CH$_2$)$_r$—CONR$^{20}$R$^{21}$; —(CH$_2$)$_{r1}$—NR$^{20}$R$^{21}$; —(CH$_2$)$_{r1}$—NR$^{20}$COR$^{21}$; —(CH$_2$)$_{r1}$—NR$^{20}$—(CH$_2$)$_s$—SO$_2$—R$^{21}$; —(CH$_2$)$_{r1}$—NH—SO$_2$—NR$^{20}$R$^{21}$; —(CH$_2$)$_{r1}$—NR$^{20}$CO$_2$R$^{21}$; —(CH$_2$)$_r$—SO$_2$NR$^{20}$R$^{21}$; phenyl optionally substituted with 1, 2, 3, 4 or 5 substituents each independently selected from halogen, C$_{1-4}$alkyl, C$_{1-4}$alkyloxy, cyano and amino; a 5- or 6-membered aromatic monocyclic heterocycle containing at least one heteroatom selected from N, O and S, said heterocycle being optionally substituted with 1, 2, 3 or 4 substituents each independently selected from halogen, C$_{1-4}$alkyl, C$_{1-4}$alkyloxy, cyano and amino; wherein said C$_{1-6}$ alkyl and C$_{3-8}$ cycloalkyl, may be optionally substituted by one or more R$^{20}$ groups R$^{20}$ and R$^{21}$ independently represent hydrogen, C$_{1-6}$ alkyl, hydroxyC$_{1-6}$alkyl, —(CH$_2$)$_n$—O—C$_{1-6}$alkyl, or when attached to a nitrogen atom R$^{20}$ and R$^{21}$ can be taken together to form with the nitrogen atom to which they are attached a monocyclic saturated 4, 5 or 6-membered ring which optionally contains a further heteroatom selected from O, S and N;

R$^{22}$ and R$^{23}$ independently represent hydrogen, C$_{1-6}$ alkyl, or hydroxyC$_{1-6}$alkyl;

m independently represents an integer equal to 0, 1 or 2;

n independently represents an integer equal to 0, 1, 2, 3 or 4;

s independently represents an integer equal to 0, 1, 2, 3 or 4;

r independently represent an integer equal to 1, 2, 3, or 4;

r1 independently represent an integer equal to 2, 3 or 4;

or an N-oxide thereof, a pharmaceutically acceptable salt thereof or a solvate thereof.

2. A method according to claim 1 wherein the compound is selected from the group consisting of a compound of formula (I-A), a tautomeric form, stereochemically isomeric form, and isotopic form thereof, or an N-oxide thereof, a pharmaceutically acceptable salt thereof or a solvate thereof.

3. A method according to claim 2 wherein the compound is selected from the group consisting of a compound of formula (I-A), a tautomeric form, stereochemically isomeric form, and isotopic form thereof, wherein X$^1$ is N, X$^2$ is CR$^{3a}$, or an N-oxide thereof, a pharmaceutically acceptable salt thereof or a solvate thereof.

4. A method according to claim 2 wherein the compound is selected from the group consisting of a compound of formula (I-A), a tautomeric form, stereochemically isomeric form, and isotopic form thereof, wherein X$^2$ is N and X$^1$ is CR$^{3a}$, or an N-oxide thereof, a pharmaceutically acceptable salt thereof or a solvate thereof.

5. A method according to claim 1 wherein the compound is selected from the group consisting of a compound of formula (I-B), a tautomeric form, stereochemically isomeric form, and isotopic form thereof, or an N-oxide thereof, a pharmaceutically acceptable salt thereof or a solvate thereof.

6. A method according to claim 1 wherein the compound is selected from the group consisting of a compound of formula (I-A) or (I-B), a tautomeric form, stereochemically isomeric form, and isotopic form thereof, wherein Y represents —CR$^{18}$=N—OR$^{19}$, or an N-oxide thereof, a pharmaceutically acceptable salt thereof or a solvate thereof.

7. A method according to claim 1 wherein the compound is selected from the group consisting of a compound of formula (I-A) or (I-B), a tautomeric form, stereochemically isomeric form, and isotopic form thereof, wherein Y is -E-D, or an N-oxide thereof, a pharmaceutically acceptable salt thereof or a solvate thereof.

8. A method according to claim 1 wherein the compound is selected from the group consisting of a compound of formula (I-A) or (I-B), a tautomeric form, stereochemically isomeric form, and isotopic form thereof, wherein E represents (i) a bond, C$_{2-4}$alkenediyl, —CO—(CR$^{22}$R$^{23}$)$_s$—, —(CR$^{22}$R$^{23}$)$_s$—CO—, —NR$^{22}$—(CR$^{22}$R$^{23}$)$_s$—, —(CR$^{22}$R$^{23}$)$_s$—NR$^{22}$—, —(CR$^{22}$R$^{23}$)$_s$—CO—NR$^{22}$—(CR$^{22}$R$^{23}$)$_s$— or —(CR$^{22}$R$^{23}$)$_s$—NR$^{22}$—CO—(CR$^{22}$R$^{23}$)$_s$—; or (ii) a bond, or an N-oxide thereof, a pharmaceutically acceptable salt thereof or a solvate thereof.

9. A method according to claim 7 wherein the compound is selected from the group consisting of a compound of formula (I-A) or (I-B), a tautomeric form, stereochemically isomeric form, and isotopic form thereof, wherein D is optionally substituted pyrazolyl, or an N-oxide thereof, a pharmaceutically acceptable salt thereof or a solvate thereof.

10. A method according to claim 1 wherein the compound is selected from the group consisting of a compound of formula (I-A) or (I-B), a tautomeric form, stereochemically isomeric form, and isotopic form thereof, wherein $R^2$:
(i) is independently selected from hydroxyl, halogen, cyano, $C_{1-4}$alkyl, $C_{2-4}$alkenyl, $C_{1-4}$alkoxy, hydroxy-$C_{1-4}$alkyl, hydroxy$C_{1-4}$alkoxy, halo$C_{1-4}$alkoxy, $C_{1-4}$alkoxy$C_{1-4}$alkyl, $R^{13}$, $C_{1-4}$alkoxy substituted with $R^{13}$, —C(=O)—$R^{13}$, $C_{1-4}$alkyl substituted with $NR^7R^8$, $C_{1-4}$alkoxy substituted with $NR^7R^8$, —$NR^7R^8$ and —C(=O)—$NR^7R^8$; or
(ii) represents $C_{1-4}$alkyloxy; or
(iii) represents $C_{1-4}$alkyloxy or fluoro,
or an N-oxide thereof, a pharmaceutically acceptable salt thereof or a solvate thereof.

11. A method according to claim 1 wherein the compound is selected from the group consisting of a compound of formula (I-A) or (I-B), a tautomeric form, stereochemically isomeric form, and isotopic form thereof, wherein $R^3$ represents:
(i) $C_{1-6}$alkyl, hydroxy$C_{1-6}$alkyl, hydroxyhalo$C_{1-6}$alkyl, halo$C_{1-6}$alkyl, $C_{1-6}$alkyl substituted with —C(=O)—$C_{1-6}$alkyl, $C_{1-6}$alkoxy$C_{1-6}$alkyl wherein each $C_{1-6}$alkyl may optionally be substituted with one or two hydroxyl groups, $C_{1-6}$alkyl substituted with $R^9$, $C_{1-6}$alkyl substituted with —$NR^{10}R^{11}$, $C_{1-6}$alkyl substituted with hydroxyl and —$NR^{10}R^{11}$, $C_{1-6}$alkyl substituted with one or two halogens and —$NR^{10}R^{11}$, $C_{1-6}$alkyl substituted with —C(=O)—O—$C_{1-6}$alkyl, $C_{1-6}$alkyl substituted with —O—C(=O)—$NR^{10}R^{11}$, $C_{1-6}$alkyl substituted with carboxyl, $C_{1-6}$alkyl substituted with —$NR^{12}$—S(=O)$_2$—$C_{1-6}$alkyl, $C_{1-6}$alkyl substituted with —$NR^{12}$—S(=O)$_2$—$NR^{14}R^{15}$, $C_{1-6}$alkyl substituted with hydroxyl and $R^9$, —$C_{1-6}$alkyl-C($R^{12}$)=N—O—$R^{12}$, $C_{1-6}$alkyl substituted with —C(=O)—$NR^{10}R^{11}$, $C_{1-6}$alkyl substituted with —C(=O)—$R^9$, $C_{2-6}$alkynyl substituted with $R^9$, hydroxy$C_{1-6}$alkoxy, $C_{2-6}$alkenyl, $C_{2-6}$alkynyl or $R^{13}$; or
(ii) hydroxy$C_{1-6}$alkyl, cyano$C_{1-6}$alkyl, halo$C_{1-6}$alkyl, $C_{1-6}$alkyl substituted with $R^9$, $C_{1-6}$alkyl substituted with —$NR^{10}R^{11}$, $C_{1-6}$alkoxy$C_{1-6}$alkyl, $C_{1-6}$alkyl substituted with —C(=O)—$NR^{10}R^{11}$, $C_{2-6}$alkynyl or $R^{13}$,
or an N-oxide thereof, a pharmaceutically acceptable salt thereof or a solvate thereof.

12. A method according to claim 11 wherein the compound is selected from the group consisting of a compound of formula (I-A) or (I-B), a tautomeric form, stereochemically isomeric form, and isotopic form thereof, wherein $R^3$ represents hydroxy$C_{1-6}$alkyl, halo$C_{1-6}$alkyl, $C_{1-6}$alkyl substituted with $R^9$, $C_{1-6}$alkyl substituted with —$NR^{10}R^{11}$, $C_{1-6}$alkoxy$C_{1-6}$alkyl, or $C_{2-6}$alkynyl, or an N-oxide thereof, a pharmaceutically acceptable salt thereof or a solvate thereof.

13. A method according to claim 1 wherein the compound is selected from the group consisting of a compound of formula (I-A) or (I-B), a tautomeric form, stereochemically isomeric form, and isotopic form thereof, wherein $R^{3a}$ represents (i) hydrogen or chlorine, or (ii) hydrogen,
or an N-oxide thereof, a pharmaceutically acceptable salt thereof or a solvate thereof.

14. A method according to claim 1 wherein the compound is selected from the group consisting of a compound of formula (I-A) or (I-B), a tautomeric form, stereochemically isomeric form, and isotopic form thereof, wherein:
(i) $X^2$ represents N and $X^1$ represent CH, n represents an integer equal to 2; and each $R^2$ represents $C_{1-4}$alkoxy, for example $CH_3O$—; $R^3$ represents hydroxy$C_{1-6}$alkyl, halo$C_{1-6}$alkyl, $C_{1-6}$alkyl substituted with $R^9$, $C_{1-6}$alkyl substituted with —$NR^{10}R^{11}$, $C_{1-6}$alkoxy$C_{1-6}$alkyl, $C_{2-6}$alkynyl; Y represents -E-D wherein E represents a bond and D represents pyrazolyl substituted with $C_{1-6}$alkyl; $R^{10}$ and $R^{11}$ represent hydrogen or $C_{1-6}$alkyl; $R^9$ represents an optionally substituted 5 membered aromatic heterocycle, such as for example optionally substituted imidazolyl; or
(ii) $X^1$ represents N and $X^2$ represents CH or $X^1$ represents CH and $X^2$ represents N; n represents an integer equal to 2, 3 or 4; and each $R^2$ represents $C_{1-4}$alkoxy, for example $CH_3O$—, or halo, for example fluoro or chloro; $R^{3a}$ represents hydrogen or chlorine; $R^3$ represents hydroxy$C_{1-6}$alkyl, cyano$C_{1-6}$alkyl, halo$C_{1-6}$alkyl, $C_{1-6}$alkyl substituted with $R^9$, $C_{1-6}$alkyl substituted with —$NR^{10}R^{11}$, $C_{1-6}$alkoxy$C_{1-6}$alkyl, $C_{1-6}$alkyl substituted with —C(=O)—$NR^{10}R^{11}$, $C_{2-6}$alkynyl or $R^{13}$; Y represents -E-D wherein E represents a bond and D represents an optionally substituted 5 or 6 membered aromatic heterocycle,
or an N-oxide thereof, a pharmaceutically acceptable salt thereof or a solvate thereof.

15. A method according to claim 1 comprising administering to the subject a compound selected from the group consisting of a compound of formula (I-A) or (I-B), a tautomeric form, stereochemically isomeric form and isotopic form thereof, or a pharmaceutically acceptable salt or solvate thereof.

16. A method according to claim 1 for treating a subject suffering from a carcinoma of the bladder, breast, colon, kidney, epidermis, liver, lung, oesophagus, head and neck, gall bladder, ovary, pancreas, stomach, cervix, endometrium, thyroid, prostate, or skin; gastrointestinal cancer; multiple myeloma; thyroid follicular cancer; melanoma; seminoma; teratocarcinoma; osteosarcoma; xeroderma pigmentosum; keratoctanthoma; Kaposi's sarcoma; colorectal cancer; or oral squamous cell carcinoma.

17. A method according to claim 1, wherein the disease state or condition is mediated by a FGFR kinase.

18. A method according to claim 17, wherein the disease state or condition is selected from multiple myeloma, myeloproliferative disorders, endometrial cancer, prostate cancer, bladder cancer, lung cancer, ovarian cancer, breast cancer, gastric cancer, colorectal cancer, and oral squamous cell carcinoma.

19. A method according to claim 17, wherein the disease state or condition is selected from lung cancer, squamous cell carcinoma, liver cancer, kidney cancer, breast cancer, colon cancer, colorectal cancer, and prostate cancer.

20. A method according to claim 1, wherein the disease state or condition is carcinoma selected from a carcinoma of the bladder, breast, colon, kidney, epidermis, liver, lung, oesophagus, head and neck, gall bladder, ovary, pancreas, stomach, cervix, endometrium, thyroid, prostate, or skin; gastrointestinal cancer; a hematopoietic tumour of lymphoid lineage; a hematopoietic tumour of myeloid lineage; multiple myeloma; thyroid follicular cancer; a tumour of mesenchymal origin; a tumour of the central or peripheral nervous system; melanoma; seminoma; teratocarcinoma; osteosarcoma; xeroderma pigmentosum; keratoctanthoma; or Kaposi's sarcoma.

21. A method of inhibiting a FGFR kinase, which method comprises contacting the kinase with a kinase-inhibiting compound selected from the group consisting of a compound of formula (I-A) or (I-B)

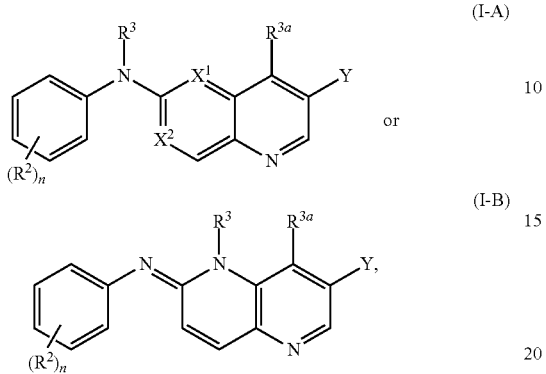

a tautomeric form, stereochemically isomeric form, and isotopic form thereof, wherein
$X^1$ is N and $X^2$ is $CR^{3a}$, or $X^2$ is N and $X^1$ is $CR^{3a}$;
each $R^2$ is independently selected from hydroxyl, halogen, cyano, $C_{1-4}$alkyl, $C_{2-4}$alkenyl, $C_{2-4}$alkynyl, $C_{1-4}$alkoxy, hydroxyC$_{1-4}$alkyl, hydroxyC$_{1-4}$alkoxy, haloC$_{1-4}$alkyl, haloC$_{1-4}$alkoxy, hydroxyhaloC$_{1-4}$alkyl, hydroxyhaloC$_{1-4}$alkoxy, $C_{1-4}$alkoxyC$_{1-4}$alkyl, haloC$_{1-4}$alkoxyC$_{1-4}$alkyl, $C_{1-4}$alkoxyC$_{1-4}$alkyl wherein each $C_{1-4}$alkyl may optionally be substituted with one or two hydroxyl groups, hydroxyhaloC$_{1-4}$alkoxy-C$_{1-4}$alkyl, $R^{13}$, $C_{1-4}$alkyl substituted with $R^{13}$, $C_{1-4}$alkyl substituted with —C(=O)—$R^{13}$, $C_{1-4}$alkoxy substituted with $R^{13}$, $C_{1-4}$alkoxy substituted with —C(=O)—$R^{13}$, —C(=O)—$R^{13}$, $C_{1-4}$alkyl substituted with —NR$^7$R$^8$, $C_{1-4}$alkyl substituted with —C(=O)—NR$^7$R$^8$, $C_{1-4}$alkoxy substituted with —NR$^7$R$^8$, $C_{1-4}$alkoxy substituted with —C(=O)—NR$^7$R$^8$, —NR$^7$R$^8$ and —C(=O)—NR$^7$R$^8$; or when two $R^2$ groups are attached to adjacent carbon atoms they may be taken together to form a radical of formula:
—O—(C(R$^{17}$)$_2$)$_p$—O—;
—X—CH=CH—; or
—X—CH=N—; wherein $R^{17}$ represents hydrogen or fluorine, p represents 1 or 2 and X represents O or S;
Y represents —CR$^{18}$=N—OR$^{19}$ or -E-D;
D represents a 3 to 12 ring membered monocyclic or bicyclic carbocyclyl or a 3 to 12 ring membered monocyclic or bicyclic heterocyclyl containing at least one heteroatom selected from N, O and S, wherein said carbocyclyl and heterocyclyl may each be optionally substituted by one or more (e.g. 1, 2 or 3) $R^1$ groups;
E represents a bond, —(CR$^{22}$R$^{23}$)$_n$—, $C_{2-4}$alkenediyl optionally substituted with $R^{22}$, $C_{2-4}$alkynediyl optionally substituted with $R^{22}$, —CO—(CR$^{22}$R$^{23}$)$_s$—, —(CR$^{22}$R$^{23}$)$_s$—CO—, —NR$^{22}$—(CR$^{22}$R$^{23}$)$_s$—, —(CR$^{22}$R$^{23}$)$_s$—NR$^{22}$—, —O—(CR$^{22}$R$^{23}$)$_s$—, —(CR$^{22}$R$^{23}$)$_s$—O—, —S(O)$_m$—(CR$^{22}$R$^{23}$)$_s$—, —(CR$^{22}$R$^{23}$)$_s$—S(O)$_m$—, —(CR$^{22}$R$^{23}$)$_s$—CO—NR$^{22}$—(CR$^{22}$R$^{23}$)$_s$— or —(CR$^{22}$R$^{23}$)$_s$—NR$^{22}$—CO—(CR$^{22}$R$^{23}$)$_s$—;
$R^1$ represents hydrogen, halo, cyano, $C_{1-6}$alkyl, $C_{1-6}$alkoxy, —C(=O)—O—$C_{1-6}$alkyl, $C_{2-4}$alkenyl, hydroxyC$_{1-6}$alkyl, haloC$_{1-6}$alkyl, hydroxyhaloC$_{1-6}$alkyl, cyanoC$_{1-4}$alkyl, $C_{1-6}$alkoxyC$_{1-6}$alkyl wherein each $C_{1-6}$alkyl may optionally be substituted with one or two hydroxyl groups, —NR$^4$R$^5$, $C_{1-6}$alkyl substituted with —O—C(=O)—$C_{1-6}$alkyl, $C_{1-6}$alkyl substituted with —NR$^4$R$^5$, —C(=O)—NR$^4$R$^5$, —C(=O)—$C_{1-6}$alkyl-NR$^4$R$^5$, $C_{1-6}$alkyl substituted with —C(=O)—NR$^4$R$^5$, —S(=O)$_2$—$C_{1-6}$alkyl, —S(=O)$_2$-haloC$_{1-6}$alkyl, —S(=O)$_2$—NR$^{14}$R$^{15}$, $C_{1-6}$alkyl substituted with —S(=O)$_2$—$C_{1-6}$alkyl, $C_{1-6}$alkyl substituted with —S(=O)$_2$-haloC$_{1-6}$alkyl, $C_{1-6}$alkyl substituted with —S(=O)$_2$—NR$^{14}$R$^{15}$, $C_{1-6}$alkyl substituted with —NH—S(=O)$_2$—$C_{1-6}$alkyl, $C_{1-6}$alkyl substituted with —NH—S(=O)$_2$-haloC$_{1-6}$alkyl, $C_{1-6}$alkyl substituted with —NR$^{12}$—S(=O)$_2$—NR$^{14}$R$^{15}$, $R^6$, $C_{1-6}$alkyl substituted with $R^6$, —C(=O)—$R^6$, $C_{1-6}$alkyl substituted with —C(=O)—$R^6$, hydroxyC$_{1-6}$alkyl substituted with $R^6$, $C_{1-6}$alkyl substituted with —Si(CH$_3$)$_3$, $C_{1-6}$alkyl substituted with —P(=O)(OH)$_2$ or $C_{1-6}$alkyl substituted with —P(=O)(OC$_{1-6}$alkyl)$_2$;
$R^{3a}$ represents hydrogen, chlorine, hydroxyl, or $C_{1-6}$alkoxy;
$R^3$ represents hydroxyl, $C_{1-6}$alkoxy, hydroxyC$_{1-6}$alkoxy, $C_{1-6}$alkoxy substituted with —NR$^{10}$R$^{11}$, $C_{1-6}$alkyl, $C_{2-6}$alkenyl, $C_{2-6}$alkynyl, haloC$_{1-6}$alkyl optionally substituted with —O—C(=O)—$C_{1-6}$alkyl, hydroxyC$_{1-6}$alkyl optionally substituted with —O—C(=O)—$C_{1-6}$alkyl, hydroxyC$_{2-6}$alkenyl, hydroxyC$_{2-6}$alkynyl, hydroxyhaloC$_{1-6}$alkyl, cyanoC$_{1-6}$alkyl, $C_{1-6}$alkyl substituted with carboxyl, $C_{1-6}$alkyl substituted with —C(=O)—$C_{1-6}$alkyl, $C_{1-6}$alkyl substituted with —C(=O)—O—$C_{1-6}$alkyl, $C_{1-6}$alkyl substituted with $C_{1-6}$alkoxyC$_{1-6}$alkyl-O—C(=O)—, $C_{1-6}$alkyl substituted with $C_{1-6}$alkoxyC$_{1-6}$alkyl-C(=O)—, $C_{1-6}$alkyl substituted with —O—C(=O)—$C_{1-6}$alkyl, $C_{1-6}$alkoxyC$_{1-6}$alkyl wherein each $C_{1-6}$alkyl may optionally be substituted with one or two hydroxyl groups or with —O—C(=O)—$C_{1-6}$alkyl, $C_{2-6}$alkenyl substituted with $C_{1-6}$alkoxy, $C_{2-6}$alkynyl substituted with $C_{1-6}$alkoxy, $C_{1-6}$alkyl substituted with $R^9$ and optionally substituted with —O—C(=O)—$C_{1-6}$alkyl, $C_{1-6}$alkyl substituted with —C(=O)—$R^9$, $C_{1-6}$alkyl substituted with hydroxyl and $R^9$, $C_{2-6}$alkenyl substituted with $R^9$, $C_{2-6}$alkynyl substituted with $R^9$, $C_{1-6}$alkyl substituted with —NR$^{10}$R$^{11}$, $C_{2-6}$alkenyl substituted with —NR$^{10}$R$^{11}$, $C_{2-6}$alkynyl substituted with —NR$^{10}$R$^{11}$, $C_{1-6}$alkyl substituted with hydroxyl and —NR$^{10}$R$^{11}$, $C_{1-6}$alkyl substituted with one or two halogens and —NR$^{10}$R$^{11}$, —$C_{1-6}$alkyl-C(R$^{12}$)=N—O—R$^{12}$, $C_{1-6}$alkyl substituted with —C(=O)—NR$^{10}$R$^{11}$, $C_{1-6}$alkyl substituted with —O—C(=O)—NR$^{10}$R$^{11}$, —S(=O)$_2$—$C_{1-6}$alkyl, —S(=O)$_2$-haloC$_{1-6}$alkyl, —S(=O)$_2$—NR$^{14}$R$^{15}$, $C_{1-6}$alkyl substituted with —S(=O)$_2$—$C_{1-6}$alkyl, $C_{1-6}$alkyl substituted with —S(=O)$_2$-haloC$_{1-6}$alkyl, $C_{1-6}$alkyl substituted with —S(=O)$_2$—NR$^{14}$R$^{15}$, $C_{1-6}$alkyl substituted with —NR$^{12}$—S(=O)$_2$—$C_{1-6}$alkyl, $C_{1-6}$alkyl substituted with —NH—S(=O)$_2$-haloC$_{1-6}$alkyl, $C_{1-6}$alkyl substituted with —NR$^2$—S(=O)$_2$—NR$^{14}$R$^{15}$, $R^{13}$, $C_{1-6}$alkyl substituted with —P(=O)(OH)$_2$ or $C_{1-6}$alkyl substituted with —P(=O)(OC$_{1-6}$alkyl)$_2$;
$R^4$ and $R^5$ each independently represent hydrogen, $C_{1-6}$alkyl, $C_{1-6}$alkyl substituted with —NR$^4$R$^{15}$ hydroxyC$_{1-6}$alkyl, haloC$_{1-6}$alkyl, hydroxyhaloC$_{1-6}$alkyl, $C_{1-6}$alkoxyC$_{1-6}$alkyl wherein each $C_{1-6}$alkyl may optionally be substituted with one or two hydroxyl groups, —S(=O)$_2$—$C_{1-6}$alkyl, —S(=O)$_2$-haloC$_{1-6}$alkyl, —S(=O)$_2$—NR$^{14}$R$^{15}$, —C(=O)—

$NR^{14}R^{15}$, —C(=O)—O—$C_{1-6}$alkyl, —C(=O)—$R^3$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with —NH—S(=O)$_2$—$NR^{14}R^{15}$, $R^{13}$ or $C_{1-6}$alkyl substituted with $R^{13}$;

$R^6$ represents $C_{3-8}$cycloalkyl, $C_{3-8}$cycloalkenyl, phenyl, 4 to 7-membered monocyclic heterocyclyl containing at least one heteroatom selected from N, O and S; said $C_{3-8}$cycloalkyl, $C_{3-8}$cycloalkenyl, phenyl, 4 to 7-membered monocyclic heterocyclyl, optionally and each independently being substituted by 1, 2, 3, 4 or 5 substituents, each substituent independently being selected from cyano, $C_{1-6}$alkyl, cyano$C_{1-6}$alkyl, hydroxyl, carboxyl, hydroxy$C_{1-6}$alkyl, halogen, halo$C_{1-6}$alkyl, hydroxyhalo$C_{1-6}$alkyl, $C_{1-6}$alkoxy, $C_{1-6}$alkoxy$C_{1-6}$alkyl, $C_{1-6}$alkyl-O—C(=O)—, —$NR^{14}R^{15}$, —C(=O)—$NR^{14}R^{15}$, $C_{1-6}$alkyl substituted with —$NR^{14}R^{15}$, $C_{1-6}$alkyl substituted with —C(=O)—$NR^{14}R^{15}$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl and $C_{1-6}$alkyl substituted with —NH—S(=O)$_2$—$NR^{14}R^{15}$;

$R^7$ and $R^8$ each independently represent hydrogen, $C_{1-6}$alkyl, hydroxy$C_{1-6}$alkyl, halo$C_{1-6}$alkyl, hydroxyhalo$C_{1-6}$alkyl or $C_{1-6}$alkoxy$C_{1-6}$alkyl;

$R^9$ represents $C_{3-8}$cycloalkyl, $C_{3-8}$cycloalkenyl, phenyl, naphthyl, or 3 to 12 membered monocyclic or bicyclic heterocyclyl containing at least one heteroatom selected from N, O and S, said $C_{3-8}$cycloalkyl, $C_{3-8}$cycloalkenyl, phenyl, naphthyl, or 3 to 12 membered monocyclic or bicyclic heterocyclyl each optionally and each independently being substituted with 1, 2, 3, 4 or 5 substituents, each substituent independently being selected from =O, $C_{1-4}$alkyl, hydroxyl, carboxyl, hydroxy$C_{1-4}$alkyl, cyano, cyano$C_{1-4}$alkyl, $C_{1-4}$alkyl-O—C(=O)—, $C_{1-4}$alkyl substituted with $C_{1-4}$alkyl-O—C(=O)—, $C_{1-4}$alkyl-C(=O)—, $C_{1-4}$alkoxy$C_{1-4}$alkyl wherein each $C_{1-4}$alkyl may optionally be substituted with one or two hydroxyl groups, halogen, halo$C_{1-4}$alkyl, hydroxyhalo$C_{1-4}$alkyl, —$NR^{14}R^{15}$, —C(=O)—$NR^{14}R^{15}$, $C_{1-4}$alkyl substituted with —$NR^{14}R^{15}$, $C_{1-4}$alkyl substituted with —C(=O)—$NR^{14}R^{15}$, $C_{1-4}$alkoxy, —S(=O)$_2$—$C_{1-4}$alkyl, —S(=O)$_2$-halo$C_{1-4}$alkyl, —S(=O)$_2$—$NR^{14}R^{15}$, $C_{1-4}$alkyl substituted with —S(=O)$_2$—$NR^{14}R^{15}$, $C_{1-4}$alkyl substituted with —NH—S(=O)$_2$—$C_{1-4}$alkyl, $C_{1-4}$alkyl substituted with —NH—S(=O)$_2$-halo$C_{1-4}$alkyl, $C_{1-4}$alkyl substituted with —NH—S(=O)$_2$—$NR^{14}R^{15}$, $R^{13}$, —C(=O)—$R^{13}$, $C_{1-4}$alkyl substituted with $R^{13}$, phenyl optionally substituted with $R^{16}$, phenyl$C_{1-6}$alkyl wherein the phenyl is optionally substituted with $R^{16}$, a 5 or 6-membered aromatic monocyclic heterocyclyl containing at least one heteroatom selected from N, O and S wherein said heterocyclyl is optionally substituted with $R^{16}$;

or when two of the substituents of $R^9$ are attached to the same atom, they may be taken together to form a 4 to 7-membered saturated monocyclic heterocyclyl containing at least one heteroatom selected from N, O and S;

$R^{10}$ and $R^{11}$ each independently represent hydrogen, carboxyl, $C_{1-6}$alkyl, cyano$C_{1-6}$alkyl, $C_{1-6}$alkyl substituted with —$NR^{14}R^{15}$, $C_{1-6}$alkyl substituted with —C(=O)—$NR^{14}R^{15}$, halo$C_{1-6}$alkyl, hydroxy$C_{1-6}$alkyl, hydroxyhalo$C_{1-6}$alkyl, $C_{1-6}$alkoxy, $C_{1-6}$alkoxy$C_{1-6}$alkyl wherein each $C_{1-6}$alkyl may optionally be substituted with one or two hydroxyl groups, $R^6$, $C_{1-6}$alkyl substituted with $R^6$, —C(=O)—$R^6$, —C(=O)—$C_{1-6}$alkyl, —C(=O)-hydroxy$C_{1-6}$alkyl, —C(=O)-halo$C_{1-6}$alkyl, —C(=O)-hydroxyhalo$C_{1-6}$alkyl, $C_{1-6}$alkyl substituted with —Si(CH$_3$)$_3$, —S(=O)$_2$—$C_{1-6}$alkyl, —S(=O)$_2$-halo$C_{1-6}$alkyl, —S(=O)$_2$—$NR^{14}R^{15}$, $C_{1-6}$alkyl substituted with —S(=O)$_2$—$C_{1-6}$alkyl, $C_{1-6}$alkyl substituted with —S(=O)$_2$-halo$C_{1-6}$alkyl, $C_{1-6}$alkyl substituted with —S(=O)$_2$—$NR^{14}R^{15}$, $C_{1-6}$alkyl substituted with —NH—S(=O)$_2$—$C_{1-6}$alkyl, $C_{1-6}$alkyl substituted with —NH—S(=O)$_2$-halo$C_{1-6}$alkyl, $C_{1-6}$alkyl substituted with carboxyl, or $C_{1-6}$alkyl substituted with —NH—S(=O)$_2$—$NR^{14}R^{15}$;

$R^{12}$ represents hydrogen or $C_{1-4}$alkyl optionally substituted with $C_{1-4}$alkoxy;

$R^{13}$ represents $C_{3-8}$cycloalkyl or a saturated 4 to 6-membered monocyclic heterocyclyl containing at least one heteroatom selected from N, O and S, wherein said $C_{3-8}$cycloalkyl or monocyclic heterocyclyl is optionally substituted with 1, 2 or 3 substituents each independently selected from halogen, hydroxyl, $C_{1-6}$alkyl, halo$C_{1-6}$alkyl, =O, cyano, —C(=O)—$C_{1-6}$alkyl, $C_{1-6}$alkoxy, and —$NR^{14}R^{15}$;

$R^{14}$ and $R^{15}$ each independently represent hydrogen, or halo$C_{1-4}$alkyl, or $C_{1-4}$alkyl optionally substituted with a substituent selected from hydroxyl, $C_{1-4}$alkoxy, amino and mono- or di($C_{1-4}$alkyl)amino;

$R^{16}$ represents hydroxyl, halogen, cyano, $C_{1-4}$alkyl, $C_{1-4}$alkoxy, —$NR^{14}R^{15}$ or —C(=O)$NR^{14}R^{15}$;

$R^{18}$ represents hydrogen, $C_{1-6}$ alkyl, $C_{3-8}$ cycloalkyl, $C_{1-4}$alkyl substituted with $C_{3-8}$ cycloalkyl;

$R^{19}$ represents hydrogen; $C_{1-6}$ alkyl; $C_{3-8}$ cycloalkyl; $C_{1-6}$alkyl substituted with —O—$R^{20}$; —(CH$_2$)$_r$—CN; —(CH$_2$)$_r$—CONR$^{20}$R$^{21}$; —(CH$_2$)$_{r-1}$—NR$^{20}$R$^{21}$; —(CH$_2$)$_{r-1}$—NR$^{20}$COR$^{21}$; —(CH$_2$)$_{r-1}$—NR$^{20}$—(CH$_2$)$_s$—SO$_2$—R$^{21}$; —(CH$_2$)$_{r-1}$—NH—SO$_2$—NR$^{20}$R$^{21}$; —(CH$_2$)$_{r-1}$—NR$^{20}$CO$_2$R$^{21}$; —(CH$_2$)$_r$—SO$_2$NR$^{20}$R$^{21}$; phenyl optionally substituted with 1, 2, 3, 4 or 5 substituents each independently selected from halogen, $C_{1-4}$alkyl, $C_{1-4}$alkyloxy, cyano and amino; a 5- or 6-membered aromatic monocyclic heterocycle containing at least one heteroatom selected from N, O and S, said heterocycle being optionally substituted with 1, 2, 3 or 4 substituents each independently selected from halogen, $C_{1-4}$alkyl, $C_{1-4}$alkyloxy, cyano and amino; wherein said $C_{1-6}$ alkyl and $C_{3-8}$ cycloalkyl, may be optionally substituted by one or more $R^{20}$ groups $R^{20}$ and $R^{21}$ independently represent hydrogen, $C_{1-6}$ alkyl, hydroxy$C_{1-6}$alkyl, —(CH$_2$)$_n$—O—$C_{1-6}$alkyl, or when attached to a nitrogen atom $R^{20}$ and $R^{21}$ can be taken together to form with the nitrogen atom to which they are attached a monocyclic saturated 4, 5 or 6-membered ring which optionally contains a further heteroatom selected from O, S and N;

$R^{22}$ and $R^{23}$ independently represent hydrogen, $C_{1-6}$ alkyl, or hydroxy$C_{1-6}$alkyl;

m independently represents an integer equal to 0, 1 or 2;

n independently represents an integer equal to 0, 1, 2, 3 or 4;
s independently represents an integer equal to 0, 1, 2, 3 or 4;
r independently represent an integer equal to 1, 2, 3, or 4;
r1 independently represent an integer equal to 2, 3 or 4;
or an N-oxide thereof, a pharmaceutically acceptable salt thereof or a solvate thereof.

* * * * *

UNITED STATES PATENT AND TRADEMARK OFFICE
CERTIFICATE OF CORRECTION

PATENT NO.         : 9,757,364 B2                         Page 1 of 1
APPLICATION NO.    : 15/339148
DATED              : September 12, 2017
INVENTOR(S)        : Angibaud et al.

It is certified that error appears in the above-identified patent and that said Letters Patent is hereby corrected as shown below:

In the Claims

Column 218, Line 2: Claim 1, Delete "-$NR^2$" and insert -- -$NR^{12}$ --

Column 218, Line 12: Claim 1, Delete "-$R^3$" and insert -- -$R^{13}$ --

Column 224, Line 58: Claim 21, Delete "-$NR^2$" and insert -- -$NR^{12}$ --

Column 225, Line 1: Claim 21, Delete "-$R^3$" and insert -- -$R^{13}$ --

Signed and Sealed this
Seventh Day of November, 2017

Joseph Matal
*Performing the Functions and Duties of the*
*Under Secretary of Commerce for Intellectual Property and*
*Director of the United States Patent and Trademark Office*